United States Patent
Adusumilli

(10) Patent No.: US 11,648,268 B2
(45) Date of Patent: May 16, 2023

(54) IMMUNE CELL COMPOSITIONS AND METHODS OF USING SAME

(71) Applicant: Memorial Sloan Kettering Cancer Center, New York, NY (US)

(72) Inventor: Prasad S. Adusumilli, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 984 days.

(21) Appl. No.: 16/060,899

(22) PCT Filed: Dec. 8, 2016

(86) PCT No.: PCT/US2016/065578
§ 371 (c)(1),
(2) Date: Jun. 8, 2018

(87) PCT Pub. No.: WO2017/100428
PCT Pub. Date: Jun. 15, 2017

(65) Prior Publication Data
US 2018/0360884 A1   Dec. 20, 2018

Related U.S. Application Data

(60) Provisional application No. 62/265,246, filed on Dec. 9, 2015, provisional application No. 62/265,411, filed on Dec. 9, 2015.

(51) Int. Cl.
| | | |
|---|---|---|
| *A61K 35/17* | (2015.01) | |
| *C07K 14/725* | (2006.01) | |
| *C07K 14/705* | (2006.01) | |
| *C12N 5/0783* | (2010.01) | |
| *A61P 37/06* | (2006.01) | |
| *A61K 9/00* | (2006.01) | |
| *A61K 38/17* | (2006.01) | |
| *A61K 39/395* | (2006.01) | |
| *C07K 16/30* | (2006.01) | |
| *A61K 39/00* | (2006.01) | |

(52) U.S. Cl.
CPC ............ *A61K 35/17* (2013.01); *A61K 9/0019* (2013.01); *A61K 38/177* (2013.01); *A61K 38/1774* (2013.01); *A61K 39/39558* (2013.01); *A61P 37/06* (2018.01); *C07K 14/7051* (2013.01); *C07K 14/70521* (2013.01); *C07K 14/70578* (2013.01); *C07K 16/3069* (2013.01); *C12N 5/0637* (2013.01); *A61K 2039/505* (2013.01); *C07K 2319/00* (2013.01); *C07K 2319/02* (2013.01); *C07K 2319/03* (2013.01); *C07K 2319/30* (2013.01); *C12N 2501/505* (2013.01); *C12N 2501/51* (2013.01); *C12N 2501/515* (2013.01); *C12N 2501/599* (2013.01); *C12N 2510/00* (2013.01)

(58) Field of Classification Search
None
See application file for complete search history.

(56) References Cited

U.S. PATENT DOCUMENTS

| | | |
|---|---|---|
| 4,956,778 A | 9/1990 | Naito |
| 5,091,513 A | 2/1992 | Huston et al. |
| 5,132,405 A | 7/1992 | Huston et al. |
| 5,399,346 A | 3/1995 | Anderson et al. |
| 7,446,190 B2 | 11/2008 | Sadelain et al. |
| 8,802,374 B2 | 8/2014 | Jensen |
| 11,242,375 B2 | 2/2022 | Adusumilli et al. |
| 2003/0105000 A1 | 6/2003 | Pero et al. |
| 2005/0196754 A1 | 9/2005 | Drmanac et al. |
| 2010/0135974 A1* | 6/2010 | Eshhar .............. C12N 5/0636 424/93.71 |
| 2014/0219975 A1 | 8/2014 | June et al. |
| 2015/0031624 A1 | 1/2015 | Feldman |
| 2015/0376296 A1 | 12/2015 | Fedorov et al. |
| 2016/0256488 A1 | 9/2016 | Wu |
| 2016/0348073 A1 | 12/2016 | Meissner et al. |
| 2017/0159025 A1* | 6/2017 | Li .......................... C12N 7/00 |

(Continued)

FOREIGN PATENT DOCUMENTS

| | | |
|---|---|---|
| JP | 2016-520302 | 7/2016 |
| WO | WO 2013/019615 A2 | 7/2013 |

(Continued)

OTHER PUBLICATIONS

Lucas et al. Disruption of T Cell Homeostasis in Mice Expressing a T Cell-Specific Dominant Negative Transforming Growth Factor β II Receptor. J Exp Med (2000) 191 (7): 1187-1196. (Year: 2000).*
Frisancho-Kiss et al., Cutting Edge: T Cell Ig Mucin-3 Reduces Inflammatory Heart Disease by Increasing CTLA-4 during Innate Immunity.J Immunol Jun. 1, 2006, 176 (11) 6411-6415 (Year: 2006).*
U.S. Appl. No. 16/329,142, filed Aug. 29, 2017 (intl. filing date), Adusumilli.
U.S. Appl. No. 62/126,804, filed Mar. 2, 2015 (filing date), Wu.
Certified English translation of U.S. Appl. No. 62/126,804, certified Feb. 11, 2020, 24 pp.

(Continued)

*Primary Examiner* — Michael D Burkhart
(74) *Attorney, Agent, or Firm* — Jones Day

(57) ABSTRACT

Disclosed herein are cells that are immunoinhibitory cell, which cells recombinantly express a dominant negative form of an inhibitor of a cell-mediated immune response of the cell. In certain embodiments, the immunoinhibitory cell is a regulatory T cell. In another aspect, provided herein is a regulatory T cell that recombinantly expresses a dominant negative form of an inhibitor of a regulatory T cell-mediated immune response. The cells can be sensitized to an antigen that is the target of a pathologic immune response associated with an immune-mediated disorder. Additionally provided are methods of using such cells to treat an immune-mediated disorder in a subject in need thereof.

Figure 1A:
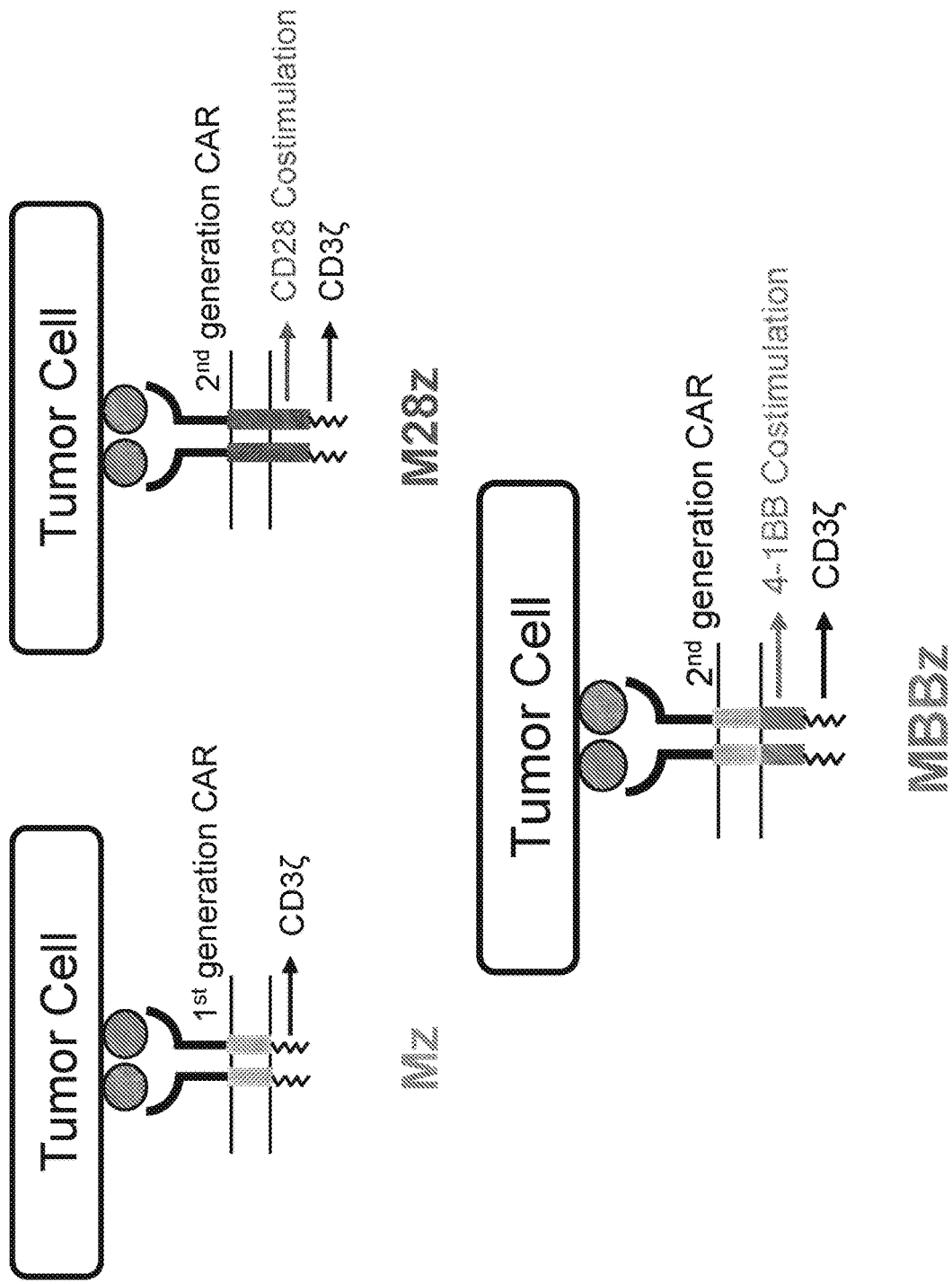

23 Claims, 41 Drawing Sheets
Specification includes a Sequence Listing.

(56) References Cited

U.S. PATENT DOCUMENTS

| | | | |
|---|---|---|---|
| 2017/0258835 A1* | 9/2017 | Zhao | A61P 17/04 |
| 2018/0273601 A1 | 9/2018 | Adusumilli et al. | |
| 2018/0291080 A1* | 10/2018 | Sentman | A61K 35/17 |
| 2020/0010803 A1 | 1/2020 | Adusumilli | |
| 2022/0112263 A1 | 4/2022 | Adusumilli et al. | |

FOREIGN PATENT DOCUMENTS

| | | |
|---|---|---|
| WO | WO 2014/107171 | 7/2014 |
| WO | WO 2014/172584 | 10/2014 |
| WO | WO 2014/184744 A1 | 11/2014 |
| WO | WO 2016/113203 A1 | 7/2016 |
| WO | WO 2016/138846 A1 | 9/2016 |
| WO | WO 2017/040945 A1 | 3/2017 |
| WO | WO 2017/100428 A1 | 6/2017 |
| WO | WO 2018/044866 A1 | 3/2018 |
| WO | WO 2018/165228 A1 | 9/2018 |

OTHER PUBLICATIONS

Definition of "truncate." The American Heritage® Stedman's Medical Dictionary, Copyright © 2002 by Houghton Mifflin Company, 1 p.
Gorelik et al., "Abrogation of TGFbeta signaling in T cells leads to spontaneous T cell differentiation and autoimmune disease," *Immunity*, 12(2):171-181 (2000).
Ataca et al., "Chimeric Antigen Receptor T Cell Therapy in Hematology," *Turk. J. Hematol.*, 32:285-294 (2015).
Adusumilli et al., "Regional delivery of mesothelin-targeted CAR T cell therapy generates potent and long-lasting CD4-dependent tumor immunity," *Sci. Transl. Med.*, 6(261):261ra151 (2014).
Agarwal et al., "Scaffold attachment region-mediated enhancement of retroviral vector expression in primary T cells," *J. Virol.*, 72:3720-3728 (1998).
Ahmad et al., "scFv antibody: principles and clinical application," *Clin. Dev. Immunol.*, 2012: ID980250 (2012).
Ali et al., "HIV-1-Specific Chimeric Antigen Receptors Based on Broadly Neutralizing Antibodies," *J. Virol.*, 90(15):6999-7006 (2016).
Amaranth et al., "The PDL1-PD1 axis converts human TH1 cells into regulatory T cells," *Sci. Transl. Med.*, 3(111):111ra120 (2011).
Anderson, "Prospects for human gene therapy," *Science*, 226:401-409 (1984).
Angaswamy et al., "Interplay between immune responses to HLA and non-HLA self-antigens in allograft rejection," *Hum. Immunol.*, 74(11):1478-1485 (2013).
Aramaki et al., "Programmed death-1-programmed death-L1 interaction is essential for induction of regulatory cells by intratracheal delivery of alloantigen," *Transplantation*, 77(1):6-12 (2004).
Bacher et al., "Antigen-specific expansion of human regulatory T cells as a major tolerance mechanism against mucosal fungi," *Mucosal. Immunol.*, 7(4):916-928 (2014).
Barese et al., "Thymidine kinase suicide gene-mediated ganciclovir ablation of autologous gene-modified rhesus hematopoiesis," *Mol. Therapy*, 20:1932-1943 (2012).
Bennet et al., *Cecil Textbook of Medicine*, 20th ed., W.B. Saunders, Philadelphia PA, pp. 2106-2113 (1996).
Bennet et al., *Cecil Textbook of Medicine*, 20th ed., W.B. Saunders, Philadelphia PA, pp. 1258-1277 (1996).
Bennet et al., *Cecil Textbook of Medicine*, 20th ed., W.B. Saunders, Philadelphia PA, pp. 1459-1466 (1996).
Bennet et al., *Cecil Textbook of Medicine*, 20th ed., W.B. Saunders, Philadelphia PA, pp. 791-792 (1996).
Bennet et al., *Cecil Textbook of Medicine*, 20th ed., W.B. Saunders, Philadelphia PA, pp. 2171-2173 (1996).
Bennet et al., *Cecil Textbook of Medicine*, 20th ed., W.B. Saunders, Philadelphia PA, p. 316 (1996).
Bennet et al., *Cecil Textbook of Medicine*, 20th ed., W.B. Saunders, Philadelphia PA, pp. 1475-1483 (1996).
Bennet et al., *Cecil Textbook of Medicine*, 20th ed., W.B. Saunders, Philadelphia PA, pp. 1408-1417 (1996).
Bennet et al., *Cecil Textbook of Medicine*, 20th ed., W.B. Saunders, Philadelphia PA, pp. 1992-1994 (1996).
Bennet et al., *Cecil Textbook of Medicine*, 20th ed., W.B. Saunders, Philadelphia PA, pp. 1517-1521 (1996).
Bennet et al., *Cecil Textbook of Medicine*, 20th ed., W.B. Saunders, Philadelphia PA, pp. 1471-1472 (1996).
Blomer et al., "Highly efficient and sustained gene transfer in adult neurons with a lentivirus vector," *J. Virol.*, 71:6641-6649 (1997).
Bluestone et al., "T cells in the control of organ-specific autoimmunity," *J. Clin. Invest.*, 125(6):2250-2260 (2015).
Bluestone et al., "Type 1 diabetes immunotherapy using polyclonal regulatory T cells," *Sci. Transl. Med.*, 7(315):315ra189 (2015).
Bollard et al., "Adapting a transforming growth factor beta-related tumor protection strategy to enhance antitumor immunity," *Blood*, 99:3179-3187 (2002).
Bottinger et al., "Expression of a dominant-negative mutant TGF-beta type II receptor in transgenic mice reveals essential roles for TGF-beta in regulation of growth and differentiation in the exocrine pancreas," *EMBO J.*, 16:2621-2633 (1997).
Bregni et al., "Human peripheral blood hematopoietic progenitors are optimal targets of retroviral-mediated gene transfer," *Blood*, 80:1418-1422 (1992).
Brentjens et al., "Genetically targeted T cells eradicate systemic acute lymphoblastic leukemia xenografts," *Clin. Cancer Res.*, 13:5426-5435 (2007).
Briscoe et al., "A rendezvous before rejection: where do T cells meet transplant antigens?," *Nat. Med.*, 8(3):220-222 (2002).
Brusko et al., "Human antigen-specific regulatory T cells generated by T cell receptor gene transfer," *PLoS One*, 5(7):e11726 (2010).
Carter et al., "PD-1:PD-L inhibitory pathway affects both CD4(+) and CD8(+) T cells and is overcome by IL-2," *Eur. J Immunol.*, 32(3):634-643 (2002).
Cayouette et al., "Adenovirus-mediated gene transfer of ciliary neurotrophic factor can prevent photoreceptor degeneration in the retinal degeneration (rd) mouse," *Hum. Gene Ther.*, 8:423-430 (1997).
Chen et al., "Direct expansion of human allospecific FoxP3+CD4+ regulatory T cells with allogeneic B cells for therapeutic application.," *J. Immunol.*, 183:4094-4102 (2009).
Chen et al., "Molecular mechanisms of T cell co-stimulation and co-inhibition," *Nat. Rev. Immunol.*, 13(4):227-242 (2013).
Chen et al., "CAR T-cell intrinsic PD-1 checkpoint blockade: a two-in-one approach for solid tumor immunotherapy," *Oncoimmunology*, 6(2):e1273302 (2017).
Cherkassky et al., "Genetic-Engineering Strategies to Enhance CAR T-Cell Therapy Efficacy against PD-L1 Expressing Lung Adenocarcinoma and Mesothelioma," *J. Thorac. Oncol.*, 10:S794, presented at the World Conference on Lung Cancer, Sep. 6-9, 2015.
Cherkassky et al., "Human CAR T cells with cell-intrinsic PD-1 checkpoint blockade resist tumor-mediated inhibition," *J Clin. Invest.*, 126(8):3130-3144 (2016).
Chmielewski et al., "TRUCKs: the fourth generation of CARs," *Exp. Opin. Biolog. Ther.*, 15(8):1145-1154 (2015).
Chuang et al., "The CD28 and CTLA-4 receptors associate with the serine/threonine phosphatase PP2A," *Immunity*, 13(3):313-322 (2000).
Cornetta et al., "Gene transfer into primates and prospects for gene therapy in humans," *Prog. Nucleic Acid Res. Mol. Biol.*, 36:311-322 (1989).
Dalakas, "Future perspectives in target-specific immunotherapies of myasthenia gravis," *Ther. Adv. Neurol. Disord.*, 8(6):316-327 (2015).
Danos et al., "Safe and efficient generation of recombinant retroviruses with amphotropic and ecotropic host ranges," *Proc. Natl. Acad. Sci. USA*, 85:6460-6464 (1988).
Di Stasi et al., "Inducible apoptosis as a safety switch for adoptive cell therapy," *N. Engl. J. Med.*, 365:1673-1683 (2011).
Dotti et al., "Design and development of therapies using chimeric antigen receptor-expressing T cells," *Immunol. Reviews*, 257(1):107-126 (2013).
Dupont et al., "Artificial antigen-presenting cells transduced with telomerase efficiently expand epitope-specific, human leukocyte antigen-restricted cytotoxic T cells," *Cancer Res.*, 65:5417-5427 (2005).

(56) References Cited

OTHER PUBLICATIONS

Dwivedi et al., "Regulatory T cells in vitiligo: Implications for pathogenesis and therapeutics," *Autoimmun. Rev.*, 14:49-56 (2015).
Eglitis et al., "Retroviral vectors for introduction of genes into mammalian cells," *BioTechniques*, 6:608-614 (1988).
Erlebacher, "Mechanisms of T cell tolerance towards the allogeneic fetus," *Nat. Rev. Immunol.*, 13(1):23-33 (2013).
Fauci et al., *Harrison's Principles of Internal Medicine*, 14th ed., McGraw-Hill, San Francisco CA, pp. 2409-2418 (1998).
Fauci et al., *Harrison's Principles of Internal Medicine*, 14th ed., McGraw-Hill, San Francisco CA, pp. 2060-2081 (1998).
Fauci et al., *Harrison's Principles of Internal Medicine*, 14th ed., McGraw-Hill, San Francisco CA, pp. 1880-1888 (1998).
Fauci et al., *Harrison's Principles of Internal Medicine*, 14th ed., McGraw-Hill, San Francisco CA, pp. 1707-1709 (1998).
Fauci et al., *Harrison's Principles of Internal Medicine*, 14th ed., McGraw-Hill, San Francisco CA, pp. 2469-2472 (1998).
Fauci et al., *Harrison's Principles of Internal Medicine*, 14th ed., McGraw-Hill, San Francisco CA, pp. 316-317 (1998).
Fauci et al., *Harrison's Principles of Internal Medicine*, 14th ed., McGraw-Hill, San Francisco CA, pp. 1874-1880 (1998).
Fauci et al., *Harrison's Principles of Internal Medicine*, 14th ed., McGraw-Hill, San Francisco CA, pp. 1860-1869 (1998).
Fauci et al., *Harrison's Principles of Internal Medicine*, 14th ed., McGraw-Hill, San Francisco CA, pp. 2348-2356 (1998).
Fauci et al., *Harrison's Principles of Internal Medicine*, 14th ed., McGraw-Hill, San Francisco CA, pp. 1935-1941 (1998).
Fauci et al., *Harrison's Principles of Internal Medicine*, 14th ed., McGraw-Hill, San Francisco CA, pp. 1949-1950 (1998).
Fedorov et al., "PD-1- and CTLA-4-based inhibitory chimeric antigen receptors (iCARs) divert off-target immunotherapy responses," *Sci. Transl. Med.*, 5(215):215ra172 (2013).
Feng et al., "A novel human monoclonal antibody that binds with high affinity to mesothelin-expressing cells and kills them by antibody-dependent cell-mediated cytotoxicity," *Mol. Cancer Ther.*, 8:1113-1118 (2009).
Finney et al., "Chimeric receptors providing both primary and costimulatory signaling in T cells from a single gene product," *J. Immunol.*, 161:2791-2797 (1998).
Foster et al., "Antitumor activity of EBV-specific T lymphocytes transduced with a dominant negative TGF-beta receptor," *J. Immunother.*, 31:500-505 (2008).
Fransson et al., "CAR/FoxP3-engineered T regulatory cells target the CNS and suppress EAE upon intranasal delivery," *J. Neuroinflammation*, 9:112 (2012).
Freeman et al., "Engagement of the PD-1 immunoinhibitory receptor by a novel B7 family member leads to negative regulation of lymphocyte activation," *J Exp. Med.*, 192(7):1027-1034 (2000).
Friedman, "Progress toward human gene therapy," *Science*, 244:1275-1281 (1989).
Gade et al., "Targeted elimination of prostate cancer by genetically directed human T lymphocytes," *Cancer Res.*, 65:9080-9088 (2005).
GenBank Accession No. AAH69566.1, "Cytotoxic T-lymphocyte-associated protein 4 [*Homo sapiens*]," (Jul. 15, 2006).
GenBank Accession No. AAP44003.1, "B and T lymphocyte attenuator [*Homo sapiens*]," (Jun. 18, 2003).
GenBank Accession No. AH002818.2, "*Homo sapiens* FKBP12C (FKBP12) gene, FK506-binding protein 12 (FKBP12) gene, complete cds; and FKBP12A (FKBP12) gene, complete sequence," (Jun. 10, 2016).
GenBank Accession No. CAA36243.3, "LAG-3 protein precursor [*Homo sapiens*]," (Sep. 12, 2001).
GenBank Accession No. NM_001229.4, "*Homo sapiens* caspase 9, apoptosis-related cysteine peptidase (CASP9), transcript variant alpha, mRNA," (Mar. 15, 2015).
GenBank Accession No. NP_000607.1, "T-cell surface glycoprotein CD4 isoform 1 precursor [*Homo sapiens*]," (Apr. 23, 2016).
GenBank Accession No. NP_001020018.1, "TGF-beta receptor type-2 isoform A precursor [*Homo sapiens*]," (Apr. 30, 2016).
GenBank Accession No. NP_001139345.1, "T-cell surface glycoprotein CD8 alpha chain isoform 1 precursor [*Homo sapiens*]," (Mar. 15, 2015).
GenBank Accession No. NP_001160135.1, "natural killer cell receptor 2B4 isoform 2 precursor [*Homo sapiens*]," (Jan. 8, 2016).
GenBank Accession No. NP_001181943.1, "T-cell surface glycoprotein CD4 isoform 2 [*Homo sapiens*]," (Mar. 15, 2015).
GenBank Accession No. NP_001181944.1, "T-cell surface glycoprotein CD4 isoform 3 [*Homo sapiens*]," (Mar. 15, 2015).
GenBank Accession No. NP_001181945.1, "T-cell surface glycoprotein CD4 isoform 3 [*Homo sapiens*]," (Mar. 15, 2015).
GenBank Accession No. NP_001181946.1, "T-cell surface glycoprotein CD4 isoform 3 [*Homo sapiens*]," (Mar. 15, 2015).
GenBank Accession No. NP_001275952.2, "leukocyte-associated immunoglobulin-like receptor 1 isoform c precursor [*Homo sapiens*]," (Aug. 28, 2016).
GenBank Accession No. NP_001275954.2, "leukocyte-associated immunoglobulin-like receptor 1 isoform e precursor [*Homo sapiens*]," (Aug. 28, 2016).
GenBank Accession No. NP_001275955.2, "leukocyte-associated immunoglobulin-like receptor 1 isoform f [*Homo sapiens*]," (Aug. 28, 2016).
GenBank Accession No. NP_001275956.2, "leukocyte-associated immunoglobulin-like receptor 1 isoform g [*Homo sapiens*]," (Aug. 28, 2016).
GenBank Accession No. NP_001552.2, "tumor necrosis factor receptor superfamily member 9 precursor [*Homo sapiens*]," (Sep. 1, 2016).
GenBank Accession No. NP_002277.4, "lymphocyte activation gene 3 protein precursor [*Homo sapiens*]," (Jan. 23, 2016).
GenBank Accession No. NP_002278.2, "leukocyte-associated immunoglobulin-like receptor 1 isoform a precursor [*Homo sapiens*]," (Aug. 28, 2016).
GenBank Accession No. NP_003318.1, "tumor necrosis factor receptor superfamily member 4 precursor [*Homo sapiens*]," (Sep. 1, 2016).
GenBank Accession No. NP_005009.2, "programmed cell death protein 1 precursor [*Homo sapiens*]," (Mar. 15, 2015).
GenBank Accession No. NP_005205.2, "cytotoxic T-lymphocyte protein 4 isoform CTLA4-TM precursor [*Homo sapiens*]," (Aug. 28, 2016).
GenBank Accession No. NP_006130.1, "T-cell-specific surface glycoprotein CD28 isoform 1 precursor [*Homo sapiens*]," (Mar. 15, 2015).
GenBank Accession No. NP_008984.1, "160 antigen precursor [*Homo sapiens*]," (Mar. 15, 2015).
GenBank Accession No. NP_036224.1, "inducible T-cell costimulator precursor [*Homo sapiens*]," (May 30, 2016).
GenBank Accession No. NP_055081.1, "hematopoietic cell signal transducer isoform 1 precursor [*Homo sapiens*]," (Mar. 15, 2015).
GenBank Accession No. NP_068352.2, "leukocyte-associated immunoglobulin-like receptor 1 isoform b precursor [*Homo sapiens*]," (Aug. 28, 2016).
GenBank Accession No. NP_116171.3, "hepatitis a virus cellular receptor 2 precursor [Homo sapiens]," (Sep. 1, 2016).
GenBank Accession No. NP_776160.2, "T-cell immunoreceptor with Ig and ITIM domains precursor [*Homo sapiens*]," (Aug. 28, 2016).
GenBank Accession No. NP_861445.3, "B- and T-lymphocyte attenuator isoform 1 precursor [*Homo sapiens*]," (Sep. 1, 2016).
GenBank Accession No. NP_932170.1, "T-cell surface glycoprotein CD3 zeta chain isoform 1 precursor [*Homo sapiens*]," (Mar. 15, 2015).
GenBank Accession No. P10747.1, "T-cell-specific surface glycoprotein CD28," (Jul. 6, 2016).
GenBank Accession No. P41273.1, "Tumor necrosis factor ligand superfamily member 9," (Jul. 6, 2016).
GenBank Accession No. P43489.1, "Tumor necrosis factor receptor superfamily member 4," (Jul. 6, 2016).
Gersbach et al., "Targeted plasmid integration into the human genome by an engineered zinc-finger recombinase," *Nucl. Acids Res.*, 39:7868-7878 (2011).
Gierasch, "Signal sequences," *Biochem.*, 28:923-930 (1989).

(56) References Cited

OTHER PUBLICATIONS

Gomez-Tourino et al., "T cells in type 1 diabetes: Instructors, regulators and effectors: A comprehensive review," *J. Autoimmun.*, 66:7-16 (2016).
Greco et al., "Improving the safety of cell therapy with the TK-suicide gene," *Frontiers Pharmacol.*, 6:95 (2015).
Guerin et al., "Regulatory T-cells and immune tolerance in pregnancy: a new target for infertility treatment?," *Hum. Reprod. Update*, 15(5):517-535 (2009).
Guillonneau et al., "CD8+ regulatory T cells in solid organ transplantation," *Curr. Opin. Organ Transplant.*, 15(6):751-756 (2010).
Hollyman et al., "Manufacturing validation of biologically functional T cells targeted to CD19 antigen for autologous adoptive cell therapy," *J. Immunother.*, 32:169-180 (2009).
Huang et al., "Alzheimer mechanisms and therapeutic strategies," *Cell*, 148(6):1204-1222 (2012).
Hughes et al. "Retroviral gene transfer to primitive normal and leukemic hematopoietic cells using clinically applicable procedures," *J. Clin. Invest.*, 89:1817-1824 (1992).
Huse et al., "Generation of a large combinatorial library of the immunoglobulin repertoire in phage lambda," *Science*, 246:1275-1281 (1989).
Huseby et al., "Role of T cell-glial cell interactions in creating and amplifying central nervous system inflammation and multiple sclerosis disease symptoms," *Front. Cell. Neurosci.*, 9:295, pp. 1-7 (2015).
Huston et al., "Protein engineering of antibody binding sites: recovery of specific activity in an anti-digoxin single-chain Fv analogue produced in *Escherichia coli,*" *Proc. Nat. Acad. Sci. USA*, 85:5879-5883 (1988).
International Search Report for International Application No. PCT/US2016/050128 dated Feb. 2, 2017.
International Search Report for International Application No. PCT/US2016/065578 dated May 3, 2017.
International Search Report for International Application No. PCT/US2017/049085 dated Jan. 11, 2018.
International Search Report for International Application No. PCT/US2018/021249 dated Aug. 10, 2018.
Jensen et al., "Design and implementation of adoptive therapy with chimeric antigen receptor-modified T cells," *Immunol. Rev.*, 257:127-133 (2014).
John et al., "Anti-PD-1 antibody therapy potently enhances the eradication of established tumors by gene-modified T cells," *Clin. Cancer Res.*, 19(20):5636-5646 (2013).
Johnson, "Gene therapy for cystic fibrosis," *Chest*, 107:77S-83S (1995).
Kachala et al., "Mesothelin overexpression is a marker of tumor aggressiveness and is associated with reduced recurrence-free and overall survival in early-stage lung adenocarcinoma," *Clin. Cancer Res.*, 20(4):1020-1028 (2014).
Kaiser et al., "Towards a commercial process for the manufacture of genetically modified T cells for therapy," *Cancer Gene Therapy*, 22:72-78 (2015).
Kershaw et al., "Gene-engineered T cells as a superior adjuvant therapy for metastatic cancer," *J. Immunol.*, 173:2143-2150 (2004).
Kido et al., "Use of a retroviral vector with an internal opsin promoter to direct gene expression to retinal photoreceptor cells," *Curr. Eye Res.*, 15:833-844 (1996).
Koehler et al., "CD28 costimulation overcomes transforming growth factor-beta-mediated repression of proliferation of redirected human CD4+ and CD8+ T cells in an antitumor cell attack," *Cancer Res.*, 67(5):2265-2273 (2007).
Koenen et al., "CD27/CFSE-based ex vivo selection of highly suppressive alloantigen-specific human regulatory T cells," *J. Immunol.*, 174(12):7573-7583 (2005).
Krause et al., "Antigen-dependent CD28 signaling selectively enhances survival and proliferation in genetically modified activated human primary T lymphocytes," *J Exp. Med.*, 188:619-626 (1998).
Kuo et al., "Molecular mechanisms of chronic rejection following transplantation," *Immunol. Red.*, 32(1-3):179-185 (2005).
Lamers et al. "Immune responses to transgene and retroviral vector in patients treated with ex vivo-engineered T cells," *Blood*, 117(1):72-82 (2011).
Lan et al., "Induced Foxp3(+) regulatory T cells: a potential new weapon to treat autoimmune and inflammatory diseases?," *J. Mol. Cell. Biol.*, 4:22-28 (2012).
Le Gal la Salle et al., "An adenovirus vector for gene transfer into neurons and glia in the brain," *Science*, 259:988-990 (1993).
Le Mercier et al., "Beyond CTLA-4 and PD-1, the Generation Z of Negative Checkpoint Regulators," *Front. Immunol.*, 6:418 (2015).
Lee et al., "In vivo inhibition of human CD19-targeted effector T cells by natural T regulatory cells in a xenotransplant murine model of B cell malignancy," *Cancer Res.*, 71(8):2871-2881 (2011).
Liu et al., "A Chimeric Switch-Receptor Targeting PD1 Augments the Efficacy of Second-Generation CAR T Cells in Advanced Solid Tumors," *Cancer Res.*, 76:1578-1590 (2016).
Liu et al., "CD127 expression inversely correlates with FoxP3 and suppressive function of human CD4+ T reg cells," *J. Exp. Med.*, 203(7):1701-1711 (2006).
Lykken et al., "Regulatory B10 cell development and function," *Int. Immunol.*, 27(10):471-477 (2015).
MacDonald et al., "Alloantigen-specific regulatory T cells generated with a chimeric antigen receptor," *J. Clin. Invest.*, 126(4):1413-1424 (2016).
MacLeod et al., "Antigen-based immunotherapy (AIT) for autoimmune and allergic disease," *Curr. Opin. Pharmacol.*, 23:11-16 (2015).
Magnani et al., "Donor-derived CD19-targeted T cells in allogeneic transplants," *Curr. Opin. Hematol.*, 22(6):497-502 (2015).
Maher et al., "Human T-lymphocyte cytotoxicity and proliferation directed by a single chimeric TCRzeta /CD28 receptor," *Nat. Biotechnol.*, 20:70-75 (2002).
Mallone et al., "T cell recognition of autoantigens in human type 1 diabetes: clinical perspectives," *Clin. Develop. Immunol.*, 2011:513210 (2011).
Markley et al., "IL-7 and IL-21 are superior to IL-2 and IL-15 in promoting human T cell-mediated rejection of systemic lymphoma in immunodeficient mice," *Blood*, 115(17):3508-3519 (2010).
Masson et al., "Purification and Immunophenotypic Characterization of Human B Cells with Regulatory Functions," *Regulatory B Cells: Methods and Protocols*, Vitale and Mion eds., Humana Press, New York, Chapter 4, pp. 45-52 (2014).
McCoy et al., "Chromium-release assay for cell-mediated cytotoxicity of human leukemia and lymphoid tissue-culture cells," *Natl. Cancer Inst. Monogr.*, 37:59-67 (1973).
McGray et al., "Immunotherapy-induced CD8+ T cells instigate immune suppression in the tumor," *Mol. Ther.*, 22(1):206-218 (2014).
Memorial Sloan Kettering Cancer Center, "Malignant Pleural Disease Treated With Autologous T Cells Genetically Engineered to Target the Cancer-Cell Surface Antigen Mesothelin," ClinicalTrials.gov archive, pp. 1-10 (Apr. 12, 2018). Retrieved from the Internet: https://clinicaltrials.gov/ct2/show/NCT02414269, on Aug. 3, 2018.
Miller et al., "Generation of helper-free amphotropic retroviruses that transduce a dominant-acting, methotrexate-resistant dihydrofolate reductase gene," *Mol. Cell. Biol.*, 5:431-437 (1985).
Miller et al., "Improved Retroviral Vectors for Gene Transfer and Expression," *Biotechniques*, 7:980-990 (1989).
Miller et al., "Redesign of retrovirus packaging cell lines to avoid recombination leading to helper virus production," *Mol. Cell. Biol.*, 6:2895-2902 (1986).
Miller, "Retrovirus packaging cells," *Hum. Gene Ther.*, 1(1):5-14 (1990).
Miller et al., "CD19-Targeted CAR T Cells: A New Tool in the Fight against B Cell Malignancies," *Oncol. Res. Treat.*, 38:683-690 (2015).
Miyagaki et al., "Regulatory B cells in human inflammatory and autoimmune diseases: from mouse models to clinical research," *Int. Immunol.*, 27(10):495-504 (2015).
Miyara et al., "TREG-cell therapies for autoimmune rheumatic diseases," *Nat. Rev. Rheumatol.*, 10(9):543-551 (2014).

(56) References Cited

OTHER PUBLICATIONS

Miyoshi et al., "Stable and efficient gene transfer into the retina using an HIV-based lentiviral vector," *Proc. Natl. Acad. Sci. U.S.A.*, 94:10319-10323 (1997).
Moen, "Directions in gene therapy," *Blood Cells*, 17:407-416 (1991).
Moon et al., "Multifactorial T-cell hypofunction that is reversible can limit the efficacy of chimeric antigen receptor-transduced human T cells in solid tumors," *Clin. Cancer Res.*, 20(16):4262-4273 (2014).
Morgan et al., "Cancer regression in patients after transfer of genetically engineered lymphocytes," *Science*, 314(5796):126-129 (2006).
Movassagh et al., "Retrovirus-mediated gene transfer into T cells: 95% transduction efficiency without further in vitro selection," *Hum. Gene Ther.*, 11:1189-1200 (2000).
Naldini et al., "In Vivo Gene Delivery and Stable Transduction of Nondividing Cells by a Lentiviral Vector," *Science*, 272:263-267 (1996).
National Cancer Institute, "CAR T Cell Receptor Immunotherapy Targeting Mesothelin for Patients With Metastatic Cancer," ClinicalTrials.gov archive, pp. 1-12 (Aug. 3, 2018). Retrieved from the Internet: https://clinicaltrials.gov/ct2/show/NCT01583686, on Aug. 3, 2018.
Noyan et al., "Isolation of human antigen-specific regulatory T cells with high suppressive function," *Eur. J. Immunol.*, 44:2592-2602 (2014).
Odegard et al., "Biomarkers for antigen immunotherapy in allergy and type 1 diabetes," *Clin. Immunol.*, 161(1):44-50 (2015).
Panelli et al., "A tumor-infiltrating lymphocyte from a melanoma metastasis with decreased expression of melanoma differentiation antigens recognizes MAGE-12," *J Immunol.*, 164:4382-4392 (2000).
Panelli et al., "Expansion of tumor—T cell pairs from fine needle aspirates of melanoma metastases," *J. Immunol.*, 164:495-504 (2000).
Papanicolaou et al., "Rapid expansion of cytomegalovirus-specific cytotoxic T lymphocytes by artificial antigen-presenting cells expressing a single HLA allele," *Blood*, 102:2498-2505 (2003).
Papapetrou et al., "Stoichiometric and temporal requirements of Oct. 4, Sox2, Klf4, and c-Myc expression for efficient human iPSC induction and differentiation," *Proc. Natl. Acad. Sci. U.S.A.*, 106(31):12759-12764 (2009).
Pardoll, "The blockade of immune checkpoints in cancer immunotherapy," *Nat. Rev. Cancer*, 12(4):252-264 (2012).
Parente-Pereira et al., "Use of retroviral-mediated gene transfer to deliver and test function of chimeric antigen receptors in human T-cells," *J. Biol. Methods*, 1(2):e7 (2014).
Parida et al., "T-Cell Therapy: Options for Infectious Diseases," *Clin. Infect. Dis.*, 61(Suppl 3):S217-S224 (2015).
Pasquet et al., "Long-term prevention of chronic allograft rejection by regulatory T-cell immunotherapy involves host Foxp3-expressing T cells," *Blood*, 121(21):4303-4310 (2013).
Petersen, "Mild cognitive impairment as a diagnostic entity," *J. Int. Med.*, 256:183-194 (2004).
Piccirillo et al., "CD4(+)CD25(+) regulatory T cells can mediate suppressor function in the absence of transforming growth factor betal production and responsiveness," *J. Exp. Med.*, 196(2):237-245 (2002).
Pihoker et al., "Autoantibodies in diabetes," *Diabetes*, 54:Suppl 2:s52-61 (2005).
Pollok et al., "Costimulation of transduced T lymphocytes via T cell receptor-CD3 complex and CD28 leads to increased transcription of integrated retrovirus," *Hum. Gene Ther.*, 10:2221-2236 (1999).
Prosser et al., "Tumor PD-L1 co-stimulates primary human CD8(+) cytotoxic T cells modified to express a PD1:CD28 chimeric receptor," *Mol. Immunol.*, 51(3-4):263-272 (2012).
Putnam et al., "Clinical grade manufacturing of human alloantigen-reactive regulatory T cells for use in transplantation," *Am. J Transplant.*, 13(11):3010-3020 (2013).
Putnam et al., "Expansion of human regulatory T-cells from patients with type 1 diabetes," *Diabetes*, 58:652-662 (2009).
Quinn et al., "T cell activation modulates retrovirus-mediated gene expression," *Hum. Gene Ther.*, 9:1457-1467 (1998).
Relander et al., "Gene transfer to repopulating human CD34+ cells using amphotropic-, GALV-, or RD114-pseudotyped HIV-1-based vectors from stable producer," *Mol. Therap.*, 11:452-459 (2005).
Rettig et al., "Transduction and selection of human T cells with novel CD34/thymidine kinase chimeric suicide genes for the treatment of graft-versus-host disease," *Mol. Ther.*, 8:29-41 (2003).
Riese et al., "Enhanced effector responses in activated CD8+ T cells deficient in diacylglycerol kinases," *Cancer Res.*, 73:3566-3577 (2013).
Riley et al., "Human T regulatory cell therapy: take a billion or so and call me in the morning," *Immunity*, 30(5):656-665 (2009).
Riviere et al., "Effects of retroviral vector design on expression of human adenosine deaminase in murine bone marrow transplant recipients engrafted with genetically modified cells," *Proc. Natl. Acad. Sci. USA*, 92:6733-6737 (1995).
Rizk et al., "Tissue and serum mesothelin are potential markers of neoplastic progression in Barrett's associated esophageal adenocarcinoma," *Cancer Epidemiol. Biomarkers Prev.*, 21(3):482-486 (2012).
Rosenberg et al., "Gene transfer into humans—immunotherapy of patients with advanced melanoma, using tumor-infiltrating lymphocytes modified by retroviral gene transduction," *N. Engl. J. Med.*, 323:570-578 (1990).
Sadelain et al., "Targeting tumours with genetically enhanced T lymphocytes," *Nat. Rev. Cancer*, 3:35-45 (2003).
Sadelain et al., "The basic principles of chimeric antigen receptor design," *Cancer Discov.*, 3(4):388-398 (2013).
Sadelain et al., "The promise and potential pitfalls of chimeric antigen receptors," *Curr. Opin. Immunol.*, 21(2):215-223 (2009).
Sage et al., "The receptor PD-1 controls follicular regulatory T cells in the lymph nodes and blood," *Nat. Immunol.*, 14(2):152-161 (2013).
Sakaguchi et al., "Regulatory T cells and immune tolerance," *Cell*, 133(5):775-787 (2008).
Saresella et al., "PD1 negative and PD1 positive CD4+ T regulatory cells in mild cognitive impairment and Alzheimer's disease," *J. Alzheimers Dis.*, 21:927-938 (2010).
Sautto et al., "Chimeric antigen receptor (CAR)-engineered T cells redirected against hepatitis C virus (HCV) E2 glycoprotein," *Gut*, 65(3):512-523 (2015).
Scholler et al., "Decade-Long Safety and Function of Retroviral-Modified Chimeric Antigen Receptor T-cells," *Sci. Transl. Med.*, 4:132ra53 (2012).
Seddiki et al., "Expression of interleukin (IL)-2 and IL-7 receptors discriminates between human regulatory and activated T cells," *J. Exp. Med.*, 203(7):1693-1700 (2006).
Servais et al., "An in vivo platform for tumor biomarker assessment," *PLoS One*, 6(10):e26722 (2011).
Servais et al., "Mesothelin overexpression promotes mesothelioma cell invasion and MMP-9 secretion in an orthotopic mouse model and in epithelioid pleural mesothelioma patients," *Clin. Cancer Res.*, 18(9):2478-2489 (2012).
Servais et al., *Current Protocols in Pharmacology*, Enna ed., John Wiley & Sons, Chapter 14, Unit14 21 (2011).
Sharp, "Gene Therapy," *Lancet*, 337:1277-1278 (1991).
Sharpe et al., "Genetically modified T cells in cancer therapy: opportunities and challenges," *Dis. Model Mech.*, 8(4):337-350 (2015).
Sheppard, "Dominant negative mutants: tools for the study of protein function in vitro and in vivo," *Am. J. Respir. Cell Mol. Biol.*, 11:1-6 (1994).
Shin et al., "Positive conversion of negative signaling of CTLA4 potentiates antitumor efficacy of adoptive T-cell therapy in murine tumor models," *Blood*, 119(24):5678-5687 (2012).
Shin et al., "Enhanced Anti-tumor Reactivity of Cytotoxic T Lymphocytes Expressing PD-1 Decoy," *Immune Netw.*, 16(2):134-139 (2016).
Smarr et al., "Antigen-specific tolerance in immunotherapy of Th2-associated allergic diseases," *Crit. Rev. Immunol.*, 33(5):389-414 (2013).

(56) References Cited

OTHER PUBLICATIONS

Snir et al., "Identification and functional characterization of T cells reactive to citrullinated vimentin in HLA-DRB1*0401-positive humanized mice and rheumatoid arthritis patients," *Arthritis Rheum.*, 63:2873-2883 (2011).
Sontheimer, "The Bacterial Origins of the CRISPR Genome-Editing Revolution," *Hum. Gene Ther.*, 26(7):413-424 (2015).
Spranger et al., "Up-regulation of PD-L1, IDO, and T(regs) in the melanoma tumor microenvironment is driven by CD8(+) T cells," *Sci. Transl. Med.*, 5(200):200ra116 (2013).
Strazza et al., "T cell chemokine receptor patterns as pathogenic signatures in autoimmunity," *Disc. Med.*, 19(103):117-125 (2015).
Su et al., "Human CD4+CD25(high)CD127 (low/neg) regulatory T cells," *Methods Mol. Biol.*, 806:287-299 (2012).
Szymczak et al., "Development of 2A peptide-based strategies in the design of multicistronic vectors," *Expert Opin. Biol. Therapy*, 5(5):627-638 (2005).
Tanaka et al., "PDL1 is required for peripheral transplantation tolerance and protection from chronic allograft rejection," *J. Immunol.*, 179(8):5204-5210 (2007).
Tembhre et al., "Alteration in regulatory T cells and programmed cell death 1-expressing regulatory T cells in active generalized vitiligo and their clinical correlation," *Br. J. Dermatol.*, 172(4):940-950 (2015).
Tolstoshev et al., "Gene expression using retroviral vectors," *Current Opin. Biotechnol.*, 1:55-61 (1990).
Tozbikian et al., "Mesothelin expression in triple negative breast carcinomas correlates significantly with basal-like phenotype, distant metastases and decreased survival," *PLoS One*, 9(12):e114900 (2014).
Tripathi et al., "Role of PD1/PDL1 pathway, and TH17 and treg cells in maternal tolerance to the fetus," *Biomed. J.*, 38(1):25-31 (2015).
Ukena et al., "Isolation strategies of regulatory T cells for clinical trials: phenotype, function, stability, and expansion capacity," *Exp. Hematol.*, 39(12):1152-1160 (2011).
University of Pennsylvania, "CART-meso in Mesothelin Expressing Cancers," ClinicalTrials.gov archive, pp. 1-7 (Nov. 9, 2017). Retrieved from the Internet: https://clinicaltrials.gov/ct2/show/NCT02159716, on Aug. 6, 2018.
Vasileva et al., "Genome-editing tools for stem cell biology," *Cell Death Dis.*, 6:e1831. (2015).
Von Heijne, "Signal sequences. The limits of variation," *J. Mol. Biol.*, 184(1):99-105 (1985).
Wang et al., "Quantitative analysis of clinically relevant mutations occurring in lymphoid cells harboring gamma-retrovirus-encoded hsvtk suicide genes," *Gene Therapy*, 15:1454-1459 (2008).
Wang et al., "Overcoming intrinsic inhibitory pathways to augment the antineoplastic activity of adoptively transferred T cells: Re-tuning your CAR before hitting a rocky road," *Oncoimmunology*, 2(11):e26492 (2013).
Ward et al., "Binding activities of a repertoire of single immunoglobulin variable domains secreted from *Escherichia coli*," *Nature*, 341:544-546 (1989).
Webb et al., "The immunogenetics of primary biliary cirrhosis: A comprehensive review," *J. Autoimmun.*, 64:42-52 (2015).
Wei et al., "Strength of PD-1 signaling differentially affects T-cell effector functions," *Proc. Natl. Acad. Sci. USA*, 110(27):E2480-E2489 (2013).
Wieser et al., "Signaling activity of transforming growth factor beta type II receptors lacking specific domains in the cytoplasmic region," *Mol. Cell. Biol.*, 13:7239-7247 (1993).
Winblad et al., "Mild cognitive impairment—beyond controversies, towards a consensus: report of the International Working Group on Mild Cognitive Impairment," *J. Int. Med.*, 256(3):240-246 (2004).
Winter et al., "Humanized antibodies," *Immunol. Today*, 14:243-246 (1993).
Wolfl et al., "Antigen-specific activation and cytokine-facilitated expansion of naive, human CD8+ T cells," *Nat. Protocols*, 9:950-966 (2014).
Wong et al., "Blockade of programmed death-1 in young (New Zealand Black x New Zealand White)F1 mice promotes the suppressive capacity of CD4+ regulatory T cells protecting from lupus-like disease.," *J. Immunol.*, 190:5402-5410 (2013).
Written Opinion for International Application No. PCT/US2016/050128 dated Feb. 2, 2017.
Written Opinion for International Application No. PCT/US2016/065578 dated May 3, 2017.
Written Opinion for International Application No. PCT/US2017/049085 dated Jan. 11, 2018.
Written Opinion for International Application No. PCT/US2018/021249 dated Aug. 10, 2018.
Wu et al., "Immunotherapies: the blockade of inhibitory signals," *Int. J. Biol. Sci.*, 8:1420-1430.
Wu et al., "Toll-like receptors: potential targets for lupus treatment," *Acta Pharmacologica Sinica*, 36:1395-1407 (2015).
Xu et al., "Correction of the enzyme deficiency in hematopoietic cells of Gaucher patients using a clinically acceptable retroviral supernatant transduction protocol," *Exp. Hemat.*, 22:223-230 (1994).
Yamagiwa et al., "A role for TGF-beta in the generation and expansion of CD4+CD25+ regulatory T cells from human peripheral blood," *J. Immunol.*, 166(12):7282-7289 (2001).
Yamagiwa et al., "Autoantibodies in primary biliary cirrhosis: recent progress in research on the pathogenetic and clinical significance," *World J Gastroenterol.*, 20(10):2606-2612 (2014).
Zhang et al., "Inhibition of TGF-β signaling in genetically engineered tumor antigen-reactive T cells significantly enhances tumor treatment efficacy," *Gene Ther.*, 20(5):575-580 (2013).
Zheng et al., "Generation ex vivo of TGF-beta-producing regulatory T cells from CD4+CD25-precursors," *J. Immunol.*, 169:4183-4189 (2002).
Zhong et al., "Chimeric antigen receptors combining 4-1BB and CD28 signaling domains augment PI3kinase/AKT/Bc1-XL activation and CD8+ T cell-mediated tumor eradication," *Molecular Therapy*, 18(2):413-420 (2010).
Rudikoff et al., 1982, "Single amino acid substitution altering antigen-binding specificity." Proc Natl Acad Sci U S A, 79(6):1979-1983.
Colman PM. 1994, "Effects of amino acid sequence changes on antibody-antigen interactions." Res Immunol. 145(1):33-36.

\* cited by examiner

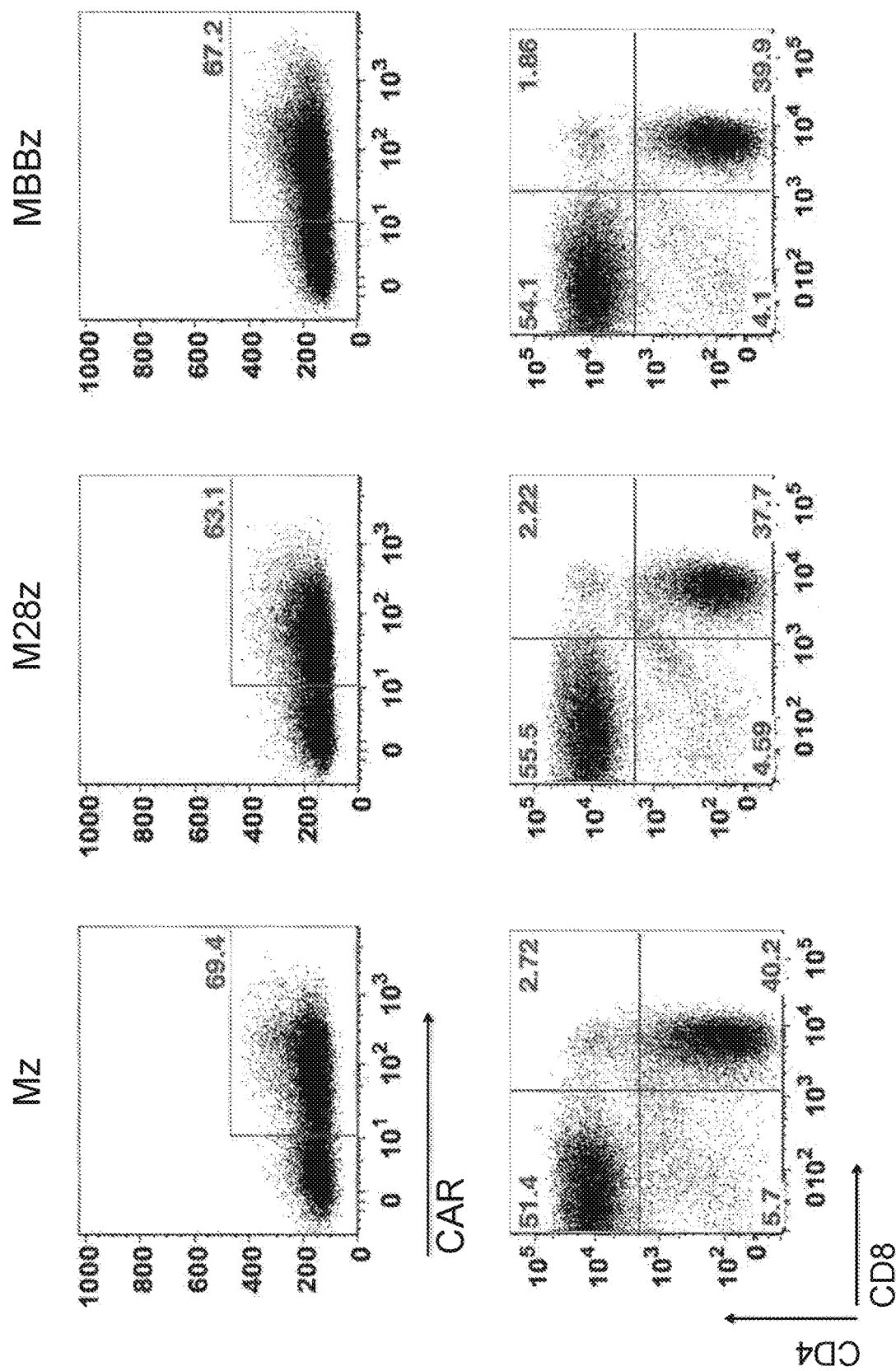

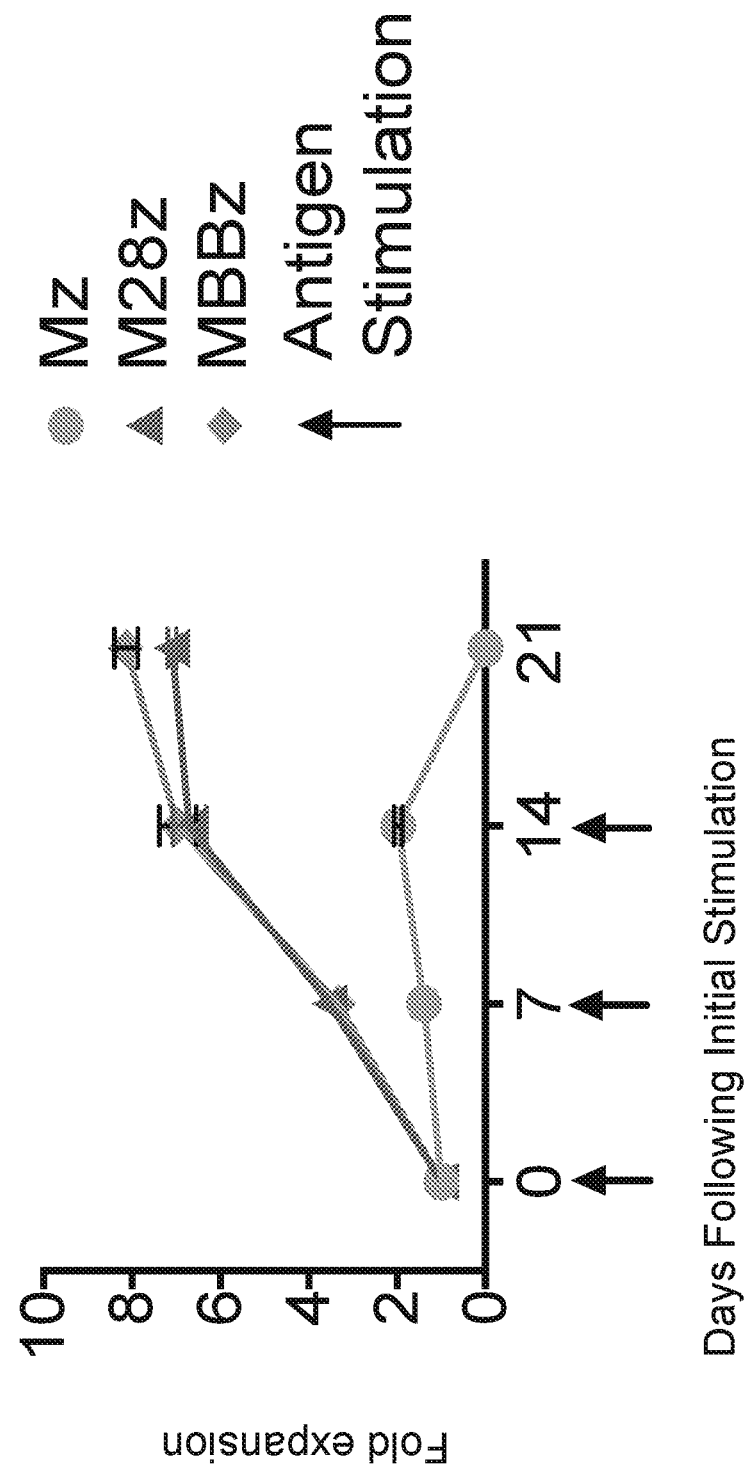

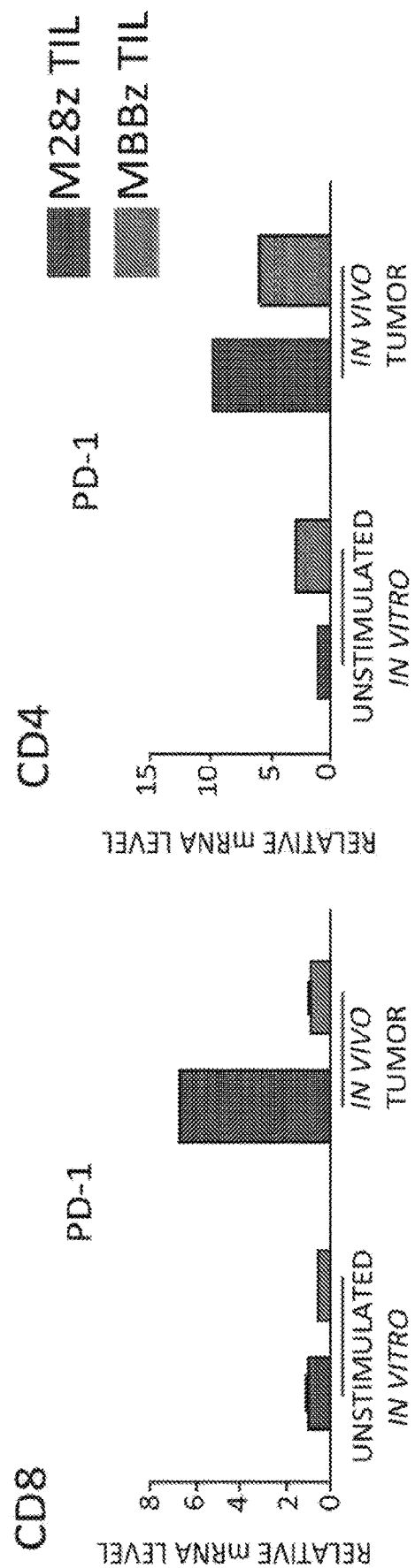

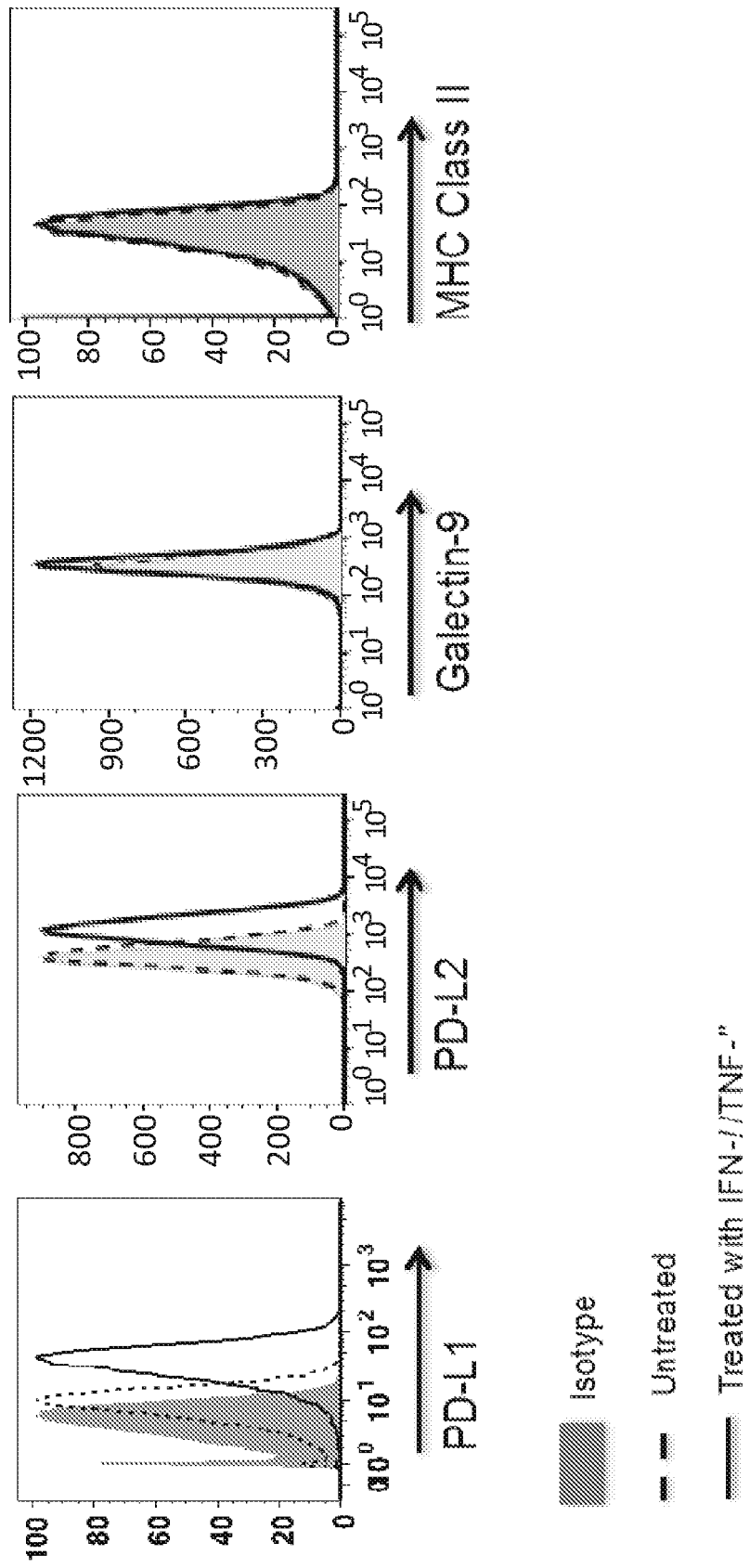

FIG. 8D
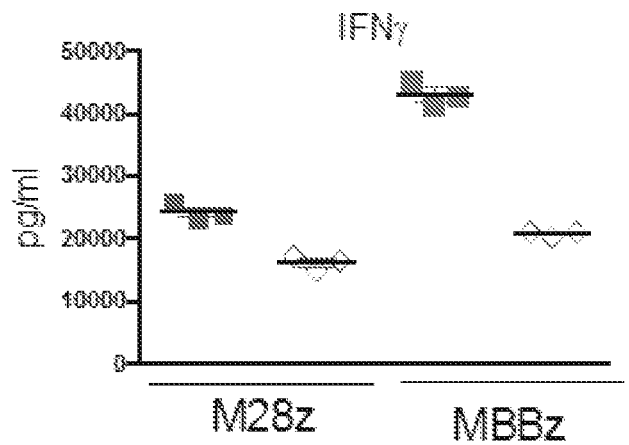
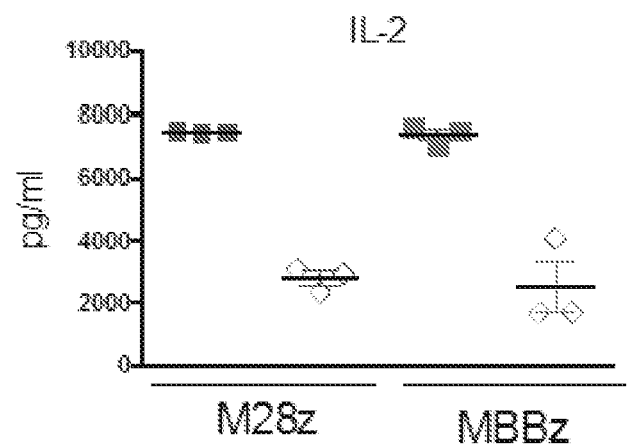
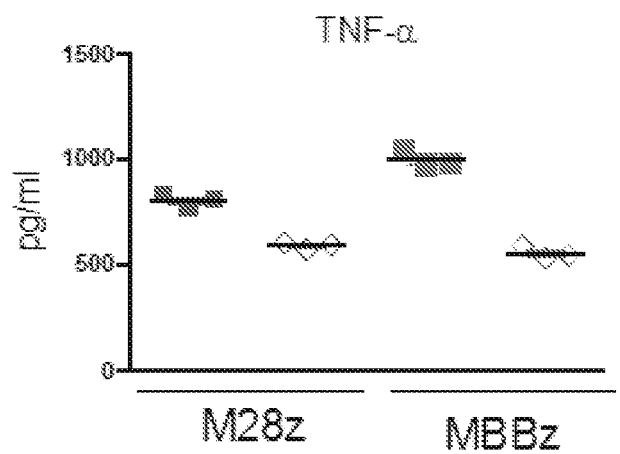

FIG. 10A
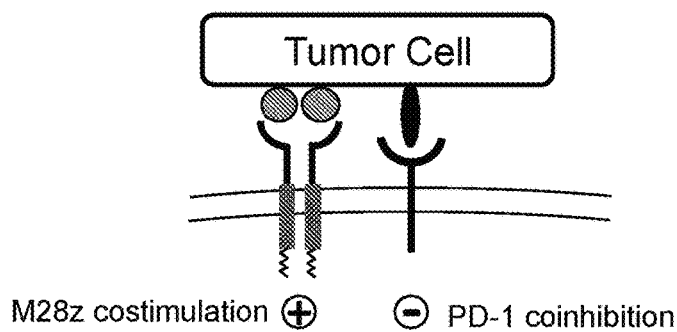
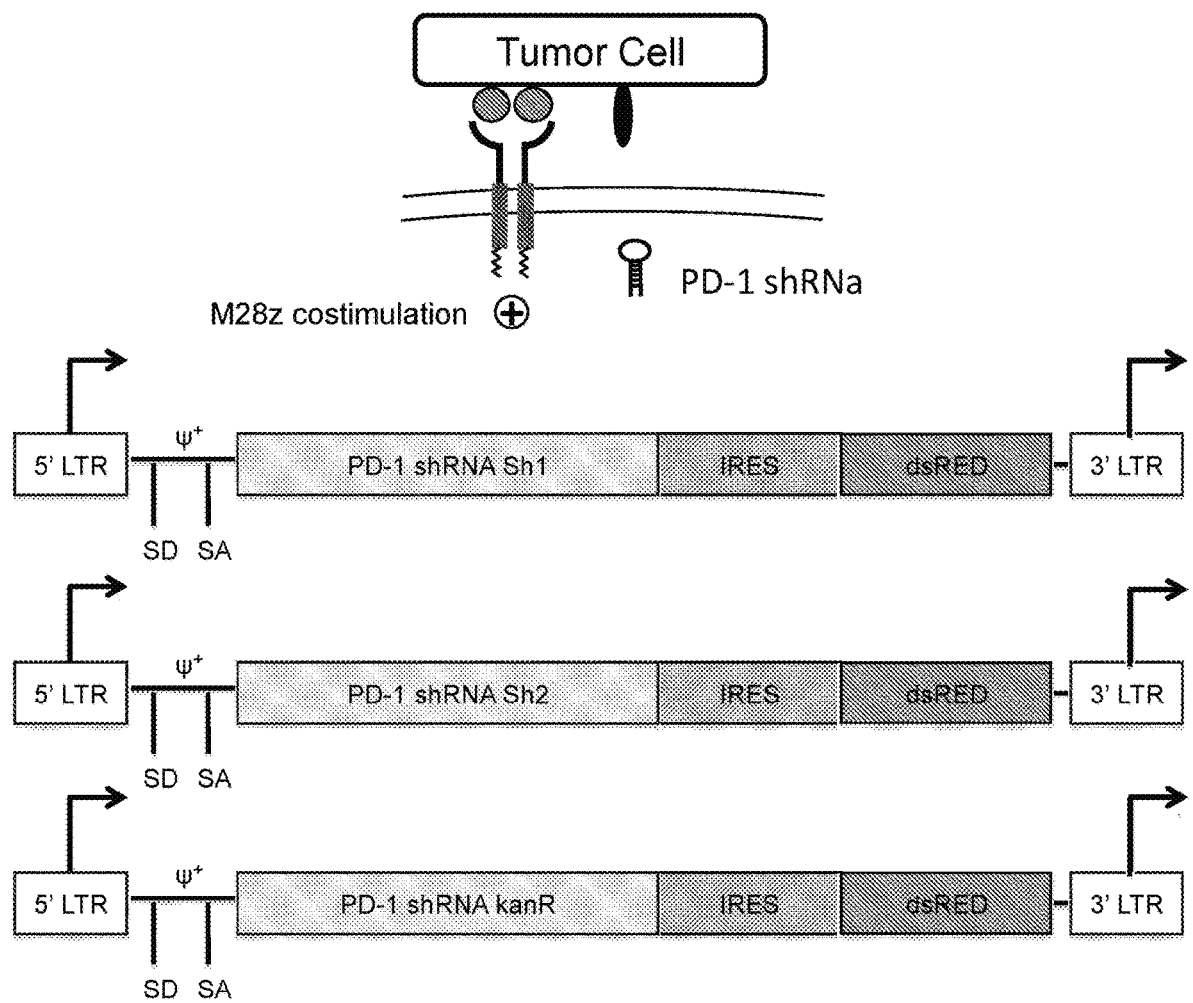

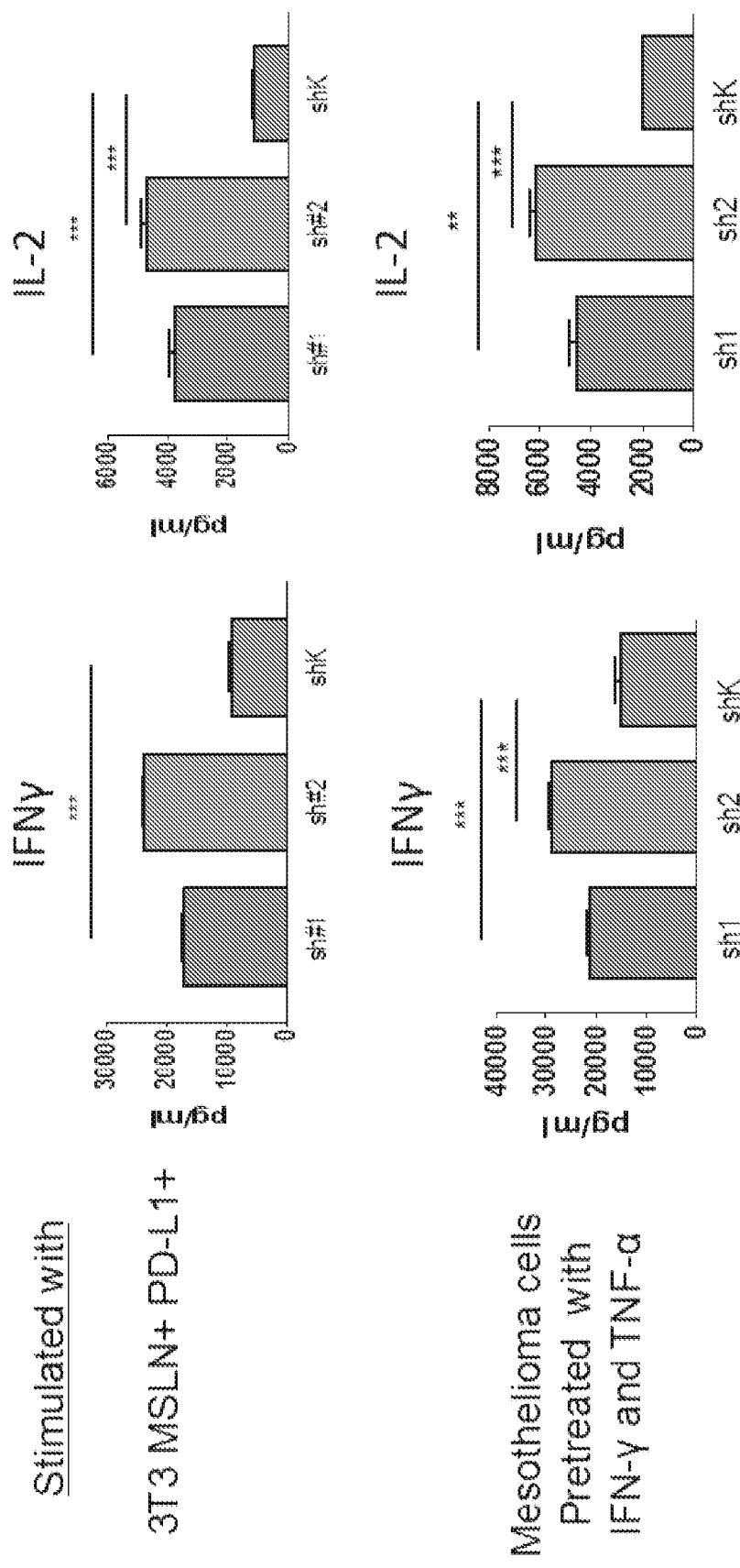

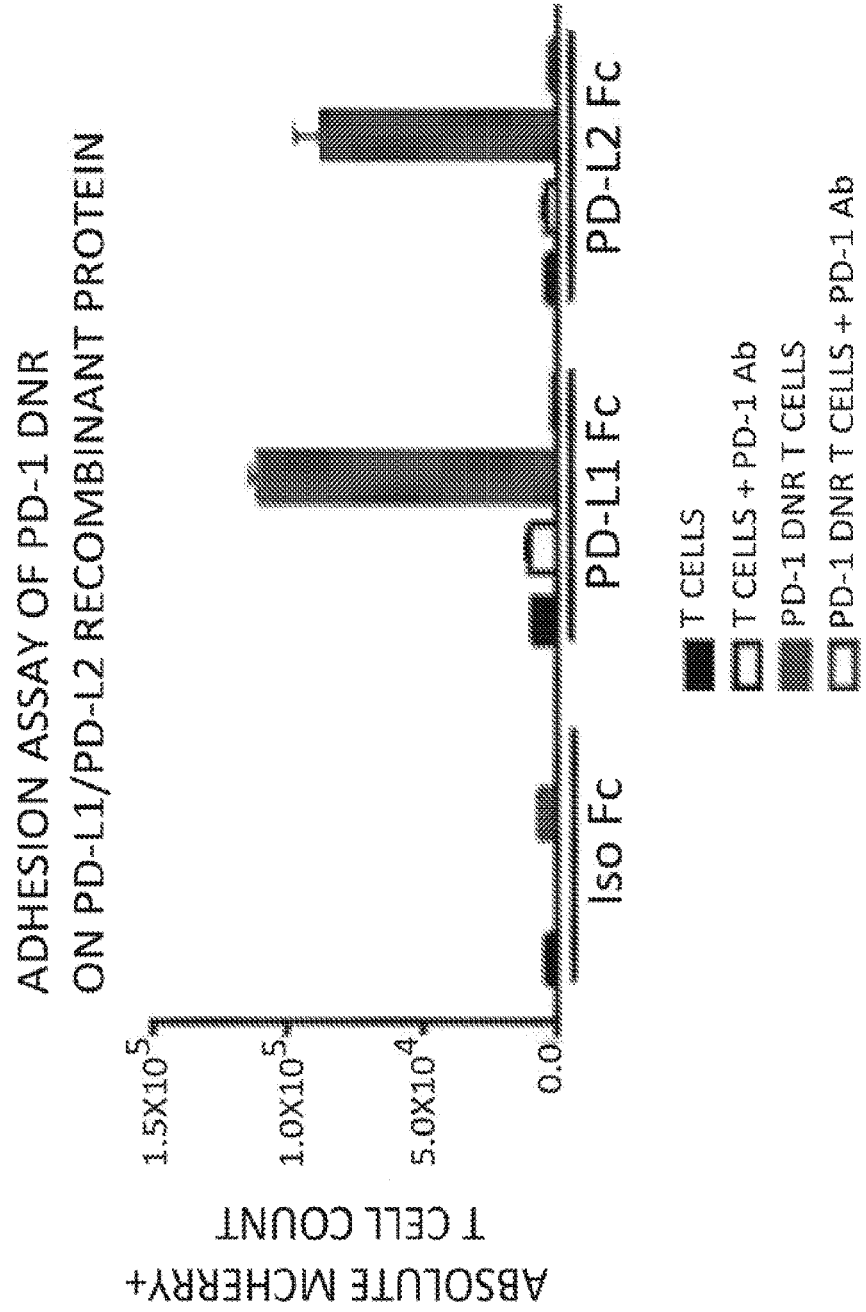

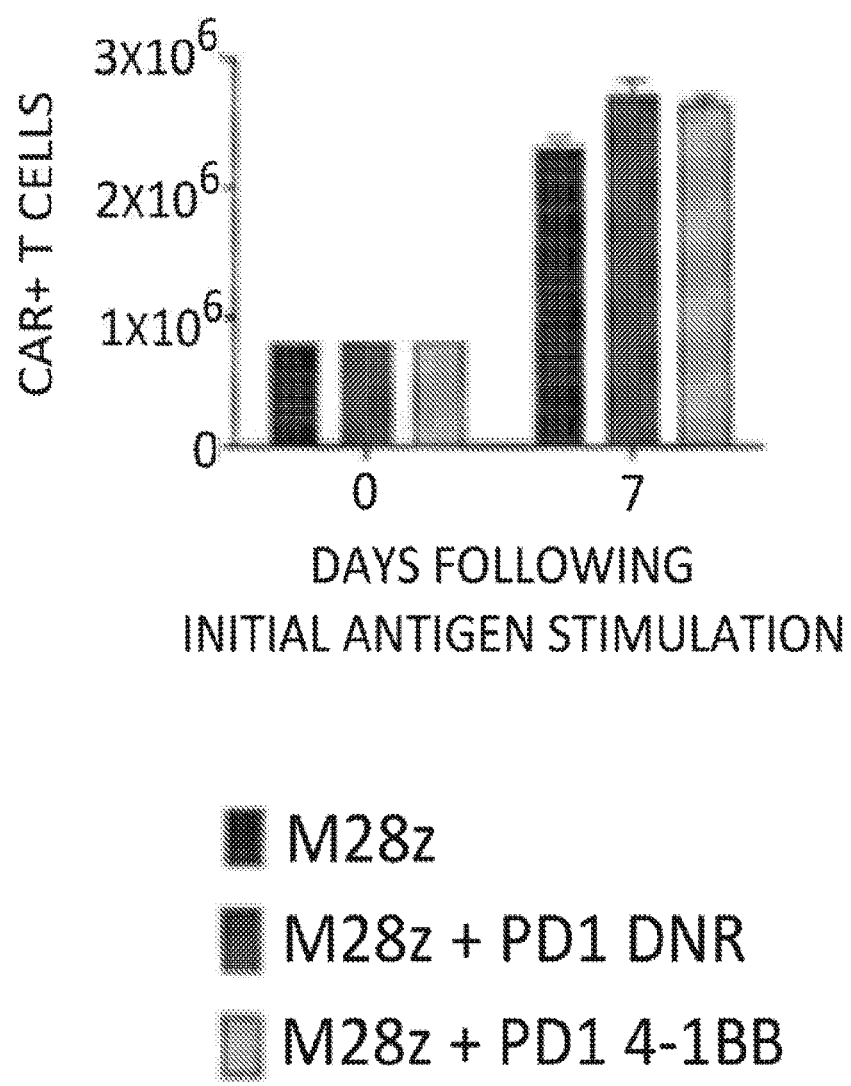

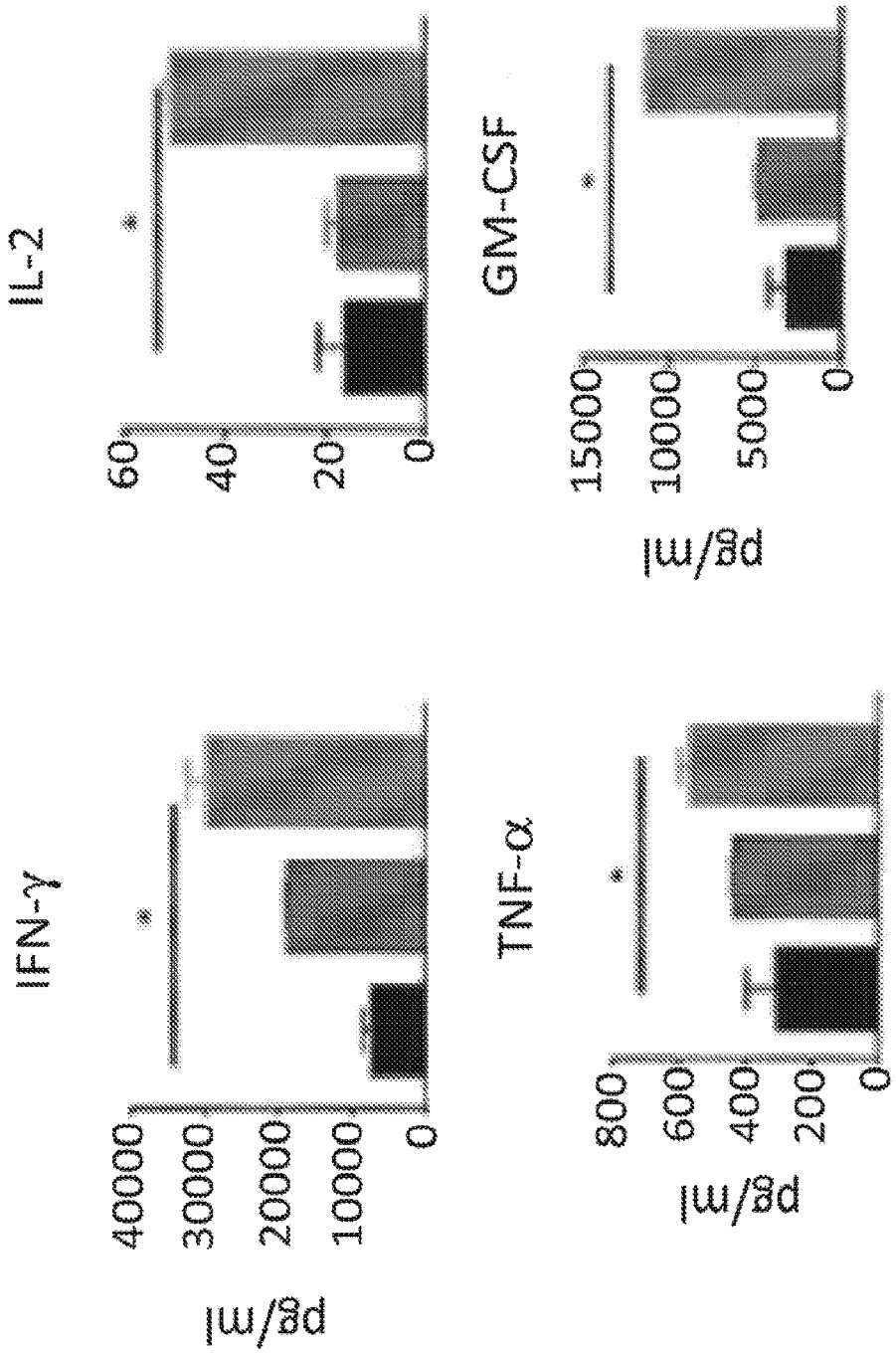

IMMUNE CELL COMPOSITIONS AND METHODS OF USING SAME

1. CROSS-REFERENCE TO RELATED APPLICATIONS

This application is a national stage application of International Patent Application No. PCT/US2016/065578, filed Dec. 8, 2016, which claims the benefit of U.S. Provisional application No. 62/265,246, filed Dec. 9, 2015, and U.S. Provisional application No. 62/265,411, filed Dec. 9, 2015 each Provisional application is incorporated by reference herein in its entirety.

REFERENCE TO SEQUENCE LISTING SUBMITTED ELECTRONICALLY

This application incorporates by reference a Sequence Listing with this application as an ASCII text file entitled "13542-037-228_SL.txt" created on Dec. 6, 2016, and having a size of 59,345 bytes.

2. FIELD

The present invention relates generally to treatment of immune-mediated disorders, and more specifically to immunotherapy for treating immune-mediated disorders.

3. BACKGROUND

The immune system has the challenge of identifying and defending against a diversity of microbial pathogens, while simultaneously avoiding self-reactivity (Paul, *Fundamental Immunology*, 5th ed., Lippincott Williams & Wilkins, New York (2003)). While the immune system has the potent ability to defend against microbial pathogens, the immune system also has mechanisms for suppressing certain immune responses in order to protect the host from being attacked by his or her own immune system.

Among the mechanisms for suppressing certain immune responses, suppressor cells, also known as regulatory cells, such as regulatory T cells, have the ability to inhibit or suppress other immune cells (Paul, supra, 2003). Regulatory T cells thus provide the host with the ability to inhibit or suppress the activity of other immune cells in their function to protect the host from pathogens. Regulatory T cells play an important role in maintaining the ability of the immune system to be unresponsive to self-antigens and for immune tolerance (Sakaguchi et al., *Cell* 133:775-787).

In certain pathological situations, the host immune system can mount an attack against self-antigens, in which case the host can develop an autoimmune disorder. In other situations, for example, in organ transplant rejection, the host cell's immune system mounts an attack against the transplanted organ, which can lead to organ transplant rejection. In these situations where the host cell's immune system is mounting a pathologic immune response in the host, either against a self-antigen or a transplanted organ, it is desirable for the host's immune system to develop tolerance to the self-antigens, in the case of autoimmune disorders, or antigens of the transplanted organ, in the case of organ transplant rejection.

It has been found that Foxp3 expression was specifically up-regulated within allografts displaying donor-specific tolerance, and their frequency decreased after PD-L1 blockade (Tanaka et al., *J. Immunol.* 179:5204-5210 (2007)). Interestingly, PD-1 mRNA is highly expressed in $CD4^+CD25^+$ regulatory T cells, suggesting several means by which PD-1 may be involved in regulating T cell tolerance (Tanaka et al., supra, 2007). Another study demonstrated that PD-1:PD-L1 interaction is essential for induction of regulatory cells by intratracheal delivery of alloantigen (Aramaki et al., *Transplantation* 77:6-12 (2004)).

It has been demonstrated that long-term prevention of chronic allograft rejection by regulatory T cell immunotherapy involves host Foxp3-expressing T cells (Pasquet et al., *Blood* 121:4303-4310 (2013)). A similar approach of enhancing $CD8^+$ regulatory T cell suppressor function has been described for enhancing organ preservation in solid organ transplantation (Guillonneau et al., *Curr. Opin. Organ Transplant* 15:751-756 (2010)).

Autoimmune disorders occur when the body's immune system attacks and destroys healthy body tissue. This occurs when the immune system does not distinguish between healthy tissue and antigens, resulting in a pathologic immune response against cells and tissues within the body. The regulation of T cell trafficking involves the coordinated expression of specific patterns of chemokines and the reciprocal expression of cognate chemokine receptors on T cell membranes, and specific patterns of chemokine receptor expression can correlate with disease activity in an autoimmune disease (Strazza et al., *Disc. Med.* 19:117-125 (2015)).

In patients with vitiligo, the percentage of regulatory T cells was decreased and the percentage of $PD-1^+$ regulatory T cells was increased (Tembhre et al., *Br. J. Immunol.* 172:940-950 (2015)). In a murine lupus model, treatment with anti-PD-1 antibody enhanced the generation of $CD4^+$ regulatory T cells, and delayed disease progression during early stages of active disease (Wong et al., *J. Immunol.* 190:5402-5410 (2013)).

It has also been found that CD4(+)CXCR5(+)Foxp3(+) follicular regulatory T cells (T(FR) cells) inhibit humoral immunity mediated by CD4(+)CXCR5(+)Foxp3(−) follicular helper T cells (T(FH) cells (Sage et al., *Nat. Immunol.* 14:152-161 (2013)). Mice deficient in PD-1 and its ligand PD-L1 had a greater abundance of T(FR) cells in the lymph nodes, and those T(FR) cells had enhanced suppressive ability. Substantial populations of T(FR) cells were found in mouse blood, and it was demonstrated that T(FR) cells in the blood homed to lymph nodes and potently inhibited T(FH) cells in vivo (Sage, supra, 2013). T(FR) cells in the blood required signaling via the costimulatory receptors CD28 and ICOS but were inhibited by PD-1 and PD-L1 (Sage, supra, 2013).

Multiple sclerosis is a condition characterized by areas of inflammation and demyelination affecting the brain, optic nerves and spinal cord, resulting from chronic inflammation and gliosis (scarring) (Bennett et al., *Cecil Textbook of Medicine*, 20th ed., pp. 2106-2113, W.B. Saunders, Philadelphia Pa. (1996); Fauci et al., *Harrison's Principles of Internal Medicine*, 14th ed., pp. 2409-2418, McGraw-Hill, San Francisco Calif. (1998)).

Type 1 diabetes is a disorder in which pancreatic beta cells are gradually destroyed by an autoimmune attack, resulting in the loss of insulin secretory activity (Bennett et al., *Cecil Textbook of Medicine*, 20th ed., pp. 1258-1277, W.B. Saunders, Philadelphia Pa. (1996); Fauci et al., *Harrison's Principles of Internal Medicine*, 14th ed., pp. 2060-2081, McGraw-Hill, San Francisco Calif. (1998)). Polyclonal regulatory T cells have been isolated from type 1 diabetes patients, expanded ex vivo, and administered to the patients in a phase 1 clinical trial (Bluestone et al., *Sci. Transl. Med.* 7(315) (doi: 10.1126/scitranslmed.aad4134)(2015)).

Rheumatoid arthritis is a chronic systemic inflammatory disease predominantly affecting diarthrodial joints and frequently other organs (Bennett et al., *Cecil Textbook of Medicine*, 20th ed., pp. 1459-1466, W.B. Saunders, Philadelphia Pa. (1996); Fauci et al., *Harrison's Principles of Internal Medicine*, 14th ed., pp. 1880-1888, McGraw-Hill, San Francisco Calif. (1998)).

Primary biliary cirrhosis is an immune-mediated disorder characterized by progressive destruction of intrahepatic bile ducts and the presence of antimitochondrial antibodies (Bennett et al., *Cecil Textbook of Medicine*, 20th ed., pp. 791-792, W.B. Saunders, Philadelphia Pa. (1996); Fauci et al., *Harrison's Principles of Internal Medicine*, 14th ed., pp. 1707-1709, McGraw-Hill, San Francisco Calif. (1998)).

Myasthenia gravis is an autoimmune disorder in which pathogenic autoantibodies induce acetylcholine receptor (AChR) deficiency at the motor end-plate (Bennett et al., *Cecil Textbook of Medicine*, 20th ed., pp. 2171-2173, W.B. Saunders, Philadelphia Pa. (1996); Fauci et al., *Harrison's Principles of Internal Medicine*, 14th ed., pp. 2469-2472, McGraw-Hill, San Francisco Calif. (1998)).

Vitiligo is a condition of progressively enlarging amelanotic macrules in a symmetric distribution around body orifices and over bony prominences (knees, elbows, hands) (Bennett et al., *Cecil Textbook of Medicine*, 20th ed., p. 316, W.B. Saunders, Philadelphia Pa. (1996); Fauci et al., *Harrison's Principles of Internal Medicine*, 14th ed., pp. 316-317, McGraw-Hill, San Francisco Calif. (1998)). Melanocytes are absent from the vitiliginous macules. In patients with vitiligo, it was observed that the percentage of regulatory T cells was decreased and the percentage of PD-1$^+$ regulatory T cells was increased (Tembhre et al., *Br. J. Immunol.* 172:940-950 (2015)).

Systemic lupus erythematosus (SLE) is a disease that may produce variable combinations of fever, rashes, hair loss, arthritis, pleuritis, pericarditis, nephritis, anemia, leukopenia, thrombocytopenia, and central nervous system disease (Bennett et al., *Cecil Textbook of Medicine*, 20th ed., pp. 1475-1483, W.B. Saunders, Philadelphia Pa. (1996); Fauci et al., *Harrison's Principles of Internal Medicine*, 14th ed., pp. 1874-1880, McGraw-Hill, San Francisco Calif. (1998)). In a murine lupus model, treatment with anti-PD-1 antibody enhanced the generation of CD4$^+$ regulatory T cells, and delayed disease progression during early stages of active disease (Wong et al., *J. Immunol.* 190:5402-5410 (2013)).

Allergic disorders, also referred to as hypersensitivity, is a condition where the immune system identifies an allergen and mounts an immune response. The immune system produces antibodies called immunoglobulin E (IgE) (Bennett et al., *Cecil Textbook of Medicine*, 20th ed., pp. 1408-1417, W.B. Saunders, Philadelphia Pa. (1996); Fauci et al., *Harrison's Principles of Internal Medicine*, 14th ed., pp. 1860-1869, McGraw-Hill, San Francisco Calif. (1998)). Allergic disorders are often treated with specific immunotherapy (SIT), consisting of gradually increasing doses of allergen (Smarr et al., *Crit. Rev. Immunol.* 33:389-414 (2013)). This procedure can result in antigen-specific tolerance to the antigen (Smarr et al., supra, 2013).

Tolerance of the fetus by the maternal immune system is regulated through various mechanisms involving different immune cells, both in the periphery and locally at the fetomaternal interface (Tripathi et al., *Biomed. J.* 38:25-31 (2015); Erlebacher, *Nat. Rev.* 13:23-33 (2013); Guerin et al., *Hum. Reprod. Update* 15:517-535 (2009)). The maternal T lymphocytes recognize the paternal fetal antigens, and a state of dynamic T cell homeostasis is maintained in the uterus during gestation, which involves an increase in antigen-specific regulatory T cell proliferation, an increase in apoptosis of antigen-specific effector T cells, and inhibition of excessive inflammation post successful implantation to ensure tolerance to the fetus (Tripathi et al., supra, 2015). The regulatory T cells play an important role in the maintenance of tolerance during gestation. In women, regulatory T cells accumulate in the decidua and are elevated in maternal blood from early in the first trimester (Guerin et al., supra, 2009). Both depletion and adoptive transfer of paternal antigen-specific regulatory T cells resulted in modulation of resorption (Tripathi et al., supra, 2015). Inadequate numbers of regulatory T cells or their functional deficiency are linked with infertility, miscarriage and pre-eclampsia (Guerin et al., supra, 2009). The PD-1/PD-L1 pathway has been shown to play an important role in the regulation of the regulatory T cell response in maintaining the fine balance between tolerance and immunity at the fetomaternal interface (Tripithi et al., supra, 2015).

Alzheimer's disease is caused by a progressive and selective degeneration of neuron populations in regions of the brain (Bennett et al., *Cecil Textbook of Medicine*, 20th ed., pp. 1992-1994, W.B. Saunders, Philadelphia Pa. (1996); Fauci et al., *Harrison's Principles of Internal Medicine*, 14th ed., pp. 2348-2356, McGraw-Hill, San Francisco Calif. (1998)). Alzheimer's disease is associated with the formation of amyloid plaques (Huang et al., *Cell* 148:1204-1222 (2012). Both regulatory T cells and PD-1$^+$ regulatory T cells are increased in patients with mild cognitive impairment and Alzheimer's disease compared to healthy controls (Saresella et al., *J. Alzheimer's Dis.* 21:927-938 (2010)). PD-1 negative regulatory T cells, the subpopulation of regulatory T cells endowed with the strongest suppressive ability, are significantly augmented in mild cognitive impairment patients alone (Saresella et al., supra, 2010). In these patients, amyloid-β-stimulated-T cell proliferation was reduced, and regulatory T cell-mediated suppression was more efficient compared to both Alzheimer's patients and healthy controls.

Arthritis is a condition involving joint pain, stiffness and inflammation or swelling. Arthritic disorders, other than rheumatoid arthritis, include, for example, osteoarthritis and psoriatic arthritis. Osteoarthritis, is a disorder of diarthrodial joints characterized by pain and functional limitations (Bennett et al., *Cecil Textbook of Medicine*, 20th ed., pp. 2171-2173, W.B. Saunders, Philadelphia Pa. (1996); Fauci et al., *Harrison's Principles of Internal Medicine*, 14th ed., pp. 1935-1941, McGraw-Hill, San Francisco Calif. (1998)). Osteoarthritis is characterized radiographically by osteophytes and joint space narrowing and histopathologically by alterations in cartilage integrity.

Psoriatic arthritis is a chronic inflammatory arthritis that affects a percentage of people with psoriasis (Bennett et al., *Cecil Textbook of Medicine*, 20th ed., pp. 1471-1472, W.B. Saunders, Philadelphia Pa. (1996); Fauci et al., *Harrison's Principles of Internal Medicine*, 14th ed., pp. 1949-1950, McGraw-Hill, San Francisco Calif. (1998)). Three major types of psoriatic arthritis are asymmetric inflammatory arthritis, symmetric arthritis and psoriatic spondylitis.

There exists a need for therapies to provide improved treatment of immune-mediated disorders, such as autoimmune disorders, organ transplant rejection, and other disorders. The object of the present invention is to satisfy this need.

4. SUMMARY OF INVENTION

The present invention relates to cells that are immunoinhibitory cells, which recombinantly express a dominant negative form of an inhibitor of a cell-mediated immune response of the cell, and to methods of using such cells.

In one aspect, provided herein is a cell that is an immunoinhibitory cell, which cell recombinantly expresses a dominant negative form of an inhibitor of a cell-mediated immune response of the cell. In certain embodiments, the immunoinhibitory cell is a regulatory T cell. In a specific embodiment, the regulatory T cell is a human CD4$^+$CD25$^+$ T cell. In another specific embodiment, the regulatory T cell is a human CD4$^+$CD127$^{lo/-}$CD25$^+$ T cell. In another specific embodiment, the immunoinhibitory cell is a follicular regulatory T cell. In another specific embodiment, the cell is FoxP3$^+$. In another specific embodiment, the immunoinhibitory cell is a regulatory B cell. In another embodiment, provided herein is a population of immunoinhibitory cells as described above.

In another aspect, provided herein is a polyclonal population of human regulatory T cells that are CD4$^+$CD25$^+$, and recombinantly express a dominant negative form of an inhibitor of a regulatory T cell-mediated immune response. In a specific embodiment, the polyclonal population of cells comprise human regulatory T cells that are CD$^{127lo/-}$.

In another aspect, provided herein is a regulatory T cell that recombinantly expresses a dominant negative form of an inhibitor of a regulatory T cell-mediated immune response. In certain embodiments, the regulatory T cell is a human CD4$^+$CD25$^+$ T cell. In a particular embodiment, the regulatory T cell is a human CD4$^+$CD127$^{lo/-}$CD25$^+$ T cell. In certain embodiments, the immunoinhibitory cell is a follicular regulatory T cell.

In certain embodiments of the immunoinhibitory cells of the invention, the inhibitor of a cell-mediated immune response is an immune checkpoint inhibitor. In certain embodiments, the immune checkpoint inhibitor is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIR1), natural killer cell receptor 2B4 (2B4), and CD160. In a particular embodiment, the inhibitor is preferably PD-1. In certain embodiments, the inhibitor is transforming growth factor β(TGF-β) receptor.

In certain embodiments of the immunoinhibitory cells of the invention as described above, the cell recognizes and is sensitized to an antigen that is the target of a pathologic immune response associated with an immune-mediated disorder. In certain embodiments of the immunoinhibitory cells of the invention as described above, the cell further expresses a chimeric antigen receptor (CAR), wherein the CAR binds to an antigen that is the target of a pathologic immune response associated with an immune-mediated disorder.

In certain embodiments of the immunoinhibitory cells of the invention as described above, the dominant negative form is a polypeptide comprising (a) at least a portion of an extracellular domain of an immune checkpoint inhibitor, wherein the portion comprises the ligand binding region, and (b) a transmembrane domain. In certain embodiments of the immunoinhibitory cells of the invention as described above, the dominant negative form further comprises a fusion to a co-stimulatory signaling domain, wherein the co-stimulatory signaling domain is carboxy-terminal to the transmembrane domain of the dominant negative form. In a particular embodiment, the co-stimulatory signaling domain of the dominant negative form is the intracellular signaling domain of 4-1BB. In certain embodiments of the immunoinhibitory cells expressing a dominant negative form that further comprises a fusion to a co-stimulatory signaling domain, the cell further expresses a CAR comprising a co-stimulatory signaling domain. In certain embodiments of such a cell, the co-stimulatory signaling domain of the dominant negative form is different from the co-stimulatory signaling domain of the CAR. In a particular embodiment, the co-stimulatory signaling domain of the CAR is the intracellular signaling domain of CD28. In a particular embodiment, the co-stimulatory signaling domain of the dominant negative form is the intracellular signaling domain of 4-1BB.

In certain embodiments of the immunoinhibitory cells of the invention expressing a CAR, the immune-mediated disorder is selected from the group consisting of organ transplant rejection, an autoimmune disorder, multiple sclerosis, type 1 diabetes, rheumatoid arthritis, primary biliary cirrhosis, myasthenia gravis, vitiligo, lupus, and an allergic disorder. In a particular embodiment, the immune-mediated disorder is organ transplant rejection. In a particular embodiment, the transplanted organ is lung. In a particular embodiment where the transplanted organ is lung, the antigen which the cell recognizes and is sensitized to, or to which the CAR binds, is selected from the group consisting of MHC class I, MHC class II, collagen type V, K alpha1 tubulin, and MHC class I related chain A (MICA). In a particular embodiment, the transplanted organ is kidney. In a particular embodiment where the transplanted organ is kidney, the antigen which the cell recognizes and is sensitized to, or to which the CAR binds, is selected from the group consisting of MHC class I, MHC class II, fibronectin, collagen type IV, collagen type VI, vimentin, angiotensin II type 1 receptor (AGTR1), perlecan, and agrin.

In a particular embodiment, the transplanted organ is liver. In a particular embodiment where the transplanted organ is liver, the antigen which the cell recognizes and is sensitized to, or to which the CAR binds, is selected from the group consisting of MHC class I, MHC class II, collagen type I, collagen type II, collagen type III, and collagen type V. In a particular embodiment, the transplanted organ is heart. In a particular embodiment where the transplanted organ is heart, the antigen which the cell recognizes and is sensitized to, or to which the CAR binds, is selected from the group consisting of MHC class I, MHC class II, cardiac myosin, vimentin, collagen type V, K alpha1 tubulin, and MHC class I related chain A (MICA). In a particular embodiment, the transplanted organ is pancreas. In a particular embodiment where the transplanted organ is pancreas, the antigen which the cell recognizes and is sensitized to, or to which the CAR binds, is selected from the group consisting of MHC class I, MHC class II, an islet cell autoantibody (ICA) antigen, insulin, and glutamic acid decarboxylase (GAD).

In particular embodiments of the invention, the immune-mediated disorder is an autoimmune disorder. In a particular embodiment, the autoimmune disorder is multiple sclerosis. In a particular embodiment where the autoimmune disorder is multiple sclerosis, the antigen which the cell recognizes and is sensitized to, or to which the CAR binds, is selected from the group consisting of myelin, myelin basic protein, myelin oligodendrocyte glycoprotein, proteolipid protein, astrocyte proteins, glial fibrillary protein (GFAP), and S100beta. In a particular embodiment, the autoimmune disorder is type 1 diabetes. In a particular embodiment where the autoimmune disorder is type 1 diabetes, the antigen which the cell recognizes and is sensitized to, or to which the CAR binds, is selected from the group consisting of a beta cell antigen, insulin, insulin B chain, proinsulin, preproinsulin, glutamic acid decarboxylase-65 (GAD65), islet-associated antigen 2, islet-specific glucose-6-phosphatase catalytic subunit-related protein (IGRP), zinc transporter 8 (ZnT8), islet antigen 2 (IA-2), heat shock protein 60 (HSP60), and chromogranin A.

In a particular embodiment, the autoimmune disorder is rheumatoid arthritis. In a particular embodiment where the autoimmune disorder is rheumatoid arthritis, the antigen which the cell recognizes and is sensitized to, or to which the CAR binds, is selected from the group consisting of dnaJ (heat shock protein), citrullinated-vimentin, and human cartilage glycoprotein-39. In a particular embodiment, the autoimmune disease is primary biliary cirrhosis. In a particular embodiment where the autoimmune disorder is primary biliary cirrhosis, the antigen which the cell recognizes and is sensitized to, or to which the CAR binds, is selected from the group consisting of a mitochondrial component, pyruvate dehydrogenase (mitochondrial); E2 component of pyruvate dehydrogenase; E2 component of branched chain 2-oxo acid dehydrogenase; E2 component of 2-oxo-glutarate dehydrogenase complex; E3 binding protein of dihydrolipoamide dehydrogenase; a nuclear component; nuclear protein sp100, nuclear pore complex protein gp120, and centromere. In a particular embodiment, the autoimmune disorder is myasthenia gravis. In a particular embodiment where the autoimmune disorder is myasthenia gravis, the antigen which the cell recognizes and is sensitized to, or to which the CAR binds, is selected from the group consisting of acetylcholine receptor (AChR), aquaporin-4 (AQP-4), CTLA-4, ICAM, LFA-3, CD40/CD154, ICOS/ICOSL, CD52, nuclear factor of activated T cells (NFAT), phospholipase C (PLC), CD25, Janus kinase, B cell activating factor (BAFF), a proliferating inducing ligand (APRIL), IL6R, IL17, IL12/IL23, an integrin, and a sphingosin receptor.

In a particular embodiment, the autoimmune disorder is vitiligo. In a particular embodiment where the autoimmune disorder is vitiligo, the antigen which the cell recognizes and is sensitized to, or to which the CAR binds, is a melanocyte antigen. In a particular embodiment, the autoimmune disorder is lupus, for example, systemic lupus erythematosus. In a particular embodiment where the autoimmune disorder is lupus, the antigen which the cell recognizes and is sensitized to, or to which the CAR binds, is selected from the group consisting of a toll-like receptor, TLR2, TLR3, TLR4, TLR5, TLR7, TLR8, TLR9, MyD88, and a IL-1R-associated kinase (IRAK).

In certain embodiments, the immune-mediated disorder is an allergic disorder. In a particular embodiment, the antigen which the cell recognizes and is sensitized to, or to which the CAR binds, is an allergen associated with the allergic disorder.

In certain embodiments of the invention, the cells of the invention further recombinantly expresses a suicide gene. In a particular embodiment, the suicide gene comprises inducible Caspase 9. In certain embodiments of the invention, the cell is derived from a human. In a particular embodiment, the cell is isolated from placenta. In a particular embodiment, the cell is derived from a human having mild cognitive impairment.

In another aspect, provided herein are pharmaceutical compositions comprising a therapeutically effective amount of the cell or population of the invention as described above; and a pharmaceutically acceptable carrier.

In another embodiment, provided herein are pharmaceutical compositions comprising a therapeutically effective amount of the cell or population of the invention as described above, wherein the dominant negative form further comprises a fusion to a co-stimulatory signaling domain; and a pharmaceutically acceptable carrier.

In yet another aspect, provided herein is a method of treating an immune-mediated disorder in a patient in need thereof, comprising administering to the patient a therapeutically effective amount of the cell or population of the invention as described above. In another embodiment, provided herein is a method of treating an immune-mediated disorder in a patient in need thereof, comprising administering to the patient the pharmaceutical composition of the invention. In certain embodiments, the immune-mediated disorder is selected from the group consisting of organ transplant rejection, an autoimmune disorder, multiple sclerosis, type 1 diabetes, rheumatoid arthritis, primary biliary cirrhosis, myasthenia gravis, vitiligo, lupus, an allergic disorder, fetomaternal intolerance, and Alzheimer's disease.

In another aspect, provided herein is a method of treating an immune-mediated disorder in a patient in need thereof, comprising administering to the patient a therapeutically effective amount of the cell or population of the invention as described above, wherein the dominant negative form further comprises a fusion to a co-stimulatory signaling domain. In another aspect, provided herein is a method of treating an immune-mediated disorder in a patient in need thereof, comprising administering to the patient a pharmaceutical composition comprising such cells expressing a dominant negative form further comprising a fusion to a co-stimulatory signaling domain. In certain embodiments, the immune-mediated disorder is selected from the group consisting of organ transplant rejection, an autoimmune disorder, multiple sclerosis, type 1 diabetes, rheumatoid arthritis, primary biliary cirrhosis, myasthenia gravis, vitiligo, lupus, an allergic disorder, fetomaternal intolerance, and Alzheimer's disease.

In another aspect, provided herein is a method of decreasing the risk of organ transplant rejection in an organ transplant recipient in need thereof comprising administering to the recipient a therapeutically effective amount of the cell or population of the invention as described above, which cell or population expresses a CAR that binds to an antigen of the organ transplant associated with organ transplant rejection. In yet another aspect, provided herein is a method of decreasing the risk of organ transplant rejection in an organ transplant recipient in need thereof comprising administering to the recipient a therapeutically effective amount of the cell or population of the invention as described above, which cell or population is the product of a process comprising isolating regulatory T cells from the recipient, and expanding the isolated regulatory T cells in cell culture.

In another aspect, provided herein is a method of treating an autoimmune disorder in a patient in need thereof, comprising administering to the patient a therapeutically effective amount of the cell or population of the invention as described above, which cell or population expresses a CAR that binds to an autoimmune antigen of the autoimmune disorder. In still another aspect, provided herein is a method of treating an autoimmune disorder in a patient in need thereof, comprising administering to the patient a therapeutically effective amount of the cell or population of the invention as described above, which cell or population is the product of a process comprising isolating regulatory T cells from the patient, and expanding the isolated regulatory T cells in cell culture. In certain embodiments, the autoimmune disorder is selected from the group consisting of multiple sclerosis, type 1 diabetes, rheumatoid arthritis, primary biliary cirrhosis, myasthenia gravis, vitiligo, and lupus.

In another aspect, provided herein is a method of treating an allergic disorder in a patient in need thereof, comprising administering to the patient a therapeutically effective amount of the cell or population of the invention as described above, which cell or population expresses a CAR that binds to an allergen associated with the allergic disorder. In yet another aspect, provided herein is a method of treating an allergic disorder in a patient in need thereof, comprising administering to the patient a therapeutically effective amount of the cell or population of the invention as described above, which cell or population is the product of a process comprising isolating regulatory T cells from the patient, and expanding the isolated regulatory T cells in cell culture. In certain embodiments, administering the cells has an effect in the patient selected from the group consisting of decreasing the duration of specific immunotherapy, increasing the efficacy of specific immunotherapy, and prolonging the effect of specific immunotherapy.

In another aspect, provided herein is a method of decreasing fetomaternal intolerance in a pregnant female in need thereof, comprising administering to the pregnant female a therapeutically effective amount of the cell or population of the invention as described above, which cell or population is the product of a process comprising isolating regulatory T cells from a placenta from a prior pregnancy of the pregnant female and transducing the regulatory T cells so that they recombinantly express a dominant negative form of an inhibitor of a regulatory T cell-mediated immune response. In a particular embodiment, the regulatory T cell is isolated from a placenta of the pregnant female being treated for fetomaternal intolerance. In another particular embodiment, the isolated regulatory T cell is paternal-antigen specific.

In another aspect, provided herein is a method of decreasing the risk of progression to Alzheimer's disease in a patient with mild cognitive impairment, comprising administering to the patient a therapeutically effective amount of the cell or population of the invention as described above, which cell or population is the product of a process comprising isolating regulatory T cells from the patient and expanding the isolated regulatory T cells in cell culture.

In another aspect, provided herein is a method of promoting self-tolerance or reestablishing immunological tolerance to a self-antigen in a patient in need thereof, comprising administering to the patient a therapeutically effective amount of the cell or population of the invention as described above, wherein the cell is a regulatory T cell specific to (that recognizes) the self-antigen, or the population comprises regulatory T cells specific to (that recognize) the self-antigen.

In certain embodiments of methods of the invention, the administering of cells of the invention is by intrapleural administration, intravenous administration, subcutaneous administration, intranodal administration, intrathecal administration, intraperitoneal administration, intracranial administration, intratracheal administration, intraarticular administration, intrauterine administration, intraocular administration, intranasal administration, intraspinal administration, epidural administration, direct administration at a tendon insertion site, or direct administration to the thymus. In a preferred embodiment, the administering is by intravenous administration.

In another aspect, the invention provides a method of treating arthritis in a patient in need thereof, comprising administering to the patient a therapeutically effective amount of the cell or population of the invention as described above, wherein the cell or population is administered intraarticularly or directly at a tendon insertion site of an arthritic joint.

In certain embodiments of methods of the invention, the cell is administered in a dose in the range of $10^4$ to $10^{10}$ cells per kilogram of body weight of the patient, recipient or pregnant female. In certain embodiments, the cell or population is administered in a dose in the range of $1\times10^5$ to $1\times10^8$ cells per kilogram of body weight of the patient, recipient or pregnant female. In certain embodiments of methods of the invention, the patient, recipient, or pregnant female is a human.

In another aspect, the invention provides a method of treating an immune-mediated disorder in a patient in need thereof, comprising isolating regulatory T cells from the patient, expanding the regulatory T cells in cell culture in vitro, and administering the expanded regulatory T cells to the patient in a therapeutically effective amount, wherein the isolated regulatory T cells are transduced to express a dominant negative form of an inhibitor of a regulatory T cell-mediated immune response.

In another aspect, the invention provides the methods of the invention described above, wherein the methods further comprise administering an immunoinhibitory cell recombinantly expressing a chimeric antigen receptor (CAR) and a switch receptor, wherein the CAR comprises a co-stimulatory signaling domain, and wherein the switch receptor is a fusion protein comprising, in amino- to carboxy-terminal order: (i) at least the extracellular ligand binding domain of an immune checkpoint inhibitor, (ii) a transmembrane domain, and (iii) a co-stimulatory signaling domain. In one embodiment, the co-stimulatory signaling domain of the switch receptor is different from the co-stimulatory signaling domain of the CAR expressed in the cell that also expresses the switch receptor. In a particular embodiment, the co-stimulatory signaling domain of the CAR expressed in the cell that also expresses the switch receptor is the intracellular signaling domain of CD28. In a particular embodiment, the co-stimulatory signaling domain of the switch receptor is the intracellular signaling domain of 4-1BB. In a specific embodiment directed to a method of decreasing the risk of organ transplant rejection an organ transplant recipient in need thereof, the CAR expressed in the cell that also expresses the switch receptor binds to an antigen of the organ transplant associated with organ transplant rejection. In a specific embodiment directed to a method of treating an autoimmune disorder a patient in need thereof, the CAR expressed in the cell that also expresses the switch receptor binds to an autoimmune antigen of the autoimmune disorder. In a specific embodiment directed to a method of treating an allergic disorder in a patient in need thereof, the CAR expressed in the cell that also expresses the switch receptor binds to an allergen associated with the allergic disorder.

In another aspect, the invention provides a method of decreasing the risk of organ transplant rejection in an organ transplant recipient in need thereof comprising administering to the recipient a therapeutically effective amount of the cell or population of the invention as described above, wherein the cells express a dominant negative form and a CAR, wherein the dominant negative form further comprises a fusion to a co-stimulatory signaling domain, and wherein the CAR binds to an antigen of the organ transplant associated with organ transplant rejection.

In another aspect, the invention provides a method of treating an autoimmune disorder in a patient in need thereof, comprising administering to the patient a therapeutically effective amount of the cell or population of the invention as described above, wherein the cells express a dominant negative form and a CAR, wherein the dominant negative form further comprises a fusion to a co-stimulatory signaling domain, and wherein the CAR binds to an autoimmune antigen of the autoimmune disorder.

In another aspect, the invention provides a method of treating an allergic disorder in a patient in need thereof, comprising administering to the patient a therapeutically effective amount of the cell or population of the invention as described above, wherein the cells express a dominant negative form and a CAR, wherein the dominant negative form further comprises a fusion to a co-stimulatory signaling domain, and wherein the CAR binds to an allergen associated with the allergic disorder.

5. DESCRIPTION OF THE DRAWINGS

Figure 1B:
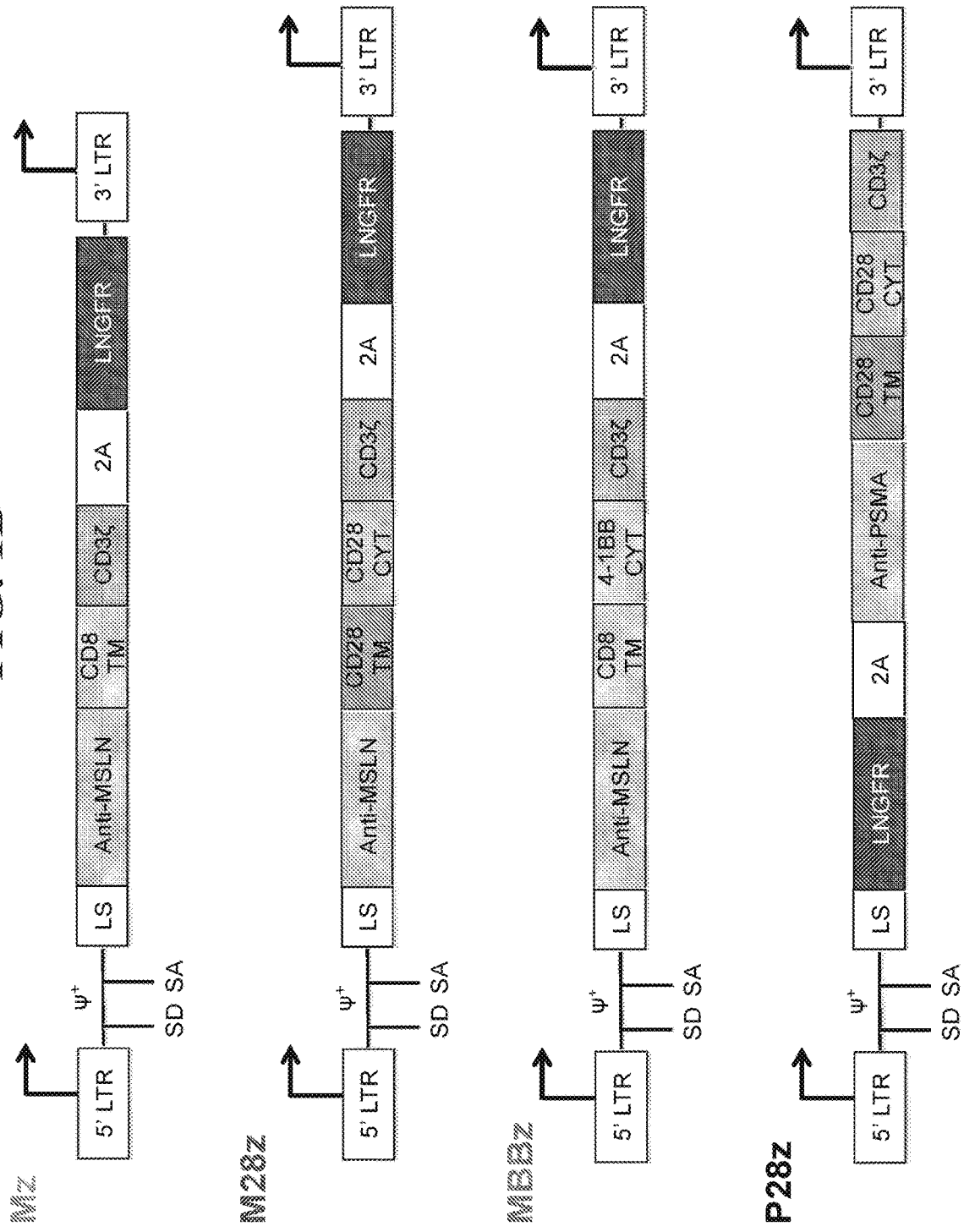
Figure 1C:
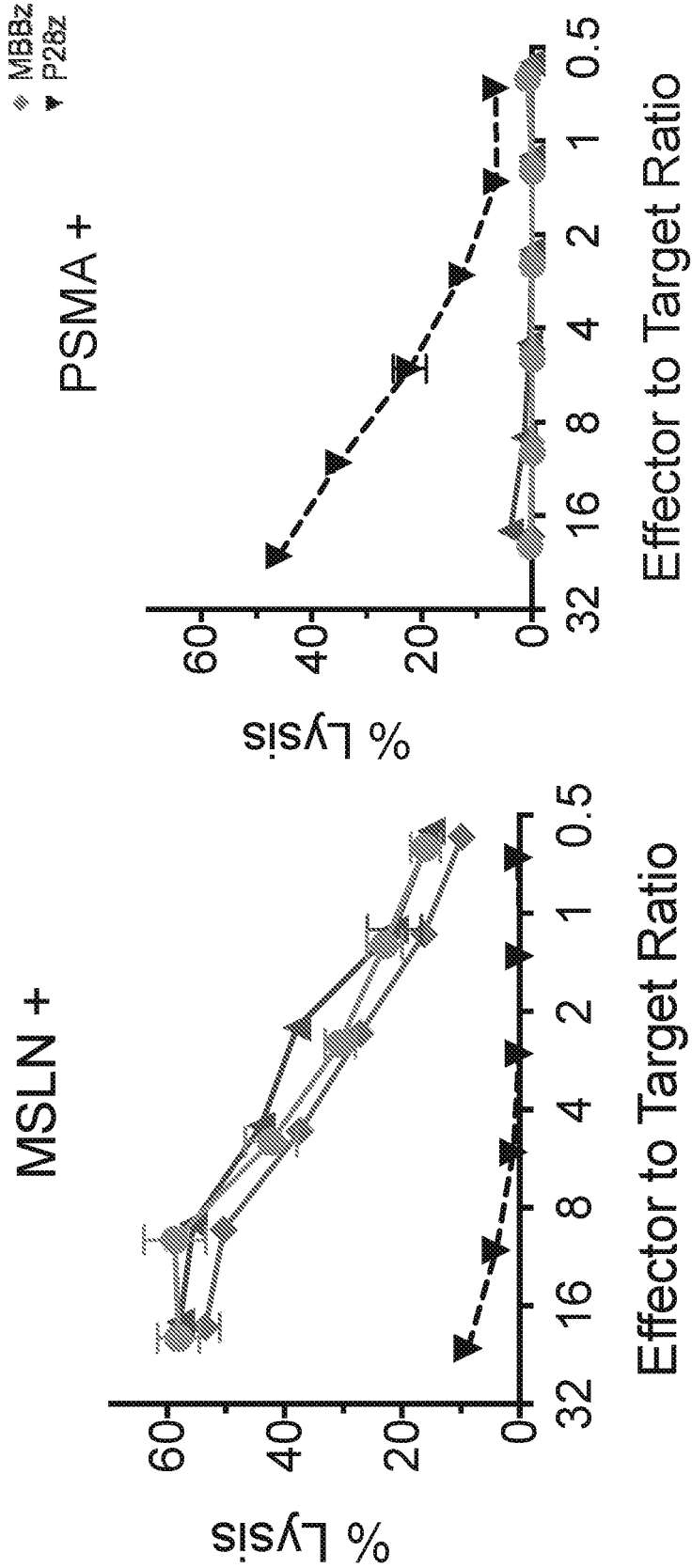
Figure 1D:
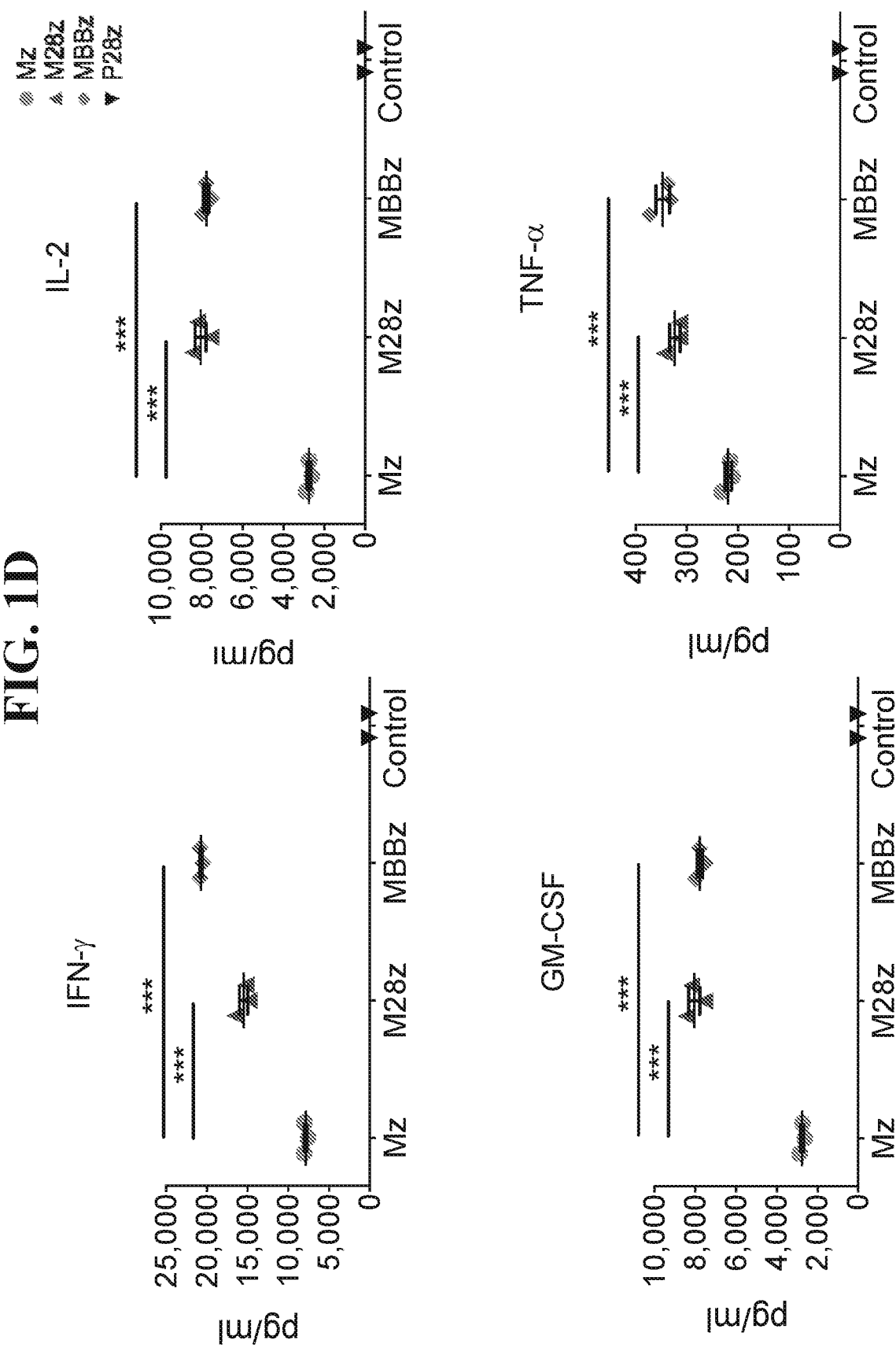
Figure 1E:
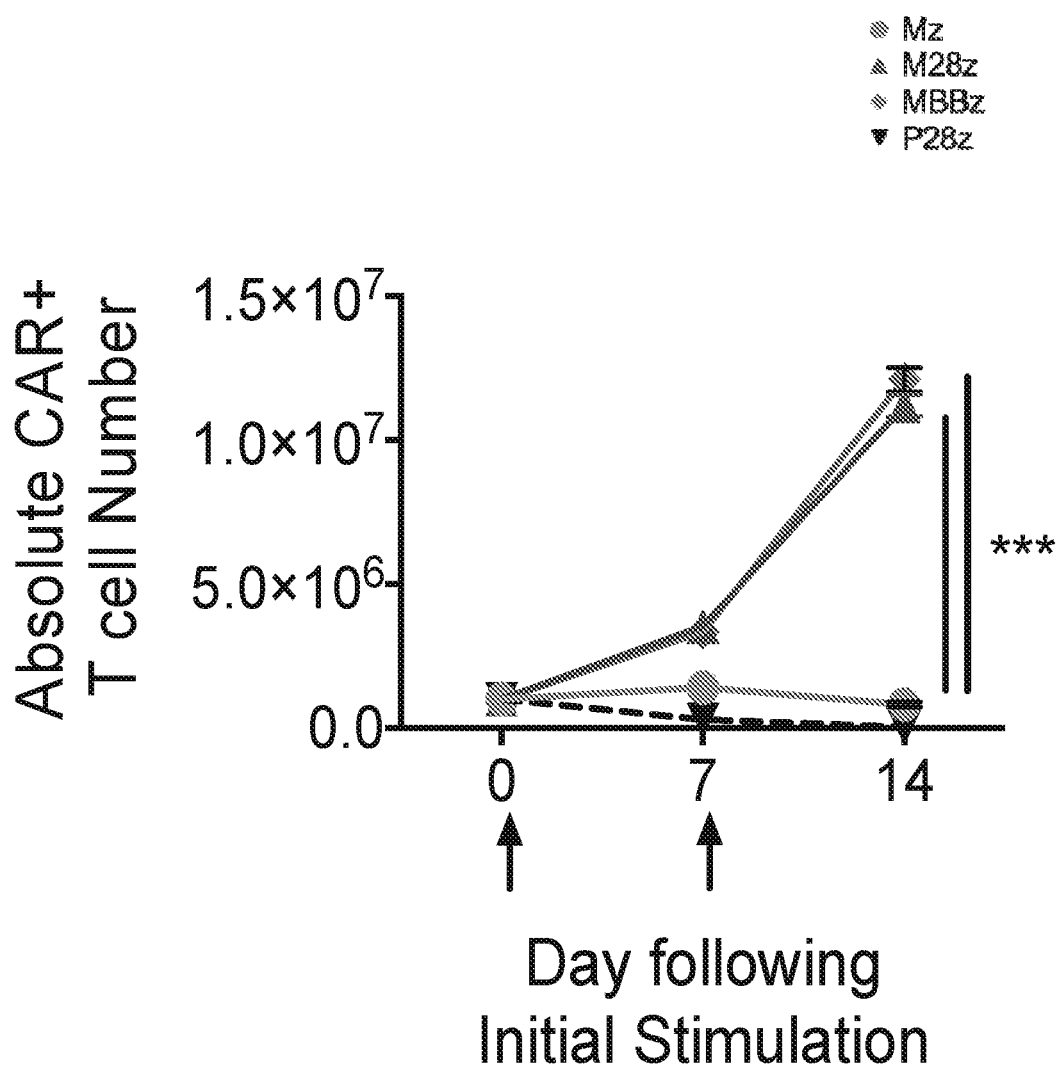

FIGS. 1A-1E show that chimeric antigen receptors (CARs) with CD28 or 4-1BB costimulation exhibit equivalent effector cytokine secretion and proliferation in vitro upon initial antigen stimulation. FIG. 1A. First- and second-generation CARs. FIG. 1B. Mesothelin (MSLN)-targeted CARs contain the CD3ζ endodomain either alone (Mz, first-generation CAR) or in combination with the CD28 (M28z) or 4-1BB (MBBz) costimulatory domain (second-generation CAR). A prostate-specific membrane antigen (PSMA)-directed CAR with CD28 costimulation (P28z) as well as PSMA-expressing targets (PSMA+) are included in experiments as negative controls. CYT, cytoplasmic domain; LS, leader sequence; LTR, long terminal repeat; SA, splice acceptor; SD, splice donor; TM, transmembrane. FIGS. 1C-1E. Antigen-specific effector functions of CAR-transduced T cells. FIG. 1C. Lysis of MSLN-expressing targets (MSLN+), but not PSMA+ targets, as measured by chromium-release assays. FIG. 1D. 4-1BB and CD28 costimulations enhance cytokine secretion, as assessed by Luminex assay, after coculture of CAR T cells with MSLN+ cells. FIG. 1E. M28z and MBBz CARs facilitate robust T-cell accumulation after stimulation with MSLN+ cells. Data represent the mean±SEM (FIGS. 1C, 1E) of three replicates or are plotted as individual points (FIG. 1D). ***P<0.001, comparing costimulated CAR T cells (M28z or MBBz) with the first-generation receptor (Mz), by Student's t test; significance was determined using the Bonferroni correction for multiple comparisons.

FIG. 2 shows efficient retroviral transduction of human T cells to express Mz, M28z, and MBBz CARs. (Top) Shown is representative FACS analysis 4 days after gene transfer. Fluorescence minus one staining was used to set positive gates after a live/dead stain excluded nonviable cells. All experiments used T cells with 50% to 70% CAR transduction efficiency; transduction percentages between T-cell groups were within 5% of each other. (Bottom) Both CD4+ and CD8+ T-cell subsets were efficiently transduced. CD4+ and CD8+ percentages after gating for CAR T cells are shown.

Figure 3A:
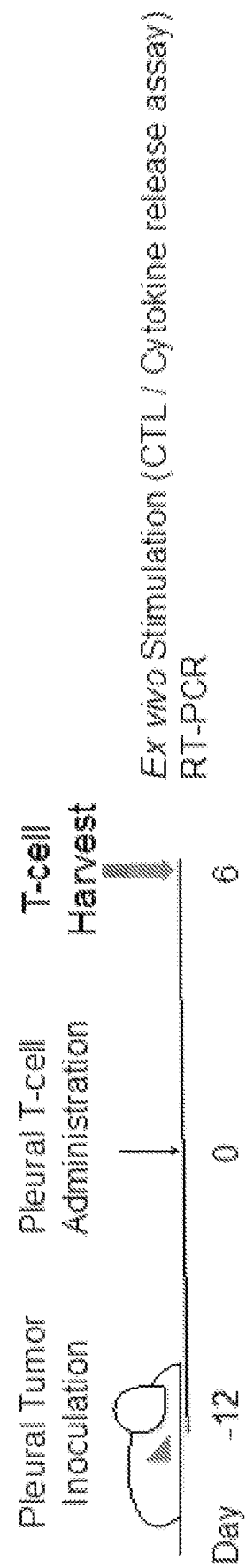
Figure 3B:
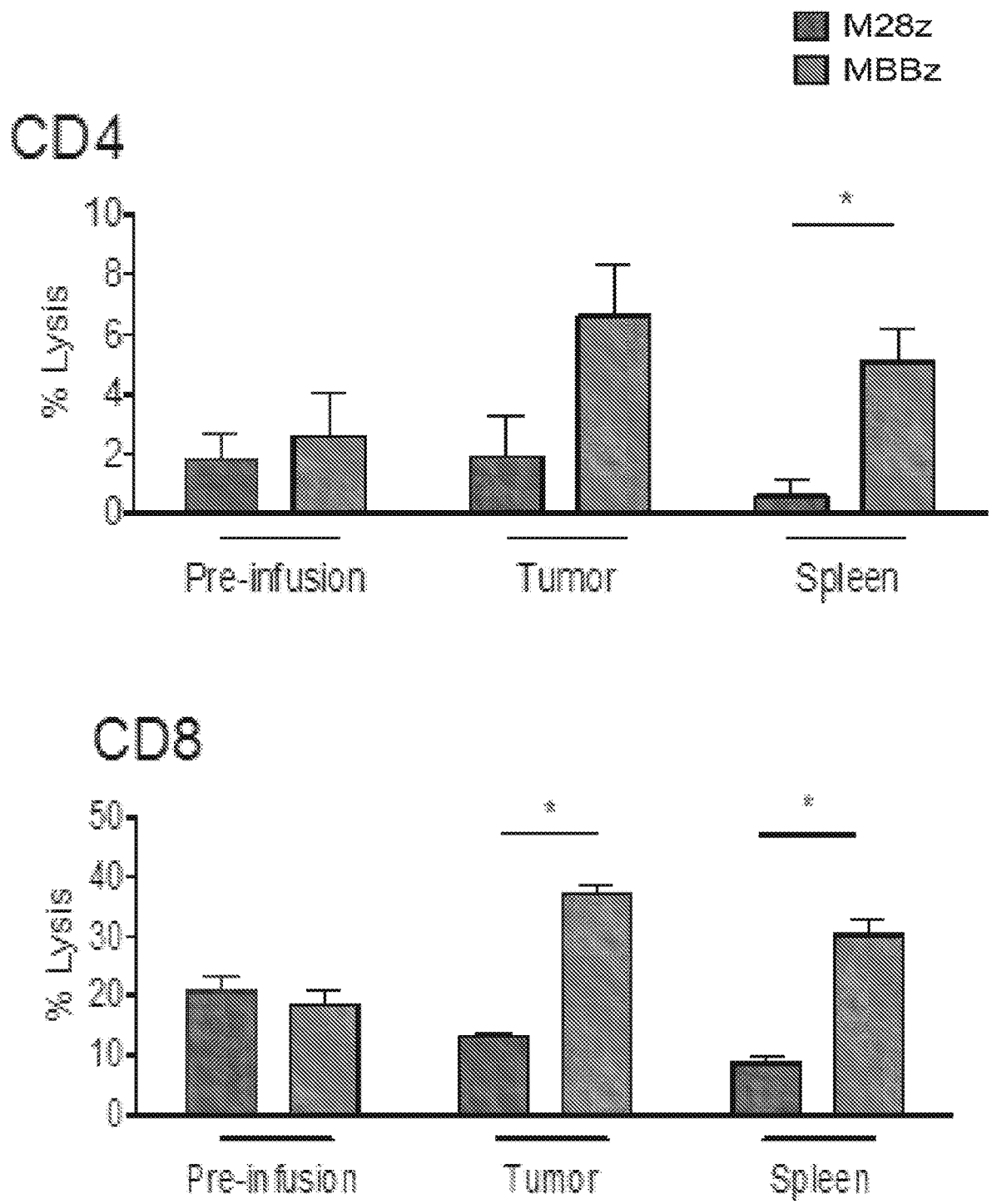
Figure 3C:
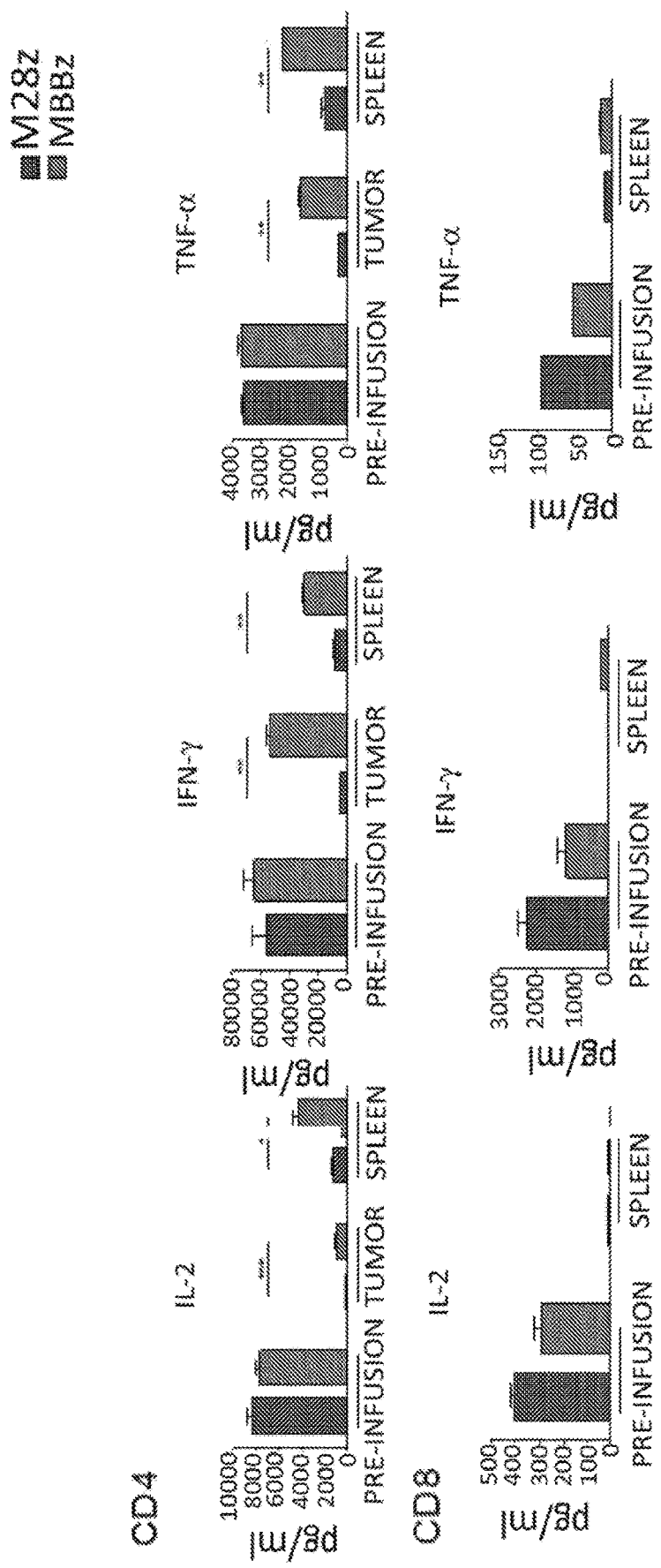
Figure 3D:
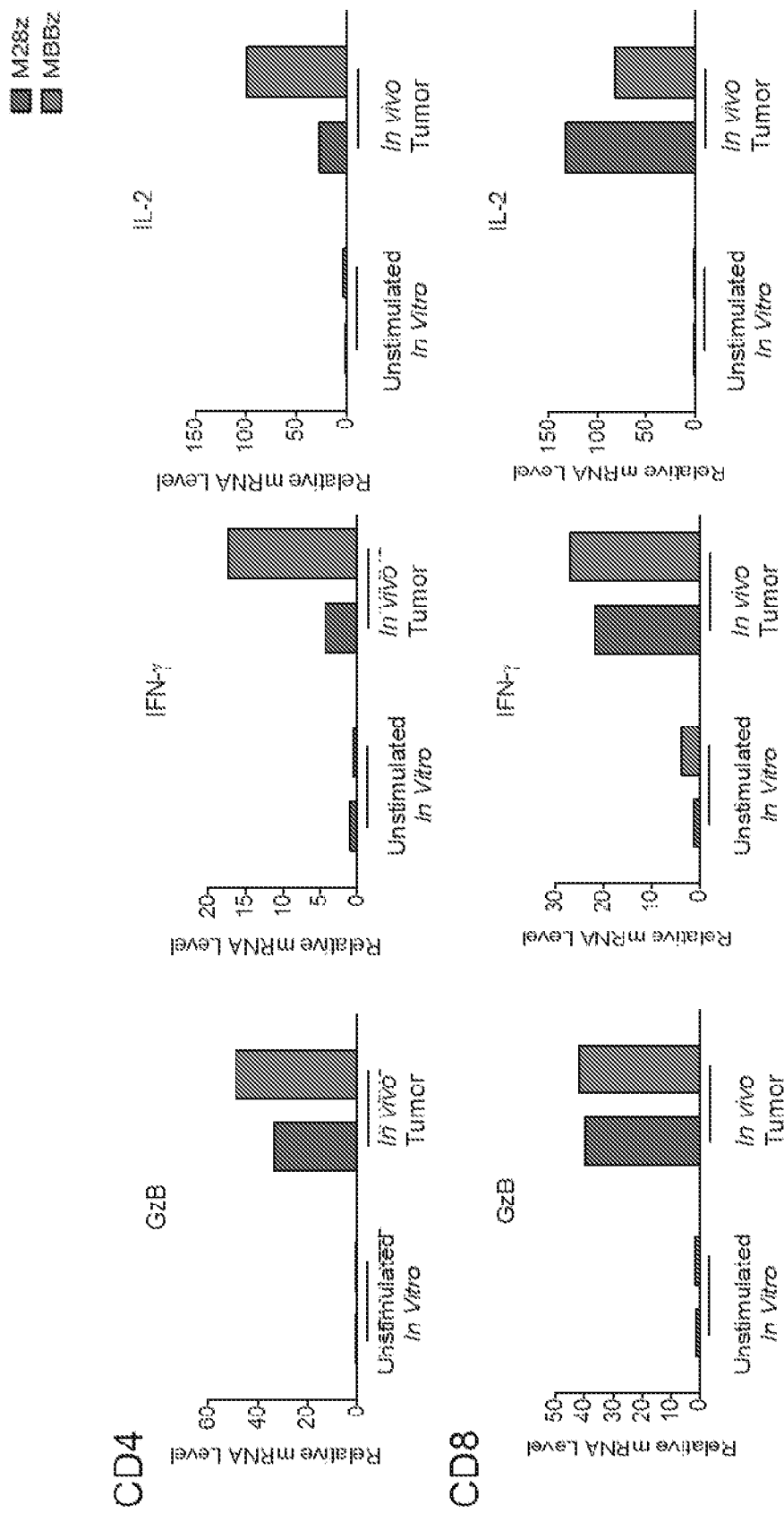

FIGS. 3A-3D show that CAR T cells become exhausted following in vivo antigen exposure, although MBBz CAR T cells preferentially retain effector cytokine secretion and cytotoxicity. FIG. 3A. Six days after intrapleural administration of CAR T cells, M28z and MBBz CAR T cells were isolated from the tumor and spleen and subjected to ex vivo antigen stimulation. FIG. 3B. Chromium-release assay upon ex vivo stimulation demonstrates a decrease in M28z but persistent MBBz cytolytic function (E:T ratio 1:5). FIG. 3C. Cytokine secretion measurements demonstrate decreases in effector cytokine secretion by CAR T cells, although MBBz CAR T cells are better able to retain secretion. FIG. 3D. RT-PCR measurements of GzB, IFN-γ, and IL-2 expression by harvested CAR T cells correlate well with protein level measurements. Data represent the fold-change relative to the mRNA expression of unstimulated M28z CAR T cell in vitro. Data represent the mean±SEM of three individual wells per condition. Student's t tests were performed, and statistical significance was determined using the Bonferroni correction for multiple comparisons (*P<0.05; P<0.01; *P<0.001). Results are reproduced in two separate cohorts of mice used for each of the two experiments. In each of FIGS. 3B-3D, each pair of bar graphs show, from left to right, M28z, MBBZ.

Figure 4B:
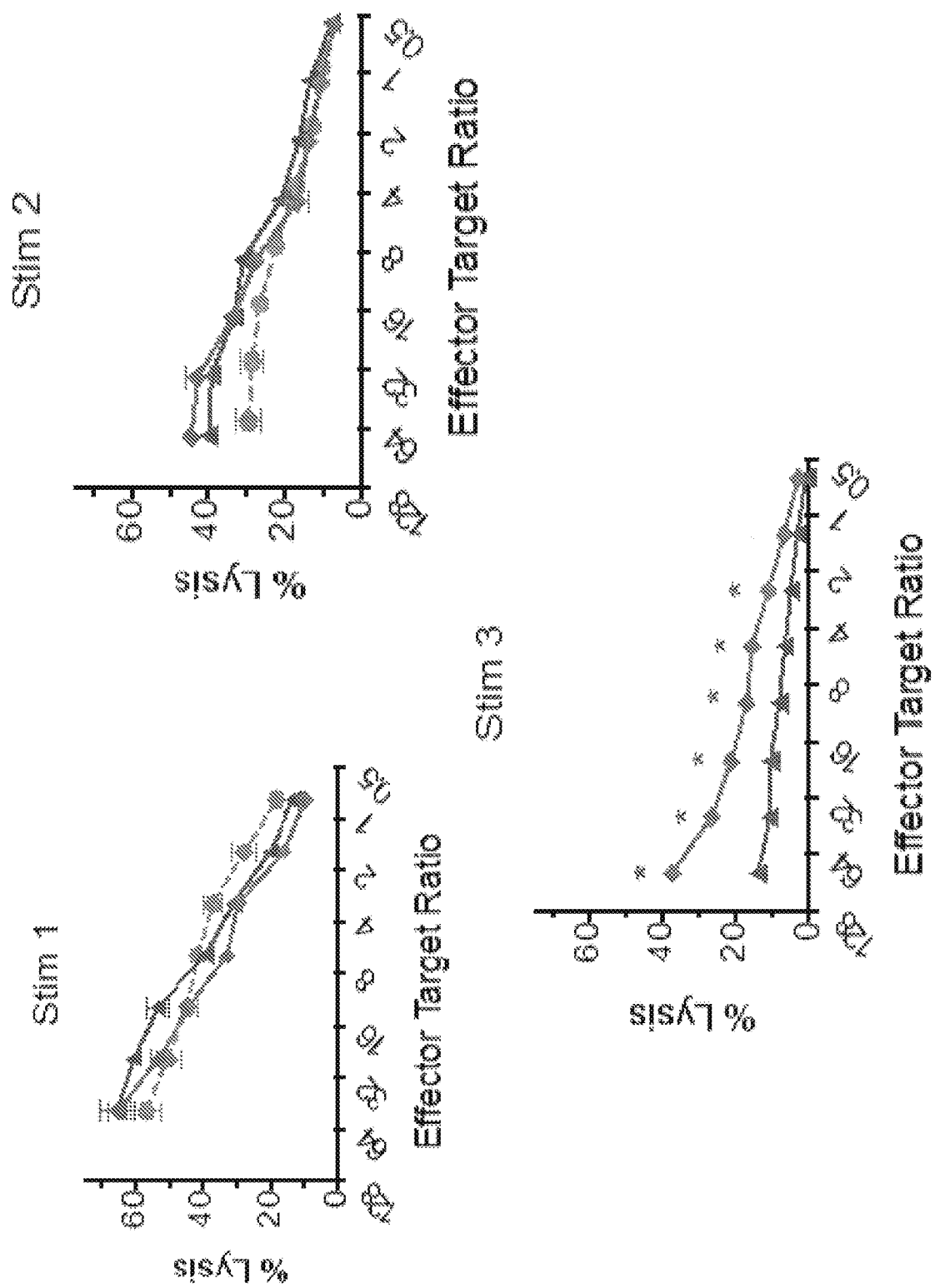
Figure 4C:
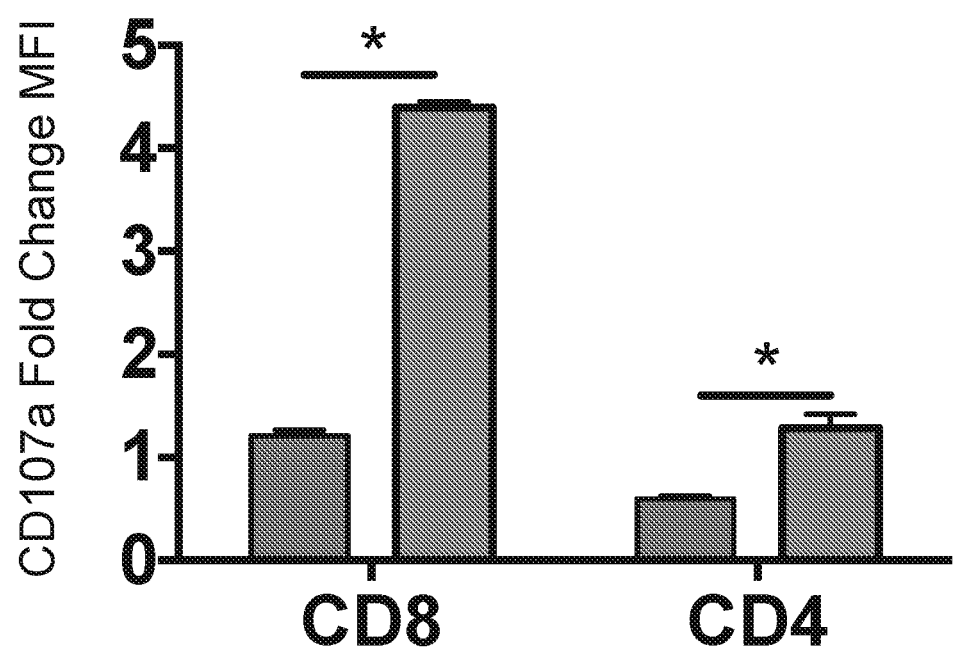
Figure 4D:
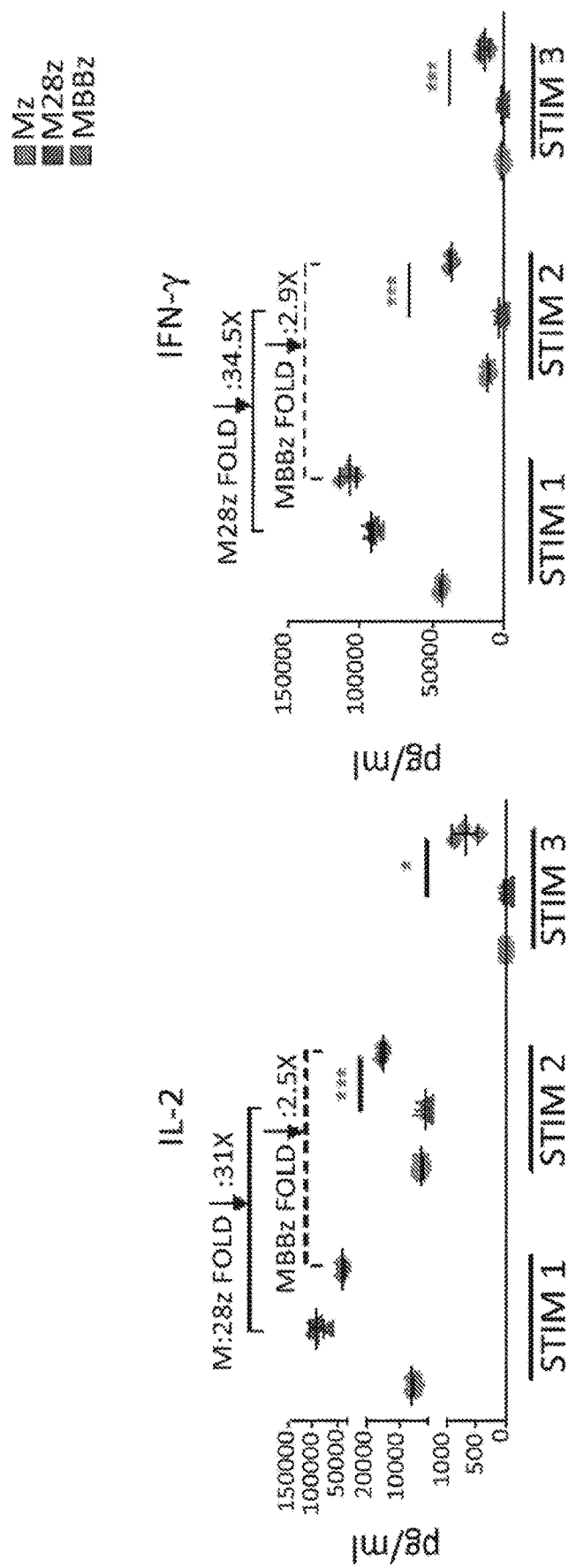
Figure 4E:
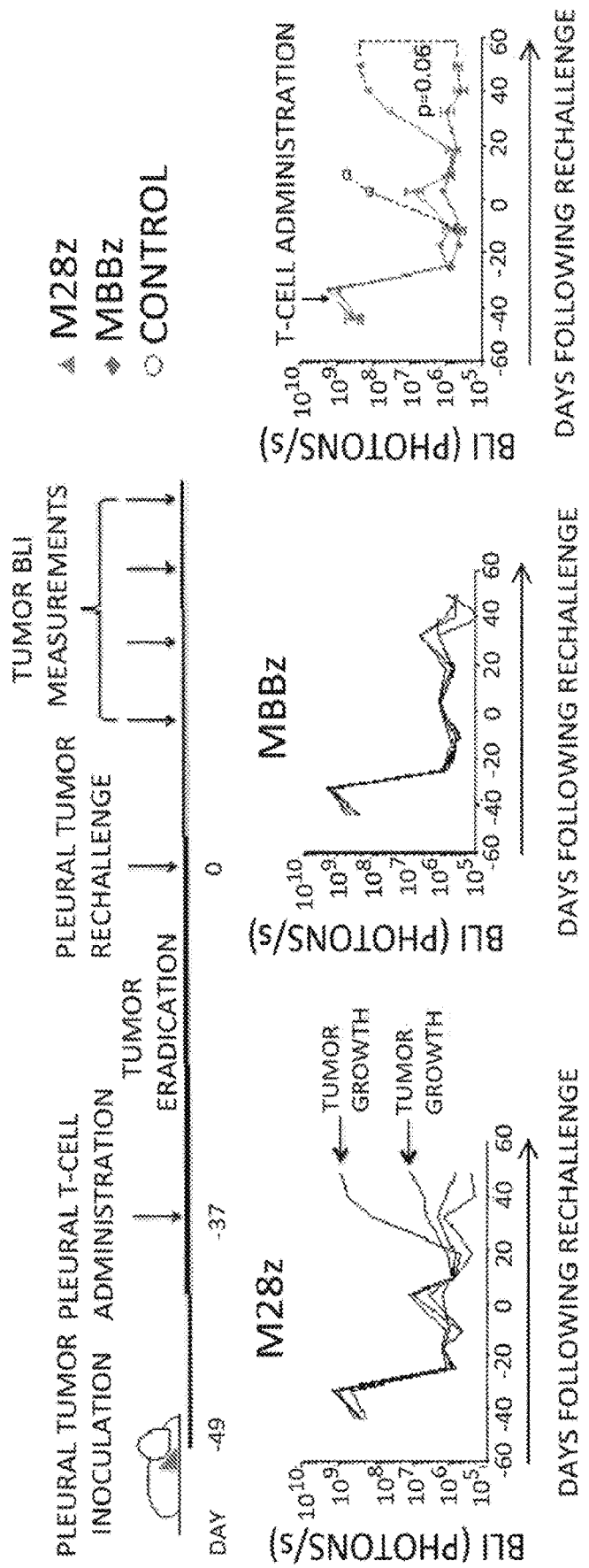

FIGS. 4A-4E show that CAR T cells become exhausted upon repeated antigen stimulation in vitro, although MBBz CAR T cells preferentially retain effector cytokine secretion and cytotoxicity in vitro and upon tumor rechallenge in vivo. FIG. 4A. Both M28z and MBBz CAR T cells retain proliferative capacity in vitro upon repeated antigen stimulation. T cells were also tested for cytotoxicity by chromium-release assay and for cytokine secretion by Luminex assay (FIGS. 4B-4D). FIG. 4B. CAR T cells demonstrate equal killing at the first stimulation (left) and loss of cytolytic function upon repeated antigen stimulation, although MBBz CAR T cells are better able to retain cytolytic function as measured by chromium-release assay (circles, MZ; triangles, M28z; diamonds, MBBz). FIG. 4C. Cytotoxic granule release as measured by CD107a expression (shown at the third stimulation) correlates with chromium release assay (FIG. 4B). Data represent the mean±SD (triplicates) of the fold-change relative to the CD107a MFI of unstimulated CAR T cells (each pair of bar graphs shows, from left to right, M28z, MBBz). FIG. 4D. Cytokine secretion measurements similarly demonstrate loss of CAR T-cell effector function upon repeated antigen encounter; again, MBBz CAR T cells are better able to preserve their function (each set of symbols above "Stim 1," "Stim 2" and "Stim 3" are, from left to right, Mz, M28z, MBBz). FIG. 4E. Although equally persistent, MBBz CAR T cells demonstrate superior functional persistence. Twenty-eight days after pleural tumor eradication (following a single dose of $1e^5$ CAR T cells), $1e^6$ MSLN+ tumor cells were injected into the pleural cavity (tumor rechallenge). MBBz CAR T cells prevented tumor growth in all mice, whereas tumor growth and death were observed in 2 of 4 mice initially treated with M28z CAR T cells. Student's t tests were performed and statistical significance was determined using the Bonferroni correction (*P<0.05; ***P<0.001). Data represent the mean±SEM of three replicates or are plotted as individual points.

Figure 5:
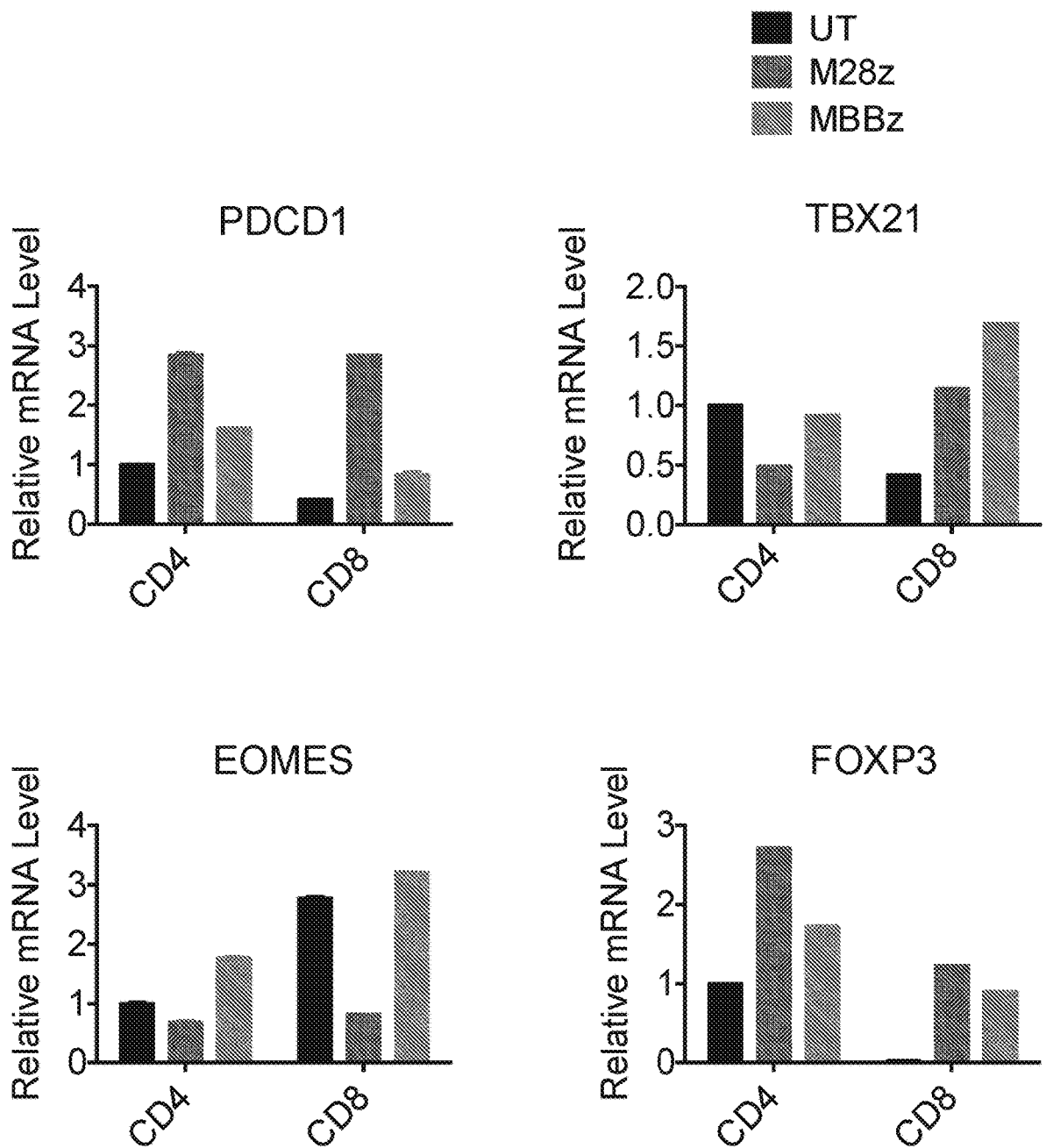

FIG. 5 shows that MBBz CAR T cells express a less exhausted, more potent phenotype compared to M28z CAR T cells. 4-1BB- and CD28-costimulated T cells were expanded with repeated antigen stimulation, and mRNA was extracted and subjected to RT-PCR analysis 20 h after the third stimulation. Data are represented in fold change relative to the mRNA expression of CD4+ unstransduced T cells. MBBz CAR T cells express higher levels of EOMES (Eomesodermin) and TBX21 (T-bet), and lower levels of PDCD1 (PD-1) and FOXP3 (Foxp3). All comparisons were significant at P<0.001. Results were similar in 3 separate experiments using different donors. Each group of bar graphs shows, left to right, UT (untransduced T cells used as a control), M28z, MBBz.

FIGS. 6A-6F show that PD-1 receptor and its ligands are upregulated in vivo (FIGS. 6A-6D, harvested T cells; FIGS.

Figure 6A:
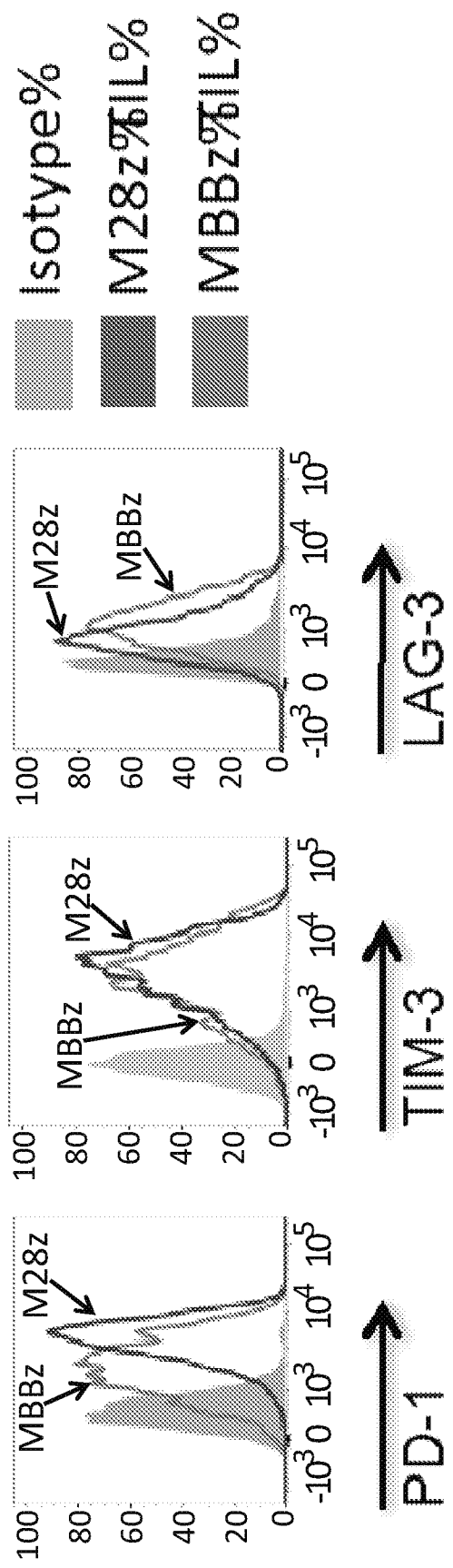
Figure 6B:
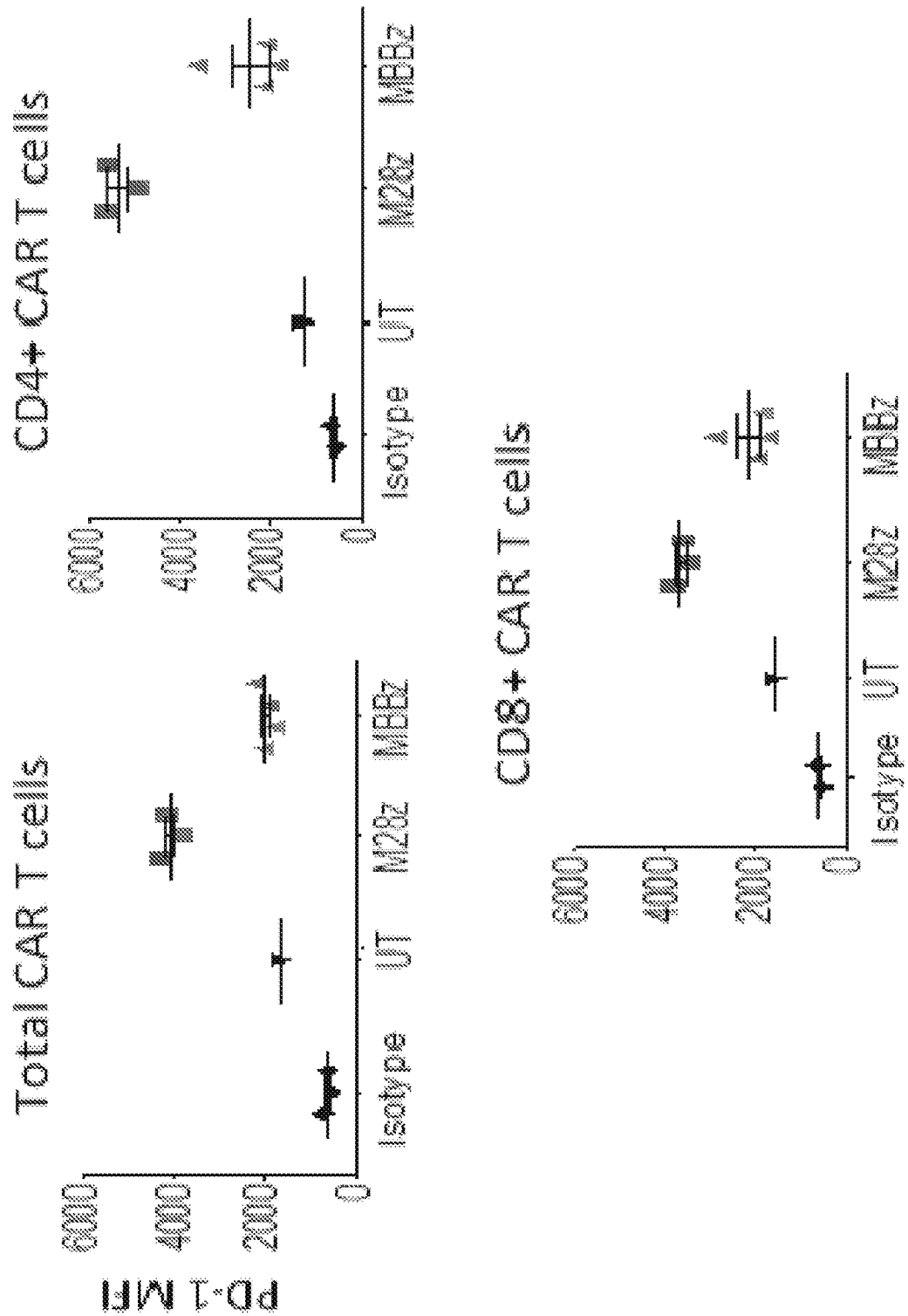
Figure 6D:
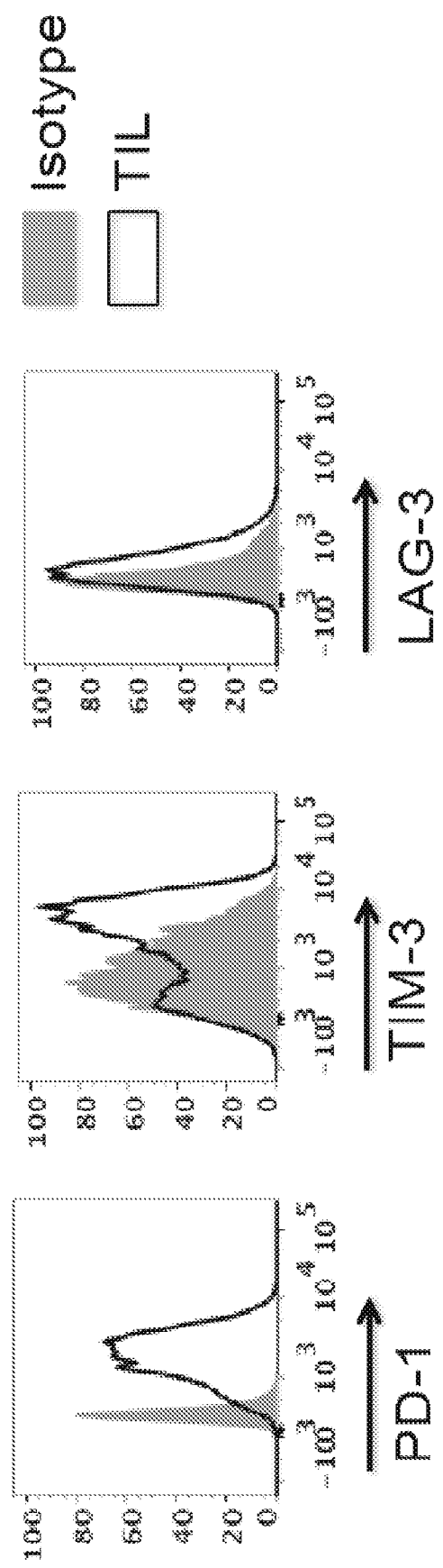
Figure 6E:
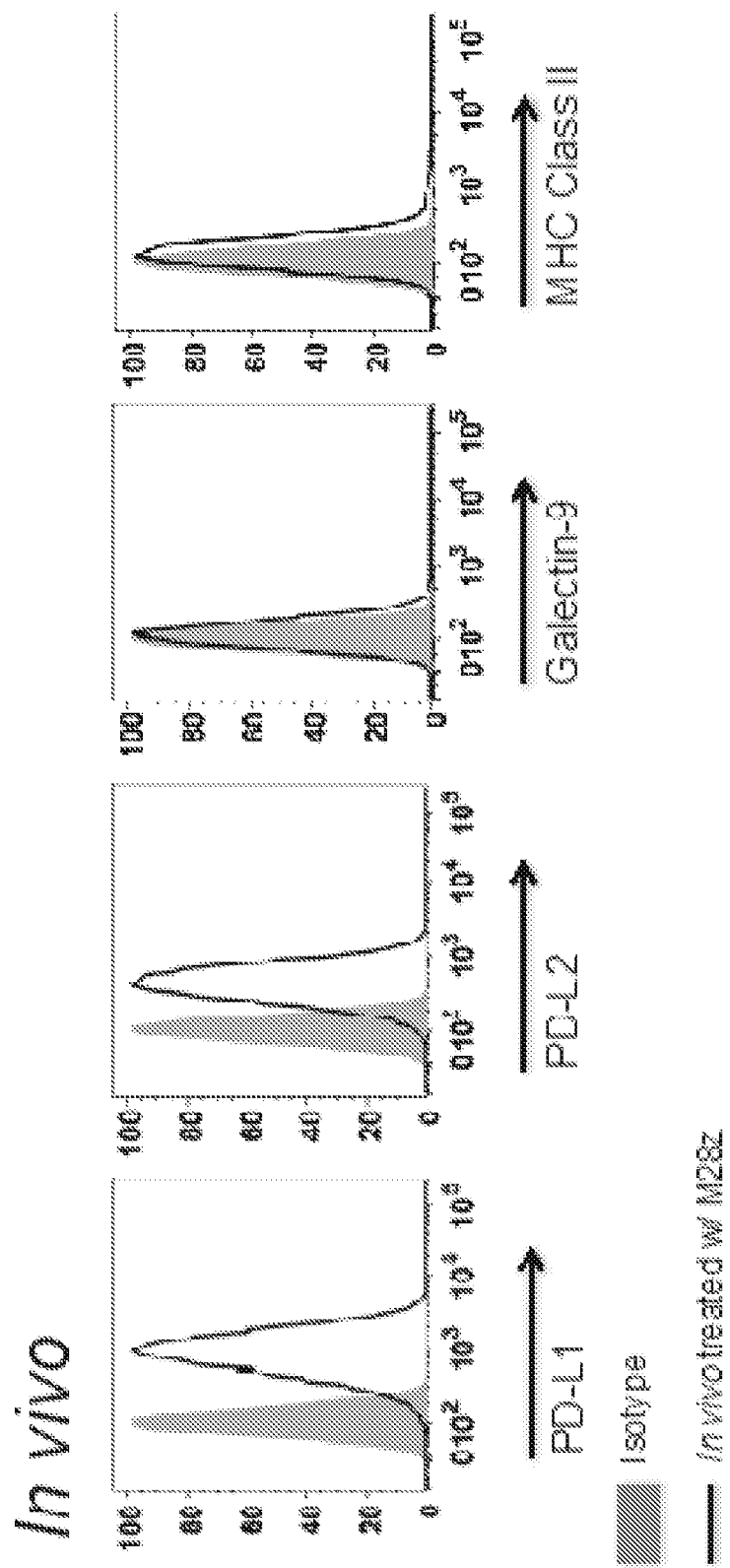

6E-6F, tumor cells). FIG. 6A. Tumor-infiltrating M28z and MBBz CAR T cells express inhibitory receptors 6 days after their administration, but MBBz CART cells express lower levels of PD-1. FIG. 6B. Mean fluorescence intensity (MFI) of PD-1 receptor expression of tumor-infiltrating CAR T cells (TIL) 6 days after intrapleural administration. FIG. 6C. Relative expression of PD-1 mRNA in CD4 and CD8 subsets of tumor-infiltrating CAR T cells 6 days after intrapleural administration. Data are represented in fold-change relative to the PD-1 mRNA expression of unstimulated M28z T cells (for each pair of bar graphs, M28z, left, MBBz, right). FIG. 6D. Tumor-infiltrating M28z CAR T cells isolated from progressing tumors express inhibitory receptors PD-1, Tim-3, and Lag-3. FIG. 6E. Single-cell tumor suspensions harvested from mice treated with M28z CAR T cells express high levels of PD-1 binding ligands. FIG. 6F. In vitro cultured mesothelioma tumor cells express the ligands (PD-L1, PD-L2) for the PD-1 receptor, and expression is further upregulated following incubation for 24 h with IFN-γ and TNF-α.

Figure 7:
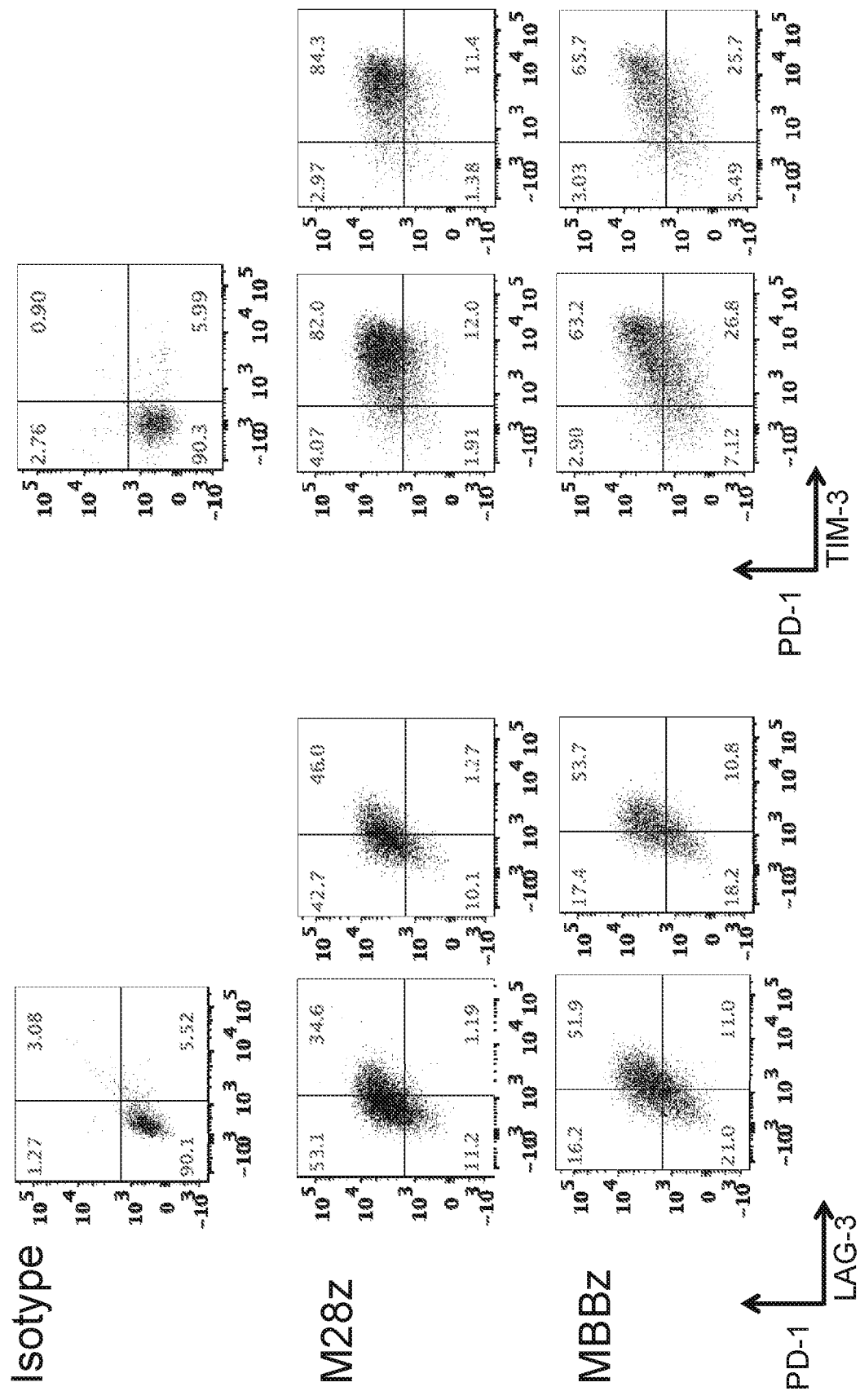

FIG. 7 shows M28z and MBBz CAR T cells coexpress PD-1 along with other inhibitory receptors. Tumor-infiltrating M28z and MBBz CAR T cells were harvested 6 days following intrapleural administration to pleural tumor bearing mice. Cells were costained with antibodies for PD-1 and for either LAG-3 (left) or TIM-3 (right) and analyzed by flow cytometry. Isotype staining controls (top) were used to establish positive gates.

Figure 8A:
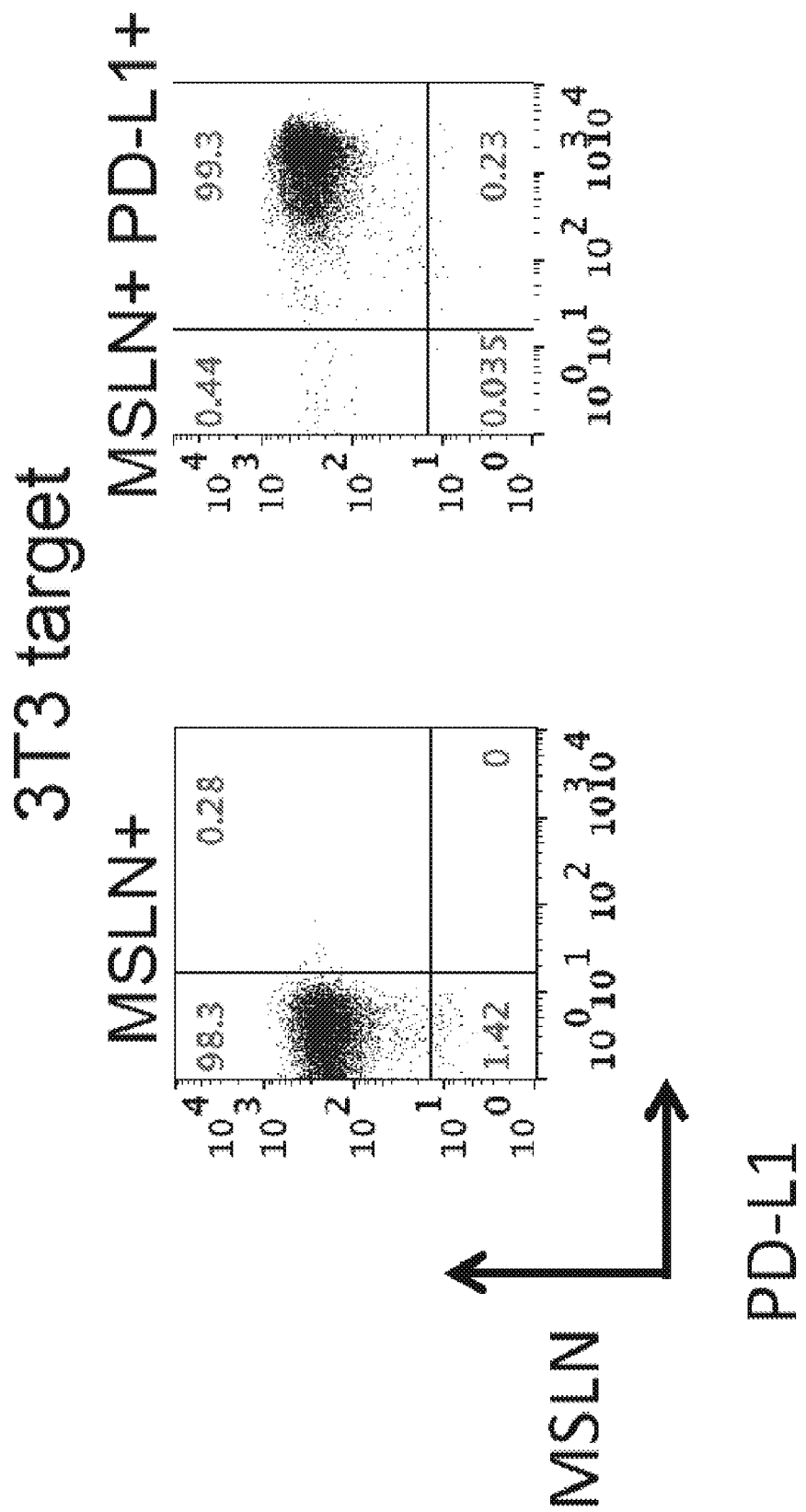
Figure 8B:
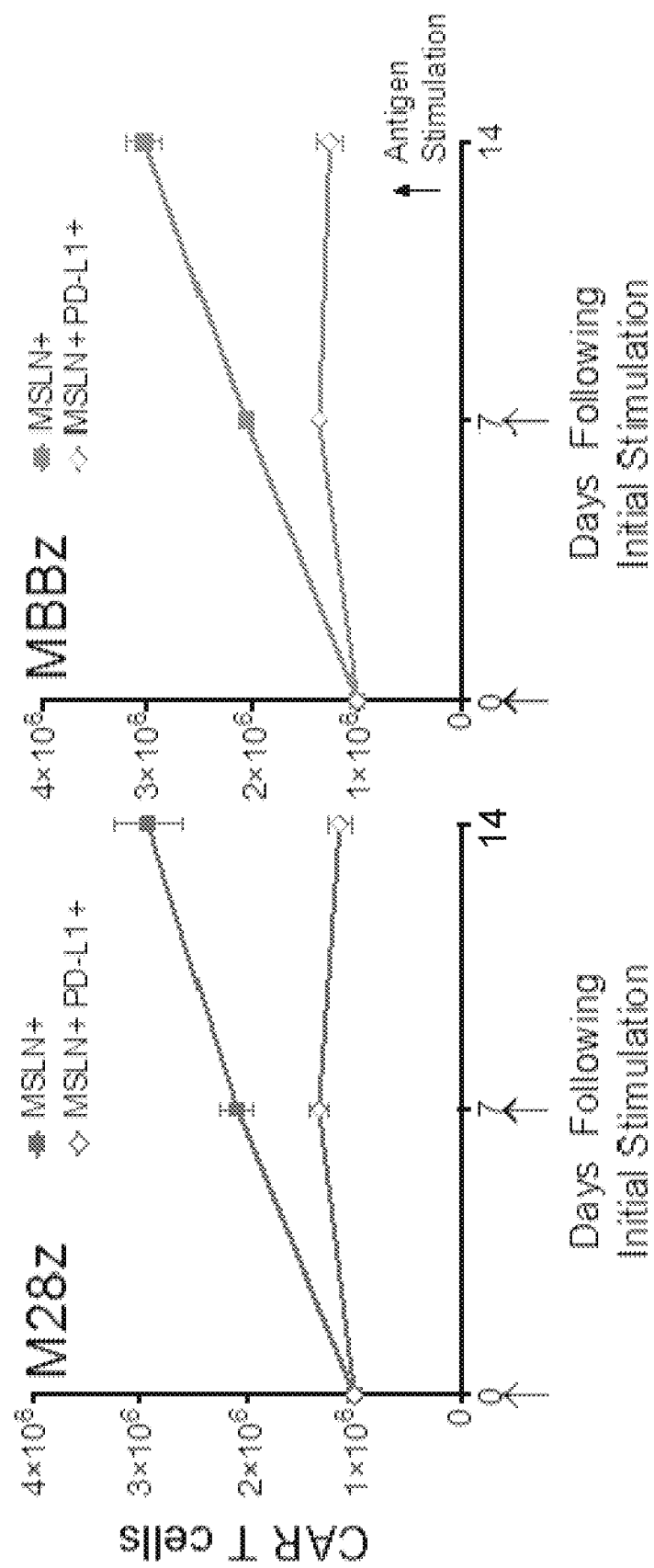
Figure 8C:
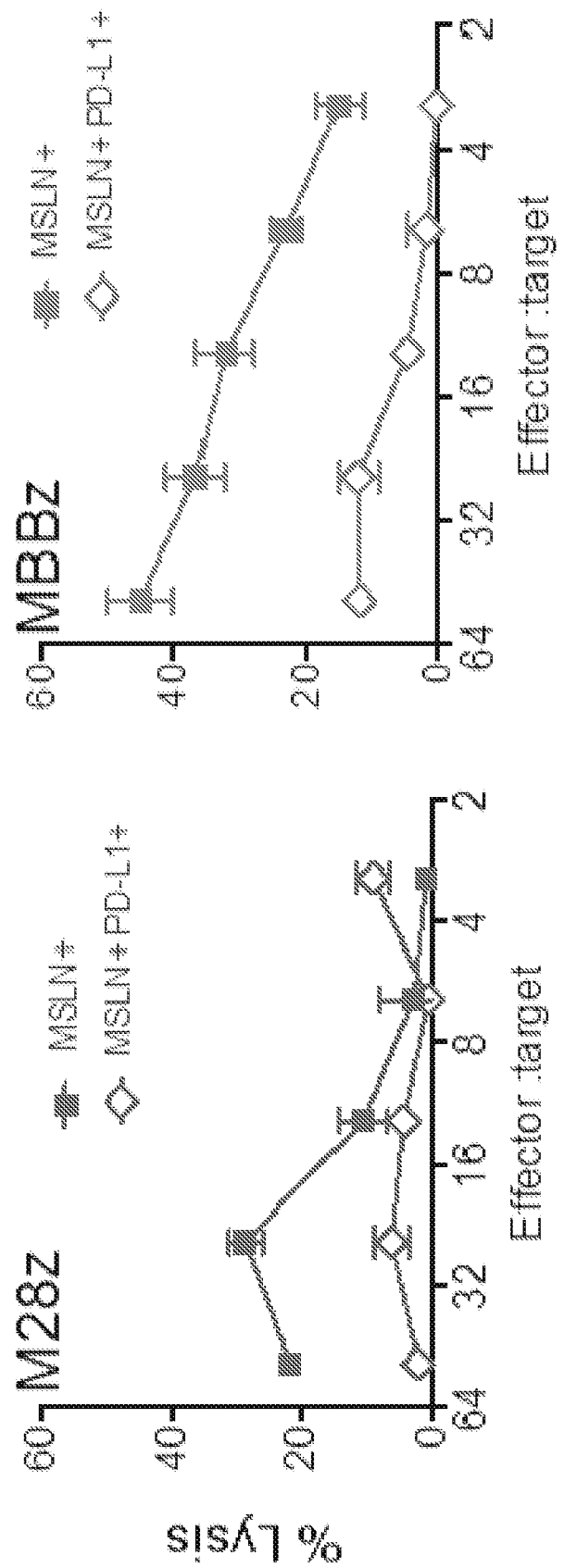

FIGS. 8A-8D show that PD-L1 inhibits CAR T-cell effector function. FIG. 8A. 3T3 fibroblasts were transduced to either express mesothelin alone (MSLN+, left) or coexpress MSLN in addition to PD-L1 (MSLN+PD-L1+, right). FIGS. 8B-8D. M28z and MBBz CAR T-cell effector functions were assessed after stimulation with 3T3 MSLN+ or MSLN+PD-L1+ targets. PD-L1 inhibits M28z and MBBz CAR T-cell accumulation upon repeated antigen stimulation (FIG. 8B), cytolytic function following two stimulations with MSLN+PD-L1+ tumor cells (FIG. 8C), and Th1 effector cytokine secretion upon the first stimulation (FIG. 8D). Data represent the mean±SEM of three replicates or are plotted as individual points.

Figure 9A:
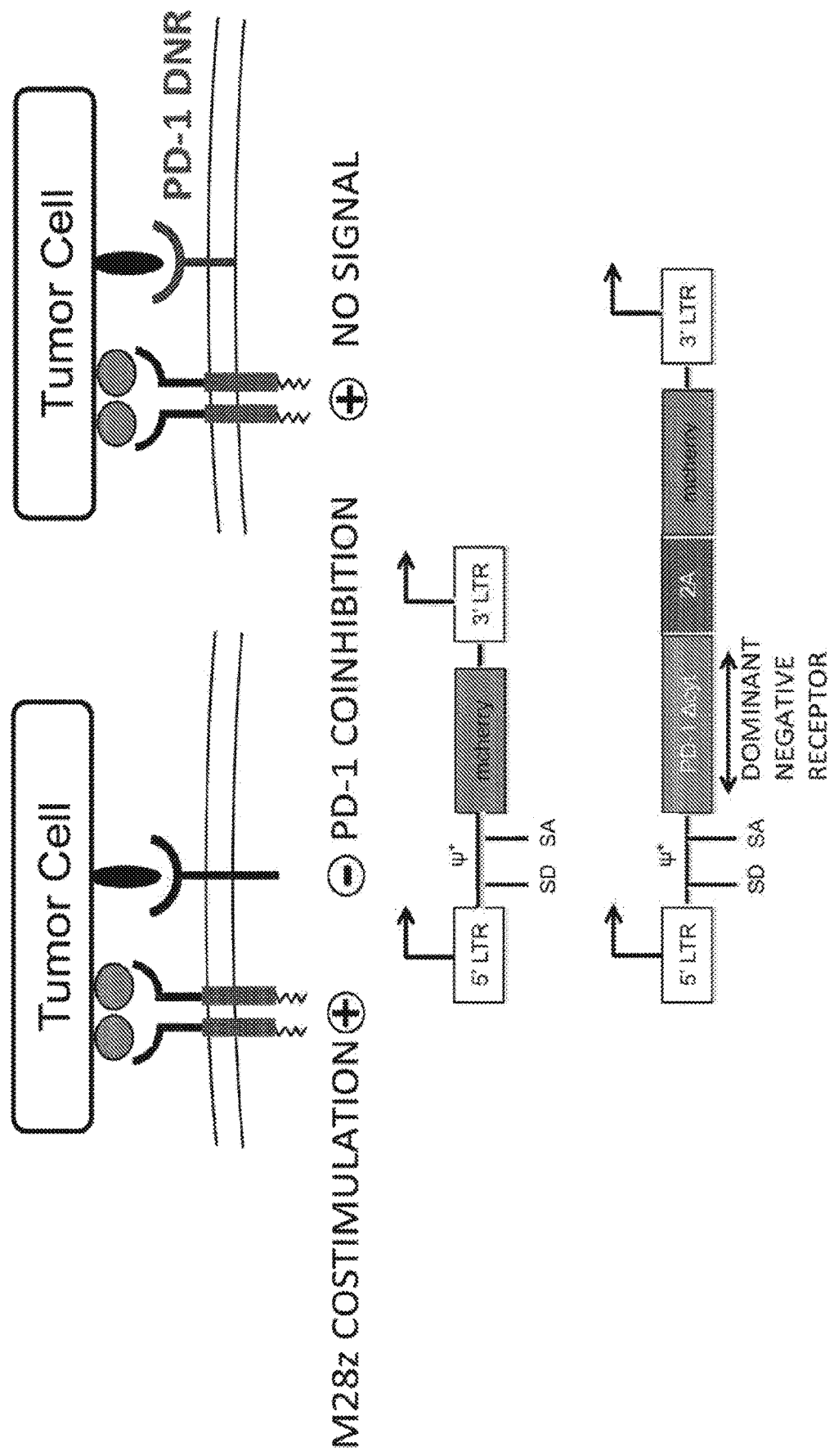
Figure 9B:
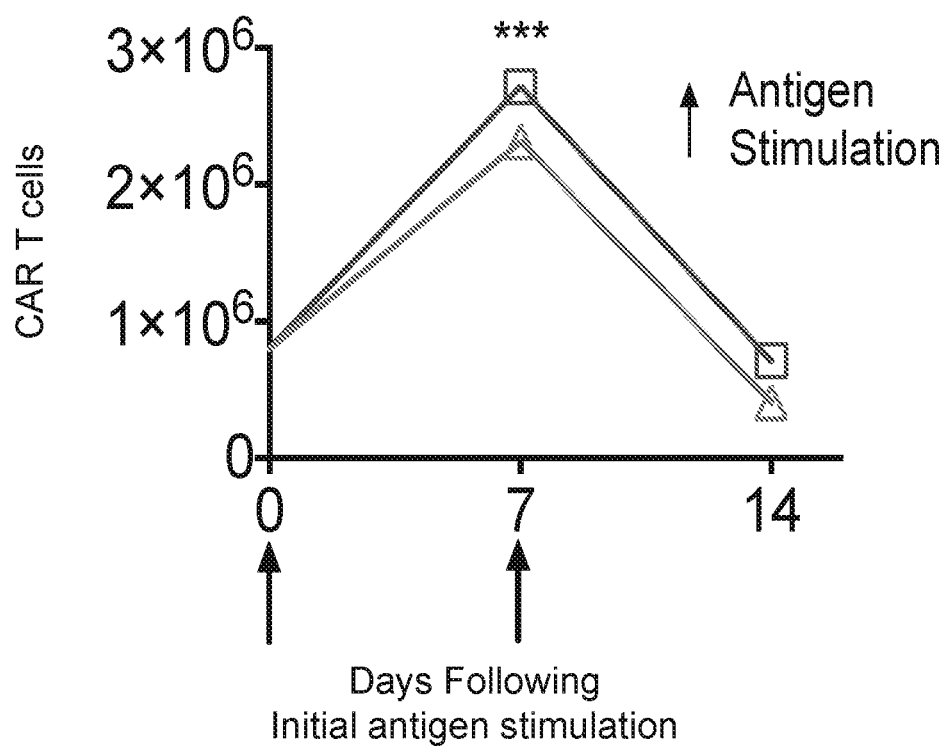
Figure 9C:
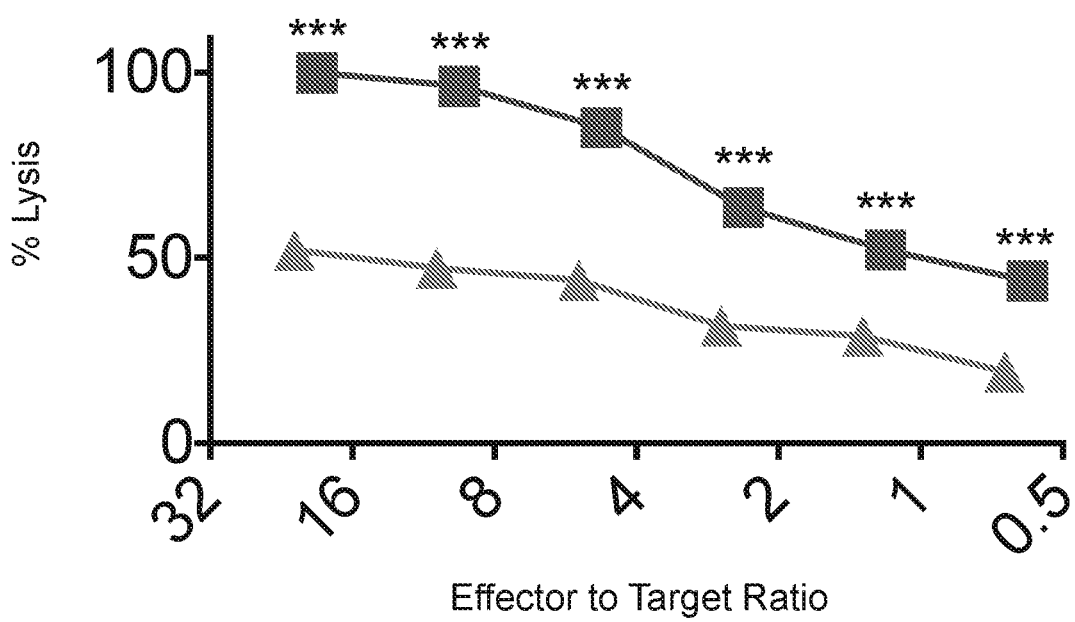
Figure 9D:
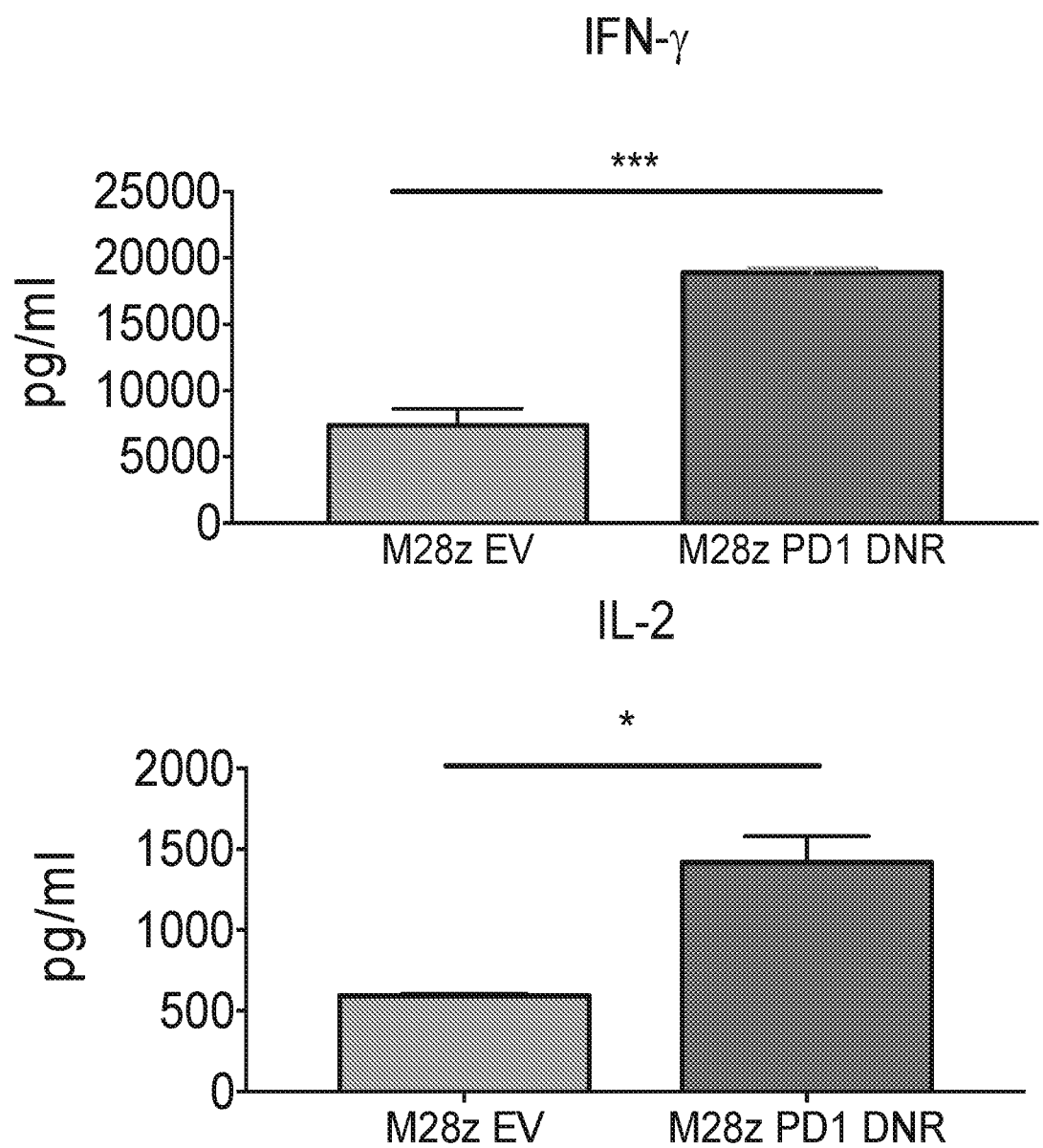
Figure 9E:
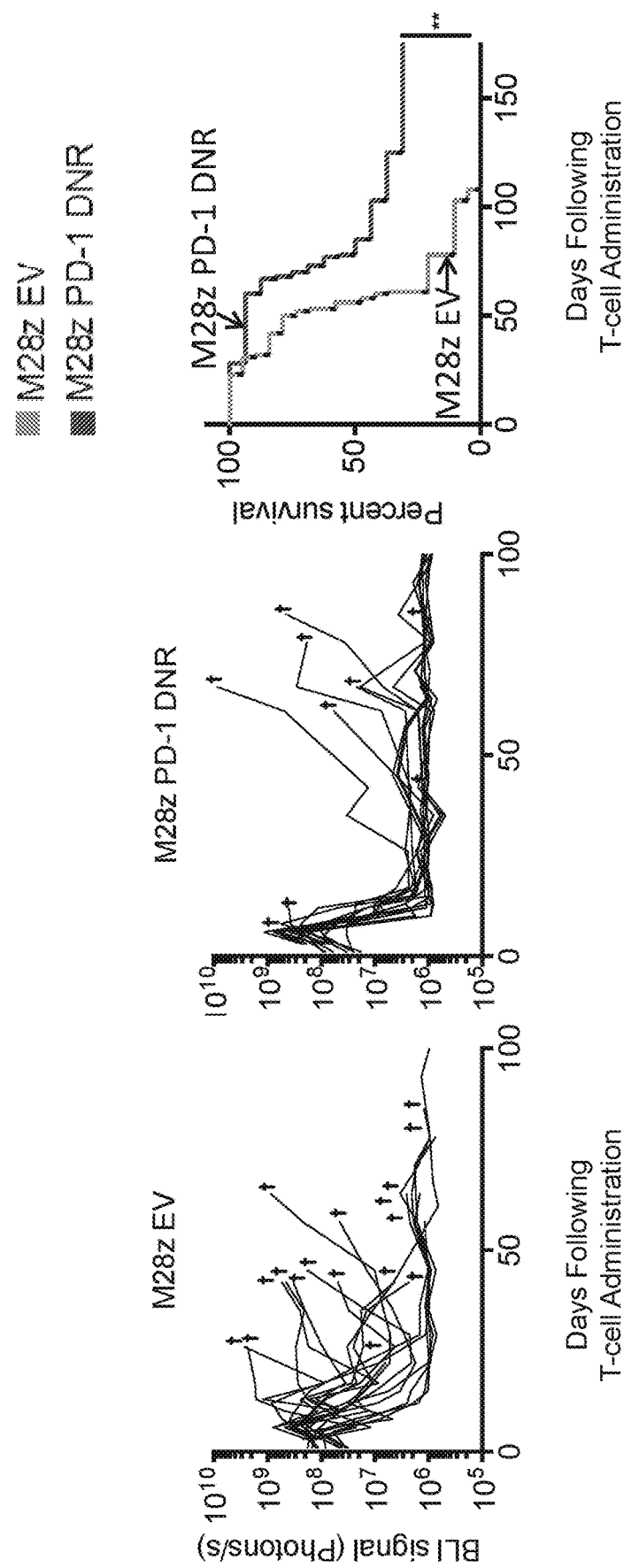

FIGS. 9A-9E show that cotransduction of a PD-1 dominant negative receptor (PD-1 DNR) rescues M28z CAR T cells from PD-1 Ligand-mediated inhibition in vitro and in vivo. FIG. 9A. (Left) Schematic representations of CD28-costimulated T cells binding tumor ligand via the endogenous PD-1 receptor (transmitting a coinhibitory signal) or a cotransduced PD-1 DNR lacking an inhibitory signaling domain. (Right) For in vitro and in vivo experiments, M28z CAR T cells were cotransduced with either empty vector (EV; SFG-mCherry) or PD-1 DNR (SFG-2A-PD-1 DNR). CAR T cells sorted for mCherry expression were then incubated for 24 h with MSLN+ tumor cells that had been treated with IFN-γ and TNF-α to upregulate PD-1 ligands. M28z PD-1 DNR CAR T cells demonstrated a small but statistically significant enhancement in accumulation upon repeated antigen stimulation (FIG. 9B; triangles, M28z EV; squares, M28z PD-1 DNR), an enhanced cytolytic function, as measured by chromium release assay upon the 3rd stimulation with MSLN+PD-L1+ tumor cells (FIG. 9C; triangles, M28z EV; squares, M28z PD-1 DNR), and an increased expression of Th1 supernatant cytokines upon initial stimulation (FIG. 9D). Student's t tests were performed, and statistical significance was determined using the Bonferroni correction for multiple comparisons (*P<0.05; P<0.01; *P<0.001). Data represent the mean±SEM of triplicates or are plotted as individual points. FIG. 9E. Tumor BLI (left) and Kaplan-Meier survival analysis (right) comparing the in vivo efficacy of a single dose of 5e4 M28z EV (n=19) or M28z PD-1 DNR (n=16) pleurally administrated. Data shown are a combination of two independent experiments. The (✝) symbol indicates death. Median survival is shown in days. The survival curve was analyzed using the log-rank test (P=0.001). The log-rank test for each independent experiment was significant to the P<0.05 level; two experiments are combined for illustration. A cohort of the mice (M28z PD-1 DNR) in this experiment survived beyond 450 days in spite of repeated tumor rechallenge, demonstrating the "functional persistence" of CAR T cells transduced with PD-1 DNR.

Figure 10B:
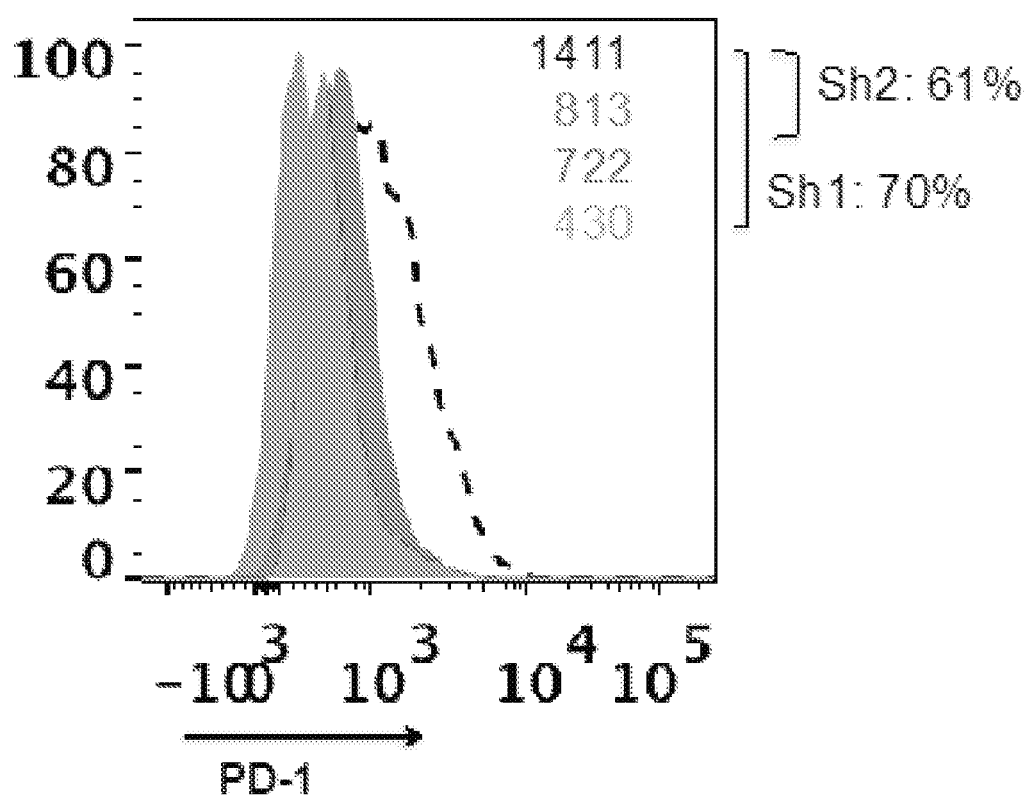
Figure 10C:
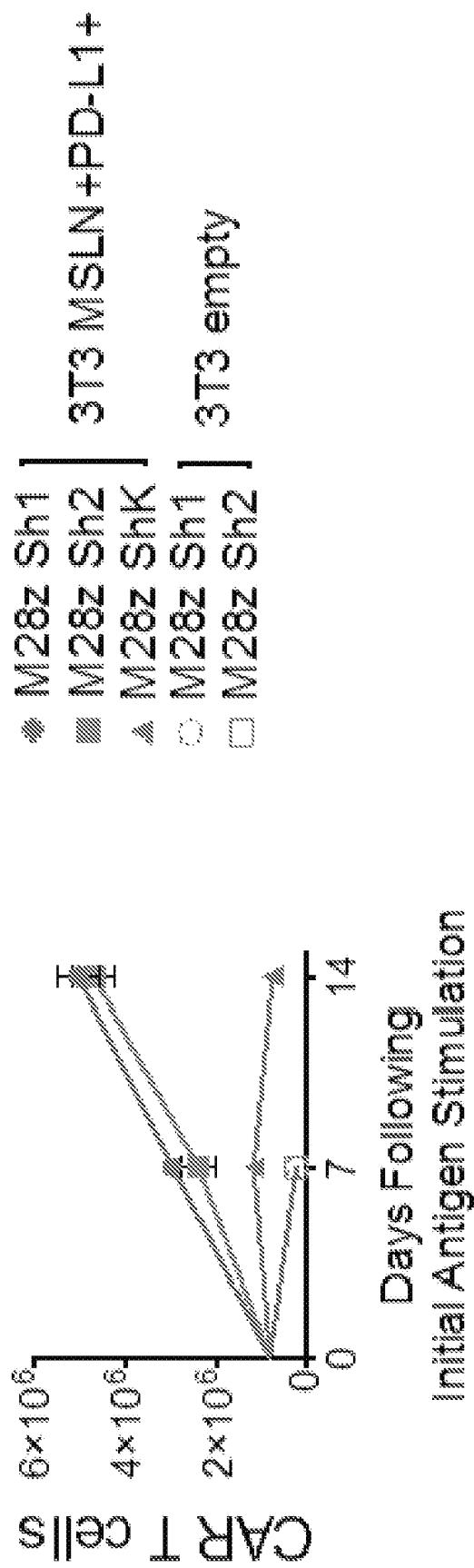
Figure 10D:
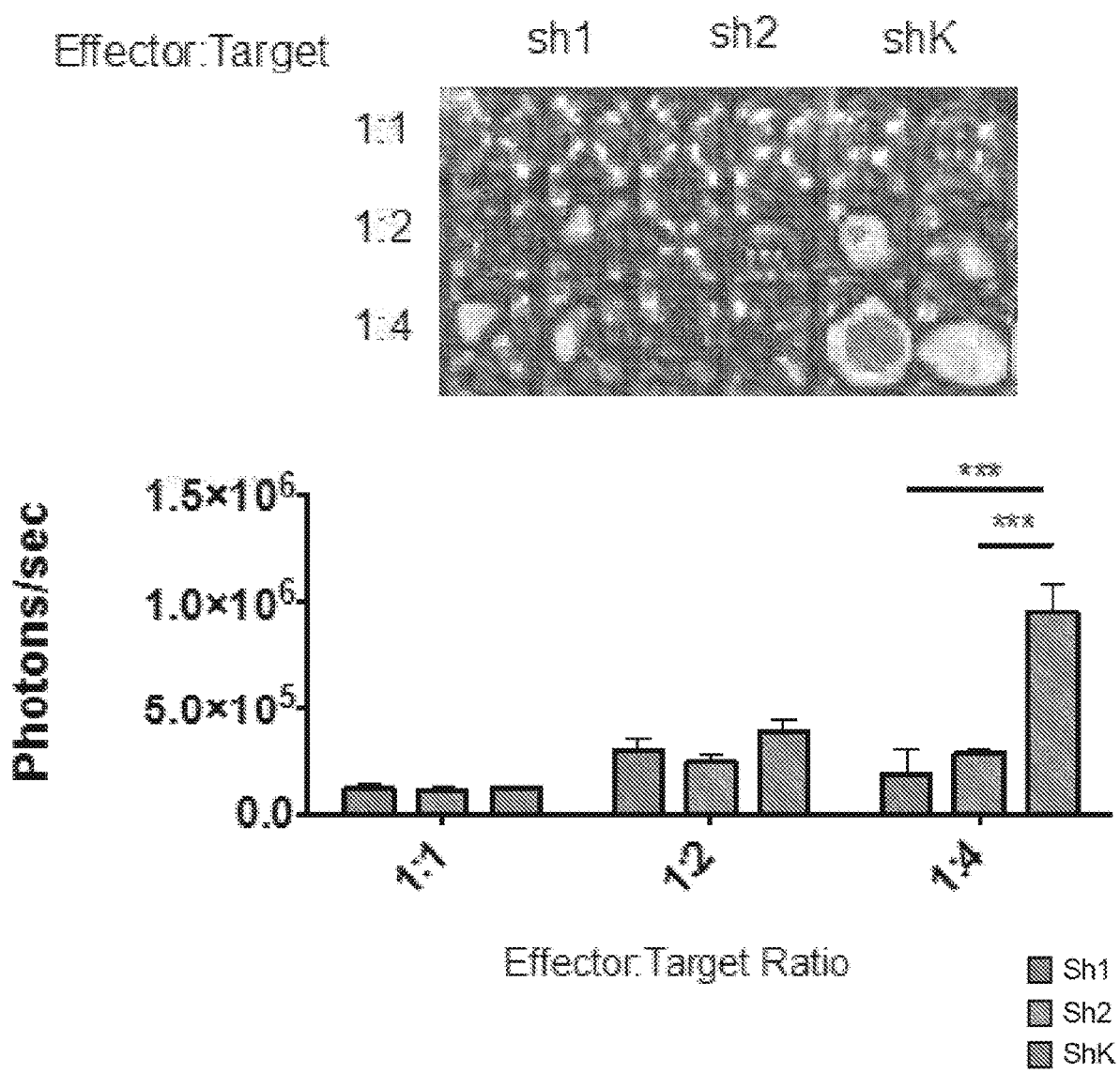

FIGS. 10A-10E show that cotransduction of PD-1 receptor-targeting shRNAs rescues M28z CAR T cells from PD-L1/PD-1-mediated inhibition in vitro. FIG. 10A. (Left) Schematic representation of CD28-costimulated T cells binding tumor-expressed PD-L1 via endogenous PD-1 receptor, with or without coexpression of PD-1-targeting shRNA. (Right) All experiments included M28z CAR T cells cotransduced with one of two PD-1-targeting shRNAs (sh1 or sh2 coexpressing a dsRED reporter) or with an shRNA targeting a bacterial sequence (KanR). FIG. 10B. Compared with KanR-transduced cells, M28z CAR T cells cotransduced with PD-1-targeting shRNAs demonstrated a 60% to 70% knockdown in PD-1 receptor protein expression upon stimulation with phytohemagglutinin (graphs left to right correspond to 430, 722, 813 and 1411). Cells were incubated with either 3T3 fibroblasts overexpressing PD-L1 (3T3 MSLN+PD-L1+) or mesothelioma tumor cells that had been treated with IFN-γ and TNF-α in order to upregulate PD-L1 and PD-L2. M28z PD1 shRNA CAR T cells demonstrate enhanced accumulation upon repeated antigen stimulation (FIG. 10C), enhanced cytolytic function at low effector to target ratios, as measured by luciferase activity of remaining live tumor cells (FIG. 10D; each group of bar grafts, from left to right, Sh1, Sh2, ShK), and increased Th1 cytokine secretion (FIG. 10E; each group of bar grafts, from left to right, Sh1, Sh2, ShK) (P<0.01; *P<0.001). Student's t tests were performed and statistical significance was determined using the Bonferroni correction for multiple comparisons. Data represent the mean±SEM of three replicates.

FIG. 11 shows an adhesion assay of PD-1 DNR to PD-L1 and PD-L2 recombinant proteins fused to an Fc domain. T cells labeled with mCherry and transduced with PD-1 DNR were exposed to plates coated with PD-L1 fused to Fc ("PD-L1 Fc"), PD-L2 fused to Fc ("PD-L2 Fc"), or control isotype Fc ("Iso Fc"). T cells bound to the plates were measured as absolute mcherry+ T cell count in the presence ("+PD-1 Ab") or absence of PD-1 antibody. The bar graphs show the binding for each of the respectively coated plates, from left to right, T cells alone ("T cells"), T cells in the presence of PD-1 antibody (T cells+PD-1 ab"), T cells transduced with PD-1 DNR ("PD-1 DNR T cells"), and T cells transduced with PD-1 DNR in the presence of PD-1 antibody ("PD-1 DNR T cells+PD-1 Ab").

Figure 12A:
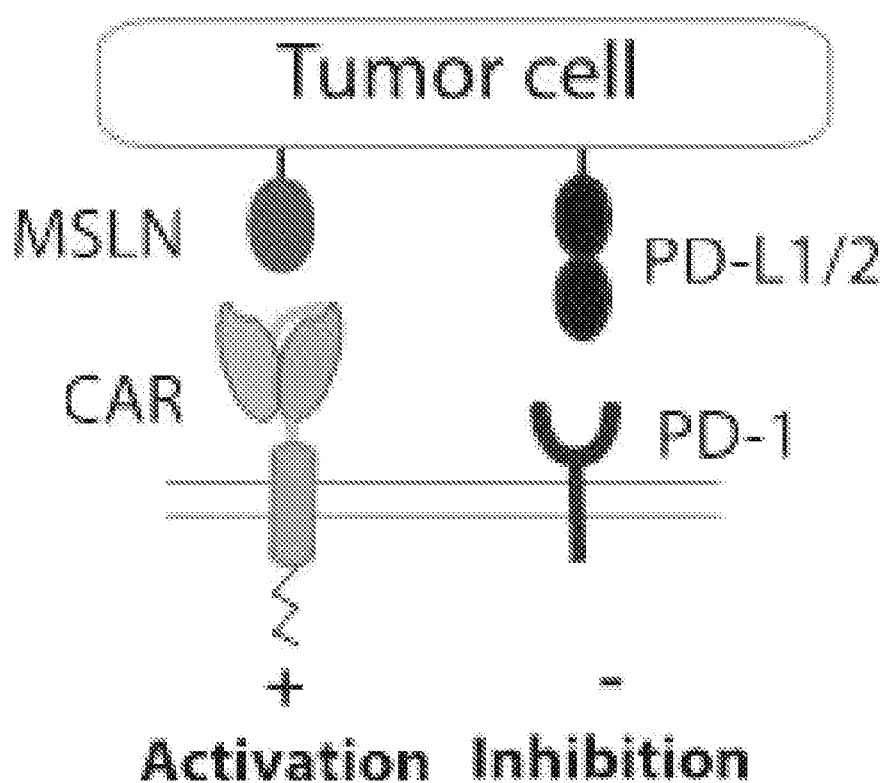
Figure 12B:
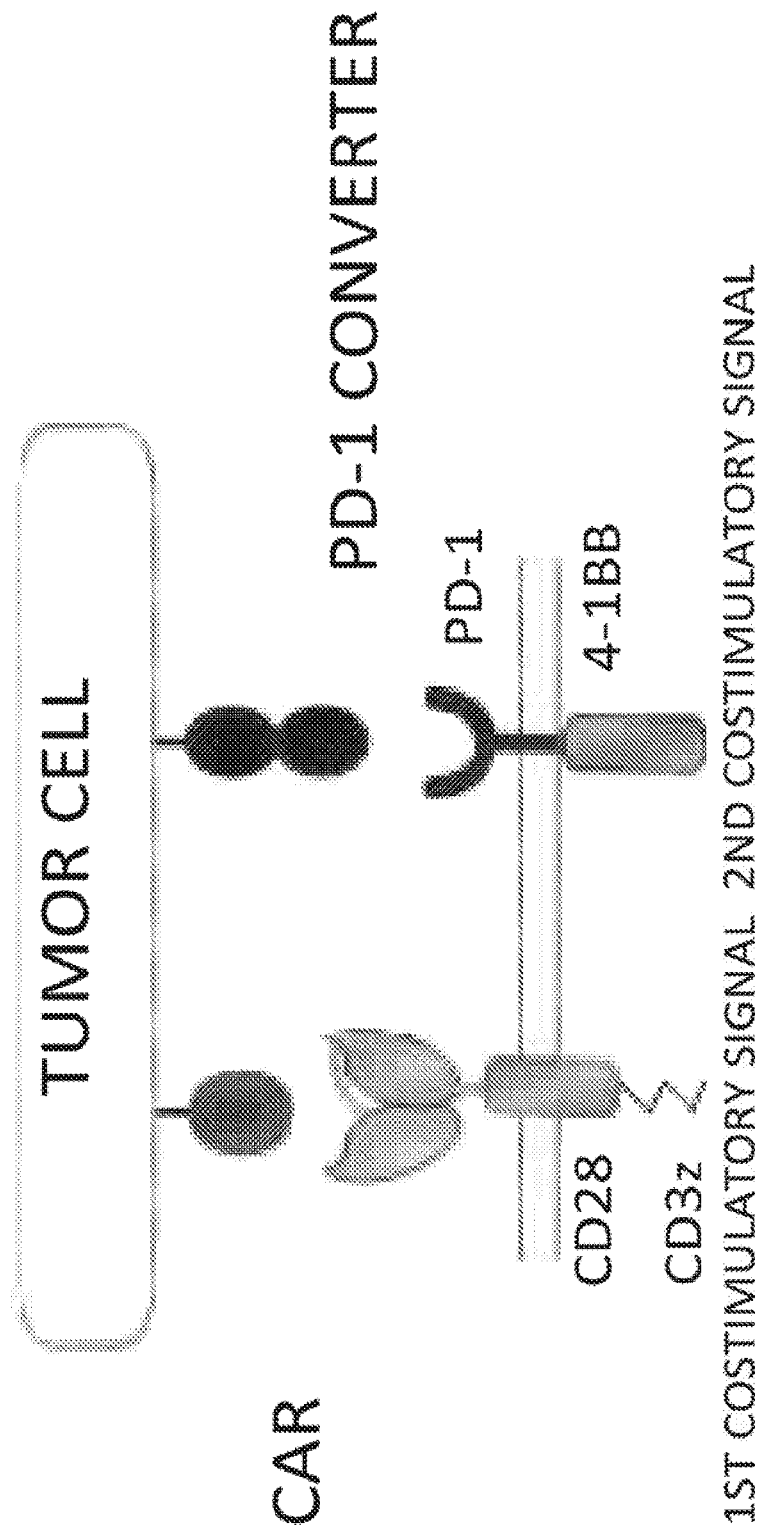

FIGS. 12A-12D show that a PD-1 DNR, which inhibits PD-L1- or PD-L2-mediated inhibition of T cell activation, can be converted into a positive co-stimulatory signal. FIG. 12A shows a schematic diagram illustrating co-expression of a CAR and a PD-1 DNR. FIG. 12B shows a schematic diagram illustrating co-expression of a CAR and a PD-1 DNR converted into a costimulatory construct by fusing a costimulatory domain, exemplified as 4-1 BB, to a transmembrane domain fused to the ligand binding domain of PD-1. FIG. 12C shows accumulation of CAR T cells at day 0 and day 7 in T cells transduced with M28z CAR, M28z CAR plus PD-1 DNR, or M28z CAR plus a PD-1 4-1BB switch receptor construct. Bars left to right respectively: M28z CAR, M28z CAR+PD-1 DNR, and M28z CAR+PD-1 4-1BB switch receptor construct. FIG. 12D shows cytokine secretion of interferon gamma (IFN-γ), interleukin 2 (IL-2), tumor necrosis factor alpha (TNF-α) and granulocyte-macrophage colony-stimulating factor (GM-CSF) in T cells transduced with M28z CAR, M28z CAR plus PD-1 DNR or M28z CAR plus a PD-1 4-1BB switch receptor construct. Bars left to right respectively: M28z CAR, M28z CAR+PD-1 DNR, and M28z CAR+PD-1 4-1BB switch receptor construct.

6. DETAILED DESCRIPTION OF THE INVENTION

The present invention relates to compositions and methods for treating immune-mediated disorders. Such disorders include, but are not limited to, organ transplant rejection, autoimmune disorders, allergic disorders, fetomaternal intolerance, and Alzheimer's disease. As described herein, immunoinhibitory cells can be genetically engineered to intrinsically express proteins that are dominant negative mutants and that inhibit blockades that limit the immunosuppressive effect of the immunoinhibitory cells. By inhibiting the blockade, the genetically engineered immunoinhibitory cells are permitted to provide a more effective immunosuppressive activity against pathological immune responses in immune-mediated disorders.

In one aspect, provided herein is a cell that is an immunoinhibitory cell, which cell recombinantly expresses a dominant negative form of an inhibitor of a cell-mediated immune response of the cell. In another aspect, provided herein is a population (preferably, a polyclonal population) of human regulatory T cells that are $CD4^+CD25^+$, and recombinantly express a dominant negative form of an inhibitor of a regulatory T cell-mediated immune response. In a specific embodiment, the polyclonal population is purified. In a specific embodiment, the polyclonal population is ex vivo. In a specific embodiment, the polyclonal population is present in a population enriched for the polyclonal population. In another aspect, provided herein is a regulatory T cell that recombinantly expresses a dominant negative form of an inhibitor of a regulatory T cell-mediated immune response. In another aspect, provided herein are pharmaceutical compositions comprising a therapeutically effective amount of a cell or population of the invention; and a pharmaceutically acceptable carrier.

In yet another aspect, provided herein is a method of treating an immune-mediated disorder in a patient in need thereof, comprising administering to the patient a therapeutically effective amount of the cell or population of the invention. In certain embodiments, the immune-mediated disorder is selected from the group consisting of organ transplant rejection, an autoimmune disorder, multiple sclerosis, type 1 diabetes, arthritis, for example, rheumatoid arthritis or other types of arthritis, primary biliary cirrhosis, myasthenia gravis, vitiligo, lupus, an allergic disorder, fetomaternal intolerance and Alzheimer's disease. In another aspect, provided herein is a method of promoting self-tolerance or reestablishing immunological tolerance to a self-antigen in a patient in need thereof, comprising administering to the patient a therapeutically effective amount of the cell or population of the invention, wherein the cell is a pathologic self-antigen specific regulatory T cell, or the population comprises pathologic self-antigen specific regulatory T cells. In another aspect, the invention provides a method of treating arthritis in a patient in need thereof, comprising administering to the patient a therapeutically effective amount of the cell or population of the invention, wherein the cell or population is administered intraarticularly or directly at a tendon insertion site of an arthritic joint. In another aspect, the invention provides a method of treating an immune-mediated disorder in a patient in need thereof, comprising isolating regulatory T cells from the patient, expanding the regulatory T cells in cell culture in vitro, and administering the expanded regulatory T cells to the patient in a therapeutically effective amount, wherein the isolated regulatory T cells are transduced to express a dominant negative form of an inhibitor of a regulatory T cell-mediated immune response.

6.1 Cells

The invention provides cells that are immunoinhibitory cells that recombinantly express a dominant negative form (hereinafter "DN form") of an inhibitor of a cell-mediated immune response, preferably of the immunoinhibitory cell. In one embodiment, the immunoinhibitory cells recognize and are sensitized to an antigen that is the target of a pathologic (or undesirable) immune response associated with an immune-mediated disorder. Such cells can be isolated, for example, from a patient, in particular a human patient, having such an immune-mediated disorder. In another embodiment, the immunoinhibitory cells expressing a DN form additionally recombinantly express a CAR that binds to an antigen that is the target of a pathologic immune response associated with an immune-mediated disorder. Such cells can be isolated, for example, from a patient, in particular a human patient, having such an immune-mediated disorder. The recombinant cells can be used to treat the immune-mediated disorder. Preferably, the cells are derived from a human (are of human origin prior to being made recombinant) (and human-derived cells are particularly preferred for administration to a human in the methods of treatment of the invention).

The immunoinhibitory cells of the invention can be cells of the lymphoid lineage. Non-limiting examples of cells of the lymphoid lineage that can be used as immunoinhibitory cells include regulatory T cells, follicular regulatory T cells, regulatory B cells, and the like. The immunoinhibitory cells of the invention express an inhibitor of a cell-mediated immune response, for example, an immune checkpoint inhibitor pathway receptor, e.g., PD-1 (while not intending to be bound by mechanism, it is submitted that expression of the DN form in the cell inhibits the inhibitor of the the cell-mediated immune response to promote sustained activation of the cell).

Immunoinhibitory cells can be isolated by methods well known in the art, including commercially available isolation methods (see, for example, Rowland-Jones et al., *Lymphocytes: A Practical Approach*, Oxford University Press, New York (1999)). Sources for the immunoinhibitory cells thereof include, but are not limited to, peripheral blood, umbilical cord blood, bone marrow, or other sources of cells of the lymphoid lineage. Various techniques can be employed to separate the cells to isolate or enrich for desired immunoinhibitory cells. For instance, negative selection methods can be used to remove cells that are not the desired immunoinhibitory cells. Additionally, positive selection methods can be used to isolate or enrich for desired immunoinhibitory cells, or a combination of positive and negative selection methods can be employed. Monoclonal antibodies (MAbs) are particularly useful for identifying markers associated with particular cell lineages and/or stages of differentiation and can be used as reagents for both positive and negative selections. A particular type of immunoinhibitory cell can be isolated based on various cell surface markers or combinations of markers, or the absence of markers, including but not limited to CD4 and/or CD8 for positive selection combined with CD127 for negative selection, as is well known in the art (see Kearse, *T Cell Protocols: Development and Activation*, Humana Press, Totowa N.J. (2000); De Libero, *T Cell Protocols*, Vol. 514 of *Methods in Molecular Biology*, Humana Press, Totowa N.J. (2009); Su et al., *Methods Mol. Biol.* 806:287-299 (2012); Bluestone et al., *Sci. Transl. Med.* 7(315) (doi: 10.1126/scitranslmed.aad4134)(2015); Miyara et al., *Nat. Rev. Rheumatol.* 10:543-551 (2014); Liu et al., *J. Exp. Med.* 203:1701-1711 (2006); Seddiki et al., *J. Exp. Med.* 203:1693-1700 (2006); Ukena et al., *Exp. Hematol.* 39:1152-1160 (2011); Chen et al., *J Immunol.* 183:4094-4102 (2009); Putnam et al., *Diabetes* 58:652-662 (2009); Putnam et al., *Am. J Tranplant.* 13:3010-3020 (2013)). In a specific embodiment, $CD4^+$ $CD25^+$ regulatory T cells are isolated, for example, using a $CD4^+CD25^+$ Regulatory T Cell Isolation Kit (Dynal brand, Invitrogen, Carlsbad, Calif.) (see Lee et al., *Cancer Res.* 71:2871-2881 (2011)). In vitro generation of regulatory T cells (iTregs) have also been described (see, for example, Lan et al., *J Mol. Cell. Biol.* 4:22-28 (2012); Yamagiwa et al., *J Immunol.* 166:7282-7289 (2001); Zheng et al., *Immunol.* 169:4183-4189 (2002)). Various methods for isolating immune cells that can be used for recombinant expression of a CAR have been described previously (Sadelain et al., *Nat. Rev. Cancer* 3:35-45 (2003); Morgan et al., *Science* 314: 126-129 (2006); Panelli et al., *J. Immunol.* 164:495-504 (2000); Panelli et al., *J. Immunol.* 164:4382-4392 (2000); Dupont et al., *Cancer Res.* 65:5417-5427 (2005); Papanicolaou et al., *Blood* 102:2498-2505 (2003); MacDonald et al., *J. Clin. Invest.* 126:1413-1424 (2016)).

Methods for isolating and expanding regulatory T cells are well known in the art (see, for example, Su et al., *Methods Mol. Biol.* 806:287-299 (2012); Bluestone et al., *Sci. Transl. Med.* 7(315) (doi: 10.1126/scitranslmed.aad4134)(2015); Miyara et al., *Nat. Rev. Rheumatol.* 10:543-551 (2014); Liu et al., *J Exp. Med.* 203:1701-1711 (2006); Seddiki et al., *J Exp. Med.* 203:1693-1700 (2006); Ukena et al., *Exp. Hematol.* 39:1152-1160 (2011); Chen et al., *J. Immunol.* 183:4094-4102 (2009); Putnam et al., *Diabetes* 58:652-662 (2009); Putnam et al., *Am. J. Tranplant.* 13:3010-3020 (2013); Lee et al., *Cancer Res.* 71:2871-2881 (2011); MacDonald et al., *J Clin. Invest.* 126:1413-1424 (2016)). In vitro generation of regulatory T cells (iTregs) have also been described (see, for example, Lan et al., *J Mol. Cell. Biol.* 4:22-28 (2012); Yamagiwa et al., *J. Immunol.* 166:7282-7289 (2001); Zheng et al., *J. Immunol.* 169:4183-4189 (2002)). Generally, regulatory T cells of the invention are $CD4^+$, for example, $CD4^+CD25^+$, and in particular $CD4^+CD127^{lo/-}CD25^+$. Such regulatory T cells express Foxp3 (forkhead box P3), which is in the forkhead/winged-helix family of transcription factors (Bluestone et al., *J. Clin. Invest.* 125:2250-2260 (2015); Riley et al., *Immunity* 30:656-665 (2009)). A regulatory T cell that is an immunoinhibitory cell of the invention can also be a $CD8^+$ regulatory T cell (Guillonneau et al., *Curr. Opin. Organ Transplant.* 15:751-756 (2010)). Methods for isolating and expanding regulatory T cells are also commercially available (see, for example, BD Biosciences, San Jose, Calif.; STEMCELL Technologies Inc., Vancouver, Canada; eBioscience, San Diego, Calif.; Invitrogen, Carlsbad, Calif.). An immunoinhibitory cell of the invention can also be a follicular regulatory T cell (T(FR)) (Sage et al., *Nat. Immunol.* 14:152-161 (2013)). In a particular embodiment, the follicular regulatory T cells of the invention are $CD4^+CXCR5^+$ and express Foxp3 (Sage et al., supra, 2013).

In some embodiments, the immunoinhibitory cells of the invention are regulatory B cells. Regulatory B cells have the unique ability in B cells to produce interleukin 10 (IL10) (see, for example, Lykken et al., *International Immunol.* 27:471-477 (2015); Miyagaki et al., *International Immunol.* 27:495-504 (2015)). Methods of isolating regulatory B cells have been described (see, for example, Masson et al., in *Regulatory B Cells: Methods and Protocols*, Vitale and Mion, eds., Chapter 4, pp. 45-52, Humana Press, New York (2014)). Such methods are based on the expression of cell surface markers, such as $CD24^{high}CD38^{high}$, and the expression of IL10 (Masson et al., supra, 2014). Other markers for regulatory B cells include $CD24^{hi}CD27^+$ (see Lykken et al., supra, 2015).

Procedures for separation of cells include, but are not limited to, density gradient centrifugation, coupling to particles that modify cell density, magnetic separation with antibody-coated magnetic beads, affinity chromatography; cytotoxic agents joined to or used in conjunction with a monoclonal antibody (mAb), including, but not limited to, complement and cytotoxins, and panning with an antibody attached to a solid matrix, for example, a plate or chip, elutriation, flow cytometry, or any other convenient technique (see, for example, Recktenwald et al., *Cell Separation Methods and Applications*, Marcel Dekker, Inc., New York (1998)). It is understood that the immunoinhibitory cells used in methods of the invention can be a substantially pure or can be a polyclonal population (see, for example, Bluestone et al., *Sci. Transl. Med.* 7(315) (doi: 10.1126/scitranslmed.aad4134)(2015)). In some embodiments, a polyclonal population can be enriched for a desired immunoinhibitory cell. Such an enrichment can take place prior to or after genetically engineering the cells to express a DN form, or a CAR and DN form, as desired.

The immunoinhibitory cells can be autologous or non-autologous to the subject to which they are administered in the methods of treatment of the invention. Autologous cells are isolated from the subject to which the engineered cells recombinantly expressing a DN form, or a CAR and DN form, are to be administered. Optionally, the cells can be obtained by leukapheresis, where leukocytes are selectively removed from withdrawn blood, made recombinant, and then retransfused into the donor. Alternatively, allogeneic cells from a non-autologous donor that is not the subject can be used. In the case of a non-autologous donor, the cells are typed and matched for human leukocyte antigen (HLA) to determine an appropriate level of compatibility, as is well known in the art. For both autologous and and non-autologous cells, the cells can optionally be cryopreserved until ready to be used for genetic manipulation and/or administration to a subject using methods well known in the art.

In one embodiment, the invention provides regulatory T cells that recognize and are sensitized to an antigen that is the target of a pathologic immune response associated with an immune-mediated disorder, and also which recombinantly express a DN form of an inhibitor of a regulatory T cell-mediated immune response. Such regulatory T cells can but need not express a CAR that binds to an antigen that is the target of a pathologic immune response associated with an immune-mediated disorder, since the cells already are antigen-specific so that the regulatory T cells are targeted to the antigen. T cells that recognize and are sensitized to an antigen can be obtained by known methods, for example, obtained from a subject that has been exposed to and is mounting a pathologic immune response associated with an immune-mediated disorder. Methods for isolating an antigen-specific regulatory T cell from a subject are well known in the art (see, for example, Noyan et al., *Eur. J. Immunol.* 44:2592-2602 (2014); Brusko et al., *PLoS One* 5(7) e11726 (doi: 10.1371) (2010); Bacher et al., *Mucosal Immunol.* 7:916-928 (2014); Koenen et al., *J. Immunol.* 174:7573-7583 (2005)). The antigen-specific regulatory T cells can be isolated using well known techniques as described above for isolating immunoinhibitory cells, which include, but are not limited to, flow cytometry, magnetic beads, panning on a solid phase, and so forth.

In a specific embodiment, isolated immunoinhibitory cells are genetically engineered ex vivo for recombinant expression of a DN form and a CAR. In a specific embodiment, isolated regulatory T cells that are antigen-specific are genetically engineered ex vivo for recombinant expression of a DN form. The cells can be genetically engineered for recombinant expression by methods well known in the art. In an embodiment where the sensitized regulatory T cells are isolated from in vivo sources, it will be self-evident that genetic engineering occurs of the already-sensitized regulatory T cells.

The immunoinhibitory cells can be subjected to conditions that favor maintenance or expansion of the immunoinhibitory cells (see Kearse, *T Cell Protocols: Development and Activation*, Humana Press, Totowa N.J. (2000); De Libero, *T Cell Protocols, Vol. 514* of *Methods in Molecular Biology*, Humana Press, Totowa N.J. (2009); Parente-Pereira et al., *J. Biol. Methods* 1(2) e7 (doi 10.14440/jbm.2014.30) (2014); Movassagh et al., *Hum. Gene Ther.* 11:1189-1200 (2000); Rettig et al., *Mol. Ther.* 8:29-41 (2003); Agarwal et al., *J. Virol.* 72:3720-3728 (1998); Pollok et al., *Hum. Gene Ther.* 10:2221-2236 (1999); Quinn et al., *Hum. Gene Ther.* 9:1457-1467 (1998); Su et al., *Methods Mol. Biol.* 806:287-299 (2012); Bluestone et al., *Sci. Transl. Med.* 7(315) (doi: 10.1126/scitranslmed.aad4134)(2015); Miyara et al., *Nat. Rev. Rheumatol.* 10:543-551 (2014); Liu et al., *J. Exp. Med.* 203:1701-1711 (2006); Seddiki et al., *J. Exp. Med.* 203:1693-1700 (2006); Ukena et al., *Exp. Hematol.* 39:1152-1160 (2011); Chen et al., *J. Immunol.* 183:4094-4102 (2009); Putnam et al., *Diabetes* 58:652-662 (2009); Putnam et al., *Am. J. Tranplant.* 13:3010-3020 (2013); Lee et al., *Cancer Res.* 71:2871-2881 (2011); MacDonald et al., *J. Clin. Invest.* 126:1413-1424 (2016)). The immunoinhibitory cells, or antigen sensitized regulatory T cells, can optionally be expanded prior to or after ex vivo genetic engineering. Expansion of the cells is particularly useful to increase the number of cells for administration to a subject. Such methods for expansion of immunoinhibitory cells are well known in the art (see Kaiser et al., *Cancer Gene Therapy* 22:72-78 (2015); Wolfl et al., *Nat. Protocols* 9:950-966 (2014); Su et al., *Methods Mol. Biol.* 806:287-299 (2012); Bluestone et al., *Sci. Transl. Med.* 7(315) (doi: 10.1126/scitranslmed.aad4134)(2015); Miyara et al., *Nat. Rev. Rheumatol.* 10:543-551 (2014); Liu et al., *J. Exp. Med.* 203:1701-1711 (2006); Seddiki et al., *J. Exp. Med.* 203:1693-1700 (2006); Ukena et al., *Exp. Hematol.* 39:1152-1160 (2011); Chen et al., *J. Immunol.* 183:4094-4102 (2009); Putnam et al., *Diabetes* 58:652-662 (2009); Putnam et al., *Am. J. Tranplant.* 13:3010-3020 (2013); Lee et al., *Cancer Res.* 71:2871-2881 (2011)). Furthermore, the cells can optionally be cryopreserved after isolation and/or genetic engineering, and/or expansion of genetically engineered cells (see Kaiser et al., supra, 2015)). Methods for cyropreserving cells are well known in the art (see, for example, Freshney, *Culture of Animal Cells: A Manual of Basic Techniques*, 4th ed., Wiley-Liss, New York (2000); Harrison and Rae, *General Techniques of Cell Culture*, Cambridge University Press (1997)).

With respect to generating cells recombinantly expressing a DN form, or a CAR and DN form, one or more nucleic acids encoding the DN form or the CAR and DN form is introduced into the immunoinhibitory cell using a suitable expression vector. The immunoinhibitory cells (for example, regulatory T cells or regulatory B cells) are preferably transduced with one or more nucleic acids encoding a DN form, or a CAR and DN form. In the case of expressing both a CAR and DN form, the CAR and DN form encoding nucleic acids can be on separate vectors or on the same vector, as desired. For example, a polynucleotide encoding a CAR or DN form of the invention can be cloned into a suitable vector, such as a retroviral vector, and introduced into the immunoinhibitory cell using well known molecular biology techniques (see Ausubel et al., *Current Protocols in Molecular Biology*, John Wiley and Sons, Baltimore, Md. (1999)). Any vector suitable for expression in a cell of the invention, particularly a human immunoinhibitory cell, can be employed. The vectors contain suitable expression elements such as promoters that provide for expression of the encoded nucleic acids in the immunoinhibitory cell. In the case of a retroviral vector, cells can optionally be activated to increase transduction efficiency (see Parente-Pereira et al., *J. Biol. Methods* 1(2) e7 (doi 10.14440/jbm.2014.30) (2014); Movassagh et al., *Hum. Gene Ther.* 11:1189-1200 (2000); Rettig et al., *Mol. Ther.* 8:29-41 (2003); Agarwal et al., *J. Virol.* 72:3720-3728 (1998); Pollok et al., *Hum. Gene Ther.* 10:2221-2236 (1998); Quinn et al., *Hum. Gene Ther.* 9:1457-1467 (1998)). Methods for use in expressing a polypeptide, such as a CAR, in a regulatory T cell can be any known in the art, e.g., those described in Lee et al., *Cancer Res.* 71:2871-2881 (2011).

In one embodiment, the vector is a retroviral vector, for example, a gamma retroviral or lentiviral vector, which is employed for the introduction of a CAR or DN form into the immunoinhibitory cell. For genetic modification of the cells to express a CAR and/or DN form, a retroviral vector is generally employed for transduction. However, it is understood that any suitable viral vector or non-viral delivery system can be used. Combinations of a retroviral vector and an appropriate packaging line are also suitable, where the capsid proteins will be functional for infecting human cells. Various amphotropic virus-producing cell lines are known, including, but not limited to, PA12 (Miller et al., *Mol. Cell. Biol.* 5:431-437 (1985)); PA317 (Miller et al., *Mol. Cell. Biol.* 6:2895-2902(1986)); and CRIP (Danos et al., *Proc. Natl. Acad. Sci. USA* 85:6460-6464 (1988)). Non-amphotropic particles are suitable too, for example, particles pseudotyped with VSVG, RD114 or GALV envelope and any other known in the art (Relander et al., *Mol. Therap.* 11:452-459 (2005)). Possible methods of transduction also include direct co-culture of the cells with producer cells (for example, Bregni et al., *Blood* 80:1418-1422 (1992)), or culturing with viral supernatant alone or concentrated vector stocks with or without appropriate growth factors and polycations (see, for example, Xu et al., *Exp. Hemat.* 22:223-230 (1994); Hughes, et al. *J. Clin. Invest.* 89:1817-1824 (1992)).

Generally, the chosen vector exhibits high efficiency of infection and stable integration and expression (see, for example, Cayouette et al., *Human Gene Therapy* 8:423-430 (1997); Kido et al., *Current Eye Research* 15:833-844 (1996); Bloomer et al., *J. Virol.* 71:6641-6649 (1997); Naldini et al., *Science* 272:263 267 (1996); and Miyoshi et al., *Proc. Natl. Acad. Sci. U.S.A.* 94:10319-10323 (1997)).

Other viral vectors that can be used include, for example, adenoviral, lentiviral, and adeno-associated viral vectors, vaccinia virus, a bovine papilloma virus derived vector, or a herpes virus, such as Epstein-Barr Virus (see, for example, Miller, *Hum. Gene Ther.* 1(1):5-14 (1990); Friedman, *Science* 244:1275-1281 (1989); Eglitis et al., *BioTechniques* 6:608-614 (1988); Tolstoshev et al., *Current Opin. Biotechnol.* 1:55-61 (1990); Sharp, *Lancet* 337:1277-1278 (1991); Cornetta et al., *Prog. Nucleic Acid Res. Mol. Biol.* 36:311-322 (1989); Anderson, *Science* 226:401-409 (1984); Moen, *Blood Cells* 17:407-416 (1991); Miller et al., *Biotechnology* 7:980-990 (1989); Le Gal La Salle et al., *Science* 259:988-990 (1993); and Johnson, *Chest* 107:77S-83S (1995)). Retroviral vectors are particularly well developed and have been used in clinical settings (Rosenberg et al., *N. Engl. J. Med.* 323:370 (1990); Anderson et al., U.S. Pat. No. 5,399, 346).

Particularly useful vectors for expressing a CAR and/or DN form of the invention include vectors that have been used in human gene therapy. In one non-limiting embodiment, a vector is a retroviral vector. The use of retroviral vectors for expression in T cells or other immune cells, including engineered CAR T cells, has been described (see Scholler et al., *Sci. Transl. Med.* 4:132-153 (2012; Parente-Pereira et al., *J. Biol. Methods* 1(2):e7 (1-9)(2014); Lamers et al., *Blood* 117(1):72-82 (2011); Reviere et al., *Proc. Natl. Acad. Sci. USA* 92:6733-6737 (1995)). In one embodiment, the vector is an SGF retroviral vector such as an SGF γ-retroviral vector, which is Moloney murine leukemia-based retroviral vector. SGF vectors have been described previously (see, for example, Wang et al., *Gene Therapy* 15:1454-1459 (2008)).

The vectors of the invention employ suitable promoters for expression in a particular host cell. The promoter can be an inducible promoter or a constitutive promoter. In a particular embodiment, the promoter of an expression vector provides expression in an immunoinhibitory cell, such as a regulatory T cell or regulatory B cell. Non-viral vectors can be used as well, so long as the vector contains suitable expression elements for expression in the immunoinhibitory cell. Some vectors, such as retroviral vectors, can integrate into the host genome. If desired, targeted integration can be implemented using technologies such as a nuclease, transcription activator-like effector nucleases (TALENs), Zinc-finger nucleases (ZFNs), and/or clustered regularly interspaced short palindromic repeats (CRISPRs), by homologous recombination, and the like (Gersbach et al., *Nucl. Acids Res.* 39:7868-7878 (2011); Vasileva, et al. *Cell Death Dis.* 6:e1831. (Jul. 23 2015); Sontheimer, *Hum. Gene Ther.* 26(7):413-424 (2015)).

The vectors and constructs can optionally be designed to include a reporter. For example, the vector can be designed to express a reporter protein, which can be useful to identify cells comprising the vector or nucleic acids provided on the vector, such as nucleic acids that have integrated into the host chromosome. In one embodiment, the reporter can be expressed as a bicistronic or multicistronic expression construct with the CAR or DN form. Exemplary reporter proteins include, but are not limited to, fluorescent proteins, such as mCherry, green fluorescent protein (GFP), blue fluorescent protein, for example, EBFP, EBFP2, Azurite, and mKalamal, cyan fluorescent protein, for example, ECFP, Cerulean, and CyPet, and yellow fluorescent protein, for example, YFP, Citrine, Venus, and YPet. In an additional embodiment, a vector construct can comprise a P2A sequence, which provides for optional co-expression of a reporter molecule. P2A is a self-cleaving peptide sequence, which can be used for bicistronic or multicistronic expression of protein sequences (see Szymczak et al., *Expert Opin. Biol. Therapy* 5(5):627-638 (2005)).

Assays can be used to determine the transduction efficiency of a CAR and/or DN form using routine molecular biology techniques. If a marker has been included in the construct, such as a fluorescent protein, gene transfer efficiency can be monitored by FACS analysis to quantify the fraction of transduced (for example, GFP$^+$) immunoinhibitory cells, such as regulatory T cells or regulatory B cells, and/or by quantitative PCR.

If desired, a nucleic acid encoding a polypeptide for genetic engineering of a cell of the invention, such as a DN form or a CAR, can be codon optimized to increase efficiency of expression in an immunoinhibitory cell. Codon optimization can be used to achieve higher levels of expression in a given cell. Factors that are involved in different stages of protein expression include codon adaptability, mRNA structure, and various cis-elements in transcription and translation. Any suitable codon optimization methods or technologies that are known to one skilled in the art can be used to modify the polynucleotides encoding the polypeptides. Such codon optimization methods are well known, including commercially available codon optimization services, for example, OptimumGene™ (GenScript; Piscataway, N.J.), Encor optimization (EnCor Biotechnology; Gainseville Fla.), Blue Heron (Blue Heron Biotech; Bothell, Wash.), and the like. Optionally, multiple codon optimizations can be performed based on different algorithms, and the optimization results blended to generate a codon optimized nucleic acid encoding a polypeptide.

Further modification can be introduced to the immunoinhibitory cells of the invention. For example, the cells can be modified to address immunological complications and/or targeting by the CAR to non-target tissues that express the same target antigens. For example, a suicide gene can be introduced into the cells to provide for depletion of the cells when desired. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. Agents are administered to the subject to which the cells containing the suicide genes have been administered, including but not limited to, gancilovir (GCV) for hsv-tk (Greco et al., *Frontiers Pharmacol.* 6:95 (2015); Barese et al., *Mol. Therapy* 20:1932-1943 (2012)), AP1903 for iCasp-9 (Di Stasi et al., *N. Engl. J. Med.* 365:1673-1683 (2011), and cetuximab for EGFRt (U.S. Pat. No. 8,802,374), to promote cell death. In one embodiment, administration of a prodrug designed to activate the suicide gene, for example, a prodrug such as AP1903 that can activate iCasp-9, triggers apoptosis in the suicide gene-activated cells. In one embodiment, iCasp9 consists of the sequence of the human FK506-binding protein (FKBP12; GenBank number, AH002818 (AH002818.1, M92422.1, GI:182645; AH002818.2, GI:1036032368)) with an F36V mutation, connected through a Ser-Gly-Gly-Gly-Ser (SEQ ID NO:28) linker to the gene encoding human caspase 9 (CASP9; GenBank number, NM001229 (NM_001229.4, GI:493798577)), which has had its endogenous caspase activation and recruitment domain deleted. FKBP12-F36V binds with high affinity to an otherwise bioinert small-molecule dimerizing agent, AP1903. In the presence of AP1903, the iCasp9 promolecule dimerizes and activates the intrinsic apoptotic pathway, leading to cell death (Di Stasi et al., *N. Engl. J. Med.* 365:1673-1683 (2011)). In another embodiment, the suicide gene is an EGFRt polypeptide. The EGFRt polypeptide can provide for cell elimination by administering anti-EGFR monoclonal antibody, for example, cetuximab. The suicide gene can be expressed on a separate vector or, optionally, expressed within the vector encoding a CAR or DN form, and can be a bicistronic or multicistronic construct joined to a CAR or DN form encoding nucleic acid.

6.2 Chimeric Antigen Receptors (CARs)

The CAR that is recombinantly expressed by a cell of the invention has an antigen binding domain that binds to an antigen that is the target of a pathologic immune response associated with an immune-mediated disorder. In specific embodiments, the CAR can be a "first generation," "second generation" or "third generation" CAR (see, for example, Sadelain et al., Cancer Discov. 3(4):388-398 (2013); Jensen et al., Immunol. Rev. 257:127-133 (2014); Sharpe et al., Dis. Model Mech. 8(4):337-350 (2015); Brentjens et al., Clin. Cancer Res. 13:5426-5435 (2007); Gade et al., Cancer Res. 65:9080-9088 (2005); Maher et al., Nat. Biotechnol. 20:70-75 (2002); Kershaw et al., J. Immunol. 173:2143-2150 (2004); Sadelain et al., Curr. Opin. Immunol. 21(2):215-223 (2009); Hollyman et al., J. Immunother. 32:169-180 (2009)).

"First generation" CARs are typically composed of an extracellular antigen binding domain, for example, a single-chain variable fragment (scFv), fused to a transmembrane domain, which is fused to a cytoplasmic/intracellular domain of the T cell receptor chain. "First generation" CARs typically have the intracellular domain from the CD3ζ-chain, which is the primary transmitter of signals from endogenous T cell receptors (TCRs) (see exemplary first generation CAR in FIG. 1A). "First generation" CARs can provide de novo antigen recognition and cause activation of T cells through their CD3ζ chain signaling domain in a single fusion molecule, independent of HLA-mediated antigen presentation. "Second-generation" CARs for use in the invention comprise an antigen-binding domain fused to an intracellular signaling domain capable of activating immunoinhibitory cells and a co-stimulatory domain designed to augment immune cell, such as T cell, potency and persistence (Sadelain et al., Cancer Discov. 3:388-398 (2013)). CAR design can therefore combine antigen recognition with signal transduction, two functions that are physiologically borne by two separate complexes, the TCR heterodimer and the CD3 complex. "Second generation" CARs include an intracellular domain from various co-stimulatory molecules, for example, CD28, 4-1BB, ICOS, OX40, and the like, in the cytoplasmic tail of the CAR to provide additional signals to the cell (see exemplary second generation CAR in FIG. 1A). "Second generation" CARs provide both co-stimulation, for example, by CD28 or 4-1BB domains, and activation, for example, by a CD3ζ signaling domain "Third generation" CARs provide multiple co-stimulation, for example, by comprising both CD28 and 4-1BB domains, and activation, for example, by comprising a CD3ζ activation domain.

In the embodiments disclosed herein, the CARs generally comprise an extracellular antigen binding domain, a transmembrane domain and an intracellular domain, as described above, where the extracellular antigen binding domain binds to an antigen that is the target of a pathologic immune response associated with an immune-mediated disorder. In a particular non-limiting embodiment, the extracellular antigen-binding domain is an scFv.

As disclosed herein, the methods of the invention involve administering cells that have been engineered to express a dominant negative form ("DN form") of an inhibitor of a cell-mediated immune response, or to co-express the DN form of an inhibitor and a CAR that binds an antigen that is a target of a pathologic immune response associated with an immune-mediated disorder. The extracellular antigen-binding domain of a CAR is usually derived from a monoclonal antibody (mAb) or from receptors or their ligands.

The design of CARs is well known in the art (see, for example, reviews by Sadelain et al., Cancer Discov. 3(4): 388-398 (2013); Jensen et al., Immunol. Rev. 257:127-133 (2014); Sharpe et al., Dis. Model Mech. 8(4):337-350 (2015), and references cited therein). A CAR directed to a desired antigen can be generated using well known methods for designing a CAR, including those as described herein. A CAR, whether a first, second or third generation CAR, can be readily designed by fusing an antigen binding activity, for example, an scFv antibody directed to the antigen, to an immune cell signaling domain, such as a T cell receptor cytoplasmic/intracellular domain. As described above, the CAR generally has the structure of a cell surface receptor, with the antigen binding activity, such as an scFv, as at least a portion of the extracellular domain, fused to a transmembrane domain, which is fused to an intracellular domain that has cell signaling activity in an immunoinhibitory cell. The CAR can include co-stimulatory molecules, as described herein. One skilled in the art can readily select appropriate transmembrane domains, as described herein and known in the art, and intracellular domains to provide the desired signaling capability in the immunoinhibitory cell of the invention.

A CAR for use in the present invention comprises an extracellular domain that includes an antigen binding domain that binds to an antigen that is the target of a pathologic immune response associated with an immune-mediated disorder. Such an antigen binding domain is generally derived from an antibody. In one embodiment, the antigen binding domain can be an scFv or a Fab, or any suitable antigen binding fragment of an antibody (see Sadelain et al., Cancer Discov. 3:388-398 (2013)). Many antibodies or antigen binding domains derived from antibodies that bind to a desired antigen are known in the art. Alternatively, such antibodies or antigen binding domains can be produced by routine methods. Methods of generating an antibody are well known in the art, including methods of producing a monoclonal antibody or screening a library to obtain an antigen binding polypeptide, including screening a library of human Fabs (Winter and Harris, Immunol. Today 14:243-246 (1993); Ward et al., Nature 341:544-546 (1989); Harlow and Lane, Antibodies: A Laboratory Manual, Cold Spring Harbor Laboratory Press (1988); Hilyard et al., Protein Engineering: A practical approach (IRL Press 1992); Borrabeck, Antibody Engineering, 2nd ed. (Oxford University Press 1995); Huse et al., Science 246:1275-1281 (1989)). For the CAR, the antigen binding domain derived from an antibody can be human, humanized, chimeric, CDR-grafted, and the like, as desired. For example, if a mouse monoclonal antibody is a source antibody for generating the antigen binding domain of a CAR, such an antibody can be humanized by grafting CDRs of the mouse antibody onto a human framework (see Borrabeck, supra, 1995), which can be beneficial for administering the CAR to a human subject. In a preferred embodiment, the antigen binding domain is an scFv. The generation of scFvs is well known in the art (see, for example, Huston, et al., Proc. Nat. Acad. Sci. USA 85:5879-5883 (1988); Ahmad et al., Clin. Dev. Immunol. 2012: ID980250 (2012); U.S. Pat. Nos. 5,091,513, 5,132,405 and 4,956,778; and U.S. Patent Publication Nos. 20050196754 and 20050196754).

With respect to obtaining an antigen binding activity, one skilled in the art can readily obtain a suitable antigen binding activity, such as an antibody, using any of the well known methods for generating and screening for an antibody that binds to a desired antigen, as disclosed herein, including the generation of an scFv that binds to an antigen that is the target of a pathologic immune response associated with an immune-mediated disorder, which is particularly useful in a CAR. In addition, a number of antibodies, in particular monoclonal antibodies directed to the target antigens listed in Table 1, are commercially available and can also be used as a source for an antigen binding activity, such as an scFv, to generate a CAR.

Alternatively to using an antigen binding domain derived from an antibody, a CAR extracellular domain can comprise a ligand or extracellular ligand binding domain of a receptor (see Sadelain et al., *Cancer Discov.* 3:388-398 (2013); Sharpe et al., *Dis. Model Mech.* 8:337-350 (2015)). In this case, the ligand or extracellular ligand binding domain of a receptor provides to the CAR the ability to target the cell expressing the CAR to the corresponding receptor or ligand. The ligand or extracellular ligand binding domain is selected such that the cell expressing the CAR is targeted to a desired site of action, such as a target tissue (see Sadelain et al., *Cancer Discov.* 3:388-398 (2013); Sharpe et al., *Dis. Model Mech.* 8:337-350 (2015), and references cited therein). In an embodiment of the invention, the ligand or extracellular ligand binding domain is selected to bind to an antigen that is the corresponding receptor or ligand (see Sadelain et al, *Cancer Discov.* 3:388-398 (2013)).

For a CAR directed to an antigen, the antigen binding domain of the CAR is selected to bind to an antigen expressed on a target cell or at the site of a pathologic immune response associated with an immune-mediated disorder. Such an antigen can be uniquely expressed on a target cell, or the antigen can be overexpressed in a target cell relative to non-target cells or tissues. The target antigen to be bound by the CAR is chosen to provide targeting of the cell expressing the CAR over non-target cells or tissues. In one embodiment of the methods of the invention for treating a disorder, an immunoinhibitory cell is designed to treat a patient by expressing in the cell a CAR that binds to a suitable antigen to target a desired site in the patient, along with a DN form, as described herein.

Any suitable target antigen can be chosen based on the type of disorder to be treated. It is understood that the selected target antigen is expressed in a manner such that the antigen is accessible for binding by the CAR. Generally, the antigen to be targeted by a cell expressing a CAR is expressed on the cell surface of a target cell or is an intracellular antigen that becomes available due to cell lysis at the site of a pathologic immune response associated with an immune-mediated disorder. It is understood that any target antigen that is accessible for binding to a CAR is suitable for targeting the CAR-expressing cell to a target cell or target site. Exemplary antigens that are targets of pathologic immune responses associated with immune-mediated disorders and exemplary disorders are provided below in Table 1.

TABLE 1

Immune-Mediated Disorders and Antigens that are Targets of Pathologic Immune Responses Associated with Immune-Mediated Disorders.

| Immune-Mediated Disorder | | Antigens that are Targets of Pathologic Immune Responses Associated with Immune-Mediated Disorders | Ref. |
|---|---|---|---|
| organ transplant | lung | MHC class I, II (HLA DR, HLA A2); collagen type V; K alpha1 tubulin (Kalpha1T; Kα1T); MHC class I related chain A (MICA) | 1, 2 |
| | kidney | MHC class I, II; fibronectin; collagen type IV, VI; vimentin; angiotensin II type 1 receptor (AGTR1); perlecan; agrin | |
| | liver | MHC class I, II; collagen type I, II, III, V | |
| | heart | MHC class I, II; cardiac myosin; vimentin; collagen type V; K alpha1 tubulin (Kalpha1T; Kα1T); MHC class I related chain A (MICA) | |
| | pancreas | MHC class I, II; islet cell autoantibody (ICA) antigens; insulin; glutamic acid decarboxylase (GAD) | |
| autoimmune disorders | multiple sclerosis | myelin; myelin basic protein; myelin oligodendrocyte glycoprotein; proteolipid protein; astrocyte proteins; glial fibrillary protein (GFAP); S100beta (S100β) | 3, 6, 9 |
| | type 1 diabetes | beta cell antigens; insulin B chain; insulin B chain derived epitope; glutamic acid decarboxylase-65 (GAD65); insulin; proinsulin; islet-associated antigen 2; preproinsulin; islet-specific glucose-6-phosphatase catalytic subunit-related protein (IGRP); zinc transporter 8 (ZnT8); islet antigen 2 (IA-2) (receptors on pancreatic B cells); heat shock protein 60 (HSP60); chromogranin A | 3, 5, 8, 9 |
| | rheumatoid arthritis | dnaJ (heat shock protein); citrullinated-vimentin; human cartilage glycoprotein-39 | 9 |
| | primary biliary cirrhosis | mitochondrial components; pyruvate dehydrogenase (mitochondrial); E2 component (subunit) of pyruvate dehydrogenase; E2 component (subunit) of branched chain 2-oxo acid dehydrogenase; E2 component (subunit) of 2-oxo-glutarate dehydrogenase complex; E3 binding protein of dihydrolipoamide dehydrogenase; nuclear components; nuclear protein sp100; nuclear pore complex protein gp120; centromere | 7 |
| | myasthenia gravis | acetylcholine receptor (AChR); aquaporin-4 (AQP-4); targets for therapy: CTLA-4; ICAM; LFA-3; CD40/CD154; ICOS/ICOSL; CD52; nuclear factor of activated T cells (NFAT); phospholipase C (PLC); | 3, 4 |

TABLE 1-continued

Immune-Mediated Disorders and Antigens that are Targets of Pathologic Immune Responses Associated with Immune-Mediated Disorders.

| Immune-Mediated Disorder | Antigens that are Targets of Pathologic Immune Responses Associated with Immune-Mediated Disorders | Ref. |
|---|---|---|
| | CD25; Janus kinase; B cell activating factor (BAFF); a proliferating inducing ligand (APRIL); IL6R; IL17; IL12/IL23; integrins; sphingosin receptors | |
| vitiligo | melanocyte antigens | 10 |
| lupus | Toll-like receptors: TLR2, TLR3, TLR4, TLR5, TLR7, TLR8, TLR9, MyD88, IL-1R-associated kinases (IRAKS) | 11 |
| allergic disorders | allergen | 8, 9 |

1. Angaswamy, et al., *Hum. Immunol.*, 74(11): 1478-1485 (2013)
2. Kuo, et al., *Immunol. Res.*, 32(1-3): 179-185 (2005)
3. Bluestone, et al., *J. Clin. Invest.*, 125(6): 2250-2260 (2015)
4. Dalakas, *Ther. Adv. Neurol. Disord.*, 8(6): 316-327 (2015)
5. Gomez-Tourino, et al., *J. Autoimmun.*, (Sep 3. pii: S0896-8411(15)30030-5. doi: 10.1016/j.jaut.2015.08.012): 1-10 (2015)
6. Huseby, et al., *Front. Cell. Neurosci.*, 9(295): 1-7 (2015)
7. Webb, et al., *J. Autoimmun.*, 64: 42-52 (2015)
8. Odegard, et al., *Clin. Immunol.*, 161(1): 44-50 (2015)
9. MacLeod, et al., *Curr. Opin. Pharmacol.*, 23: 11-16 (2015)
10. Dwivedi et al., *Autimmun. Rev.* 14: 49-56 (2015)
11. Wu et al., *Acta Pharmacologica Sinica* 36: 1395-1407 (2015)

Suitable antigens include, but are not limited to, those described in Table 1 or known in the art (see references 1-11 of Table 1 and, for example, Snir et al., *Arthritis Rheum.* 63:2873-2883 (2011); Yamagiwa et al., *World J. Gastroenterol.* 20:2606-2612 (2014); Mallone et al., *Clin. Develop. Immunol.* 2011:513210 (doi: 10.1155/2011/513210)(2011); Pihoker et al., *Diabetes* 54:Suppl 2:S52-61 (2005)). It is understood that these or other antigens that target a pathologic immune response associated with an immune-mediated disorder can be utilized for targeting an antigen with a CAR.

As described above, a CAR also contains a signaling domain that functions in the immunoinhibitory cell thereof expressing the CAR. Such a signaling domain can be, for example, derived from CDζ or Fc receptor γ (see Sadelain et al., *Cancer Discov.* 3:388-398 (2013)). In general, the signaling domain will induce persistence, trafficking and/or effector functions in the transduced immunoinhibitory cells of the invention (Sharpe et al., *Dis. Model Mech.* 8:337-350 (2015); Finney et al., *J. Immunol.* 161:2791-2797 (1998); Krause et al., *J. Exp. Med.* 188:619-626 (1998)). In the case of CDζ or Fc receptor γ, the signaling domain corresponds to the intracellular domain of the respective polypeptides, or a fragment of the intracellular domain that is sufficient for signaling. Exemplary signaling domains are described below in more detail.

Exemplary polypeptides are described herein with reference to GenBank numbers, GI numbers and/or SEQ ID NOS. It is understood that one skilled in the art can readily identify homologous sequences by reference to sequence sources, including but not limited to GenBank (ncbi.nlm.nih.gov/genbank/) and EMBL (embl.org/).

CD3ζ.

In a non-limiting embodiment, a CAR can comprise a signaling domain derived from a CD3ζ polypeptide, for example, a signaling domain derived from the intracellular domain of CD3ζ, which can activate or stimulate an immunoinhibitory cell of the invention. CD3ζ comprises 3 Immune-receptor-Tyrosine-based-Activation-Motifs (ITAMs), and transmits an activation signal to the cell, for example, a cell of the lymphoid lineage such as a T cell, after antigen is bound. A CD3ζ polypeptide can have an amino acid sequence corresponding to the sequence having GenBank No. NP_932170 (NP_932170.1, GI:37595565; see below), or fragments thereof. In one embodiment, the CD3ζ polypeptide has an amino acid sequence of amino acids 52 to 164 of the CD3ζ polypeptide sequence provided below, or a fragment thereof that is sufficient for signaling activity. An exemplary CAR is Mz, which has an intracellular domain comprising a CD3ζ polypeptide comprising amino acids 52 to 164 of the CD3ζ polypeptide sequence provided below. Another exemplary CAR is M28z, which has an intracellular domain comprising a CD3ζ polypeptide comprising amino acids 52 to 164 of the CD3ζ polypeptide provided below. Still another exemplary CAR is MBBz, which has an intracellular domain comprising a CD3ζ polypeptide comprising amino acids 52 to 164 of the CD3ζ polypeptide provided below. Yet another exemplary CAR is P28z, which has an intracellular domain derived from a CD3ζ polypeptide. See GenBank NP_932170 for reference to domains within CD3, for example, signal peptide, amino acids 1 to 21; extracellular domain, amino acids 22 to 30; transmembrane domain, amino acids 31 to 51; intracellular domain, amino acids 52 to 164.

```
                                            (NP_932170; SEQ ID NO: 1)
  1 MKWKALFTAA ILQAQLPITE AQSFGLLDPK LCYLLDGILF IYGVILTALF LRVKFSRSAD

61 APAYQQGQNQ LYNELNLGRR EEYDVLDKRR GRDPEMGGKP QRRKNPQEGL YNELQKDKMA

121 EAYSEIGMKG ERRRGKGHDG LYQGLSTATK DTYDALHMQA LPPR
```

It is understood that a "CD3ζ nucleic acid molecule" refers to a polynucleotide encoding a CD3ζ polypeptide. In one embodiment, the CD3ζ nucleic acid molecule encoding the CD3ζ polypeptide comprised in the intracellular domain of a CAR, including exemplary CARs Mz, M28z, or MBBz, comprises a nucleotide sequence as set forth below.

(SEQ ID NO: 2)
AGAGTGAAGTTCAGCAGGAGCGCAGACGCCCCCGCGTACCAGCAGGGCC

AGAACCAGCTCTATAACGAGCTCAATCTAGGACGAAGAGAGGAGTACGA

TGTTTTGGACAAGAGACGTGGCCGGGACCCTGAGATGGGGGAAAGCCG

AGAAGGAAGAACCCTCAGGAAGGCCTGTACAATGAACTGCAGAAAGATA

AGATGGCGGAGGCCTACAGTGAGATTGGGATGAAAGGCGAGCGCCGGAG

GGGCAAGGGGCACGATGGCCTTTACCAGGGTCTCAGTACAGCCACCAAG

GACACCTACGACGCCCTTCACATGCAGGCCCTGCCCCCTCGCTAA

In certain non-limiting embodiments, an intracellular domain of a CAR can further comprise at least one co-stimulatory signaling domain. Such a co-stimulatory signaling domain can provide increased activation of an immunoinhibitory cell. A co-stimulatory signaling domain can be derived from a CD28 polypeptide, a 4-1BB polypeptide, an OX40 polypeptide, an ICOS polypeptide, a DAP10 polypeptide, a 2B4 polypeptide, and the like. CARs comprising an intracellular domain that comprises a co-stimulatory signaling region comprising 4-1BB, ICOS or DAP-10 have been described previously (see U.S. Pat. No. 7,446,190, which is incorporated herein by reference, which also describes representative sequences for 4-1BB, ICOS and DAP-10). In some embodiments, the intracellular domain of a CAR can comprise a co-stimulatory signaling region that comprises two co-stimulatory molecules, such as CD28 and 4-1BB (see Sadelain et al., Cancer Discov. 3(4):388-398 (2013)), or CD28 and OX40, or other combinations of co-stimulatory ligands, as disclosed herein.

CD28.

Cluster of Differentiation 28 (CD28) is a protein expressed on T cells that provides co-stimulatory signals for T cell activation and survival. CD28 is the receptor for CD80 (B7.1) and CD86 (B7.2) proteins. In one embodiment, a CAR can comprise a co-stimulatory signaling domain derived from CD28. For example, as disclosed herein, a CAR can include at least a portion of an intracellular/cytoplasmic domain of CD28, for example an intracellular/cytoplasmic domain that can function as a co-stimulatory signaling domain (see FIG. 1B). A CD28 polypeptide can have an amino acid sequence corresponding to the sequence having GenBank No. P10747 (P10747.1, GI:115973) or NP_006130 (NP_006130.1, GI:5453611), as provided below, or fragments thereof. If desired, CD28 sequences additional to the intracellular domain can be included in a CAR of the invention. For example, a CAR can comprise the transmembrane of a CD28 polypeptide. In one embodiment, a CAR can have an amino acid sequence comprising the intracellular domain of CD28 corresponding to amino acids 180 to 220 of CD28, or a fragment thereof. In another embodiment, a CAR can have an amino acid sequence comprising the transmembrane domain of CD28 corresponding to amino acids 153 to 179, or a fragment thereof. M28z is an exemplary CAR, which comprises a co-stimulatory signaling domain corresponding to an intracellular domain of CD28 (see FIG. 1B). M28z also comprises a transmembrane domain derived from CD28 (see FIG. 1B). Thus, M28z exemplifies a CAR that comprises two domains from CD28, a co-stimulatory signaling domain and a transmembrane domain. In one embodiment, a CAR has an amino acid sequence comprising the transmembrane domain and the intracellular domain of CD28 and comprises amino acids 153 to 220 of CD28. In another embodiment, a CAR is exemplified by M28z CAR and comprises amino acids 117 to 220 of CD28. Another exemplary CAR having a transmembrane domain and intracellular domain of CD28 is P28z (see FIG. 1B). In one embodiment, a CAR can comprise a transmembrane domain derived from a CD28 polypeptide comprising amino acids 153 to 179 of the CD28 polypeptide provided below. See GenBank NP_006130 for reference to domains within CD28, for example, signal peptide, amino acids 1 to 18; extracellular domain, amino acids 19 to 152; transmembrane domain, amino acids 153 to 179; intracellular domain, amino acids 180 to 220. It is understood that sequences of CD28 that are shorter or longer than a specific delineated domain can be included in a CAR, if desired.

(NP_006130; SEQ ID NO: 3)
```
  1 MLRLLLALNL FPSIQVTGNK ILVKQSPMLV AYDNAVNLSC KYSYNLFSRE FRASLHKGLD

61 SAVEVCVVYG NYSQQLQVYS KTGFNCDGKL GNESVTFYLQ NLYVNQTDIY FCKIEVMYPP

121 PYLDNEKSNG TIIHVKGKHL CPSPLFPGPS KPFWVLVVVG GVLACYSLLV TVAFIIFWVR

181 SKRSRLLHSD YMNMTPRRPG PTRKHYQPYA PPRDFAAYRS
```

It is understood that a "CD28 nucleic acid molecule" refers to a polynucleotide encoding a CD28 polypeptide. In one embodiment, the CD28 nucleic acid molecule encoding the CD28 polypeptide of M28z comprising the transmembrane domain and the intracellular domain, for example, the co-stimulatory signaling region, comprises a nucleotide sequence as set forth below.

(SEQ ID NO: 4)
ATTGAAGTTATGTATCCTCCTCCTTACCTAGACAATGAGAAGAGCAATG

GAACCATTATCCATGTGAAAGGGAAACACCTTTGTCCAAGTCCCCTATT

TCCCGGACCTTCTAAGCCCTTTTGGGTGCTGGTGGTGGTTGGTGGAGTC

CTGGCTTGCTATAGCTTGCTAGTAACAGTGGCCTTTATTATTTTCTGGG

TGAGGAGTAAGAGGAGCAGGCTCCTGCACAGTGACTACATGAACATGAC

TCCCCGCCGCCCCGGGCCCACCCGCAAGCATTACCAGCCCTATGCCCCA

CCACGCGACTTCGCAGCCTATCGCTCC 4-1BB.

4-1BB, also referred to as tumor necrosis factor receptor superfamily member 9, can act as a tumor necrosis factor (TNF) ligand and have stimulatory activity. In one embodiment, a CAR can comprise a co-stimulatory signaling domain derived from 4-1BB. A 4-1BB polypeptide can have an amino acid sequence corresponding to the sequence having GenBank No. P41273 (P41273.1, GI:728739) or NP_001552 (NP_001552.2, GI:5730095) or fragments thereof. In one embodiment, a CAR can have a co-stimulatory domain comprising the intracellular domain of 4-1BB corresponding to amino acids 214 to 255, or a fragment thereof. In another embodiment, a CAR can have a transmembrane domain of 4-1BB corresponding to amino acids 187 to 213, or a fragment thereof. An exemplary CAR is MBBz, which has an intracellular domain comprising a 4-1BB polypeptide (for example, amino acids 214 to 255 of NP_001552, SEQ ID NO:5) (see FIG. 1B). See GenBank NP_001552 for reference to domains within 4-1BB, for example, signal peptide, amino acids 1 to 17; extracellular domain, amino acids 18 to 186; transmembrane domain, amino acids 187 to 213; intracellular domain, amino acids 214 to 255. It is understood that sequences of 4-1BB that are shorter or longer than a specific delineated domain can be included in a CAR, if desired. It is also understood that a "4-1BB nucleic acid molecule" refers to a polynucleotide encoding a 4-1BB polypeptide.

(NP_001552; SEQ ID NO: 5)

```
  1 MGNSCYNIVA TLLLVLNFER TRSLQDPCSN CPAGTFCDNN RNQICSPCPP NSFSSAGGQR

61 TCDICRQCKG VFRTRKECSS TSNAECDCTP GFHCLGAGCS MCEQDCKQGQ ELTKKGCKDC

121 CFGTFNDQKR GICRPWTNCS LDGKSVLVNG TKERDVVCGP SPADLSPGAS SVTPPAPARE

181 PGHSPQIISF FLALTSTALL FLLFFLTLRF SVVKRGRKKL LYIFKQPFMR PVQTTQEEDG

241 CSCRFPEEEE GGCEL
```

OX40.

OX40, also referred to as tumor necrosis factor receptor superfamily member 4 precursor or CD134, is a member of the TNFR-superfamily of receptors. In one embodiment, a CAR can comprise a co-stimulatory signaling domain derived from OX40. An OX40 polypeptide can have an amino acid sequence corresponding to the sequence having GenBank No. P43489 (P43489.1, GI:1171933) or NP_003318 (NP_003318.1, GI:4507579), provided below, or fragments thereof. In one embodiment, a CAR can have a co-stimulatory domain comprising the intracellular domain of OX40 corresponding to amino acids 236 to 277, or a fragment thereof. In another embodiment, a CAR can have an amino acid sequence comprising the transmembrane domain of OX40 corresponding to amino acids 215 to 235 of OX40, or a fragment thereof. See GenBank NP_003318 for reference to domains within OX40, for example, signal peptide, amino acids 1 to 28; extracellular domain, amino acids 29 to 214; transmembrane domain, amino acids 215 to 235; intracellular domain, amino acids 236 to 277. It is understood that sequences of OX40 that are shorter or longer than a specific delineated domain can be included in a CAR, if desired. It is also understood that an "OX40 nucleic acid molecule" refers to a polynucleotide encoding an OX40 polypeptide.

(NP_003318; SEQ ID NO: 6)

```
  1 MCVGARRLGR GPCAALLLLG LGLSTVTGLH CVGDTYPSND RCCHECRPGN GMVSRCSRSQ

61 NTVCRPCGPG FYNDVVSSKP CKPCTWCNLR SGSERKQLCT ATQDTVCRCR AGTQPLDSYK

121 PGVDCAPCPP GHFSPGDNQA CKPWTNCTLA GKHTLQPASN SSDAICEDRD PPATQPQETQ

181 GPPARPITVQ PTEAWPRTSQ GPSTRPVEVP GGRAVAAILG LGLVLGLLGP LAILLALYLL

241 RRDQRLPPDA HKPPGGGSFR TPIQEEQADA HSTLAKI
```

ICOS.

Inducible T-cell costimulator precursor (ICOS), also referred to as CD278, is a CD28-superfamily costimulatory molecule that is expressed on activated T cells. In one embodiment, a CAR can comprise a co-stimulatory signaling domain derived from ICOS. An ICOS polypeptide can have an amino acid sequence corresponding to the sequence having GenBank No. NP_036224 (NP_036224.1, GI:15029518), provided below, or fragments thereof. In one embodiment, a CAR can have a co-stimulatory domain comprising the intracellular domain of ICOS corresponding to amino acids 162 to 199 of ICOS. In another embodiment, a CAR can have an amino acid sequence comprising the transmembrane domain of ICOS corresponding to amino acids 141 to 161 of ICOS, or a fragment thereof. See GenBank NP_036224 for reference to domains within ICOS, for example, signal peptide, amino acids 1 to 20; extracellular domain, amino acids 21 to 140; transmembrane domain, amino acids 141 to 161; intracellular domain, amino acids 162 to 199. It is understood that sequences of ICOS that are shorter or longer than a specific delineated domain can be included in a CAR, if desired. It is also understood that an "ICOS nucleic acid molecule" refers to a polynucleotide encoding an ICOS polypeptide.

the cell surface. It is understood that, once a polypeptide containing a signal peptide is expressed at the cell surface, the signal peptide has generally been proteolytically removed during processing of the polypeptide in the endoplasmic reticulum and translocation to the cell surface. Thus, a polypeptide such as a CAR is generally expressed at the cell surface as a mature protein lacking the signal peptide, whereas the precursor form of the polypeptide includes the signal peptide. A signal peptide or leader can be essential if a CAR is to be glycosylated and/or anchored in the cell membrane. The signal sequence or leader is a peptide sequence generally present at the N-terminus of newly synthesized proteins that directs their entry into the secretory pathway. The signal peptide is covalently joined to the N-terminus of the extracellular antigen-binding domain of a CAR as a fusion protein. In one embodiment, the signal peptide comprises a CD8 polypeptide comprising amino acids MALPVTALLLPLALLLHAARP (SEQ ID NO:9). It is understood that use of a CD8 signal peptide is exemplary. Any suitable signal peptide, as are well known in the art, can be applied to a CAR to provide cell surface expression in an immunoinhibitory cell (see Gierasch *Biochem.* 28:923-930 (1989); von Heijne, *J. Mol. Biol.* 184 (1):99-105 (1985)). Particularly useful signal peptides can be derived from cell

```
                                                    (NP_036224; SEQ ID NO: 7)
  1 MKSGLWYFFL FCLRIKVLTG EINGSANYEM FIFHNGGVQI LCKYPDIVQQ FKMQLLKGGQ

61 ILCDLTKTKG SGNTVSIKSL KFCHSQLSNN SVSFFLYNLD HSHANYYFCN LSIFDPPPFK

121 VTLTGGYLHI YESQLCCQLK FWLPIGCAAF VVVCILGCIL ICWLTKKKYS SSVHDPNGEY

181 MFMRAVNTAK KSRLTDVTL
```

DAP10.

DAP10, also referred to as hematopoietic cell signal transducer, is a signaling subunit that associates with a large family of receptors in hematopoietic cells. In one embodiment, a CAR can comprise a co-stimulatory domain derived from DAP10. A DAP10 polypeptide can have an amino acid sequence corresponding to the sequence having GenBank No. NP_055081.1 (GI:15826850), provided below, or fragments thereof. In one embodiment, a CAR can have a co-stimulatory domain comprising the intracellular domain of DAP10 corresponding to amino acids 70 to 93, or a fragment thereof. In another embodiment, a CAR can have a transmembrane domain of DAP10 corresponding to amino acids 49 to 69, or a fragment thereof. See GenBank NP_055081.1 for reference to domains within DAP10, for example, signal peptide, amino acids 1 to 19; extracellular domain, amino acids 20 to 48; transmembrane domain, amino acids 49 to 69; intracellular domain, amino acids 70 to 93. It is understood that sequences of DAP10 that are shorter or longer than a specific delineated domain can be included in a CAR, if desired. It is also understood that a "DAP10 nucleic acid molecule" refers to a polynucleotide encoding an DAP10 polypeptide.

surface proteins naturally expressed in the immunoinhibitory cell, including any of the signal peptides of the polypeptides disclosed herein. Thus, any suitable signal peptide can be utilized to direct a CAR to be expressed at the cell surface of an immunoinhibitory cell.

In certain non-limiting embodiments, an extracellular antigen-binding domain of a CAR can comprise a linker sequence or peptide linker connecting the heavy chain variable region and light chain variable region of the extracellular antigen-binding domain. In one non-limiting example, the linker comprises amino acids having the sequence set forth in GGGGSGGGGSGGGGS (SEQ ID NO:10).

In certain non-limiting embodiments, a CAR can also comprise a spacer region or sequence that links the domains of the CAR to each other. For example, a spacer can be included between a signal peptide and an antigen binding domain, between the antigen binding domain and the transmembrane domain, between the transmembrane domain and the intracellular domain, and/or between domains within the intracellular domain, for example, between a stimulatory domain and a co-stimulatory domain. The spacer region can be flexible enough to allow interactions of various domains

```
                                                 (NP_055081.1; SEQ ID NO: 8)
 1 MIHLGHILFL LLLPVAAAQT TPGERSSLPA FYPGTSGSCS GCGSLSLPLL AGLVAADAVA

61 SLLIVGAVFL CARPRRSPAQ EDGKVYINMP GRG
```

The extracellular domain of a CAR can be fused to a leader or a signal peptide that directs the nascent protein into the endoplasmic reticulum and subsequent translocation to with other polypeptides, for example, to allow the antigen binding domain to have flexibility in orientation in order to facilitate antigen recognition. The spacer region can be, for example, the hinge region from an IgG, the CH₂CH₃ (constant) region of an immunoglobulin, and/or portions of CD3 (cluster of differentiation 3) or some other sequence suitable as a spacer.

The transmembrane domain of a CAR generally comprises a hydrophobic alpha helix that spans at least a portion of the membrane. Different transmembrane domains result in different receptor stability. After antigen recognition, receptors cluster and a signal is transmitted to the cell. In an embodiment, the transmembrane domain of a CAR can be derived from another polypeptide that is naturally expressed in the immunoinhibitory cell. In one embodiment, a CAR can have a transmembrane domain derived from CD8, CD28, CD3ζ, CD4, 4-1BB, OX40, ICOS, CTLA-4, PD-1, LAG-3, 2B4, BTLA, or other polypeptides expressed in the immunoinhibitory cell having a transmembrane domain, including others as disclosed herein. Optionally, the transmembrane domain can be derived from a polypeptide that is not naturally expressed in the immunoinhibitory cell, so long as the transmembrane domain can function in transducing signal from antigen bound to the CAR to the intracellular signaling and/or co-stimulatory domains. It is understood that the portion of the polypeptide that comprises a transmembrane domain of the polypeptide can include additional sequences from the polypeptide, for example, additional sequences adjacent on the N-terminal or C-terminal end of the transmembrane domain, or other regions of the polypeptide, as desired.

CD8.

Cluster of differentiation 8 (CD8) is a transmembrane glycoprotein that serves as a co-receptor for the T cell receptor (TCR). CD8 binds to a major histocompatibility complex (MHC) molecule and is specific for the class I MHC protein. In one embodiment, a CAR can comprise a transmembrane domain derived from CD8. A CD8 polypeptide can have an amino acid sequence corresponding to the sequence having GenBank No. NP_001139345.1 (GI: 225007536), as provided below, or fragments thereof. In one embodiment, a CAR can have an amino acid sequence comprising the transmembrane domain of CD8 corresponding to amino acids 183 to 203, or fragments thereof. In one embodiment, an exemplary CAR is Mz, which has a transmembrane domain derived from a CD8 polypeptide (see FIG. 1B). In another embodiment, an exemplary CAR is MBBz, which has a transmembrane domain derived from a CD8 polypeptide (see FIG. 1B). In one non-limiting embodiment, a CAR can comprise a transmembrane domain derived from a CD8 polypeptide comprising amino acids 183 to 203. In addition, a CAR can comprise a hinge domain comprising amino acids 137-182 of the CD8 polypeptide provided below. In another embodiment, a CAR can comprise amino acids 137-203 of the CD8 polypeptide provided below. In yet another embodiment, a CAR can comprise amino acids 137 to 209 of the CD8 polypeptide provided below. See GenBank NP_001139345.1 for reference to domains within CD8, for example, signal peptide, amino acids 1 to 21; extracellular domain, amino acids 22 to 182; transmembrane domain amino acids, 183 to 203; intracellular domain, amino acids 204 to 235. It is understood that additional sequence of CD8 beyond the transmembrane domain of amino acids 183 to 203 can be included in a CAR, if desired. It is further understood that sequences of CD8 that are shorter or longer than a specific dilineated domain can be included in a CAR, if desired. It also is understood that a "CD8 nucleic acid molecule" refers to a polynucleotide encoding a CD8 polypeptide.

```
                                    (NP_001139345.1; SEQ ID NO: 11)
  1 MALPVTALLL PLALLLHAAR PSQFRVSPLD RTWNLGETVE LKCQVLLSNP TSGCSWLFQP

61 RGAAASPTFL LYLSQNKPKA AEGLDTQRFS GKRLGDTFVL TLSDFRRENE GYYFCSALSN

121 SIMYFSHFVP VFLPAKPTTT PAPRPPTPAP TIASQPLSLR PEACRPAAGG AVHTRGLDFA

181 CDIYIWAPLA GTCGVLLLSL VITLYCNHRN RRRVCKCPRP VVKSGDKPSL SARYV
```

CD4.

Cluster of differentiation 4 (CD4), also referred to as T-cell surface glycoprotein CD4, is a glycoprotein found on the surface of immune cells such as T helper cells, monocytes, macrophages, and dendritic cells. In one embodiment, a CAR can comprise a transmembrane domain derived from CD4. CD4 exists in various isoforms. It is understood that any isoform can be selected to achieve a desired function. Exemplary isoforms include isoform 1 (NP_000607.1, GI:10835167), isoform 2 (NP_001181943.1, GI:303522479), isoform 3 (NP_001181944.1, GI:303522485; or NP_001181945.1, GI:303522491; or NP_001181946.1, GI:303522569), and the like. One exemplary isoform sequence, isoform 1, is provided below. In one embodiment, a CAR can have an amino acid sequence comprising the transmembrane domain of CD4 corresponding to amino acids 397 to 418, or fragments thereof. See GenBank NP_000607.1 for reference to domains within CD4, for example, signal peptide, amino acids 1 to 25; extracellular domain, amino acids 26 to 396; transmembrane domain amino acids, 397 to 418; intracellular domain, amino acids 419 to 458. It is understood that additional sequence of CD4 beyond the transmembrane domain of amino acids 397 to 418 can be included in a CAR, if desired. It is further understood that sequences of CD4 that are shorter or longer than a specific dilineated domain can be included in a CAR, if desired. It also is understood that a "CD4 nucleic acid molecule" refers to a polynucleotide encoding a CD4 polypeptide.

```
                                    (NP_000607.1; SEQ ID NO: 12)
  1 MNRGVPFRHL LLVLQLALLP AATQGKKVVL GKKGDTVELT CTASQKKSIQ FHWKNSNQIK

61 ILGNQGSFLT KGPSKLNDRA DSRRSLWDQG NFPLIIKNLK IEDSDTYICE VEDQKEEVQL

121 LVFGLTANSD THLLQGQSLT LTLESPPGSS PSVQCRSPRG KNIQGGKTLS VSQLELQDSG
```

```
-continued
181 TWTCTVLQNQ KKVEFKIDIV VLAFQKASSI VYKKEGEQVE FSFPLAFTVE KLTGSGELWW

241 QAERASSSKS WITFDLKNKE VSVKRVTQDP KLQMGKKLPL HLTLPQALPQ YAGSGNLTLA

301 LEAKTGKLHQ EVNLVVMRAT QLQKNLTCEV WGPTSPKLML SLKLENKEAK VSKREKAVWV

361 LNPEAGMWQC LLSDSGQVLL ESNIKVLPTW STPVQPMALI VLGGVAGLLL FIGLGIFFCV

421 RCRHRRRQAE RMSQIKRLLS EKKTCQCPHR FQKTCSPI
```

As disclosed herein, mesothelin CARs exemplify CARs that can target an antigen, and CARs directed to other antigens can be generated using similar methods and others well known in the art, as described above. It is understood that domains of the polypeptides described herein can be used in a CAR, as useful to provide a desired function such as a signal peptide, antigen binding domain, transmembrane domain, intracellular signaling domain and/or co-stimulatory domain. For example, a domain can be selected such as a signal peptide, a transmembrane domain, an intracellular signaling domain, or other domain, as desired, to provide a particular function to a CAR of the invention. Possible desirable functions can include, but are not limited to, providing a signal peptide and/or transmembrane domain.

6.3. Dominant Negative Forms of an Inhibitor of a Cell-Mediated Immune Response

According to the invention, an immunoinhibitory cell is engineered to express a dominant negative form (DN form) of an inhibitor of a cell-mediated immune response. It has been shown that PD-1 activation inhibits the suppressor function of regulatory T cells (Amaranth et al., Sci. Transl. Med. 3(111) (111ra120. doi: 10.1126/scitranslmed.3003130) (2011)). A DN form of an inhibitor of a cell-mediated immune response, such as PD-1 or another inhibitor disclosed herein, can be transduced into immunoinhibitory cells, such as regulatory T cells or other immunoinhibitory cells, as disclosed herein, to potentiate antigen-specific or non-specific immune inhibitory responses. The cells transduced with a DN form of an inhibitor of a cell-mediated immune response, such as PD-1, can have enhanced immunosuppressive effects that can benefit patients with a number of immune-mediated disorders, as described herein. Such immune-mediated disorders are described herein and include, but are not limited to, organ transplant rejection, an autoimmune disorder, multiple sclerosis, type 1 diabetes, arthritis, including rheumatoid arthritis or other forms of arthritis, primary biliary cirrhosis, myasthenia gravis, vitiligo, lupus, an allergic disorder, fetomaternal intolerance, and Alzheimer's disease. The immunoinhibitory cells of the invention expressing a DN form of an inhibitor of a cell-mediated immune response can be readily translated to the clinic. Without being bound by a particular mechanism or theory, the immunoinhibitory cells of the invention can be administered to a patient having an immune-mediated disorder without adding toxicity since the DN form simply binds (consumes) a negative signal induced by the ligand corresponding to the inhibitor molecule (e.g., PD-L1 in the case of PD-1) and avoids downstream signaling.

An inhibitor of a cell-mediated immune response of the immunoinhibitory cell refers to a molecule that acts to inhibit or suppress the immune response effected by the immunoinhibitory cell. In one embodiment, the inhibitor of a cell-mediated immune response is an immune checkpoint inhibitor, also referred to as a checkpoint blockade.

In one embodiment, the invention provides immunoinhibitory cells that co-express a CAR and a dominant negative form of an inhibitor of a cell-mediated immune response of the immunoinhibitory cell, for example, a receptor that functions in an immune checkpoint inhibitor pathway. Immune checkpoint pathways are inhibitory pathways that suppress the immune response of an immunoinhibitory cell. The pathways deliver negative signals to the immunoinhibitory cells and attenuate TCR-mediated signals, leading to decreased cell proliferation, cytokine production and cell cycle progression (see Pardoll, Nat. Rev. 12:252-264 (2012); Wu et al., Int. J. Biol. Sci. 8:1420-1430 (2012)). The immune checkpoint inhibitor pathway generally involves a ligand-receptor pair. Exemplary immune checkpoint inhibitor pathway receptors include, for example, PD-1, CTLA-4, BTLA, TIM-3, LAG-3, CD160, TIGIT, LAIR1, 2B4, and the like (see Chen et al., Nat. Rev. Immunol. 13(4):227-242 (2013)). The corresponding ligands for these receptors include, for example, PD-L1 (for PD-1); PD-L2 (for PD-1); CD80, CD86 (for CTLA-4); HVEM (for BTLA); Galectin-9, HMGB1 (for TIM-3); MHC II (for LAG-3); HVEM (for CD160); CD155, CD112, CD113 (for TIGIT); C1q, collagen (for LAIR1); CD48 (for 2B4), and the like (Chen et al., supra, 2013). Expression of a DN form in the immunoinhibitory cell provides for inhibition of a checkpoint inhibitor pathway that is intrinsic to the cell.

A DN form of an inhibitor of a cell-mediated immune response that is a cell-surface receptor such as an immune checkpoint inhibitor pathway receptor can be generated by deleting some portion of the receptor to prevent intracellular signaling, thereby suppressing the immune checkpoint pathway and sustaining activation of the immunoinhibitory cell. In a specific embodiment, a DN form of the invention is a polypeptide comprising (a) at least a portion of an extracellular domain of an immune checkpoint inhibitor, where the portion comprises the ligand binding region, and (b) a transmembrane domain, where the polypeptide is a dominant negative form of the immune checkpoint inhibitor. Generally, a DN form of an inhibitor of an immune checkpoint inhibitor pathway receptor retains most or all of an extracellular domain of the receptor such that the extracellular domain retains sufficient protein interaction activity to bind to its respective ligand. Thus, in a specific embodiment, a polypeptide encoding a DN form comprises substantially all of an extracellular domain of an immune checkpoint inhibitor. It is understood that a polypeptide comprising "substantially all" of an extracellular domain includes a polypeptide that comprises the entire extracellular domain or a portion of the extracellular domain in which one to a few amino acids have been deleted from the N-terminus and/or C-terminus of the extracellular domain, for example deletion of 1, 2, 3, 4, or 5 amino acids from the N-terminus and/or C-terminus, so long as the remaining portion of the extracellular domain retains sufficient protein interaction activity to bind to its respective ligand. A DN form of the invention generally also lacks some portion or all of a signaling domain, such as the intracellular/cytoplasmic domain, such that the DN form has reduced activity or is inactive for signaling in the immune checkpoint pathway. Without being bound by a particular mechanism or theory, binding of the ligand to the DN form decreases binding of the ligand to the intact endogenous receptor, and/or the DN form complexes with signaling molecules, including the endogenous receptor, resulting in decreased signaling of an immune checkpoint pathway.

A DN form of the invention generally has certain functional characteristics including, but not limited to, the ability to be expressed at the cell surface of an immunoinhibitory cell, the ability to bind to its respective ligand, and the inability or reduced ability to propagate an intracellular signal of an immune checkpoint pathway. One skilled in the art can readily generate a DN form of an inhibitor of a cell-mediated immune response by engineering the inhibitor to have such functional characteristics. In one embodiment, a DN form is constructed to retain the extracellular domain of inhibitor of a cell-mediated immune response, or at least a sufficient portion of the extracellular domain to retain ligand binding activity. In an exemplary embodiment, a DN form can be constructed using the extracellular domain of an inhibitor of a cell-mediated immune response, including, but not limited to, the extracellular domains of PD-1, CTLA-4, BTLA, TIM-3, LAG-3, CD160, TIGIT, LAIR1, 2B4, as disclosed herein. One skilled in the art will readily understand that it is not required to retain the entire extracellular domain of an inhibitor of a cell-mediated immune response, and that deletions from the N-terminus and/or C-terminus of the extracellular domain can be introduced so long as ligand binding activity is retained. One skilled in the art can readily determine the appropriateness of such N-terminal and/or C-terminal deletions based on the analysis of the receptor sequence to identify protein motifs known to provide ligand binding activity (see, for example, ExPASy (expasy.org), in particular PROSITE (prosite.expasy.org)). In addition or alternatively, suitable N-terminal and/or C-terminal deletions can be determined empirically by introducing deletions in a polypeptide and measuring binding activity for the respective ligand. Thus, one skilled in the art can readily determine an appropriate sequence of an inhibitor of a cell-mediated immune response to provide ligand binding activity to a DN form of the invention.

It is understood that, whether an entire extracellular domain or a portion of the extracellular domain of a receptor is used in a DN form, additional sequences can optionally be included in the extracellular domain of the DN form. Such additional sequences can be derived from the parent polypeptide of the DN form, or the additional sequences can be derived from a different polypeptide. Such a polypeptide comprising sequences from a parent polypeptide and a different polypeptide is a non-naturally occurring, chimeric polypeptide. For example, a signal peptide or leader peptide is generally included so that the DN form will be expressed at the cell surface of the immunoinhibitory cell. It is understood that, once a polypeptide containing a signal peptide is expressed at the cell surface, the signal peptide has generally been proteolytically removed during processing of the polypeptide in the endoplasmic reticulum and translocation to the cell surface. Thus, a polypeptide such as a DN form is generally expressed at the cell surface as a mature protein lacking the signal peptide, whereas the precursor form of the polypeptide includes the signal peptide. The signal peptide can be the naturally occurring signal peptide of the receptor, or alternatively can be derived from a different protein. Exemplary signal peptides are described herein, including those described herein as being suitable for a CAR. To additionally provide expression at the cell surface, the DN form will generally include a transmembrane domain that provides for retention of the DN form at the cell surface. The transmembrane domain can be the naturally occurring transmembrane of the receptor, or alternatively can be derived from a different protein. In a particular embodiment, the transmembrane domain derived from another protein is derived from another receptor expressed on the cell surface of the immunoinhibitory cell. Exemplary transmembrane domains are described herein, including those described herein as being suitable for a CAR.

In the case of an immune checkpoint pathway receptor, generally the signaling domain resides within the intracellular/cytoplasmic domain. The signaling activity of an immune checkpoint pathway receptor is generally mediated by protein-protein interactions with cell surface receptor(s) and/or intracellular signaling molecules. In one embodiment, a DN form lacks the entire intracellular domain, or a portion thereof, that functions in propagating the signal of an immune checkpoint pathway. It is understood that it is not necessary to delete the entire intracellular domain of the receptor so long as a sufficient portion of the intracellular signaling domain is deleted to inhibit or reduce signaling from the DN form. In addition or alternatively, mutations can be introduced into the intracellular signaling domain to inhibit or reduce signaling from the DN form. In addition or alternatively, a heterologous sequence with no signaling activity can be substituted for the intracellular signaling domain of the receptor to generate a DN form. One skilled in the art will readily understand that these and other well known methods can be utilized to generate a DN form of the invention.

One exemplary embodiment of a dominant negative form of an immune checkpoint inhibitor is a dominant negative form of PD-1. A dominant negative form of PD-1 is exemplary of a DN form of an inhibitor of a cell-mediated immune response, including an immune checkpoint inhibitor. It is understood that a PD-1 DN form as disclosed herein is exemplary.

As described herein, a DN form of an inhibitor of a cell-mediated immune response is designed to have reduced or inhibited intracellular signaling. The DN forms of the invention are generally based on inhibiting a receptor of an immune checkpoint pathway, which function to inhibit activation of an immunoinhibitory cell, for example, cell proliferation, cytokine production and/or cell cycle progression, in particular the immunosuppressive function of an immunoinhibitory cell of the invention. The DN forms of the invention are designed to remove the intracellular signaling domain, or a portion thereof, so that the signaling ability of the receptor is reduced or inhibited. The DN form also functions to inhibit signaling of the endogenous receptor. In a particular embodiment, the reduced or inhibited signaling overcomes the checkpoint blockade, resulting in sustained signaling and activation of the immunoinhibitory cell. It is understood that the signaling activity of the DN form can be completely knocked out or partially knocked out, so long as the partial reduction in activity is sufficient for the effect of providing enhanced activation of the immunoinhibitory cell in comparison to the absence of the DN form. Also, the DN form is not required to result in complete inactivation of signaling from the endogenous receptor but can reduce the activation of the endogenous receptor sufficient to overcome the checkpoint blockade and allow activation of the immunoinhibitory cell. One skilled in the art can readily determine the effect of a DN form on the activity of a parent receptor using assay methods well known in the art, including assays using in vivo models, such as animal models, to assess the effect of the DN form on the effectiveness of CAR expressing cells.

As with a CAR for use in the invention, optional linker or spacer sequences can be included in a DN form, for example, a linker or spacer between a signal peptide and the extracellular ligand binding domain, particularly when heterologous sequences are fused. A linker or spacer can also optionally be included between the extracellular ligand binding domain and the transmembrane domain. Similarly, a linker or spacer can optionally be included between the transmembrane domain and any remaining intracellular domain. Such optional linkers or spacers are described herein. In addition, such linkers or spacers can be derived from a heterologous sequence. For example, as described above, a transmembrane domain derived from a heterologous polypeptide can optionally include additional sequences at the N-terminus and/or C-terminus derived from the heterologous polypeptide. Such additional sequences can function as a linker or spacer.

In one embodiment, a dominant negative form of the invention can optionally further comprise a fusion to a co-stimulatory signaling domain, wherein the co-stimulatory signaling domain is carboxy-terminal to the transmembrane domain of the dominant negative form. Such a DN form is also referred to herein as a "switch receptor." Such a DN form, or switch receptor, comprises at least a ligand binding domain of the extracellular region of an inhibitor of a cell-mediated immune response of the cell, such as an immune checkpoint inhibitor, fused to a transmembrane domain, fused to a co-stimulatory domain (i.e., cytoplasmic signaling domain) of an immunostimulatory molecule, thereby switching the activity upon ligand binding from inhibitory of the cell immune activity to stimulatory of the cell immune activity (see e.g., Liu et al., *Cancer Res.* 76:1578-1590 (2016)). A DN form further comprising a fusion to a co-stimulatory domain (i.e., switch receptor) also functions as a dominant negative form in such a construct since the signaling domain of the immune checkpoint inhibitor has been deleted. In one embodiment, a DN form further comprising a fusion to a co-stimulatory signaling domain is expressed in an immunoinhibitory cell. In another embodiment, a DN form further comprising a fusion to a co-stimulatory signaling domain is co-expressed with a CAR in an immunoinhibitory cell.

A co-stimulatory signaling domain in a DN form fusion polypeptide can be derived, for example, from a cytoplasmic signaling domain of a receptor such as the co-stimulatory molecules described herein for use in a CAR, including but not limited to a 4-1BB polypeptide, a CD28 polypeptide, an OX40 polypeptide, an ICOS polypeptide, a DAP10 polypeptide, and a 2B4 polypeptide. In a DN form comprising a fusion to a co-stimulatory signaling domain, the transmembrane domain can be derived from the polypeptide from which the co-stimulatory domain is derived, from the polypeptide from which the extracellular ligand binding domain of DN form is derived, or it can be a transmembrane domain from another polypeptide, similar to the description herein of the transmembrane domains that can be utilized to generate a CAR or DN form.

In one embodiment, the invention provides an immunoinhibitory cell that recombinantly expresses a DN form, wherein the DN form further comprises a fusion to a co-stimulatory signaling domain, wherein the co-stimulatory signaling domain is fused carboxy-terminal to the transmembrane domain of the DN form. In certain embodiments of the invention, the cell or population of the invention recombinantly expresses a dominant negative form of an inhibitor of a cell-mediated immune response of the cell, wherein the dominant negative form further comprises a co-stimulatory signaling domain, wherein the co-stimulatory signaling domain is fused to the transmembrane domain of the dominant negative form (which in turn is fused to the at least a portion of the extracellular domain of an immune checkpoint inhibitor containing the ligand binding region of the dominant negative form). Such cells can be used to treat an immune-mediated disorder as disclosed herein. The invention provides for recombinant expression by an immunoinhibitory cell of a switch receptor (i.e., a DN form further comprising a co-stimulatory signaling domain), which switch receptor comprises (i) at least the extracellular ligand binding domain of an immune checkpoint inhibitor, (ii) a transmembrane domain, and (iii) a co-stimulatory signaling domain. The invention also provides for recombinant expression by an immunoinhibitory cell of both a CAR and a DN form further comprising a fusion to a co-stimulatory signaling domain (switch receptor), which comprises (i) at least the extracellular ligand binding domain of an immune checkpoint inhibitor, (ii) a transmembrane domain, and (iii) a co-stimulatory signaling domain. It is understood that, in such immunoinhibitory cells co-expressing a CAR and a DN form further comprising a fusion to a co-stimulatory signaling domain (switch receptor), the CAR binds to an antigen of the same disease or disorder as being treated. In one embodiment of cells co-expressing a CAR and a DN form comprising a fusion to a co-stimulatory signaling domain, the co-stimulatory signaling domain of the DN form is different from the co-stimulatory signaling domain of the CAR. In a particular embodiment, the co-stimulatory signaling domain of the DN form is the intracellular signaling domain of 4-1BB. In another particular embodiment, in an immunoinhibitory cell co-expressing a CAR and a DN form that further comprises a fusion to a co-stimulatory signaling domain, the co-stimulatory signaling domain of the CAR is the intracellular signaling domain of CD28. In another particular embodiment, the invention provides an immunoinhibitory cell co-expressing a CAR and a DN form that further comprises a fusion to a co-stimulatory signaling domain and a CAR, where the co-stimulatory signaling domain of the DN form is the intracellular signaling domain of 4-1BB and the co-stimulatory signaling domain of the CAR is the intracellular signaling domain of CD28.

Exemplary DN forms of immune checkpoint inhibitors are described below in more detail. DN forms consisting essentially of the described sequences are also envisioned.

PD-1.

Programmed cell death protein 1 (PD-1) is a negative immune regulator of activated T cells upon engagement with its corresponding ligands, PD-L1 and PD-L2, expressed on endogenous macrophages and dendritic cells. PD-1 is a type I membrane protein of 268 amino acids. PD-1 has two ligands, PD-L1 and PD-L2, which are members of the B7 family. The protein's structure comprises an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif. PD-1 negatively regulates TCR signals. SHP-1 and SHP-2 phosphatases bind to the cytoplasmic tail of PD-1 upon ligand binding. Upregulation of PD-L1 is one mechanism tumor cells use to evade the host immune system. In pre-clinical and clinical trials, PD-1 blockade by antagonistic antibodies induced anti-tumor responses mediated through the host endogenous immune system.

A PD-1 polypeptide can have an amino acid corresponding to GenBank No. NP_005009.2 (GI:167857792), as provided below, or fragments thereof. See GenBank NP_005009.2 for reference to domains within PD-1, for example, signal peptide, amino acids 1 to 20; extracellular domain, amino acids 21 to 170; transmembrane domain, amino acids 171 to 191; intracellular domain, amino acids 192 to 288. It is understood that an "PD-1 nucleic acid molecule" refers to a polynucleotide encoding an PD-1 polypeptide.

```
                                                       (NP_005009.2; SEQ ID NO: 13)
  1 MQIPQAPWPV VWAVLQLGWR PGWFLDSPDR PWNPPTFSPA LLVVTEGDNA TFTCSFSNTS

61 ESFVLNWYRM SPSNQTDKLA AFPEDRSQPG QDCRFRVTQL PNGRDFHMSV VRARRNDSGT

121 YLCGAISLAP KAQIKESLRA ELRVTERRAE VPTAHPSPSP RPAGQFQTLV VGVVGGLLGS

181 LVLLVWVLAV ICSRAARGTI GARRTGQPLK EDPSAVPVFS VDYGELDFQW REKTPEPPVP

241 CVPEQTEYAT IVFPSGMGTS SPARRGSADG PRSAQPLRPE DGHCSWPL
```

In one embodiment, the invention provides an inhibitor of a cell-mediated immune response that is a PD-1 dominant negative form (DN form). In one embodiment, the PD-1 DN form comprises the extracellular ligand binding domain of PD-1. In one embodiment, the PD-1 DN form comprises the extracellular ligand binding domain of PD-1 and a transmembrane domain (e.g., mature form). In another embodiment, the PD-1 DN form comprises the extracellular ligand binding domain of PD-1, a transmembrane domain and a signal peptide (e.g., precursor form). The invention also provides encoding polypeptides and nucleic acids of the PD-1 DN forms of the invention. In a particular embodiment, the PD-1 extracellular ligand binding domain is fused to one or more heterologous polypeptide sequences, that is, the PD-1 DN form is a chimeric sequence. For example, the PD-1 extracellular ligand binding domain can be fused at its N-terminus to a signal peptide that is optionally a heterologous signal peptide, including various signal peptides described herein. In addition, a PD-1 DN form can comprise a transmembrane domain that is optionally a heterologous transmembrane domain, including any of various transmembrane domains described herein. Although the PD-1 DN form exemplified in the Example herein comprises heterologous sequences fused to the extracellular domain of PD-1, it is understood that a PD-1 DN form can comprise PD-1 sequence only.

In one embodiment, the invention provides a PD-1 DN form that comprises the extracellular domain, or a ligand binding portion thereof, of PD-1, for example, amino acids 21 to 170 corresponding to the extracellular domain of PD-1 (GenBank NP_005009.2; SEQ ID NO:13). A cell expressing such a PD-1 DN form should lack the ability or have reduced ability to signal in a PD-1 immune checkpoint pathway. In one embodiment, a PD-1 DN form is a deletion mutant having a deletion of the intracellular domain, for example, amino acids 192 to 288 of PD-1 (GenBank NP_005009.2; SEQ ID NO:13), or a portion thereof, such that intracellular signaling of the immune checkpoint pathway mediated by PD-1 is reduced or inhibited. Additional embodiments of a DN form of PD-1 are described below.

In one embodiment, a PD-1 DN form comprises an amino acid sequence comprising the extracellular domain of PD-1 fused to the transmembrane and hinge domains of CD8. In one embodiment, a PD-1 DN form comprises amino acids 21 to 165 of a PD-1 sequence (NP_005009.2; SEQ ID NO:13). Such a PD-1 DN form comprises the extracellular domain of PD-1. In another embodiment, the invention provides a PD-1 DN form comprising amino acids 1 to 165 (precursor form) or amino acids 21 to 165 (mature form) of a PD-1 sequence (NP_005009.2; SEQ ID NO:13). Such a DN form comprises the signal peptide of PD-1, amino acids 1 to 20, and extracellular domain amino acids 21 to 165, whereas the mature form lacks the signal peptide. In one embodiment, a PD-1 DN form comprises amino acids 21 to 151 of a PD-1 sequence (NP_005009.2; SEQ ID NO:13). In another embodiment, the invention provides a PD-1 DN form comprising amino acids 1 to 151 (precursor form) or amino acids 21 to 151 (mature form) of a PD-1 sequence (NP_005009.2; SEQ ID NO:13). Optionally, a PD-1 DN form comprises an extracellular ligand binding domain starting at amino acid 21 through an amino acid between amino acids 151 to 165 of a PD-1 sequence (NP_005009.2; SEQ ID NO:13). In another embodiment, a PD-1 DN form comprises the transmembrane domain of CD8, amino acids 183 to 203 of a CD8 sequence (NP_001139345.1; SEQ ID NO:11). Such an embodiment is representative of a chimeric DN form comprising a transmembrane domain from a different (heterologous) polypeptide. As described above, a DN form comprising a heterologous domain such as a transmembrane domain can optionally include additional sequence from the heterologous polypeptide. In one such embodiment, a DN form is provided that comprises additional sequence from the heterologous polypeptide N-terminal of the transmembrane domain. In one embodiment, the DN form comprises the hinge domain of CD8. In a particular embodiment, the heterologous sequence comprises additional N-terminal sequence of amino acids 137 to 182, or optionally starting at amino acids 138 or 139, of a CD8 sequence (NP_001139345.1; SEQ ID NO:11). In another embodiment, a DN form is provided that comprises additional sequence from the heterologous polypeptide C-terminal of the transmembrane domain. In a particular embodiment, the heterologous sequence comprises additional C-terminal sequence from amino acids 204 to 209 of a CD8 sequence (NP_001139345.1; SEQ ID NO:11). In one embodiment, the PD-1 DN form comprises the transmembrane domain of CD8, amino acids 183 to 203, optionally a hinge domain comprising amino acids 137 to 182 (or optionally starting at amino acids 138 or 139), and/or additional C-terminal sequence comprising amino acids 204 to 209. In a particular embodiment of the invention, a PD-1 DN form is provided that comprises amino acids 1 to 165 of a PD-1 sequence (NP_005009.2; SEQ ID NO:13), and amino acids 137 to 209, optionally starting at amino acids 138 or 139, of a CD8 sequence (NP_001139345.1; SEQ ID NO:11).

In a further particular embodiment, the invention provides a PD-1 DN form comprising the sequence provided below, where the underlined sequence is derived from PD-1 and the italicized sequence is derived from CD8.

(SEQ ID NO: 14)
MQIPQAPWPVVWAVLQLGWRPGWFLDSPDRPWNPPTFSPALLVVTEGDNA
TFTCSFSNTSESFVLNWYRMSPSNQTDKLAAFPEDRSQPGQDCRFRVTQL
PNGRDFHMSVVRARRNDSGTYLCGAISLAPKAQIKESLRAELRVTERRAE
VPTAHPSPSPRPAGQAAAPTTTPAPRPPTPAPTIASQPLSLRPEACRPAA
GGAVHTRGLDFACDIYIWAPLAGTCGVLLLSLVITLYCNHRRIQ

In an additional embodiment, a DN form of the invention optionally comprises a P2A sequence, which provides for optional co-expression of a reporter molecule. P2A is a self-cleaving peptide sequence, which can be used for bicistronic or multicistronic expression of protein sequences (see Szymczak et al., *Expert Opin. Biol. Therapy* 5(5):627-638 (2005)). An exemplary P2A sequence is GSGATNFSLLKQAGDVEENPGPM (SEQ ID NO:15). In a further embodiment, a DN form of the invention is co-expressed with a reporter protein. In a particular embodiment, the reporter protein is mCherry fluorescent protein. In a particular embodiment, the mCherry polypeptide sequence is as provided below. It is understood that mCherry is merely exemplary and that any desired reporter molecule, such as a fluorescent protein can be included as a reporter, as described herein.

(SEQ ID NO: 16)
MVSKGEEDNMAIIKEFMRFKVHMEGSVNGHEFEIEGEGEGRPYEGTQTAK
LKVTKGGPLPFAWDILSPQFMYGSKAYVKHPADIPDYLKLSFPEGFKWER
VMNFEDGGVVTVTQDSSLQDGEFIYKVKLRGTNFPSDGPVMQKKTMGWEA
SSERMYPEDGALKGEIKQRLKLKDGGHYDAEVKTTYKAKKPVQLPGAYNV
NIKLDITSHNEDYTIVEQYERAEGRHSTGGMDELYK

In a further particular embodiment, a PD-1 DN form is expressed as a polypeptide construct as provided below, where the underlined sequence is derived from PD-1, the italicized sequence is derived from CD8, the P2A sequence is double underlined, and the mCherry sequence is underlined and italicized.

(SEQ ID NO: 17)
MQIPQAPWPVVWAVLQLGWRPGWFLDSPDRPWNPPTFSPALLVVTEGDNA
TFTCSFSNTSESFVLNWYRMSPSNQTDKLAAFPEDRSQPGQDCRFRVTQL
PNGRDFHMSVVRARRNDSGTYLCGAISLAPKAQIKESLRAELRVTERRAE
VPTAHPSPSPRPAGQAAAPTTTPAPRPPTPAPTIASQPLSLRPEACRPAA
GGAVHTRGLDFACDIYIWAPLAGTCGVLLLSLVITLYCNHRRIQGSGATN
FSLLKQAGDVEENPGPMVSKGEEDNMAIIKEFMRFKVHMEGSVNGHEFEI
EGEGEGRPYEGTQTAKLKVTKGGPLPFAWDILSPQFMYGSKAYVKHPADI
PDYLKLSFPEGFKWERVMNFEDGGVVTVTQDSSLQDGEFIYKVKLRGTNF
PSDGPVMQKKTMGWEASSERMYPEDGALKGEIKQRLKLKDGGHYDAEVKT
TYKAKKPVQLPGAYNVNIKLDITSHNEDYTIVEQYERAEGRHSTGGMDEL
YK

In a particular embodiment, a nucleic acid encoding a PD-1 DNR form construct is provided below, where the underlined sequence encodes amino acids derived from PD-1 DN, the italicized sequence encodes amino acids derived from CD8, the P2A encoding sequence is double underlined, the mCherry encoding sequence is underlined and italicized, a Kozak sequence is bolded with a dashed underline, and restriction sites Age I and Xho I are underlined with a dotted line at the 5' and 3' ends, respectively.

(SEQ ID NO: 18)
ACCGGTGGTACCTCACCCTTACCGAGTCGGCGACACAGTGTGGGTCCGCCGACACC
AGACTAAGAACCTAGAACCTCGCTGGAAAGGACCTTACACAGTCCTGCTGACCACC
CCCACCGCCCTCAAAGTAGACGGCATCGCAGCTTGGATACACGCCGCCCACGTGAA
GGCTGCCGACCCCGGGGGTGGACCATCCTCTAGACTGGCCACCATGCAGATCCCAC
AGGCGCCCTGGCCAGTCGTCTGGGCGGTGCTACAACTGGGCTGGCGGCCAGGATGG
TTCTTAGACTCCCCAGACAGGCCCTGGAACCCCCCACCTTCTCCCCAGCCCTGCTC
GTGGTGACCGAAGGGGACAACGCCACCTTCACCTGCAGCTTCTCCAACACATCGGA
GAGCTTCGTGCTAAACTGGTACCGCATGAGCCCCAGCAACCAGACGGACAAGCTGG
CCGCTTTCCCGAGGACCGCAGCCAGCCCGGCCAGGACTGCCGCTTCCGTGTCACAC
AACTGCCCAACGGGCGTGACTTCCACATGAGCGTGGTCAGGGCCCGGCGCAATGAC
AGCGGCACCTACCTCTGTGGGGCCATCTCCCTGGCCCCCAAGGCGCAGATCAAAGA
GAGCCTGCGGGCAGAGCTCAGGGTGACAGAGAGAAGGGCAGAAGTGCCCACAGCC
CACCCCAGCCCCTCACCCAGGCCAGCCGGCCAGGCGGCCGCACCCACCACGACGCCA
*GCGCCGCGACCACCAACCCCGGCGCCCACGATCGCGTCGCAGCCCCTGTCCCTGCGCC*
*CAGAGGCGTGCCGGCCAGCGGCGGGGGGCGCAGTGCACACGAGGGGGCTGGACTTCG*
*CCTGTGATATCTACATCTGGGCGCCCCTGGCCGGGACTTGTGGGGTCCTTCTCCTGTCAC*

```
-continued
TGGTTATCACCCTTTACTGCAACCACAGGCGGATCCAAGGATCTGGAGCAACAAACTT

CTCACTACTCAAACAAGCAGGTGACGTGGAGGAGAATCCCGGCCCCATGGTGAGCAA

GGGCGAGGAGGATAACATGGCCATCATCAAGGAGTTCATGCGCTTCAAGGTGCACATGGA

GGGCTCCGTGAACGGCCACGAGTTCGAGATCGAGGGCGAGGGCGAGGGCCGCCCCTAC

GAGGGCACCCAGACCGCCAAGCTGAAGGTGACCAAGGGTGGCCCCCTGCCCTTCGCCT

GGGACATCCTGTCCCCTCAGTTCATGTACGGCTCCAAGGCCTACGTGAAGCACCCCGCC

GACATCCCCGACTACTTGAAGCTGTCCTTCCCCGAGGGCTTCAAGTGGGAGCGCGTGATG

AACTTCGAGGACGGCGGCGTGGTGACCGTGACCCAGGACTCCTCCCTGCAGGACGGCG

AGTTCATCTACAAGGTGAAGCTGCGCGGCACCAACTTCCCCTCCGACGGCCCCGTAATGC

AGAAGAAGACCATGGGCTGGGAGGCCTCCTCCGAGCGGATGTACCCCGAGGACGGCGC

CCTGAAGGGCGAGATCAAGCAGAGGCTGAAGCTGAAGGACGGCGGCCACTACGACGCT

GAGGTCAAGACCACCTACAAGGCCAAGAAGCCCGTGCAGCTGCCCGGCGCCTACAACGT

CAACATCAAGTTGGACATCACCTCCCACAACGAGGACTACACCATCGTGGAACAGTACGA

ACGCGCCGAGGGCCGCCACTCCACCGGCGGCATGGACGAGCTGTACAAGTAACTCGAG
```

CTLA-4.

Cytotoxic T-lymphocyte-associated protein 4 (CTLA-4) is an inhibitory receptor expressed by activated T cells, which when engaged by its corresponding ligands (CD80 and CD86; B7-1 and B7-2, respectively), mediates activated T cell inhibition or anergy. In both preclinical and clinical studies, CTLA-4 blockade by systemic antibody infusion enhanced the endogenous anti-tumor response albeit, in the clinical setting, with significant unforeseen toxicities. CTLA-4 contains an extracellular V domain, a transmembrane domain, and a cytoplasmic tail. Alternate splice variants, encoding different isoforms, have been characterized. The membrane-bound isoform functions as a homodimer interconnected by a disulfide bond, while the soluble isoform functions as a monomer. The intracellular domain is similar to that of CD28, in that it has no intrinsic catalytic activity and contains one YVKM (SEQ ID NO:29) motif able to bind PI3K, PP2A and SHP-2 and one proline-rich motif able to bind SH3 containing proteins. One role of CTLA-4 in inhibiting T cell responses seems to be directly via SHP-2 and PP2A dephosphorylation of TCR-proximal signaling proteins such as CD3 and LAT. CTLA-4 can also affect signaling indirectly via competing with CD28 for CD80/86 binding. CTLA-4 has also been shown to bind and/or interact with PI3K, CD80, AP2M1, and PPP2R5A.

A CTLA-4 polypeptide can have an amino acid sequence corresponding to GenBank No. AAH69566.1 (GI: 46854814) or NP_005205.2 (GI:21361212), sequence as provided below, or fragments thereof. See GenBank NP_005205.2 for reference to domains within CTLA-4, for example, signal peptide, amino acids 1 to 35; extracellular domain, amino acids 36 to 161; transmembrane domain, amino acids 162 to 182; intracellular domain, amino acids 183 to 223. It is understood that a "CTLA-4 nucleic acid molecule" refers to a polynucleotide encoding a CTLA-4 polypeptide.

(NP_005205.2; SEQ ID NO: 19)
```
  1 MACLGFQRHK AQLNLATRTW PCTLLFFLLF IPVFCKAMHV AQPAVVLASS RGIASFVCEY

61 ASPGKATEVR VTVLRQADSQ VTEVCAATYM MGNELTFLDD SICTGTSSGN QVNLTIQGLR

121 AMDTGLYICK VELMYPPPYY LGIGNGTQIY VIDPEPCPDS DFLLWILAAV SSGLFFYSFL

181 LTAVSLSKML KKRSPLTTGV YVKMPPTEPE CEKQFQPYFI PIN
```

In one embodiment, the invention provides a CTLA-4 DN form. In one embodiment, the CTLA-4 DN form comprises the extracellular ligand binding domain of CTLA-4. In one embodiment, the CTLA-4 DN form comprises the extracellular ligand binding domain of CTLA-4 and a transmembrane domain (e.g., mature form). In another embodiment, the CTLA-4 DN form comprises the extracellular ligand binding domain of CTLA-4, a transmembrane domain and a signal peptide (e.g., precursor form). The invention also provides encoding polypeptides and nucleic acids of the CTLA-4 DN forms of the invention. In a particular embodiment, the CTLA-4 extracellular ligand binding domain is fused to one or more heterologous polypeptide sequences, that is, the CTLA-4 DN form is chimeric. For example, the CTLA-4 extracellular ligand binding domain can be fused at its N-terminus to a signal peptide that is optionally a heterologous signal peptide, including various signal peptides described herein. In addition, a CTLA-4 DN form can comprise a transmembrane domain that is optionally a heterologous transmembrane domain, including any of various transmembrane domains described herein.

In an embodiment of the invention, the CTLA-4 DN form can comprise the extracellular domain, or a ligand binding portion thereof, of CTLA-4, for example, amino acids 36 to 161 corresponding to the extracellular domain of CTLA-4

(GenBank NP_005205.2; SEQ ID NO:19). A cell expressing such a CTLA-4 DN form should lack the ability or have reduced ability to signal in a CTLA-4 immune checkpoint pathway. In one embodiment, a CTLA-4 DN form is a deletion mutant having a deletion of the intracellular domain, for example, amino acids 183 to 223 of CTLA-4 (GenBank NP_005205.2; SEQ ID NO:19), or a portion thereof, such that intracellular signaling of the immune checkpoint pathway mediated by CTLA-4 is reduced or inhibited.

BTLA.

B- and T-lymphocyte attenuator (BTLA) expression is induced during activation of T cells, and BTLA remains expressed on Th1 cells but not Th2 cells. BTLA interacts with a B7 homolog, B7H4. BTLA displays T-Cell inhibition via interaction with tumor necrosis family receptors (TNF-R), not just the B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses. BTLA activation has been shown to inhibit the function of human CD8$^+$ cancer-specific T cells. BTLA has also been designated as CD272 (cluster of differentiation 272).

A BTLA polypeptide can have an amino acid sequence corresponding homologous to GenBank No. AAP44003.1 (GI:31880027) or NP_861445.3 (GI:145580621), sequence provided below, or fragments thereof. See GenBank NP_861445.3 for reference to domains within BTLA, for example, signal peptide, amino acids 1 to 30; extracellular domain, amino acids 31 to 157; transmembrane domain, amino acids 158 to 178; intracellular domain, amino acids 179 to 289. It is understood that a "BTLA nucleic acid molecule" refers to a polynucleotide encoding a BTLA polypeptide.

BTLA extracellular ligand binding domain is fused to one or more heterologous polypeptide sequences, that is, the BTLA DN form is chimeric. For example, the BTLA extracellular ligand binding domain can be fused at its N-terminus to a signal peptide that is optionally a heterologous signal peptide, including various signal peptides described herein. In addition, a BTLA DN form can comprise a transmembrane domain that is optionally a heterologous transmembrane domain, including any of various transmembrane domains described herein.

In an embodiment of the invention, the BTLA DN form can comprise the extracellular domain, or a ligand binding portion thereof, of BTLA, for example, amino acids 31 to 157 corresponding to the extracellular domain of BTLA (GenBank NP_861445.3; SEQ ID NO:20). A cell expressing such a BTLA DN form should lack the ability or have reduced ability to signal in a BTLA immune checkpoint pathway. In one embodiment, a BTLA DN form is a deletion mutant having a deletion of the intracellular domain, for example, amino acids 179 to 289 of BTLA (GenBank NP_861445.3; SEQ ID NO:20), or a portion thereof, such that intracellular signaling of the immune checkpoint pathway mediated by BTLA is reduced or inhibited.

TIM-3.

T cell immunoglobulin mucin-3 (TIM-3), also referred to as hepatitis A virus cellular receptor 2 precursor, is a Th1-specific cell surface protein that regulates macrophage activation. Tim-3 was first identified as a molecule selectively expressed on IFN-γ-producing CD4+T helper 1 (Th1) and CD8+T cytotoxic 1 (Tc1) T cells. TIM-3 possess an N-terminal Ig domain of the V type, followed by a mucin domain.

```
                                            (NP_861445.3; SEQ ID NO: 20)
  1 MKTLPAMLGT GKLFWVFFLI PYLDIWNIHG KESCDVQLYI KRQSEHSILA GDPFELECPV

61 KYCANRPHVT WCKLNGTTCV KLEDRQTSWK EEKNISFFIL HFEPVLPNDN GSYRCSANFQ

121 SNLIESHSTT LYVTDVKSAS ERPSKDEMAS RPWLLYSLLP LGGLPLLITT CFCLFCCLRR

181 HQGKQNELSD TAGREINLVD AHLKSEQTEA STRQNSQVLL SETGIYDNDP DLCFRMQEGS

241 EVYSNPCLEE NKPGIVYASL NHSVIGPNSR LARNVKEAPT EYASICVRS
```

In one embodiment, the invention provides a BTLA DN form. In one embodiment, the BTLA DN form comprises the extracellular ligand binding domain of BTLA. In one embodiment, the BTLA DN form comprises the extracellular ligand binding domain of BTLA and a transmembrane domain (e.g., mature form). In another embodiment, the BTLA DN form comprises the extracellular ligand binding domain of BTLA, a transmembrane domain and a signal peptide (e.g., precursor form). The invention also provides encoding polypeptides and nucleic acids of the BTLA DN forms of the invention. In a particular embodiment, the A TIM-3 polypeptide can have an amino acid sequence corresponding to GenBank No. NP_116171.3 (GI: 49574534), sequence provided below, or fragments thereof. See GenBank NP_116171.3 for reference to domains within TIM-3, for example, signal peptide, amino acids 1 to 21; extracellular domain, amino acids 22 to 202; transmembrane domain, amino acids 203 to 223; intracellular domain, amino acids 224 to 301. It is understood that a "TIM-3 nucleic acid molecule" refers to a polynucleotide encoding a TIM-3 polypeptide.

```
                                            (NP_116171.3; SEQ ID NO: 21)
  1 MFSHLPFDCV LLLLLLLLTR SSEVEYRAEV GQNAYLPCFY TPAAPGNLVP VCWGKGACPV

61 FECGNVVLRT DERDVNYWTS RYWLNGDFRK GDVSLTIENV TLADSGIYCC RIQIPGIMND

121 EKFNLKLVIK PAKVTPAPTR QRDFTAAFPR MLTTRGHGPA ETQTLGSLPD INLTQISTLA

181 NELRDSRLAN DLRDSGATIR IGIYIGAGIC AGLALALIFG ALIFKWYSHS KEKIQNLSLI

241 SLANLPPSGL ANAVAEGIRS EENIYTIEEN VYEVEEPNEY YCYVSSRQQP SQPLGCRFAM

301 P
```

In one embodiment, the invention provides a TIM-3 DN form. In one embodiment, the TIM-3 DN form comprises the extracellular ligand binding domain of TIM-3. In one embodiment, the TIM-3 DN form comprises the extracellular ligand binding domain of TIM-3 and a transmembrane domain (e.g., mature form). In another embodiment, the TIM-3 DN form comprises the extracellular ligand binding domain of TIM-3, a transmembrane domain and a signal peptide (e.g., precursor form). The invention also provides encoding polypeptides and nucleic acids of the TIM-3 DN forms of the invention. In a particular embodiment, the TIM-3 extracellular ligand binding domain is fused to one or more heterologous polypeptide sequences, that is, the TIM-3 DN form is chimeric. For example, the TIM-3 extracellular ligand binding domain can be fused at its N-terminus to a signal peptide that is optionally a heterologous signal peptide, including various signal peptides described herein. In addition, a TIM-3 DN form can comprise a transmembrane domain that is optionally a heterologous transmembrane domain, including any of various transmembrane domains described herein.

In an embodiment of the invention, the TIM-3 DN form can comprise the extracellular domain, or a ligand binding portion thereof, of TIM-3, for example, amino acids 22 to 202 corresponding to the extracellular domain of TIM-3 (GenBank NP_116171.3; SEQ ID NO:21). A cell expressing such a TIM-3 DN form should lack the ability or have reduced ability to signal in a TIM-3 immune checkpoint pathway. In one embodiment, a TIM-3 DN form is a deletion mutant having a deletion of the intracellular domain, for example, amino acids 224 to 301 of TIM-3 (GenBank NP_116171.3; SEQ ID NO:21), or a portion thereof, such that intracellular signaling of the immune checkpoint pathway mediated by TIM-3 is reduced or inhibited.

LAG-3.

Lymphocyte-activation protein 3 (LAG-3) is a negative immune regulator of immune cells. LAG-3 belongs to the immunoglobulin (Ig) superfamily and contains 4 extracellular Ig-like domains. The LAG3 gene contains 8 exons. The sequence data, exon/intron organization, and chromosomal localization all indicate a close relationship of LAG-3 to CD4. LAG-3 has also been designated CD223 (cluster of differentiation 223).

A LAG-3 polypeptide can have an amino acid sequence corresponding to GenBank No. CAA36243.3 (GI: 15617341) or NP_002277.4 (GI:167614500), sequence provided below, or fragments thereof. See GenBank NP_002277.4 for reference to domains within LAG-3, for example, signal peptide, amino acids 1 to 22; extracellular domain, amino acids 23 to 450; transmembrane domain, amino acids 451 to 471; intracellular domain, amino acids 472 to 525. It is understood that a "LAG-3 nucleic acid molecule" refers to a polynucleotide encoding a LAG-3 polypeptide.

```
                                       (NP_002277.4; SEQ ID NO: 22)
  1 MWEAQFLGLL FLQPLWVAPV KPLQPGAEVP VVWAQEGAPA QLPCSPTIPL QDLSLLRRAG

61 VTWQHQPDSG PPAAAPGHPL APGPHPAAPS SWGPRPRRYT VLSVGPGGLR SGRLPLQPRV

121 QLDERGRQRG DFSLWLRPAR RADAGEYRAA VHLRDRALSC RLRLRLGQAS MTASPPGSLR

181 ASDWVILNCS FSRPDRPASV HWFRNRGQGR VPVRESPHHH LAESFLFLPQ VSPMDSGPWG

241 CILTYRDGFN VSIMYNLTVL GLEPPTPLTV YAGAGSRVGL PCRLPAGVGT RSFLTAKWTP

301 PGGGPDLLVT GDNGDFTLRL EDVSQAQAGT YTCHIHLQEQ QLNATVTLAI ITVTPKSFGS

361 PGSLGKLLCE VTPVSGQERF VWSSLDTPSQ RSFSGPWLEA QEAQLLSQPW QCQLYQGERL

421 LGAAVYFTEL SSPGAQRSGR APGALPAGHL LLFLILGVLS LLLLVTGAFG FHLWRRQWRP

481 RRFSALEQGI HPPQAQSKIE ELEQEPEPEP EPEPEPEPEP EPEQL
```

In one embodiment, the invention provides a LAG-3 DN form. In one embodiment, the LAG-3 DN form comprises the extracellular ligand binding domain of LAG-3. In one embodiment, the LAG-3 DN form comprises the extracellular ligand binding domain of LAG-3 and a transmembrane domain (e.g., mature form). In another embodiment, the LAG-3 DN form comprises the extracellular ligand binding domain of LAG-3, a transmembrane domain and a signal peptide (e.g., precursor form). The invention also provides encoding polypeptides and nucleic acids of the LAG-3 DN forms of the invention. In a particular embodiment, the LAG-3 extracellular ligand binding domain is fused to one or more heterologous polypeptide sequences, that is, the LAG-3 DN form is chimeric. For example, the LAG-3 extracellular ligand binding domain can be fused at its N-terminus to a signal peptide that is optionally a heterologous signal peptide, including various signal peptides described herein. In addition, a LAG-3 DN form can comprise a transmembrane domain that is optionally a heterologous transmembrane domain, including any of various transmembrane domains described herein.

In an embodiment of the invention, the LAG-3 DN form can comprise the extracellular domain, or a ligand binding portion thereof, of LAG-3, for example, amino acids 23 to 450 corresponding to the extracellular domain of LAG-3 (GenBank NP_002277.4; SEQ ID NO:22). A cell expressing such a LAG-3 DN form should lack the ability or have reduced ability to signal in a LAG-3 immune checkpoint pathway. In one embodiment, a LAG-3 DN form is a deletion mutant having a deletion of the intracellular domain, for example, amino acids 472 to 525 of LAG-3 (GenBank NP_002277.4; SEQ ID NO:22), or a portion thereof, such that intracellular signaling of the immune checkpoint pathway mediated by LAG-3 is reduced or inhibited.

TIGIT.

T-cell immunoreceptor with Ig and ITIM domains (TIGIT) is a cell surface protein that suppresses T-cell activation. It belongs to the poliovirus receptor (PVR) family of immunoglobulin (Ig) proteins that share 3 conserved sequence motifs in their N-terminal Ig domains. A TIGIT polypeptide can have an amino acid sequence corresponding to GenBank No. NP_776160.2 (GI:256600228), sequence provided below, or fragments thereof. See GenBank NP_776160.2 for reference to domains within TIGIT, for example, signal peptide, amino acids 1 to 21; extracellular domain, amino acids 22 to 141; transmembrane domain, amino acids 142 to 162; intracellular domain, amino acids 163 to 244. It is understood that a "TIGIT nucleic acid molecule" refers to a polynucleotide encoding a TIGIT polypeptide.

negative regulatory role on cytolytic function of natural killer (NK) cells, B-cells and T-cells. LAIR exists in various isoforms. It is understood that any isoform can be selected to achieve a desired function. Exemplary isoforms include isoform a (NP_002278.2, GI:612407859), isoform b (NP_068352.2, GI:612407861), isoform c (NP_001275952.2, GI:612407867), isoform e (NP_001275954.2, GI:612407869), isoform f

```
                                         (NP_776160.2; SEQ ID NO: 23)
  1 MRWCLLLIWA QGLRQAPLAS GMMTGTIETT GNISAEKGGS IILQCHLSST TAQVTQVNWE

61 QQDQLLAICN ADLGWHISPS FKDRVAPGPG LGLTLQSLTV NDTGEYFCIY HTYPDGTYTG

121 RIFLEVLESS VAEHGARFQI PLLGAMAATL VVICTAVIVV VALTRKKKAL RIHSVEGDLR

181 RKSAGQEEWS PSAPSPPGSC VQAEAAPAGL CGEQRGEDCA ELHDYFNVLS YRSLGNCSFF

241 TETG
```

In one embodiment, the invention provides a TIGIT DN form. In one embodiment, the TIGIT DN form comprises the extracellular ligand binding domain of TIGIT. In one embodiment, the TIGIT DN form comprises the extracellular ligand binding domain of TIGIT and a transmembrane domain (e.g., mature form). In another embodiment, the TIGIT DN form comprises the extracellular ligand binding domain of TIGIT, a transmembrane domain and a signal peptide (e.g., precursor form). The invention also provides encoding polypeptides and nucleic acids of the TIGIT DN forms of the invention. In a particular embodiment, the TIGIT extracellular ligand binding domain is fused to one or more heterologous polypeptide sequences, that is, the TIGIT DN form is chimeric. For example, the TIGIT extracellular ligand binding domain can be fused at its N-terminus to a signal peptide that is optionally a heterologous signal peptide, including various signal peptides described herein. In addition, a TIGIT DN form can comprise a transmembrane domain that is optionally a heterologous transmembrane domain, including any of various transmembrane domains described herein.

In an embodiment of the invention, the TIGIT DN form can comprise the extracellular domain, or a ligand binding portion thereof, of TIGIT, for example, amino acids 22 to 141 corresponding to the extracellular domain of TIGIT (GenBank NP_776160.2; SEQ ID NO:23). A cell expressing such a TIGIT DN form should lack the ability or have reduced ability to signal in a TIGIT immune checkpoint pathway. In one embodiment, a TIGIT DN form is a deletion mutant having a deletion of the intracellular domain, for example, amino acids 163 to 244 of TIGIT (GenBank NP_776160.2; SEQ ID NO:23), or a portion thereof, such that intracellular signaling of the immune checkpoint pathway mediated by TIGIT is reduced or inhibited.

LAIR1.

Leukocyte-associated immunoglobulin-like receptor 1 (LAIR1) is an inhibitory receptor that plays a constitutive (NP_001275955.2, GI:612407863), isoform g (NP_001275956.2, GI:612407865), and the like. One exemplary isoform sequence, isoform a, is provided below. In one embodiment, a LAIR1 polypeptide can have an amino acid sequence corresponding to NP_002278.2, sequence provided below, or fragments thereof. See GenBank NP_002278.2 for reference to domains within LAIR1, for example, signal peptide, amino acids 1 to 21; extracellular domain, amino acids 22 to 165; transmembrane domain, amino acids 166 to 186; intracellular domain, amino acids 187 to 287. It is understood that a "LAIR1 nucleic acid molecule" refers to a polynucleotide encoding a LAIR1 polypeptide.

```
                                         (NP_002278.2; SEQ ID NO: 24)
  1 MSPHPTALLG LVLCLAQTIH TQEEDLPRPS ISAEPGTVIP LGSHVTFVCR GPVGVQTFRL

61 ERDSRSTYND TEDVSQASPS ESEARFRIDS VREGNAGLYR CIYYKPPKWS EQSDYLELLV

121 KESSGGPDSP DTEPGSSAGP TQRPSDNSHN EHAPASQGLK AEHLYILIGV SVVFLFCLLL

181 LVLFCLHRQN QIKQGPPRSK DEEQKPQQRP DLAVDVLERT ADKATVNGLP EKDRETDTSA

241 LAAGSSQEVT YAQLDHWALT QRTARAVSPQ STKPMAESIT YAAVARH
```

In one embodiment, the invention provides a LAIR1 DN form. In one embodiment, the LAIR1 DN form comprises the extracellular ligand binding domain of LAIR1. In one embodiment, the LAIR1 DN form comprises the extracellular ligand binding domain of LAIR1 and a transmembrane domain (e.g., mature form). In another embodiment, the LAIR1 DN form comprises the extracellular ligand binding domain of LAIR1, a transmembrane domain and a signal peptide (e.g., precursor form). The invention also provides encoding polypeptides and nucleic acids of the LAIR1 DN forms of the invention. In a particular embodiment, the LAIR1 extracellular ligand binding domain is fused to one or more heterologous polypeptide sequences, that is, the LAIR1 DN form is chimeric. For example, the LAIR1 extracellular ligand binding domain can be fused at its N-terminus to a signal peptide that is optionally a heterologous signal peptide, including various signal peptides described herein. In addition, a LAIR1 DN form can comprise a transmembrane domain that is optionally a heterologous transmembrane domain, including any of various transmembrane domains described herein.

In an embodiment of the invention, the LAIR1 DN form can comprise the extracellular domain, or a ligand binding portion thereof, of LAIR1, for example, amino acids 22 to 165 corresponding to the extracellular domain of LAIR1 (GenBank NP_002278.2; SEQ ID NO:24). A cell expressing such a LAIR1 DN form should lack the ability or have reduced ability to signal in a LAIR1 immune checkpoint pathway. In one embodiment, a LAIR1 DN form is a deletion mutant having a deletion of the intracellular domain, for example, amino acids 187 to 287 of LAIR1 (GenBank NP_002278.2; SEQ ID NO:24), or a portion thereof, such that intracellular signaling of the immune checkpoint pathway mediated by LAIR1 is reduced or inhibited.

2B4.

Natural Killer Cell Receptor 2B4 (2B4) mediates non-MHC restricted cell killing on NK cells and subsets of T cells. The 2B4-S isoform is believed to be an activating receptor, and the 2B4-L isoform is believed to be a negative immune regulator of immune cells. 2B4 becomes engaged upon binding its high-affinity ligand, CD48. 2B4 contains a tyrosine-based switch motif, a molecular switch that allows the protein to associate with various phosphatases. 2B4 has also been designated CD244 (cluster of differentiation 244).

A 2B4 polypeptide can have an amino acid sequence corresponding to GenBank No. NP_001160135.1 (GI: 262263435), sequence provided below, or fragments thereof. See GenBank NP_001160135.1 for reference to domains within 2B4, for example, signal peptide, amino acids 1 to 18; extracellular domain, amino acids 19 to 229; transmembrane domain, amino acids 230 to 250; intracellular domain, amino acids 251 to 370. It is understood that a "2B4 nucleic acid molecule" refers to a polynucleotide encoding a 2B4 polypeptide.

and nucleic acids of the 2B4 DN forms of the invention. In a particular embodiment, the 2B4 extracellular ligand binding domain is fused to one or more heterologous polypeptide sequences, that is, the 2B4 DN form is chimeric. For example, the 2B4 extracellular ligand binding domain can be fused at its N-terminus to a signal peptide that is optionally a heterologous signal peptide, including various signal peptides described herein. In addition, a 2B4 DN form can comprise a transmembrane domain that is optionally a heterologous transmembrane domain, including any of various transmembrane domains described herein.

In an embodiment of the invention, the 2B4 DN form can comprise the extracellular domain, or a ligand binding portion thereof, of 2B4, for example, amino acids 19 to 229 corresponding to the extracellular domain of 2B4 (GenBank NP_001160135.1; SEQ ID NO:25). A cell expressing such a 2B4 DN form should lack the ability or have reduced ability to signal in a 2B4 immune checkpoint pathway. In one embodiment, a 2B4 DN form is a deletion mutant having a deletion of the intracellular domain, for example, amino acids 251 to 370 of 2B4 (GenBank NP_001160135.1; SEQ ID NO:25), or a portion thereof, such that intracellular signaling of the immune checkpoint pathway mediated by 2B4 is reduced or inhibited.

CD160.

CD160 is a glycosylphosphatidylinositol-anchored molecule containing a single IgV-like domain that binds to HVEM and functions as a co-inhibitory receptor on T cells. A CD160 polypeptide can have an amino acid sequence corresponding to GenBank NP_008984.1 (GI:5901910),

```
                                                           (NP_001160135.1; SEQ ID NO: 25)
  1 MLGQVVTLIL LLLLKVYQGK GCQGSADHVV SISGVPLQLQ PNSIQTKVDS IAWKKLLPSQ

61 NGFHHILKWE NGSLPSNTSN DRFSFIVKNL SLLIKAAQQQ DSGLYCLEVT SISGKVQTAT

121 FQVFVFESLL PDKVEKPRLQ GQGKILDRGR CQVALSCLVS RDGNVSYAWY RGSKLIQTAG

181 NLTYLDEEVD INGTHTYTCN VSNPVSWESH TLNLTQDCQN AHQEFRFWPF LVIIVILSAL

241 FLGTLACFCV WRRKRKEKQS ETSPKEFLTI YEDVKDLKTR RNHEQEQTFP GGGSTIYSMI

301 QSQSSAPTSQ EPAYTLYSLI QPSRKSGSRK RNHSPSFNST IYEVIGKSQP KAQNPARLSR

361 KELENFDVYS
```

In one embodiment, the invention provides a 2B4 DN form. In one embodiment, the 2B4 DN form comprises the extracellular ligand binding domain of 2B4. In one embodiment, the 2B4 DN form comprises the extracellular ligand binding domain of 2B4 and a transmembrane domain (e.g., mature form). In another embodiment, the 2B4 DN form comprises the extracellular ligand binding domain of 2B4, a transmembrane domain and a signal peptide (e.g., precursor form). The invention also provides encoding polypeptides sequence provided below, or fragments thereof. See GenBank NP_008984.1 for reference to domains within CD160, for example, signal peptide, amino acids 1 to 26; extracellular domain, amino acids 27 to 159. It is understood that a "CD160 nucleic acid molecule" refers to a polynucleotide encoding a CD160 polypeptide.

```
                                                           (NP_008984.1; SEQ ID NO: 26)
  1 MLLEPGRGCC ALAILLAIVD IQSGGCINIT SSASQEGTRL NLICTVWHKK EEAEGFVVFL

61 CKDRSGDCSP ETSLKQLRLK RDPGIDGVGE ISSQLMFTIS QVTPLHSGTY QCCARSQKSG

121 IRLQGHFFSI LFTETGNYTV TGLKQRQHLE FSHNEGTLSS GFLQEKVWVM LVTSLVALQA

181 L
```

In one embodiment, the invention provides a CD160 DN form. In one embodiment, the CD160 DN form comprises the extracellular ligand binding domain of CD160. In one embodiment, the CD160 DN form comprises the extracellular ligand binding domain of CD160 and a transmembrane domain (e.g., mature form). In another embodiment, the CD160 DN form comprises the extracellular ligand binding domain of CD160, a transmembrane domain and a signal peptide (e.g., precursor form). The invention also provides encoding polypeptides and nucleic acids of the CD160 DN forms of the invention. In a particular embodiment, the CD160 extracellular ligand binding domain is fused to one or more heterologous polypeptide sequences, that is, the CD160 DN form is chimeric. For example, the CD160 extracellular ligand binding domain can be fused at its N-terminus to a signal peptide that is optionally a heterologous signal peptide, including various signal peptides described herein. In addition, a CD160 DN form can comprise a transmembrane domain that is a heterologous transmembrane domain, including any of various transmembrane domains described herein.

In an embodiment of the invention, the CD160 DN form can comprise the extracellular domain, or a ligand binding portion thereof, of CD160, for example, amino acids 27 to 159 corresponding to the extracellular domain of CD160 (GenBank NP_008984.1; SEQ ID NO:26). A cell expressing such a CD160 DN form should lack the ability or have reduced ability to signal in an immune checkpoint pathway. In one embodiment, the CD160 DN form comprises the extracellular domain of CD160, or a ligand binding portion thereof, and a transmembrane domain derived from a heterologous polypeptide, including but not limited to one of the transmembrane domains described herein. In one non-limiting embodiment, the CD160 DN form comprises the transmembrane domain of CD8. In a cell expressing the CD160 DN form, intracellular signaling of the immune checkpoint pathway mediated by CD160 should be reduced or inhibited.

TGF-β Receptor Type 2.

TGF-β receptor type 2 binds to TGF-β and a type I receptor dimer forming a heterotetrameric complex with the ligand. A TGF-β receptor type 2 polypeptide can have an amino acid sequence corresponding to GenBank No. NP_001020018.1 (GI:67782326), sequence provided below, or fragments thereof. See GenBank NP_001020018.1 for reference to domains within TGF-β receptor type 2, for example, signal peptide, amino acids 1 to 22; extracellular domain, amino acids 23 to 191; transmembrane domain, amino acids 192 to 212; intracellular domain, amino acids 213 to 592 (see also annotation in UniProtKB-P37173). It is understood that a "TGF-β receptor type 2 nucleic acid molecule" refers to a polynucleotide encoding a TGF-β receptor type 2 polypeptide.

```
                                          (NP_001020018.1, SEQ ID NO: 27)
  1 MGRGLLRGLW PLHIVLWTRI ASTIPPHVQK SDVEMEAQKD EIICPSCNRT AHPLRHINND

61 MIVTDNNGAV KFPQLCKFCD VRFSTCDNQK SCMSNCSITS ICEKPQEVCV AVWRKNDENI

121 TLETVCHDPK LPYHDFILED AASPKCIMKE KKKPGETFFM CSCSSDECND NIIFSEEYNT

181 SNPDLLLVIF QVTGISLLPP LGVAISVIII FYCYRVNRQQ KLSSTWETGK TRKLMEFSEH

241 CAIILEDDRS DISSTCANNI NHNTELLPIE LDTLVGKGRF AEVYKAKLKQ NTSEQFETVA

301 VKIFPYEEYA SWKTEKDIFS DINLKHENIL QFLTAEERKT ELGKQYWLIT AFHAKGNLQE

361 YLTRHVISWE DLRKLGSSLA RGIAHLHSDH TPCGRPKMPI VHRDLKSSNI LVKNDLTCCL

421 CDFGLSLRLD PTLSVDDLAN SGQVGTARYM APEVLESRMN LENVESFKQT DVYSMALVLW

481 EMTSRCNAVG EVKDYEPPFG SKVREHPCVE SMKDNVLRDR GRPEIPSFWL NHQGIQMVCE

541 TLTECWDHDP EARLTAQCVA ERFSELEHLD RLSGRSCSEE KIPEDGSLNT TK
```

In one embodiment, the invention provides a TGFβ receptor DN form. In one embodiment, the TGFβ receptor DN form comprises the extracellular ligand binding domain of TGFβ receptor. In one embodiment, the TGFβ receptor DN form comprises the extracellular ligand binding domain of TGFβ receptor and a transmembrane domain (e.g., mature form). In another embodiment, the TGFβ receptor DN form comprises the extracellular ligand binding domain of TGFβ receptor, a transmembrane domain and a signal peptide (e.g., precursor form). The invention also provides encoding polypeptides and nucleic acids of the TGF-β receptor DN forms of the invention. In a particular embodiment, the TGFβ receptor extracellular ligand binding domain is fused to one or more heterologous polypeptide sequences, that is, the TGFβ receptor DN form is chimeric. For example, the TGFβ receptor extracellular ligand binding domain can be fused at its N-terminus to a signal peptide that is optionally a heterologous signal peptide, including various signal peptides described herein. In addition, a TGFβ receptor DN form can comprise a transmembrane domain that is a heterologous transmembrane domain, including any of various transmembrane domains described herein.

TGFβ receptor DN forms have been described previously (see, for example, Bottinger et al., *EMBO J.* 16:2621-2633 (1997), describing a DN form comprising TGFβ receptor extracellular and transmembrane domains; Foster et al., *J. Immunother.* 31:500-505 (2008); Bollard et al., *Blood* 99:3179-3187 (2002); Wieser et al., *Mol. Cell. Biol.* 13:7239-7247 (1993)). In an embodiment of the invention, the TGFβ receptor DN form can comprise the extracellular domain, or a ligand binding portion thereof, of TGFβ receptor, for example, amino acids 23 to 191 corresponding to the extracellular domain of TGFβ receptor (GenBank NP_001020018.1, SEQ ID NO:27). A cell expressing such a TGFβ receptor DN form lacks the ability or has reduced ability to signal in the cell. In one embodiment, a TGFβ receptor DN form is a deletion mutant having a deletion of the intracellular domain, for example, amino acids 213 to 592 of TGFβ receptor (GenBank NP_001020018.1, SEQ ID NO:27), or a portion thereof, such that intracellular signaling of mediated by TGFβ receptor is reduced or inhibited (see also Bottinger et al., *EMBO J.* 16:2621-2633 (1997); Foster et al., *J. Immunother.* 31:500-505 (2008); Bollard et al., *Blood* 99:3179-3187 (2002); Wieser et al., *Mol. Cell. Biol.* 13:7239-7247 (1993)).

It is understood that, optionally, a second DN form of an inhibitor of a cell-mediated immune response, such as an immune checkpoint inhibitor, can be expressed in a cell of the invention. In this case, it can be desirable to inhibit more than one cell-mediated immune response in the same cell. Thus, a cell can express two or more DN forms, each directed to a different inhibitor of a cell-mediated immune response, including those described above. For example, a DN form of PD-1 can be co-expressed in a cell with a DN form of TGF-β receptor, a DN form of PD-1 can be co-expressed with a DN form of CTLA-4, a CTLA-4 DN form can be co-expressed with a DN form of TGF-β, and so forth, as desired, including combinations of any of the DN forms described above

6.4. Methods of Treatment

The invention also relates to methods of treating disorders, such as an immune-mediated disorder, using the immunoinhibitory cells of the invention. The methods are used to treat a patient having an immune-mediated disorder. The methods of the invention relate to suppressing a pathologic immune response using the immunoinhibitory cells of the invention. Such pathologic immune responses include, but are not limited to, organ transplant rejection, autoimmune disorders, allergic disorders, fetomaternal intolerance, Alzheimer's disease, arthritis, and the like. It is understood that a pathologic immune response need not be the primary cause of a disorder, disease or condition. An immune-mediated disorder refers to a disorder, disease or condition associated with a pathologic immune response. Exemplary immune-mediated disorders include, but are not limited to, organ transplant rejection, autoimmune disorders, allergic disorders, fetomaternal intolerance, Alzheimer's disease, and the like, as discussed below in more detail.

In one embodiment, the invention provides a method of treating an immune-mediated disorder in a patient in need thereof, comprising administering to the patient a therapeutically effective amount of an immunoinhibitory cell or population of cells of the invention, or a pharmaceutical composition comprising such cell or cells. In a particular embodiment, the immune-mediated disorder is selected from the group consisting of organ transplant rejection, an autoimmune disorder, multiple sclerosis, type 1 diabetes, rheumatoid arthritis, primary biliary cirrhosis, myasthenia gravis, vitiligo, lupus, an allergic disorder, fetomaternal intolerance and Alzheimer's disease. In a particular embodiment, the immunoinhibitory cells are specific to (sensitized to, or recognize) an antigen that is the target of a pathologic immune response associated with an immune-mediated disorder. In another particular embodiment, immunoinhibitory cells express a chimeric antigen receptor (CAR), wherein the CAR binds to an antigen that is the target of a pathologic immune response associated with an immune-mediated disorder.

Organ Transplant Rejection.

In response to a foreign organ transplant, the host immune system normally launches an immune attack against the transplanted organ, which may result in ultimate rejection of the organ. T-cell recognition of alloantigen is the central and primary event in organ transplant rejection, which ultimately leads to graft rejection (Briscoe et al., *Nat. Med.* 8:220-222 (2002)). To prevent solid organ rejection (liver, lung, kidney, pancreas, small bowel, etc), lifelong immunosuppressive agents are used as standard-of-care to suppress host effector immune responses against the transplanted organ. Antigen-specific responses that are causative of the organ rejection have been identified (see, for example, Table 1).

Transduction of immunoinhibitory cells, such as regulatory T cells, with a dominant negative form (DN form) of an inhibitor of a cell-mediated immune response, for example, PD-1, can be used to promote immunosuppression within the transplanted organ and decrease organ transplant rejection. Furthermore, transplanted organ-specific antigen-responsive immunoinhibitory cells, such as regulatory T cells, can either be isolated as antigen-responsive cells, transduced with a DN form of an inhibitor of a cell-mediated immune response, and cultured ex vivo, or immunoinhibitory cells can be cotransduced with a DN form of an inhibitor of a cell-mediated immune response and a CAR that targets an antigen of the organ transplant to make the immunoinhibitory cells, such as regulatory T cells, antigen-specific. The transduced immunoinhibitory cells, such as regulatory T cells, can provide transplanted organ-specific immunosuppression, thereby enhancing the innate ability for immune tolerance in place of the conventional methods of immunosuppression.

In one embodiment, the invention provides a method of decreasing the risk of organ transplant rejection in an organ transplant recipient in need thereof comprising administering to the recipient a therapeutically effective amount of an immunoinhibitory cell or cell population of the invention. In a particular embodiment, the immunoinhibitory cells express a CAR that binds to an antigen of the organ transplant associated with organ transplant rejection. In another particular embodiment, the immunoinhibitory cells used in the method are the product of a process comprising isolating regulatory T cells from the recipient, and expanding the isolated regulatory T cells in cell culture. Exemplary organ transplant target antigens are described in Table 1. In a particular embodiment, the immunoinhibitory cells are isolated from the transplanted organ or from the area surrounding the transplanted organ. For example, during liver transplantation, regulatory T cells, for example, from the transplanted liver, can be harvested, transduced with a dominant negative form of an inhibitor of an cell-mediated immune response, and administered to the patient, the organ recipient, to reduce or prevent rejection of the transplanted liver.

In a particular embodiment, the transplanted organ is lung. In a particular embodiment where the transplanted organ is lung, the antigen which the cell recognizes and is sensitized to, or to which the CAR binds, is selected from the group consisting of MHC class I, MHC class II, collagen type V, K alpha1 tubulin, and MHC class I related chain A (MICA). In a particular embodiment, the transplanted organ is kidney. In a particular embodiment where the transplanted organ is kidney, the antigen which the cell recognizes and is sensitized to, or to which the CAR binds, is selected from the group consisting of MHC class I, MHC class II, fibronectin, collagen type IV, collagen type VI, vimentin, angiotensin II type 1 receptor (AGTR1), perlecan, and agrin.

In a particular embodiment, the transplanted organ is liver. In a particular embodiment where the transplanted organ is liver, the antigen which the cell recognizes and is sensitized to, or to which the CAR binds, is selected from the group consisting of MHC class I, MHC class II, collagen type I, collagen type II, collagen type III, and collagen type V. In a particular embodiment, the transplanted organ is heart. In a particular embodiment where the transplanted organ is heart, the antigen which the cell recognizes and is sensitized to, or to which the CAR binds, is selected from the group consisting of MHC class I, MHC class II, cardiac myosin, vimentin, collagen type V, K alpha1 tubulin, and MHC class I related chain A (MICA). In a particular embodiment, the transplanted organ is pancreas. In a particular embodiment where the transplanted organ is pancreas, the antigen which the cell recognizes and is sensitized to, or to which the CAR binds, is selected from the group consisting of MHC class I, MHC class II, an islet cell autoantibody (ICA) antigen, insulin, and glutamic acid decarboxylase (GAD).

Autoimmune Disorders.

Transduction of DN forms of a cell-mediated immune response, such as PD-1, in an immunoinhibitory cell, such as a regulatory T cell, can be used to treat autoimmune disorders. In a specific embodiment, a DN form of an inhibitor of a cell-mediated immune response, such as PD-1, can be transduced into immunoinhibitory cells that are follicular regulatory T cells to promote their suppressive ability. Such cells can be used to suppress autoantibody production while leaving other arms of the immune system intact in patients with autoimmune disorders.

In one embodiment, the invention provides a method of treating an autoimmune disorder in a patient in need thereof, comprising administering to the patient a therapeutically effective amount of the immunoinhibitory cells of the invention. In a particular embodiment, the immunoinhibitory cells express a CAR that binds to an autoimmune antigen of the autoimmune disorder. In another particular embodiment, the immunoinhibitory cells are the product of a process comprising isolating regulatory T cells from the patient, and expanding the isolated regulatory T cells in cell culture. In a particular embodiment, the autoimmune disorder is selected from the group consisting of multiple sclerosis, type 1 diabetes, rheumatoid arthritis, primary biliary cirrhosis, myasthenia gravis, vitiligo, and lupus, for example, systemic lupus erythematosus.

In one embodiment, the invention provides a method of promoting self-tolerance or reestablishing immunological tolerance to a self-antigen in a patient in need thereof, comprising administering to the patient a therapeutically effective amount of the immunoinhibitory cells of the invention, wherein the cell is a pathologic self-antigen specific regulatory T cell, or the cell population comprises pathologic self-antigen specific regulatory T cells. Such a method can be used to alleviate the pathological effects of an autoimmune disorder.

Multiple Sclerosis.

In one embodiment, the invention provides a method of treating an immune-mediated disorder that is multiple sclerosis in a patient in need thereof, comprising administering to the patient a therapeutically effective amount of an immunoinhibitory cell or population of cells of the invention, or a pharmaceutical composition comprising such cell or cells. In a particular embodiment, the immunoinhibitory cells are the product of a process comprising isolating regulatory T cells from the patient, and expanding the isolated regulatory T cells in cell culture. In another particular embodiment, the immunoinhibitory cells express a CAR that binds to an autoimmune antigen of the autoimmune disorder. In yet another particular embodiment, the antigen which the immunoinhibitory cell recognizes and is sensitized to, or to which the CAR binds to, is selected from the group consisting of myelin, myelin basic protein, myelin oligodendrocyte glycoprotein, proteolipid protein, astrocyte proteins, glial fibrillary protein (GFAP), and S100beta.

Type 1 Diabetes.

In one embodiment, the invention provides a method of treating an immune-mediated disorder that is type 1 diabetes in a patient in need thereof, comprising administering to the patient a therapeutically effective amount of an immunoinhibitory cell or population of cells of the invention, or a pharmaceutical composition comprising such cell or cells. In a particular embodiment, the immunoinhibitory cells are the product of a process comprising isolating regulatory T cells from the patient, and expanding the isolated regulatory T cells in cell culture. In another particular embodiment, the immunoinhibitory cells express a CAR that binds to an autoimmune antigen of the autoimmune disorder. In yet another particular embodiment, the antigen which the immunoinhibitory cell recognizes and is sensitized to, or to which the CAR binds to, is selected from the group consisting of a beta cell antigen, insulin, insulin B chain, proinsulin, preproinsulin, glutamic acid decarboxylase-65 (GAD65), islet-associated antigen 2, islet-specific glucose-6-phosphatase catalytic subunit-related protein (IGRP), zinc transporter 8 (ZnT8), islet antigen 2 (IA-2), heat shock protein 60 (HSP60), and chromogranin A.

Rheumatoid Arthritis.

In one embodiment, the invention provides a method of treating an immune-mediated disorder that is rheumatoid arthritis in a patient in need thereof, comprising administering to the patient a therapeutically effective amount of an immunoinhibitory cell or population of cells of the invention, or a pharmaceutical composition comprising such cell or cells. In a particular embodiment, the immunoinhibitory cells are the product of a process comprising isolating regulatory T cells from the patient, and expanding the isolated regulatory T cells in cell culture. In another particular embodiment, the immunoinhibitory cells express a CAR that binds to an autoimmune antigen of the autoimmune disorder. In yet another particular embodiment, the antigen which the immunoinhibitory cell recognizes and is sensitized to, or to which the CAR binds to, is selected from the group consisting of a dnaJ (heat shock protein), citrullinated-vimentin, and human cartilage glycoprotein-39.

Primary Biliary Cirrhosis.

In one embodiment, the invention provides a method of treating an immune-mediated disorder that is primary biliary cirrhosis in a patient in need thereof, comprising administering to the patient a therapeutically effective amount of an immunoinhibitory cell or population of cells of the invention, or a pharmaceutical composition comprising such cell or cells. In a particular embodiment, the immunoinhibitory cells are the product of a process comprising isolating regulatory T cells from the patient, and expanding the isolated regulatory T cells in cell culture. In another particular embodiment, the immunoinhibitory cells express a CAR that binds to an autoimmune antigen of the autoimmune disorder. In yet another particular embodiment, the antigen which the immunoinhibitory cell recognizes and is sensitized to, or to which the CAR binds to, is selected from the group consisting of a mitochondrial component, pyruvate dehydrogenase (mitochondrial); E2 component of pyruvate dehydrogenase; E2 component of branched chain 2-oxo acid dehydrogenase; E2 component of 2-oxo-glutarate dehydrogenase complex; E3 binding protein of dihydrolipoamide dehydrogenase; a nuclear component; nuclear protein sp100, nuclear pore complex protein gp120, and centromere.

Myasthenia Gravis.

In one embodiment, the invention provides a method of treating an immune-mediated disorder that is myasthenia gravis in a patient in need thereof, comprising administering to the patient a therapeutically effective amount of an immunoinhibitory cell or population of cells of the invention, or a pharmaceutical composition comprising such cell or cells. In a particular embodiment, the immunoinhibitory cells are the product of a process comprising isolating regulatory T cells from the patient, and expanding the isolated regulatory T cells in cell culture. In another particular embodiment, the immunoinhibitory cells express a CAR that binds to an autoimmune antigen of the autoimmune disorder. In yet another particular embodiment, the antigen which the immunoinhibitory cell recognizes and is sensitized to, or to which the CAR binds to, is selected from the group consisting of acetylcholine receptor (AChR), aquaporin-4 (AQP-4), CTLA-4, ICAM, LFA-3, CD40/CD154, ICOS/ICOSL, CD52, nuclear factor of activated T cells (NFAT), phospholipase C (PLC), CD25, Janus kinase, B cell activating factor (BAFF), a proliferating inducing ligand (APRIL), IL6R, IL17, IL12/IL23, an integrin, and a sphingosin receptor. Regulatory T cells naturally accumulate in the thymus. In a particular embodiment, the immunoinhibitory cells, such as regulatory T cells, accumulate in the thymus and can facilitate treatment of myasthenia gravis.

Vitiligo.

In one embodiment, the invention provides a method of treating an immune-mediated disorder that is vitiligo in a patient in need thereof, comprising administering to the patient a therapeutically effective amount of an immunoinhibitory cell or population of cells of the invention, or a pharmaceutical composition comprising such cell or cells. In a particular embodiment, the immunoinhibitory cells are the product of a process comprising isolating regulatory T cells from the patient, and expanding the isolated regulatory T cells in cell culture. In another particular embodiment, the immunoinhibitory cells express a CAR that binds to an autoimmune antigen of the autoimmune disorder. In yet another particular embodiment, the antigen which the immunoinhibitory cell recognizes and is sensitized to, or to which the CAR binds to, is a melanocyte antigen.

Systemic Lupus Erythematosus.

In one embodiment, the invention provides a method of treating an immune-mediated disorder that is lupus, in particular, systemic lupus erythematosus, in a patient in need thereof, comprising administering to the patient a therapeutically effective amount of an immunoinhibitory cell or population of cells of the invention, or a pharmaceutical composition comprising such cells. In a particular embodiment, the immunoinhibitory cells are the product of a process comprising isolating regulatory T cells from the patient, and expanding the isolated regulatory T cells in cell culture. In another particular embodiment, the immunoinhibitory cells express a CAR that binds to an autoimmune antigen of the autoimmune disorder. In yet another particular embodiment, the antigen which the immunoinhibitory cell recognizes and is sensitized to, or to which the CAR binds to, is selected from the group consisting of a toll-like receptor, TLR2, TLR3, TLR4, TLR5, TLR7, TLR8, TLR9, MyD88, and a IL-1R-associated kinase (IRAK).

Allergic Disorders.

In one embodiment, the invention provides a method of treating an allergic disorder in a patient in need thereof, comprising administering to the patient a therapeutically effective amount of an immunoinhibitory cell or population of such cells. In a particular embodiment, the immunoinhibitory cells are the product of a process comprising isolating regulatory T cells from the patient, and expanding the isolated regulatory T cells in cell culture. In another particular embodiment, the immunoinhibitory cells express a CAR that binds to an allergen associated with the allergic disorder. In yet another particular embodiment, the antigen to which the immunoinhibitory cell recognizes and is sensitized to, or to which the CAR binds to, is an allergen associated with the allergic disorder.

In a specific embodiment, in patients undergoing specific immunotherapy (SIT), along with the subcutaneous injection of the small but increasing doses of allergen peptide(s), immunoinhibitory cells that recognize and are sensitized to an antigen that is the allergen, or which express a CAR that binds to the allergen, can be coinjected with the allergen peptide(s). In a specific embodiment, this can result in the effect in the patient of decreasing the duration of specific immunotherapy, increasing the efficacy of specific immunotherapy, and/or prolonging the effect of specific immunotherapy, for example, using an allergen as the specific antigen, providing clinical improvement that can be prolonged for years. For example, the patient can be undergoing SIT for wasp-venom or a monoagent allergy (e.g., house dust mite). In a particular embodiment, administering the immunoinhibitory cells of the invention has an effect in the patient selected from the group consisting of decreasing the duration of SIT, increasing the efficacy of SIT, and/or prolonging the effect of SIT. Thus, the methods of the invention utilizing the immunoinhibitory cells of the invention can be used to improve the effectiveness of specific immunotherapy (SIT) with an allergen.

Fetomaternal Intolerance.

Regulatory T cells specific to (sensitized to) paternal antigen can be harvested from placenta in a lost pregnancy. These regulatory T cells specific to paternal antigen are transduced with a DN form of an inhibitor of a cell-mediated immune response, such as PD-1, cultured, and reinfused at a subsequent pregnancy, resulting in an increase in fetal implantation and a decrease in fetal loss.

In one embodiment, the invention provides a method of decreasing fetomaternal intolerance in a pregnant female in need thereof, comprising administering to the pregnant female a therapeutically effective amount of an immunoinhibitory cell or cell population, which cell or cell population is the product of a process comprising isolating regulatory T cells from a placenta from a prior pregnancy of the pregnant female and transducing the regulatory T cells so that they recombinantly express a dominant negative form of an inhibitor of a regulatory T cell-mediated immune response. In a particular embodiment, the regulatory T cell is isolated from a placenta of the pregnant female being treated for fetomaternal intolerance. In a further embodiment, the isolated regulatory T cell is paternal-antigen specific. The method can be used to increase the likelihood of fetal implantation and to decrease the likelihood of fetal loss.

Alzheimer's Disease.

The observation that PD-1 negative regulatory T cells are increased in mild cognitive impairment patients reinforces the inflammatory origin of Alzheimer's disease and supports a beneficial role of PD-1 negative regulatory T cells in mild cognitive impairment that is lost in patients with full-blown Alzheimer's disease.

In a specific embodiment, regulatory T cells are harvested from patients with mild cognitive impairment, and the cells transduced with a DN form of an inhibitor of a cell mediated immune response, such as PD-1. The cells are reinfused into the patient to prevent or slow the progression to Alzheimer's disease.

The criteria for diagnosing mild cognitive impairment have been described (Saresella et al., *J. Alzheimer's Disease* 21:927-938 (2010); Petersen, *J. Int. Med.* 256:183-194 (2004); Winblad et al., *J. Int. Med.* 256:240-246 (2004)). Exemplary criteria include reported cognitive decline, impaired cognitive function, essentially normal functional activities, and exclusion of dementia.

In one embodiment, the invention provides a method of decreasing the risk of progression to Alzheimer's disease in a patient with mild cognitive impairment, comprising administering to the patient a therapeutically effective amount of the immunoinhibitory cells or cell or cell population of the invention, wherein the immunoinhibitory cells are the product of a process comprising isolating regulatory T cells from the patient and expanding the isolated regulatory T cells in cell culture. In a particular embodiment, the regulatory T cells are isolated from a patient having mild cognitive impairment.

Arthritis.

Currently, in patients with arthritis and severe pain, steroid injections are administered locally, which alleviates the inflammatory response and relieves pain. Unlike steroids, which kill inflammatory cells, regulatory T cells counteract inflammation by suppression and PD-1 DNR increases suppression. In one embodiment, the invention provides a method of treating arthritis in a patient in need thereof, comprising administering to the patient a therapeutically effective amount of the immunoinhibitory cells of the invention. In a specific embodiment, the cells are administered regionally into the arthritic joints, for example, intraarticularly or directly at a tendon insertion site of an arthritic joint. In a specific embodiment, the arthritis being treated is osteoarthritis. In another specific embodiment, the arthritis being treated is psoriatic arthritis, which can be but is not limited to asymmetric inflammatory arthritis, symmetric arthritis and psoriatic spondylitis. In one embodiment, non-antigen specific regulatory T cells, or regulatory T cells not selected for a particular antigen specificity, are administered.

Dosages and Administration.

In the methods of the invention, the immunoinhibitory cells of the invention are administered to a subject or patient in need of treatment. The subject or patient can be a mammal, in particular a human. Preferably, the subject or patient is a human. The human can be a child or an adult.

For treatment, the amount administered is an amount effective for producing the desired effect. An effective amount or therapeutically effective amount is an amount sufficient to provide a beneficial or desired clinical result upon treatment. An effective amount can be provided in a single administration or a series of administrations (one or more doses). An effective amount can be provided in a bolus or by continuous perfusion. In terms of treatment, an effective amount is an amount that is sufficient to palliate, ameliorate, stabilize, reverse or slow the progression of the disease, or otherwise reduce the pathological consequences of the disease. The effective amount can be determined by the physician for a particular subject. Several factors are typically taken into account when determining an appropriate dosage to achieve an effective amount. These factors include age, sex and weight of the subject, the condition being treated, the severity of the condition and the form and effective concentration of the cells of the invention being administered.

The cells of the invention are generally administered as a dose based on cells per kilogram (cells/kg) of body weight of the subject to which the cells are administered. Generally the cell doses are in the range of about $10^4$ to about $10^{10}$ cells/kg of body weight, for example, about $10^5$ to about $10^9$, about $10^5$ to about $10^8$, about $10^5$ to about $10^7$, or about $10^5$ to $10^6$ cells/kg, depending on the mode and location of administration. In general, in the case of systemic administration, a higher dose is used than in regional administration, where the immunoinhibitory cells of the invention are administered in the region of pathologic immune response. Exemplary dose ranges include, but are not limited to, $1\times10^4$ to $1\times10^8$, $2\times10^4$ to $1\times10^8$, $3\times10^4$ to $1\times10^8$, $4\times10^4$ to $1\times10^8$, $5\times10^4$ to $1\times10^8$, $6\times10^4$, to $1\times10^8$, $7\times10^4$ to $1\times10^8$, $8\times10^4$ to $1\times10^8$, $9\times10^4$ to $1\times10^8$, $1\times10^5$ to $1\times10^8$, for example, $1\times10^5$ to $9\times10^7$, $1\times10^5$ to $8\times10^7$, $1\times10^5$ to $7\times10^7$, $1\times10^5$ to $6\times10^7$, $1\times10^5$ to $5\times10^7$, $1\times10^5$ to $4\times10^7$, $1\times10^5$ to $3\times10^7$, $1\times10^5$ to $2\times10^7$, $1\times10^5$ to $1\times10^7$, $1\times10^5$ to $9\times10^6$, $1\times10^5$ to $8\times10^6$, $1\times10^5$ to $7\times10^6$, $1\times10^5$ to $6\times10^6$, $1\times10^5$ to $5\times10^6$, $1\times10^5$ to $4\times10^6$, $1\times10^5$ to $3\times10^6$, $1\times10^5$ to $2\times10^6$, $1\times10^5$ to $1\times10^6$, $2\times10^5$ to $9\times10^7$, $2\times10^5$ to $8\times10^7$, $2\times10^5$ to $7\times10^7$, $2\times10^5$ to $6\times10^7$, $2\times10^5$ to $5\times10^7$, $2\times10^5$ to $4\times10^7$, $2\times10^5$ to $3\times10^7$, $2\times10^5$ to $2\times10^7$, $2\times10^5$ to $1\times10^7$, $2\times10^5$ to $9\times10^6$, $2\times10^5$ to $8\times10^6$, $2\times10^5$ to $7\times10^6$, $2\times10^5$ to $6\times10^6$, $2\times10^5$ to $5\times10^6$, $2\times10^5$ to $4\times10^6$, $3\times10^5$ to $3\times10^6$ cells/kg, and the like. Such dose ranges can be particularly useful for regional administration. In a particular embodiment, cells are provided in a dose of $1\times10^5$ to $1\times10^8$, for example $1\times10^5$ to $1\times10^7$, $1\times10^5$ to $1\times10^6$, $1\times10^6$ to $1\times10^8$, $1\times10^6$ to $1\times10^7$, $1\times10^7$ to $1\times10^8$, $1\times10^5$ to $5\times10^6$, $1\times10^5$ to $3\times10^6$ or $3\times10^5$ to $3\times10^6$ cells/kg for regional administration. Exemplary dose ranges also can include, but are not limited to, $5\times10^5$ to $1\times10^8$, for example, $6\times10^5$ to $1\times10^8$, $7\times10^5$ to $1\times10^8$ $8\times10^5$ to $1\times10^8$ $9\times10^5$ to $1\times10^8$ $1\times10^6$ to $1\times10^8$ $1\times10^6$ to $9\times10^7$ $1\times10^6$ to $8\times10^7$ $1\times10^6$ to $7\times10^7$, $1\times10^6$ to $6\times10^7$, $1\times10^6$ to $5\times10^7$, $1\times10^6$ to $4\times10^7$, $1\times10^6$ to $3\times10^7$ cells/kg, and the like. Such does can be particularly useful for systemic administration. In a particular embodiment, cells are provided in a dose of $1\times10^6$ to $3\times10^7$ cells/kg for systemic administration. Exemplary cell doses include, but are not limited to, a dose of $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10$, $1\times10^6$, $2\times10^6$, $3\times10^6$, $4\times10^6$, $5\times10^6$, $6\times10^6$, $7\times10^6$, $8\times10^6$, $9\times10^7$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$ and so forth in the range of about $10^4$ to about $10^{10}$ cells/kg. In addition, the dose can also be adjusted to account for whether a single dose is being administered or whether multiple doses are being administered. The precise determination of what would be considered an effective dose can be based on factors individual to each subject, including their size, age, sex, weight, and condition of the particular subject, as described above. Dosages can be readily determined by those skilled in the art based on the disclosure herein and knowledge in the art.

In a specific embodiment, the dosage for human administration is in the range of $1\times10^5$ to $1\times10^8$ cells/kg body weight of the human.

The cells of the invention can be administered by any methods known in the art, including, but not limited to, pleural administration, intravenous administration, subcutaneous administration, intranodal administration, intrathecal administration, intrapleural administration, intraperitoneal administration, intracranial administration, intratracheal administration, intraarticular administration, intrauterine administration, intraocular administration, intranasal administration, intraspinal administration, epidural administration, direct administration at a tendon insertion site, and direct administration to the thymus. In one embodiment, the cells of the invention can be delivered regionally to desired site using well known methods, including but not limited to, hepatic or aortic pump; limb, lung or liver perfusion; in the portal vein; through a venous shunt; in a cavity or in a vein that is nearby a desired site, and the like, such that the cells of the invention are delivered to a region such as the site of an organ transplant or the site of a pathologic immune response in an immune-mediated disorder. For example, in the case of a condition such as arthritis, the cells of the invention can be administered in the joint using intraarticular administration of direct administration at a tendon insertion site. In another embodiment, the cells of the invention can be administered systemically. In a preferred embodiment, the cells are administered regionally at a desired site. One skilled in the art can select a suitable mode of administration based on the type of immune-mediated disorder to be treated. The cells can be introduced by injection or catheter. In one embodiment, the cells are administered by intravenous infusion. Optionally, expansion and/or differentiation agents can be administered to the subject prior to, during or after administration of cells to increase production of the cells of the invention in vivo.

Proliferation of the cells of the invention is generally done ex vivo, prior to administration to a subject, and can be desirable in vivo after administration to a subject (see Kaiser et al., *Cancer Gene Therapy* 22:72-78 (2015)). Cell proliferation should be accompanied by cell survival to permit cell expansion and persistence. Cell isolation and/or expansion can be carried out using any method known in the art, e.g., as described in Lee et al., *Cancer Res.* 71:2871-2881 (2011).

The methods of the invention can further comprise adjuvant therapy in combination with, either prior to, during, or after treatment with the cells of the invention. Thus, the cell therapy methods of the invention can be used with other standard care and/or therapies for treating a particular disorder that are compatible with administration of the cells of the invention.

Optionally, the methods of administering cells of the invention can additionally include combination therapy that comprises immunomodulation of the host to facilitate the effectiveness of the administered cells of the invention. In an embodiment of the invention, the methods of the invention can further comprise administering at least one immunomodulatory agent. Non-limiting examples of immunomodulatory agents include immunoinhibitory agents.

In one embodiment, the immunoinhibitory cells of the invention expressing a DN form can be co-administered with immunoinhibitory cells co-expressing a CAR and a switch receptor. In such immunoinhibitory cells co-expressing a CAR and a switch receptor that are to be co-administered with immunoinhibitory cells expressing a DN form that does not contain a co-stimulatory domain (i.e., is not a switch receptor), the CAR binds to an antigen of the same disease or disorder as being treated. In another embodiment, the switch receptor can be transduced into the same cell in which a CAR and DN form are transduced, so that the cell recombinantly expresses all three constructs. Alternatively and preferably, the switch receptor is transduced into a cell in which the CAR, but not DN form is transduced, so as to produce a cell expressing both the switch receptor and CAR, which can be used in combination therapy with cells that express the DN form, or both the CAR and DN form, but not the switch receptor. In this case, two types of cells, either cells expressing a DN form and cells expressing a CAR and a switch receptor, or cells expressing a CAR and DN form and cells expressing a CAR and a switch receptor, are administered to the subject. Generally, the two types of cells are administered concurrently, but can also be administered sequentially, for example, within 1 or 2 hours, or within 1 or 2 days, or on the same day, as each other, as desired. In a particular embodiment, the co-stimulatory signaling domain of the CAR is different than the co-stimulatory signaling domain of the switch receptor being expressed in the same cell. This should result in two co-stimulatory signaling domains in the same cell and enhanced efficacy of the cells for immune cell therapy. In the case where it is believed that the administered immunoinhibitory cells will proliferate sufficiently in the subject being treated such that additional doses of cells need not be administered, it may be suitable to administer the immunoinhibitory cells of the invention at the initiation of immune cell therapy. Optionally, the immunoinhibitory cells of the invention, including optionally immunoinhibitory cells that express a switch receptor, can be administered more than once, as needed.

Administering an immunomodulatory agent, or cells expressing a CAR and a switch receptor, in a combination therapy with an immunoinhibitory cell of the invention expressing a DN form can occur concurrently with administration of the immunoinhibitory cells of the invention, for example, when immune cell therapy is initiated, or can occur sequentially at any time during the immune cell therapy, as desired. A person skilled in the art can readily determine appropriate regimens for administering cells of the invention and an immunomodulatory agent, or cells expressing a CAR and a switch receptor, in a combination therapy, including the timing and dosing of an immunomodulatory agent to be used in a combination therapy, based on the needs of the subject being treated.

6.5. Pharmaceutical Compositions

The invention additionally provides pharmaceutical compositions comprising the cells of the invention. The pharmaceutical composition comprises an effective amount of a cell of the invention and a pharmaceutically acceptable carrier. The cells of the invention and compositions comprising the cells can be conveniently provided in sterile liquid preparations, for example, typically isotonic aqueous solutions with cell suspensions, or optionally as emulsions, dispersions, or the like, which are typically buffered to a selected pH. The compositions can comprise carriers, for example, water, saline, phosphate buffered saline, and the like, suitable for the integrity and viability of the cells, and for administration of a cell composition.

Sterile injectable solutions can be prepared by incorporating cells of the invention in a suitable amount of the appropriate solvent with various amounts of the other ingredients, as desired. Such compositions can include a pharmaceutically acceptable carrier, diluent, or excipient such as sterile water, physiological saline, glucose, dextrose, or the like, that are suitable for use with a cell composition and for administration to a subject such as a human. Suitable buffers for providing a cell composition are well known in the art. Any vehicle, diluent, or additive used is compatible with preserving the integrity and viability of the cells of the invention.

The compositions will generally be isotonic, that is, they have the same osmotic pressure as blood and lacrimal fluid. The desired isotonicity of the cell compositions of the invention can be accomplished using sodium chloride, or other pharmaceutically acceptable agents such as dextrose, boric acid, sodium tartrate, or other inorganic or organic solutes. Sodium chloride is preferred particularly for buffers containing sodium ions. One particularly useful buffer is saline, for example, normal saline. Those skilled in the art will recognize that the components of the compositions should be selected to be chemically inert and will not affect the viability or efficacy of the cells of the invention and will be compatible for administration to a subject, such as a human. The skilled artisan can readily determine the amount of cells and optional additives, vehicles, and/or carrier in compositions to be administered in methods of the invention.

The cells of the invention can be administered in any physiologically acceptable vehicle. Suitable doses for administration are described herein. A cell population comprising cells of the invention can comprise a purified population of cells. Those skilled in the art can readily determine the percentage of cells in a cell population using various well-known methods, as described herein. The ranges of purity in cell populations comprising genetically modified cells of the invention can be from about 50% to about 55%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. Dosages can be readily adjusted by those skilled in the art; for example, a decrease in purity may require an increase in dosage.

The invention also provides kits for preparation of cells of the invention. In one embodiment, the kit comprises one or more vectors for generating a genetically engineered immunoinhibitory cell, such as a regulatory T cell, that expresses a DN form or co-expresses a CAR and DN form of an inhibitor of a cell-mediated immune response. The kits can be used to generate genetically engineered immunoinhibitory cells from autologous cells derived from a subject or from non-autologous cells to be administered to a compatible subject. In another embodiment, the kits can comprise cells of the invention, for example, autologous or non-autologous cells, for administration to a subject. In specific embodiments, the kits comprise the immunoinhibitory cells of the invention in one or more containers.

It is understood that modifications which do not substantially affect the activity of the various embodiments of this invention are also provided within the definition of the invention provided herein. Accordingly, the following example is intended to illustrate but not limit the present invention.

7. EXAMPLE

This example describes the construction and use of T cells expressing CARs and a dominant negative PD-1 mutant. Although this example relates to the use of CD4$^+$ T cells and CD8$^+$ T cells that are not regulatory T cells to enhance the immune response, instead of regulatory T cells to provide immunosuppression, it describes methodology that can be applied in the instant invention. Furthermore, the results described below, although with CD4$^+$ T cells and CD8$^+$ T cells, show that a dominant negative form of PD-1 can function as a dominant negative and can sustain the activity of a T cell expressing the dominant negative form of PD-1.

7.1. Methods and Procedures

The experimental procedures were approved by the Institutional Animal Care and Use Committee of Memorial Sloan Kettering Cancer Center (MSKCC). Each experiment was performed multiple times, using different donor T cells. To avoid confounding variables—such as differences due to transduction efficiencies, donor-related variability, and E:T ratios—data are presented using a representative experiment, with sample replicates of more than 3.

Cell Lines.

MSTO-211H human pleural mesothelioma cells (ATCC, Manassas, Va.) were retrovirally transduced to express GFP and firefly luciferase fusion protein (MSTO GFP-ffLuc$^+$). These cells were then transduced with the human MSLN variant 1 subcloned into an SFG retroviral vector to generate MSTO MSLN$^+$ GFP-ffLuc$^+$ Similarly, A549 cells and 3T3 murine fibroblasts were transduced with human MSLN variant 1 alone to generate A549 MSLN+ and 3T3 MSLN+ cell lines. 3T3 cells were also cotransduced with PD-L1 to generate 3T3 MSLN+ PDL1+ cells.

γ-Retroviral Vector Construction and Viral Production.

To generate MSLN-specific CARs, a cDNA encoding for a fully human scFv m912 specific for MSLN (provided by D. Dimitrov, National Cancer Institute at Frederick) (Feng et al., *Mol. Cancer Ther.* 8(5):1113-1118 (2009)), linked to the human CD8 leader domain and the CD8/CD3ζ, CD28/CD3ζ, or CD8/4-1BB/CD3ζ domain was engineered, as previously described (Zhong et al., *Mol. Ther.* 18(2):413-420 (2010)). The control PSMA-specific CAR was generated similarly, using a previously characterized PSMA-targeting scFv (Gade et al., *Cancer Res.* 65(19):9080-9088 (2005)). For construction of the PD-1 DNR, commercial gene synthesis was used to encode the extracellular portion of the PD-1 receptor (amino acids 1-151) fused to the CD8 transmembrane and hinge domains. The CAR sequence was inserted into the SFG γ-retroviral vector (provided by I. Riviere, MSKCC) and linked to a P2A sequence to induce coexpression of the LNGFR reporter (truncated low-affinity nerve growth factor receptor) or, in the case of the PD-1 DNR, the mCherry fluorescent protein reporter (Markley et al., *Blood* 115(17):3508-3519 (2010); Papapetrou et al., *Proc. Natl. Acad. Sci. USA* 106(31):12759-12764 (2009)). The CAR and PD-1 DNR encoding plasmids were then transfected into 293T H29 packaging cell lines to produce the retrovirus, as previously described (Hollyman et al., *J. Immunother.* 32(2):169-180 (2009)).

T-Cell Isolation, Gene Transfer, and CD4/CD8 Isolation.

Peripheral blood leukocytes were isolated from the blood of healthy volunteer donors under an institutional review board—approved protocol. Peripheral blood mononuclear cells (PBMCs) were isolated by low-density centrifugation on Lymphoprep (Stem Cell Technology, Vancouver, Canada) and activated with phytohemagglutinin (2 μg/mL, Remel, Lenexa, Kans.). Two days after isolation, PBMCs were transduced with 293T RD114-produced retroviral particles encoding for CARs and PD-1 DNR and spinoculated for 1 h at 3000 rpm on plates coated with retronectin (15 μg/mL; r-Fibronectin, Takara, Tokyo, Japan). After 1 day, transduced PBMCs were maintained in IL-2 (20 UI/mL; Novartis, Basel, Switzerland). Transduction efficiencies were determined by flow cytometric analysis. Pure populations of CD4+ and CD8+ CAR+ T cells, or mCherry-positive PD-1 DNR-expressing and mCherry-positive EV-expressing CAR+ T cells, were obtained by flow cytometric-based sorting (BD Aria Sorter; BD Biosciences, San Jose, Calif.).

Flow Cytometry.

Human MSLN expression was detected using a phycoerythrin- or allophycocyanin-conjugated anti-human MSLN rat IgG2a (R&D Systems, Minneapolis, Minn.). Expression of costimulation or inhibitory proteins on tumor cells was analyzed using the following antibodies: 4-1BBL (PE, clone 5F4; BioLegend, San Diego, Calif.), MHC HLA-DR (PE, clone L203; R&D Systems), PD-L1 (APC, clone MIH1; eBioscience, San Diego, Calif.), PD-L2 (APC, clone MIH18; eBioscience), and galectin-9 (APC, clone 9M13; BioLegend). T-cell phenotype and transduction efficiency were determined with monoclonal antibodies for CD3, CD4, CD8, and CD69m LNGFR. Expression of T-cell inhibitory receptors was analyzed using PD1 (APC, eBioJIU5; eBioscience), TIM-3 (PE, clone 344823; R&D Systems), and Lag-3 (PE, clone C9B7W; BioLegend). Cell staining was analyzed using a BD LSRII flow cytometer (BD, Franklin Lakes, N.J.) and FlowJo analysis software (FlowJo, Ashland, Oreg.).

T-Cell Functional Assays.

The cytotoxicity of T cells transduced with a CAR or vector control was determined by standard $^{51}$Cr-release assays, as previously described (McCoy et al., *National Cancer Institute Monograph* 37:59-67 (1973)). To perform the luciferase-activity assay, CAR+ T cells and MSTO-211H cells expressing MSLN and firefly luciferase were incubated for 18 h at different E:T ratios. Tumor-cell quantity was determined by BLI using IVIS 100/lumina II, after the addition of 100 μL of D-luciferin (15 mg/mL) per well, and was compared to the signal emitted by the tumor cells alone. CD107a and intracellular staining were performed after incubation of effector cells and irradiated MSTO-211H MSLN tumor cells for 18 h in 24-well plates at a ratio of 5:1. For the CD107a assay, 5 μL of CD107a-PeCy7 antibody (BD Biosciences, San Jose, Calif.) and Golgi STOP (4 μL/6 mL; BD Biosciences) were added at the time of stimulation. For intracellular staining, Golgi Plug (1 μL/1 mL; BD Biosciences) was added at the time of stimulation. After incubation, effector cells were stained for CD4, CD8, LNGFR, and CD3 marker, then fixed and permeabilized in accordance with the manufacturer's instructions (Cytofix/Cytoperm Kit; BD Biosciences). Staining for intracellular cytokines was performed using granzyme B-APC, perforin-PE, and IFN-γ-FITC antibodies (BD Biosciences).

Cytokine-release assays were performed by coculturing $3×10^4$ to $5×10^3$ T cells with target cells in a 1:1 to 5:1 ratio, in 200 μL of medium, in 96-well round-bottomed plates as triplicates. After 6 to 24 h of coculture, supernatants were collected. Cytokine levels were determined using a multiplex bead Human Cytokine Detection kit, in accordance with the manufacturer's instructions (Millipore, Darmstadt, Germany).

To analyze the proliferation capacity of T cells, $1×10^6$ CAR+ T cells were stimulated over irradiated MSTO-211H or 3T3 cells with or without MSLN expression (and, in the case of 3T3, with or without PD-L1). Proliferation assays were performed in the absence of exogenous IL-2. Cells were counted every 7 days and then overlaid on irradiated target cells for repeated stimulations. The CAR+ T cell number versus time was plotted for each T-cell group.

Orthotopic Pleural Mesothelioma Animal Model and Ex Vivo Experiments.

To develop the orthotopic mouse model of pleural mesothelioma, female NOD/SCIDγ mice (The Jackson Laboratory, Bar Harbor, Me.) aged 4 to 6 weeks were used. All procedures were performed under approved Institutional Animal Care and Use Committee protocols. Mice were anesthetized using inhaled isoflurane and oxygen, with bupivacaine administered for analgesia. Direct intrapleural injection of $1×10^5$ to $1×10^6$ tumor cells in 200 μL of serum-free medium via a right thoracic incision was performed to establish orthotopic MPM tumors, as previously described (Adusumilli et al., *Science Translational Medicine* 6(261):261ra151 (2014); Servais et al., *Clin. Cancer Res.* 18(9):2478-2489 (2012); Servais et al., in *Current Protocols in Pharmacology*, Enna, ed., Chapter 14 (Unit14 21), John Wiley & Sons (2011)). In total, $3×10^4$ to $1×10^5$ transduced T cells (in 200 μL of serum-free medium) were adoptively transferred into tumor-bearing mice, either into the thoracic cavity by direct intrapleural injection or systemically by tail vein injection. Tumor growth was monitored and quantified in vivo by BLI performed 20 minutes after a single intraperitoneal dose of D-luciferin (150 mg/kg; Perkin Elmer, Waltham, MA). BLI data were analyzed using Living Image software (version 2.60; Perkin Elmer); BLI signal was reported as total flux (photons per second), which represents the average of ventral and dorsal flux. To analyze the functional capacity of CAR T cells ex vivo, tumor tissues and mouse spleen were processed as follows: Tissues were weighed and harvested into ice-cold RPMI 1640. The tissues were manually morselized with a scalpel and then mechanically disaggregated through 40- to 100-μm filters. Next, samples were analyzed by FACS (fluorescence activated cell sorting) for phenotyping, or CAR+CD4+ or CD8+ T cells were sorted using a FACS Aria sorter then rested for 24 h in RPMI with IL-2 (60 UI/mL), and $^{51}$Cr-release and cytokine-release assays were performed as described above.

Histologic Analysis and Immunostaining.

Histopathologic evaluation of tumors was performed after hematoxylin and eosin (H&E) staining of paraffin-embedded, 4% paraformaldehyde-fixed tissue samples. Immunohistochemical analysis for human MSLN was performed with mouse anti-human MSLN immunoglobulin G, as previously described (Kachala et al., *Clin. Cancer Res.* 20(4): 1020-1028 (2014); Rizk et al., *Cancer Epidemiol. Biomarkers Prev.* 21(3):482-486 (2012); Tozbikian et al., *PLoS One* 9(12):e114900 (2014)).

Quantitative Real-Time PCR.

The mRNA from CD4+ LNGFR+ or CD8+ LNGFR+ sorted T cells were extracted and reverse transcribed into cDNA using μMACS One-Step cDNA kit (MACS molecular, Miltenyi Biotech Inc, Auburn, USA). Quantitative Real Time PCR (RT-PCR) was performed with the Taqman® method using Applied Biosystems® 7500 systems (Foster, Calif., USA), Taqman® Universal PCR Mastermix and Taqman® probes labeled with 6-carboxyfluorescein (FAM-MBG) and designed by Life Technologies (Carlsbad, Calif.): Tbet (Hs00203436_m1); Eomes (Hs00172872 ml); Granzyme B (Hs01554355 ml); IFN-γ (Hs00989291_m1); IL-2 (Hs00174114 ml); PD-1 (Hs01550088_m1). The comparative threshold cycle (CT) of the gene of interest was used and normalized to the β2m housekeeping gene using the following formula: ΔCt (sample)=Ct (gene of interest)-Ct ((β2m). Then, the $2^{-\Delta\Delta ct}$ method was used to analyze the relative fold change expression compared to control condition and calculated as follow: $2^{-\Delta\Delta ct}=2^{\wedge}$-(ΔCt(sample)-ΔCt (control)).

Statistical Methods.

Data were analyzed using Prism (version 6.0; GraphPad Software, La Jolla, Calif.) software and are presented as mean±SEM, as stated in the figure legends. Results were analyzed using the unpaired Student's t test (two-tailed), with the Bonferroni correction used for multiple comparisons, when applicable. Survival curves were analyzed using the log-rank test. Statistical significance was defined as P<0.05. All statistical analyses were performed with Prism software.

7.2. CARs with CD28 or 4-1BB Costimulation Exhibit Equivalent Effector Cytokine Secretion and Proliferation In Vitro Upon Initial Antigen Stimulation Three CARs were constructed that incorporated a human MSLN-specific scFv (Feng et al., *Mol. Cancer Ther.* 8(5): 1113-1118 (2009)) and either CD3ζ, CD28/CD3ζ or 4-1BB/CD3ζ signaling domains (Mz, M28z, MBBz) (FIGS. 1A and 1B). The P28z CAR, which is specific for prostate-specific membrane antigen (PSMA), served as a negative effector to control for alloreactivity and xenoreactivity. Both CD4+ and CD8+ human peripheral blood T lymphocytes were effectively transduced using the SFG-retroviral vector (50%-70% transduction) (FIG. 2). MSLN-transduced MSTO-211H cells (MSLN+) and PSMA-transduced EL-4 mouse lymphoma cells (MSLN−) served as MSLN-positive and -negative targets in the in vitro experiments. Mz-, M28z-, and MBBz-transduced T cells demonstrated similar MSLN-specific lysis in vitro (FIG. 1C). P28z CAR T cells did not lyse MSTO MSLN+ cells, and MSLN-targeted CARs did not lyse EL4 PSMA+ cells, demonstrating that lysis is antigen specific. Validating the functionality of costimulatory signaling (Brentjens et al., Clin. Cancer Res. 13(18 Pt 1):5426-5435 (2007)), M28z and MBBz CART cells secreted 2- to 15-fold higher levels of Th1 cytokines (FIG. 1D) and achieved 14-fold greater T-cell accumulation upon repeated exposure to MSLN+ cells when compared to Mz in the absence of exogenous IL-2 (FIG. 1E). Having established antigen specificity and validated the functionality of costimulatory signaling domains, evaluation of the therapeutic potential of MSLN-targeted CAR T cells in mice bearing established pleural tumors was performed.

These results demonstrate that CARs with CD28 or 4-1BB costimulation exhibit equivalent effector cytokine secretion and proliferation in vitro upon initial antigen stimulation.

7.3. Mesothelin CAR T Cells Become Exhausted Following In Vivo Antigen Exposure

To assess whether there is ongoing immuno inhibition of CAR T cells and to compare the relative abilities of M28z and MBBz CAR T cells to overcome tumor-mediated immuno inhibition, $1 \times 10^6$ CAR T cells were injected into the pleural cavities of MSTO MSLN+ tumor—bearing mice, allowed sufficient time for repeated antigen encounter and T-cell activation (confirmed by forward- and side-scatter and upregulation of the activation marker CD69), and then performed ex vivo stimulation of harvested CD4 or CD8 CAR tumor-infiltrating or splenic T cells with MSLN+ targets (schematic shown in FIG. 3A). Uninjected in vitro resting T cells ("preinfusion cells") were used to establish the baseline level of function (before antigen exposure). Compared with resting M28z CD8+ CAR T cells, T cells exposed to MSLN antigen in vivo had lower levels of cytolytic function (FIG. 3A) (preinfusion cell lysis, 20.5%; tumor-infiltrating T-cell lysis, 13.1%; splenic T-cell lysis, 8.7%). In contrast, MBBz CART cells retained cytolytic function (preinfusion cell lysis, 18.3%; tumor-infiltrating T-cell lysis, 37.2%; splenic T-cell lysis, 22.2%). Sorted CD4+ CAR T cells demonstrated a similar pattern of results.

Cytokine levels were also measured upon ex vivo stimulation of tumor-infiltrating and splenic CAR T cells, and a decrease in Th1 cytokine secretion was observed for CD4+ M28z CAR T cells exposed in vivo to MSLN+ antigen. CD4+ MBBz CAR T cells also demonstrated a decrease in Th1 cytokine secretion, although these cells were better able to retain cytokine secretion when compared with M28z CAR T cells (FIG. 3B). CD8+ T cell supernatants contained significantly lower levels of cytokines, compared with CD4+ T cell supernatants (a finding previously observed Adusumilli et al., Science Translational Medicine 6(261): 261ra151 (2014)). CD8+ T cells also had a decreased ability to secrete cytokines upon in vivo antigen exposure; CD8+ MBBz CAR T cells preferentially retained their ability to secrete IFN-γ. The mRNA levels of T cells harvested from tumor and spleen on day 3 after administration were assessed, and it was found that the in vivo expression levels of GzB, IL-2, and IFN-γ were mostly greater for CD4+ and CD8+ MBBz CAR T cells than for M28z CAR T cells, with the exception of IL-2 expression in the CD8+ subset (FIG. 3C).

These results demonstrate that mesothelin CAR T cells become exhausted following in vivo antigen exposure.

7.4. MBBz CAR T Cells Show Delayed Exhaustion In Vivo

Having demonstrated inhibition of both the cytolytic function and effector cytokine secretion in costimulated CAR T cells exposed to antigen in vivo, it was reasoned that repeated antigen stimulation may, similar to models of chronic infection, play a role in T-cell inhibition and that differing abilities to retain function upon repeated antigen encounter might explain enhanced efficacy of MBBz CAR T cells. Therefore, Mz, M28z, and MBBz CAR T cells were tested for their ability to withstand repeated antigen encounter in an in vitro model system, wherein cells were assessed for proliferation, cytolytic function, and cytokine secretion upon MSLN+ antigen stimulation every 7 days. M28z and MBBz CAR T cells had similar abilities to expand upon serial MSLN+ stimulation, expanding to levels 14-fold greater than those of Mz CAR T cells; they lost the ability to expand following the third stimulation (FIG. 4A). Both MBBz and M28z CAR T cells lost cytolytic function upon repeated antigen stimulation, although MBBz CAR T cells were better able to retain lytic function. Whereas lysis was equal among the three T-cell groups at the first stimulation, by the third stimulation, M28z lytic function was inhibited to a more pronounced level, such that MBBz CAR T cells had enhanced tumor lysis at multiple E:T ratios (FIG. 4B, right). Lytic function (as assessed by a degranulation assay measuring CD107a expression) at the third stimulation correlated with the results of chromium-release assays (FIG. 4C).

Next, Th1 cytokine secretion was measured. Similar levels between M28z and MBBz CAR T cells were noted at the first stimulation, as well as a successive decrease with each stimulation. As with cytotoxicity, MBBz CAR T cells preferentially retained cytokine secretion; cytokine concentrations decreased >30-fold for M28z and only around 2-fold for MBBz CAR T cells, when levels at the first and second stimulations were compared (FIG. 4D). The differences in cytokine production were confirmed by measuring intracellular levels of cytokines at the second stimulation. Reverse-transcriptase PCR analysis of CAR T cells at the time of antigen stimulation revealed that MBBz CAR T cells expressed markers that correlate with lower levels of exhaustion and inhibition, compared with M28z CAR T cells; MBBz CAR T cells expressed higher levels of Tbet and Eomesodermin and lower levels of PD1 and FoxP3 (FIG. 5). The in vivo function of persisting CAR T cells that had already been exposed to tumor antigen was tested. Although quantitative persistence is equal between M28z and MBBz CAR T cells, it was thought that MBBz CAR T cells would demonstrate enhanced function upon tumor rechallenge. Mice with established MSLN+ pleural tumors were administered intrapleural M28z or MBBz CAR T cells (at a dose of $1 \times 10^5$, E:T ratio 1:3000) to eradicate pleural tumor (FIG. 4E). Twenty days after the initial T-cell injection, tumor rechallenge was performed by injecting MSLN+ tumor cells (lx $10^6$) into the pleural cavity of survivors; tumor burden was monitored using BLI. Persisting MBBz CAR T cells were better able to control tumor burden (4 of 4 MBBz-treated mice had a BLI signal at baseline levels vs. 2 of 4 M28z-treated mice) (FIG. 4E).

These results demonstrate that MBBz CAR T cells show delayed exhaustion in vivo.

7.5. Tumor Cell PD-L1 Inhibits Mesothelin CAR T-Cell Effector Functions

Having established that CAR T cells are inhibited by the in vivo tumor environment and that MBBz CAR T cells are better able to overcome this inhibition, at least in part because of their ability to retain function upon repeated antigen encounter (see above), it was next sought to assess the role that inhibitory receptor and ligand pathways play in the model. Tumor-infiltrating T cells, in M28z-treated mice with tumor progression, were stained for the expression of well-known pathways of inhibition. High levels of expression of PD-1, Tim-3, and LAG-3 were found (FIG. 6A). Tumor-infiltrating MBBz CAR T cells harvested 6 days after administration demonstrated upregulation of inhibitory receptors as well, although they expressed significantly lower levels of PD-1 receptor at both the protein and the mRNA level (FIG. 6B-D). CD4+ T cells expressed higher levels of PD-1, compared with CD8+ T cells. It was also observed that a significant fraction of both M28z and MBBz CAR T cells coexpressed PD-1 and LAG-3 or PD-1 and Tim-3, suggesting that multiple inhibitory pathways could be functioning simultaneously (FIG. 7). Next, tumor-expressed ligands were assessed: PD-L1 and PD-L2 (ligands for PD-1), galectin-9 (ligand for Tim-3), and MHC class II (ligand for LAG-3). Only PD-1 ligands were expressed on pleural tumor cells harvested after intrapleural administration of M28z CAR T cells (FIG. 6E). As reported elsewhere (McGray et al., *Mol. Ther.* 22(1):206-218 (2014); Spranger et al., *Science Translational Medicine* 5(200):200ra116 (2013)), coculture of tumor cells with IFN-γ and TNF-α (at concentrations similar to those secreted by T cells in FIGS. 1 and 4) resulted in a similar level of upregulation of PD-L1 and PD-L2 expression on tumor cells (FIG. 6F), reflecting an adaptation of tumor cells to resist immune attack ("adaptive immunoresistance"). The unique presence of expression of both PD-1 receptor and ligand in vivo suggests that this pathway may play a significant inhibitory role.

As some studies have suggested that costimulation may be sufficient to overcome inhibition by PD-1 (Carter et al., *Eur. J. Immunol.* 32(3):634-643 (2002); Freeman et al., *J. Exp. Med.* 192(7):1027-1034 (2000); Koehler et al., *Cancer Res.* 67(5):2265-2273 (2007)), it was next assessed whether overexpressed PD-L1 can inhibit CAR T-cell function in an in vitro model of PD-L1-mediated immuno inhibition (using 3T3 mouse fibroblasts transduced with either MSLN alone (MSLN+) or both MSLN and PD-L1 (MSLN+PD-L1+)) (FIG. 8A). In both M28z and MBBz CAR T cells, PD-L1 overexpression resulted in decreased accumulation upon successive stimulation (FIG. 8B) and Th1 effector cytokine secretion (FIG. 8D). Although tumor-cell lysis was not inhibited upon initial stimulation, chromium release assay performed with 3T3s as targets following two stimulations against MSTO MSLN+ tumor cells demonstrates decreased lytic function in both M28z and MBBz CAR T cells, a higher extent of decrease in M28z CAR T cells (FIG. 8C). This result may be due to the differential upregulation of PD-1 on M28z and MBBz CAR T cells following exposure to MSTO MSLN+ tumor cells.

These results demonstrate that tumor cell PD-L1 inhibits mesothelin CAR T-cell effector functions.

7.6. Cell Intrinsic PD-1 Resistance Rescues M28z CAR T-Cell Function In Vivo

The above results indicate that the PD-1 pathway is a functioning mechanism of tumor-mediated immuno inhibition and that PD-1 upregulation following repeated antigen stimulation decreases CAR T-cell efficacy. Therefore, checkpoint blockade was combined with CD28 costimulatory signaling. Since the goal was to provide CAR T-cell-specific checkpoint blockade that was not reliant on repeated dosing of systemically administered antibodies, the studies were focused on genetically engineered methods of overcoming immuno inhibition. A PD-1 dominant negative receptor (DNR) was constructed that contained the extracellular ligand binding domain of the receptor fused to a CD8 transmembrane domain. Since the PD-1 DNR lacks any signaling domain, it was thought that sufficiently overexpressed receptor would enhance T-cell efficacy by saturating PD-1 ligands and thereby blocking signaling through the endogenous PD-1 receptor. M28z CAR T cells were cotransduced with either the PD-1 DNR linked by a P2A element to an mCherry reporter (PD-1 DNR) or an empty vector containing only the reporter (EV) (FIG. 9A). M28z CAR T cells cotransduced with the PD-1 DNR had slight but statistically significant advantages in proliferative ability (FIG. 9B), enhanced cytotoxicity (FIG. 9C) at multiple E:T ratios, as well as augmented levels of IL-2 and IFN-γ secretion (FIG. 9D).

Next, it was assessed whether intrapleural administration of M28z CAR T cells cotransduced with a genetically engineered PD-1 resistance would provide an in vivo advantage. Mice with established pleural MSLN+-expressing tumors were administered a single intrapleural dose of $5 \times 10^4$ CAR+M28z EV or M28z PD-1 DNR T cells, and treatment response was monitored by tumor burden measurements (using serial BLI) and median survival. Mice treated with M28z PD-1 DNR T cells had significantly enhanced tumor burden control and prolonged median survival (FIG. 9E); however, only some mice (7/16, 44%) had long-term tumor-free survival, suggesting that there are redundant mechanisms of immuno inhibition that must be overcome. A cohort of the mice (M28z PD-1 DNR) in this experiment survived beyond 450 days in spite of repeated tumor rechallenge, demonstrating the "functional persistence" of CAR T cells transduced with PD-1 DNR. These results demonstrate that, with an injection of 50,000 CAR T cells, not only was a large tumor burden eradicated but tumor relapse was prevented in spite of multiple tumor rechallenge over more than 15 months.

To investigate an alternative genetic strategy for overcoming PD-1-mediated immuno inhibition, M28z CAR T cells were cotransduced with vectors expressing PD-1-targeting shRNAs (FIG. 10A), which generated >60% PD-1 receptor knockdown at the protein level (FIG. 10B). In M28z CAR T cells, cotransduction with PD-1 shRNAs enhanced proliferative function upon MSLN+ antigen stimulation (FIG. 10C), augmented cytotoxicity (FIG. 10D), and enhanced cytokine secretion upon stimulation with either mesothelioma cells or MSLN+ PDL1+3T3 mouse fibroblasts (FIG. 10E), compared with cotransduction with an shRNA targeting a non-mammalian gene (M28z KanR). M28z PD-1 shRNA-transduced T cells did not achieve greater in vivo tumor rejection efficacy than M28z KanR T cells, but it is noteworthy that the level of knockdown was significantly lower in vivo than in vitro. Thus, the PD1 DNR proved to be the more effective strategy in vivo than the RNA interference approach. These results demonstrate that cell intrinsic PD-1 resistance rescues M28z CAR T-cell function in vivo.

7.7 PD-1 DNR Binds Efficiently to Both PD-L1 and PD-L2

To test the binding of PD-1 DNR to the ligands PD-L1 and PD-L2, T cells labeled with mCherry and transduced with PD-1 DNR were exposed to plates coated with PD-L1 fused to an Fc ("PD-L1 Fc"), PD-L2 fused to an Fc ("PD-L2 Fc"), or control isotype Fc ("iso Fc"). Human T cells were transduced with an mCherry construct to label the T cells with mCherry essentially as described in section 7.6. The PD-L1 Fc fusion, PD-L2 Fc fusion and control Fc were purchased commercially.

Plates coated with PD-L1 Fc fusion protein, PD-L2 Fc protein, or control isotype Fc were exposed to mCherry labeled T cells alone, mCherry labeled T cells in the presence of a PD-1 antibody, mCherry labeled T cells transduced with PD-1 DNR, and mCherry labeled T cells transduced with PD-1 DNR in the presence of PD-1 antibody.

As shown in FIG. 11, compared to control T cells with mCherry and without PD-1 DNR transduction, T cells transduced with PD-1 DNR bound to both PD-L1 and PD-L2 efficiently. These results demonstrate that the PD-1 DNR binds to both PD-L1 and PD-L2. Since some tumor cells express either PD-L1 or PD-L2, and since some immune cells (T cells and non-T cells such as macrophages, etc.) express either PD-L1 or PD-L2, it is significant that the PD-1 DNR binds to both PD-L1 and PD-L2. Thus, the T cells transduced with PD-1 DNR can neutralize both PD-L1 and PD-L2.

7.8 Addition of Intracellular 4-1BB Signaling to PD-1 DNR Improves CAR T Cell Efficiency A PD-1 DNR, which inhibits PD-L1- or PD-L2-mediated inhibition of T cell activation, can be converted into a positive co-stimulatory signal. Human T cells were transduced with a mesothelin-specific (MSLN-specific) CAR having CD28 and CD3zeta domains (M28z) (see also description of m28z above in section 7.2). To counteract PD-1/PD-L1 inhibition, cell-intrinsic genetic-engineering strategies were evaluated by cotranducing M28z CAR T cells with a PD-1 dominant negative receptor (PD-1 DNR) fused to a transmembrane domain fused to a 4-1BB intracellular signaling domain, also referred to as a switch receptor.

FIG. 12A shows a schematic diagram illustrating co-expression of a CAR and a PD-1 DNR. The lower portion of FIG. 12A represents a T cell expressing a CAR that binds to an antigen on a target cell, exemplified in FIG. 12A as a tumor cell expressing the tumor cell antigen mesothelin (MSLN). Binding of the T cell expressing a tumor cell antigen-specific CAR to a tumor cell expressing the tumor cell antigen results in activation of the T cell. Co-expression of the PD-1 DNR inhibits the immune checkpoint inhibitor pathway mediated by the binding of PD-L1 or PD-L2 to wild type PD-1. FIG. 12B shows a schematic diagram illustrating co-expression of a CAR and a PD-1 DNR, where the PD-1 DNR has been converted into a costimulatory construct by fusing a costimulatory molecule, exemplified as 4-1 BB, to a transmembrane domain fused to the ligand binding domain of PD-1. Such a construct is an example of a construct referred to herein as a switch receptor (see Liu et al., *Cancer Res.* 76:1578-1590 (2016)). The 4-1BB domain acts as a second costimulatory signal for T cell activation.

Human T cells were transduced with M28z CAR, both M28z CAR and PD-1 DNR, or both M28z CAR and a PD-1/4-1BB switch receptor construct. Transduced cells were antigen stimulated and analyzed for T cell accumulation in culture. As shown in FIG. 12C, M28z CAR T cell accumulation was increased at day 7, and the accumulation was enhanced when the T cells expressing M28z CAR were cotransduced with PD-1 DNR or a PD-1/4-1BB switch receptor construct.

FIG. 12D shows cytokine secretion of interferon gamma (IFN-γ), interleukin 2 (IL-2), tumor necrosis factor alpha (TNF-α) and granulocyte-macrophage colony-stimulating factor (GM-CSF) in human T cells transduced with M28z CAR, both M28z CAR and PD-1 DNR, or both M28z CAR and a PD-1/4-1BB switch receptor construct. Cytokine secretion assays were performed essentially as described above in section 7.1. As shown in FIG. 12D, secretion of IFN-γ, IL-2, TNF-α and GM-CSF was enhanced in cells expressing M28z CAR and a PD-1/4-1BB switch receptor construct relative to the cytokine secretion observed in cells expressing M28z CAR or cells coexpressing M28z CAR and PD-1 DNR. These results demonstrate that PD-L1 (or PD-L2) inhibition can be converted into a positive costimulatory signal by cotransducing in T cells a PD-1/4-1BB switch receptor construct with M28z CAR, resulting in enhanced cytokine secretion and T-cell accumulation.

7.9. Overview and Discussion of Experimental Results

As described above, CAR T-cell therapy and PD-1 checkpoint blockade have been demonstrated to be a rational combination in a solid tumor model. In vitro and ex vivo stimulation assays were performed to assess the impact of PD-1/PD-L1 inhibition on mesothelin CAR T-cell function. To directly counteract PD-1-mediated inhibition, retroviral vectors were used to combine CAR-mediated costimulation with a PD-1 DNR. Optimal signaling provided by this combinatorial strategy (costimulation and checkpoint blockade) enhanced T-cell function in the presence of tumor-encoded PD-L1 expression, resulting in long-term tumor-free survival following a single low dose of CAR T cells. These studies are relevant to the clinical practice of adoptive T-cell therapy and are immediately translational for the following reasons: (1) the costimulatory signaling domains tested—CD28 and 4-1BB—are the two costimulatory domains used in ongoing clinical trials (NCT02414269, NCT02159716, NCT01583686), (2) the models of pleural mesothelioma recapitulate human disease and uses large, clinically relevant tumor burdens that elucidate the relevance of T-cell exhaustion (Adusumilli et al., *Science Translational Medicine* 6(261): 261ra151 (2014); Servais et al., *Clin. Cancer Res.* 18(9):2478-2489 (2012); Servais et al., in *Current Protocols in Pharmacology*, Enna, ed., Chapter 14 (Unit14 21), John Wiley & Sons (2011); Servais et al., *PLoS One* 6(10):e26722 (2011)), and (3) the strategy of potentiating CAR T cells by genetically encoded checkpoint blockade uses human sequences that can be readily applied in the clinic (Adusumilli et al., *Science Translational Medicine* 6(261):261ra151 (2014); Feng et al., *Mol. Cancer Ther.* 8(5):1113-1118 (2009)).

The relatively higher expression of PD-1 in M28z CAR T cells led to the focus on CD28-stimulated CAR T cells. On the basis of this analysis, genetic strategies were pursued for counteracting PD-1 inhibitory signaling, such as generating a PD-1 dominant negative receptor (PD-1 DNR) and shRNAs targeting PD-1. When expressed at sufficient levels, the PD-1 DNR competes with the endogenous PD-1 receptor for binding PD-1 ligands (PD-L1 and PD-L2). CD28-costimulated T cells cotransduced with PD-1 DNR demonstrated enhanced in vitro T-cell functions and in vivo T-cell efficacy, suggesting PD-1 signaling as a significant mechanism by which tumor cells evade CAR T cells in the tumor model. Although only in vitro efficacy was demonstrated for PD-1-targeting shRNAs, the absence of in vivo efficacy is likely related to saturation of shRNA machinery by the high volume of PD-1 transcripts induced following multiple in vivo antigen encounters, a conclusion supported by the finding that PD-1 knockdown was significantly lower in vivo than in vitro. The findings described above point to the therapeutic usefulness of adoptively transferred T cells that are genetically engineered to resist tumor-mediated immune inhibition. A DNR that targets TGF-β has been validated in preclinical models and is currently being tested in clinical trials (Foster et al., *J. Immunother.* 31(5):500-505 (2008); Bollard et al., *Blood* 99(9):3179-3187 (2002)).

Whereas others have combined T-cell therapy with PD-1-blocking antibodies either in vivo or in vitro, the addition of a genetic strategy for coinhibitory blockade described in the experiments above overcomes several major obstacles limiting antibody therapy, including (1) the reliance on repeated administrations of antibodies and (2) the incidence of immune-related adverse events. T-cell therapy, then, has advantages over antibody therapy because it can establish long-term engraftment of T cells programmed for resistance to inhibition after a single dose and because it provides blockade of inhibitory pathways that is limited to a tumor-targeted T-cell repertoire, which may limit the autoimmunity that results from a more broadly applied antibody checkpoint blockade. Furthermore, it is possible that perhaps PD-L1 blocking antibodies can further prolong the efficacy of M28z and M28z PD-1 DNR CAR T cells.

The studies described above have identified one of the inhibitory mechanisms responsible for CAR T-cell and highlighted differences in the ability of costimulatory strategies to withstand immuno inhibition. Other inhibitory pathways may also function to potentially limit T-cell function. That a proportion of mice treated with PD-1 DNR-cotransduced M28z CAR T cells died of tumor progression suggests the action of other inhibitory mechanisms. Furthermore, the literature on chronic infection suggests the existence of other mechanisms of inhibition, both cell intrinsic and cell extrinsic, which are being assessed in tumor-targeted T-cell therapies (Moon et al., *Clin. Cancer Res.* 20(16):4262-4273 (2014); Riese et al., *Cancer Res.* 73(12):3566-3577 (2013)). Additional studies on inhibitory signaling can use an immunocompetent model that includes elements such as myeloid-derived suppressor cells and endogenous T cells, which have been shown to play important roles in tumor immune evasion.

The results described above have established the importance of tumor-mediated inhibition of CAR T-cell effector functions. By performing a comprehensive analysis of T-cell effector functions, it has been established that even costimulated CAR T cells, although they demonstrate enhanced persistence, are subject to inhibition upon repeated antigen encounter, both in vitro and within the tumor microenvironment. The results described demonstrate that CAR T-cell therapy can be used to counteract inhibitory signaling and provides the flexibility to engineer signaling domains that provide optimal costimulation and directly counteract inhibitory signals such as PD-1. Furthermore, in ongoing CAR T-cell therapy clinical trials in patients who show T-cell infiltration but a limited clinical response, combining PD-1/PD-L1 blockade following CAR T-cell therapy can be utilized to improve the efficacy of CAR T-cell therapy. The knowledge acquired from the clinical trials and the strategies presented herein are highly valuable to improve immunotherapy methods using CAR T cells, which is particularly use for therapy of solid tumors. Thus, the results described above exemplify methods that can be applied in a clinical setting to improve the efficacy of CAR T-cell therapy.

As described above, low-level tumor infiltration was modeled, and it was found that CAR T cells can be susceptible to tumor cell-mediated immune-inhibition, resulting in impaired T-cell function and diminished tumor rejection. T cells engineered to resist PD-1 signaling displayed enhanced anti-tumor potency. Following a single low-dose CAR T-cell therapy of advanced tumors, it was observed that, in response to CAR T-cell secreted cytokines, tumor cells upregulate PD-L1 leading to CAR T-cell inhibition and tumor relapse. To directly overcome the PD-L1-mediated immunosuppression, a PD-1 dominant negative receptor (PD-1 DNR) lacking the intracellular inhibitory signaling domain was designed. The cotransduction of PD-1 DNR with a CAR enhanced CAR T-cell function, resulting in a long-term cancer free survival following a single low-dose of CAR T cells. The coexpression of an immune checkpoint pathway receptor DNR with a CAR is immediately translatable to the clinic since a DNR can be added to any CAR without inhibiting CAR function or adding toxicity. Without being bound by a particular theory, it is believed that the DNR simply binds (consumes) negative signal induced by its corresponding ligand (for example, PD-L1 in the case of PD-1) and avoids downstream signaling.

The effectiveness of an immune cell expressing a CAR and a dominant negative form of an immune checkpoint inhibitor can also be enhanced by expression of a switch receptor, in which an intracellular co-stimulatory signaling domain is fused to a transmembrane domain fused to the extracellular ligand binding domain of an immune checkpoint inhibitor, such as PD-1. The results described above show that expression of a PD-1 extracellular domain fused to a transmembrane domain fused to the cytoplasmic domain of 4-1BB increased cytokine production and increased accumulation of CAR T cells. Expression of a switch receptor in an immune cell expressing a CAR can improve the efficacy of the immune cell for immunotherapy. Alternatively, a switch receptor can be expressed in a cell without a CAR, in which case the switch receptor functions as a dominant negative. Immune cells expressing a CAR and a switch receptor can be administered, concurrently or sequentially, with immune cells expressing a dominant negative form of an immune checkpoint inhibitor (that does not contain the co-stimulatory signaling domain, and thus is not a switch receptor), or with cells co-expressing a CAR and a dominant negative form of an immune checkpoint inhibitor (that does not contain the co-stimulatory signaling domain, and thus is not a switch receptor), to enhance the effectiveness of immunotherapy using such immune cells.

8. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A cell that is an immunoinhibitory cell that recombinantly expresses
    (a) a dominant negative form of programmed death 1 (PD-1), wherein the dominant negative form of PD-1 comprises (i) at least a portion of an extracellular domain of PD-1, said portion comprising the ligand binding region, and (ii) a transmembrane domain derived from a heterologous polypeptide; wherein the dominant negative form of PD-1 lacks any functional signaling domain; and
    (b) a chimeric antigen receptor (CAR) that binds to an antigen that is the target of a pathologic immune response associated with an immune-mediated disorder.

2. The cell of claim 1, wherein the immunoinhibitory cell is a regulatory T cell.

3. A polyclonal population of human regulatory T cells that are CD4$^+$CD25$^+$, and recombinantly express
    (a) a dominant negative form of programmed death 1 (PD-1), wherein the dominant negative form of PD-1 comprises (a) at least a portion of an extracellular domain of PD-1, said portion comprising the ligand binding region, and (b) a transmembrane domain derived from a heterologous polypeptide; wherein the dominant negative form of PD-1 lacks any functional signaling domain; and
    (b) a chimeric antigen receptor (CAR) that binds to an antigen that is the target of a pathologic immune response associated with an immune-mediated disorder.

4. A pharmaceutical composition comprising a therapeutically effective amount of the cell of claim 1; and a pharmaceutically acceptable carrier.

5. A method of treating an immune-mediated disorder in a patient in need thereof, comprising administering to the patient a therapeutically effective amount of the cell of claim 1.

6. The method of claim 5, wherein the immune-mediated disorder is selected from the group consisting of organ transplant rejection, an autoimmune disorder, multiple sclerosis, type 1 diabetes, rheumatoid arthritis, primary biliary cirrhosis, myasthenia gravis, vitiligo, lupus, an allergic disorder, fetomaternal intolerance, and Alzheimer's disease.

7. A method of decreasing the risk of organ transplant rejection in an organ transplant recipient in need thereof comprising administering to the recipient a therapeutically effective amount of the cell of claim 1, which cell expresses a CAR that binds to an antigen of the organ transplant associated with organ transplant rejection.

8. A method of promoting self-tolerance or reestablishing immunological tolerance to a self-antigen in a patient in need thereof, comprising administering to the patient a therapeutically effective amount of the cell of claim 1, wherein the cell is a regulatory T cell specific to the self-antigen, or the population comprises regulatory T cells specific to the self-antigen.

9. A method of treating arthritis in a patient in need thereof, comprising administering to the patient a therapeutically effective amount of the cell of claim 1, wherein the cell is administered intraarticularly or directly at a tendon insertion site of an arthritic joint.

10. The cell of claim 1, wherein the transmembrane domain is the transmembrane domain of CD8.

11. The cell of claim 2, wherein the transmembrane domain is the transmembrane domain of CD8.

12. The polyclonal population of claim 3, wherein the transmembrane domain is the transmembrane domain of CD8.

13. A pharmaceutical composition comprising a therapeutically effective amount of the cell of claim 2; and a pharmaceutically acceptable carrier.

14. A pharmaceutical composition comprising a therapeutically effective amount of the polyclonal population of claim 3; and a pharmaceutically acceptable carrier.

15. A pharmaceutical composition comprising a therapeutically effective amount of the cell of claim 10; and a pharmaceutically acceptable carrier.

16. A pharmaceutical composition comprising a therapeutically effective amount of the cell of claim 11; and a pharmaceutically acceptable carrier.

17. A pharmaceutical composition comprising a therapeutically effective amount of the cell of claim 12; and a pharmaceutically acceptable carrier.

18. The cell of claim 2, wherein the regulatory T cell is a human $CD4^+CD25^+$ T cell.

19. The cell of claim 2, wherein the regulatory T cell is a human $CD4^+CD127^{lo/-}CD25^+$ T cell.

20. The cell of claim 1, wherein the immunoinhibitory cell is a follicular regulatory T cell.

21. The cell of claim 1, wherein the cell is $FoxP3^+$.

22. The cell of claim 1, wherein the immunoinhibitory cell is a regulatory B cell.

23. The cell of claim 1, wherein the immune-mediated disorder is selected from the group consisting of organ transplant rejection, an autoimmune disorder, multiple sclerosis, type 1 diabetes, rheumatoid arthritis, primary biliary cirrhosis, myasthenia gravis, vitiligo, lupus, and an allergic disorder.

* * * * *

SEQUENCE LISTING

<160> NUMBER OF SEQ ID NOS: 29

<210> SEQ ID NO 1

-continued

```
<211> LENGTH: 164
<212> TYPE: PRT
<213> ORGANISM: Homo sapiens

<400> SEQUENCE: 1

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 2
<211> LENGTH: 339
<212> TYPE: DNA
<213> ORGANISM: Homo sapiens

<400> SEQUENCE: 2
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga agataagat ggcggaggcc tacagtgaga ttgggatgaa aggcgagcgc      240
cggaggggca aggggcacga tggcctttac cagggtctca gtacagccac caaggacacc     300
tacgacgccc ttcacatgca ggccctgccc cctcgctaa                             339

<210> SEQ ID NO 3
<211> LENGTH: 220
<212> TYPE: PRT
<213> ORGANISM: Homo sapiens

<400> SEQUENCE: 3

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
```

```
                65                  70                  75                  80
Lys Thr Gly Phe Asn Cys Asp Gly Lys Leu Gly Asn Glu Ser Val Thr
                    85                  90                  95

Phe Tyr Leu Gln Asn Leu Tyr Val Asn Gln Thr Asp Ile Tyr Phe Cys
                100                 105                 110

Lys Ile Glu Val Met Tyr Pro Pro Tyr Leu Asp Asn Glu Lys Ser
                115                 120                 125

Asn Gly Thr Ile Ile His Val Lys Gly Lys His Leu Cys Pro Ser Pro
            130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
210                 215                 220

<210> SEQ ID NO 4
<211> LENGTH: 321
<212> TYPE: DNA
<213> ORGANISM: Homo sapiens

<400> SEQUENCE: 4
attgaagtta tgtatcctcc tccttaccta gacaatgaga agagcaatgg aaccattatc      60
catgtgaaag ggaaacacct tgtccaagt cccctatttc ccggaccttc taagcccttt     120
tgggtgctgg tggtggttgg tggagtcctg gcttgctata gcttgctagt aacagtggcc     180
tttattattt tctgggtgag gagtaagagg agcaggctcc tgcacagtga ctacatgaac     240
atgactcccc gccgccccgg gcccaccgc aagcattacc agccctatgc cccaccacgc     300
gacttcgcag cctatcgctc c                                               321

<210> SEQ ID NO 5
<211> LENGTH: 255
<212> TYPE: PRT
<213> ORGANISM: Homo sapiens

<400> SEQUENCE: 5

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
```

```
            115                 120                 125
Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 6
<211> LENGTH: 277
<212> TYPE: PRT
<213> ORGANISM: Homo sapiens

<400> SEQUENCE: 6

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240
```

```
Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 7
<211> LENGTH: 199
<212> TYPE: PRT
<213> ORGANISM: Homo sapiens

<400> SEQUENCE: 7

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195

<210> SEQ ID NO 8
<211> LENGTH: 93
<212> TYPE: PRT
<213> ORGANISM: Homo sapiens

<400> SEQUENCE: 8

Met Ile His Leu Gly His Ile Leu Phe Leu Leu Leu Leu Pro Val Ala
1               5                   10                  15

Ala Ala Gln Thr Thr Pro Gly Glu Arg Ser Ser Leu Pro Ala Phe Tyr
            20                  25                  30

Pro Gly Thr Ser Gly Ser Cys Ser Gly Cys Gly Ser Leu Ser Leu Pro
        35                  40                  45

Leu Leu Ala Gly Leu Val Ala Ala Asp Ala Val Ala Ser Leu Leu Ile
    50                  55                  60

Val Gly Ala Val Phe Leu Cys Ala Arg Pro Arg Arg Ser Pro Ala Gln
65                  70                  75                  80
```

-continued

Glu Asp Gly Lys Val Tyr Ile Asn Met Pro Gly Arg Gly
                85                  90

<210> SEQ ID NO 9
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Met Ala Leu Pro Val Thr Ala Leu Leu Leu Pro Leu Ala Leu Leu
1               5                   10                  15

His Ala Ala Arg Pro
            20

<210> SEQ ID NO 10
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic linker peptide"

<400> SEQUENCE: 10

Gly Gly Gly Gly Ser Gly Gly Gly Ser Gly Gly Gly Gly Ser
1               5                   10                  15

<210> SEQ ID NO 11
<211> LENGTH: 235
<212> TYPE: PRT
<213> ORGANISM: Homo sapiens

<400> SEQUENCE: 11

Met Ala Leu Pro Val Thr Ala Leu Leu Leu Pro Leu Ala Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
                100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
        130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

```
Cys Gly Val Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
210                 215                 220

Gly Asp Lys Pro Ser Leu Ser Ala Arg Tyr Val
225                 230                 235

<210> SEQ ID NO 12
<211> LENGTH: 458
<212> TYPE: PRT
<213> ORGANISM: Homo sapiens

<400> SEQUENCE: 12

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
```

```
            325                 330                 335
Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
            355                 360                 365

Gln Cys Leu Leu Ser Asp Ser Gly Gln Val Leu Leu Glu Ser Asn Ile
            370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Gln Ala Glu Arg Met
                420                 425                 430

Ser Gln Ile Lys Arg Leu Leu Ser Glu Lys Lys Thr Cys Gln Cys Pro
                435                 440                 445

His Arg Phe Gln Lys Thr Cys Ser Pro Ile
                450                 455

<210> SEQ ID NO 13
<211> LENGTH: 288
<212> TYPE: PRT
<213> ORGANISM: Homo sapiens

<400> SEQUENCE: 13

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240
```

```
Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 14
<211> LENGTH: 244
<212> TYPE: PRT
<213> ORGANISM: Homo sapiens

<400> SEQUENCE: 14

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Ala Ala Pro Thr Thr Thr Pro Ala Pro Arg
                165                 170                 175

Pro Pro Thr Pro Ala Pro Thr Ile Ala Ser Gln Pro Leu Ser Leu Arg
            180                 185                 190

Pro Glu Ala Cys Arg Pro Ala Ala Gly Gly Ala Val His Thr Arg Gly
        195                 200                 205

Leu Asp Phe Ala Cys Asp Ile Tyr Ile Trp Ala Pro Leu Ala Gly Thr
    210                 215                 220

Cys Gly Val Leu Leu Leu Ser Leu Val Ile Thr Leu Tyr Cys Asn His
225                 230                 235                 240

Arg Arg Ile Gln

<210> SEQ ID NO 15
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Ser Gly Ala Thr Asn Phe Ser Leu Leu Lys Gln Ala Gly Asp Val
1               5                   10                  15
```

Glu Glu Asn Pro Gly Pro Met
            20

<210> SEQ ID NO 16
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 17
<211> LENGTH: 502
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp

```
                35                  40                  45
Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
                130                 135                 140

Thr Glu Arg Arg Ala Glu Val Pro Thr Ala His Pro Ser Pro Ser Pro
145                 150                 155                 160

Arg Pro Ala Gly Gln Ala Ala Ala Pro Thr Thr Thr Pro Ala Pro Arg
                165                 170                 175

Pro Pro Thr Pro Ala Pro Thr Ile Ala Ser Gln Pro Leu Ser Leu Arg
                180                 185                 190

Pro Glu Ala Cys Arg Pro Ala Ala Gly Gly Ala Val His Thr Arg Gly
                195                 200                 205

Leu Asp Phe Ala Cys Asp Ile Tyr Ile Trp Ala Pro Leu Ala Gly Thr
                210                 215                 220

Cys Gly Val Leu Leu Leu Ser Leu Val Ile Thr Leu Tyr Cys Asn His
225                 230                 235                 240

Arg Arg Ile Gln Gly Ser Gly Ala Thr Asn Phe Ser Leu Leu Lys Gln
                245                 250                 255

Ala Gly Asp Val Glu Glu Asn Pro Gly Pro Met Val Ser Lys Gly Glu
                260                 265                 270

Glu Asp Asn Met Ala Ile Ile Lys Glu Phe Met Arg Phe Lys Val His
                275                 280                 285

Met Glu Gly Ser Val Asn Gly His Glu Phe Glu Ile Glu Gly Glu Gly
290                 295                 300

Glu Gly Arg Pro Tyr Glu Gly Thr Gln Thr Ala Lys Leu Lys Val Thr
305                 310                 315                 320

Lys Gly Gly Pro Leu Pro Phe Ala Trp Asp Ile Leu Ser Pro Gln Phe
                325                 330                 335

Met Tyr Gly Ser Lys Ala Tyr Val Lys His Pro Ala Asp Ile Pro Asp
                340                 345                 350

Tyr Leu Lys Leu Ser Phe Pro Glu Gly Phe Lys Trp Glu Arg Val Met
                355                 360                 365

Asn Phe Glu Asp Gly Gly Val Val Thr Val Thr Gln Asp Ser Ser Leu
                370                 375                 380

Gln Asp Gly Glu Phe Ile Tyr Lys Val Lys Leu Arg Gly Thr Asn Phe
385                 390                 395                 400

Pro Ser Asp Gly Pro Val Met Gln Lys Lys Thr Met Gly Trp Glu Ala
                405                 410                 415

Ser Ser Glu Arg Met Tyr Pro Glu Asp Gly Ala Leu Lys Gly Glu Ile
                420                 425                 430

Lys Gln Arg Leu Lys Leu Lys Asp Gly Gly His Tyr Asp Ala Glu Val
                435                 440                 445

Lys Thr Thr Tyr Lys Ala Lys Lys Pro Val Gln Leu Pro Gly Ala Tyr
                450                 455                 460
```

```
Asn Val Asn Ile Lys Leu Asp Ile Thr Ser His Asn Glu Asp Tyr Thr
465                 470                 475                 480

Ile Val Glu Gln Tyr Glu Arg Ala Glu Gly Arg His Ser Thr Gly Gly
                485                 490                 495

Met Asp Glu Leu Tyr Lys
            500

<210> SEQ ID NO 18
<211> LENGTH: 1726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
accggtggta cctcacccctt accgagtcgg cgacacagtg tgggtccgcc gacaccagac      60
taagaaccta gaacctcgct ggaaaggacc ttacacagtc ctgctgacca cccccaccgc     120
cctcaaagta gacggcatcg cagcttggat acacgccgcc cacgtgaagg ctgccgaccc     180
cgggggtgga ccatcctcta gactggccac catgcagatc ccacaggcgc cctggccagt     240
cgtctgggcg gtgctacaac tgggctggcg gccaggatgg ttcttagact ccccagacag     300
gccctggaac cccccaccct tctcccccagc cctgctcgtg gtgaccgaag ggacaacgc     360 caccttcacc tgcagcttct ccaacacatc ggagagcttc gtgctaaact ggtaccgcat     420
gagccccagc aaccagacgg acaagctggc cgctttcccc gaggaccgca gccagcccgg     480
ccaggactgc cgcttccgtg tcacacaact gcccaacggg cgtgacttcc acatgagcgt     540
ggtcagggcc cggcgcaatg acagcggcac ctacctctgt ggggccatct ccctggcccc     600
caaggcgcag atcaaagaga gcctgcgggc agagctcagg gtgacagaga aagggcaga     660 agtgcccaca gcccaccccca gcccctcacc caggccagcc ggccaggcgg ccgcaccac     720 cacgacgcca gcgccgcgac caccaacccc ggcgcccacg atcgcgtcgc agcccctgtc     780
cctgcgccca gaggcgtgcc ggccagcggc gggggcgca gtgcacacga gggggctgga     840
cttcgcctgt gatatctaca tctgggcgcc cctggccggg acttgtgggg tccttctcct     900
gtcactggtt atcaccccttt actgcaacca caggcggatc caaggatctg agcaacaaa     960 cttctcacta ctcaaacaag caggtgacgt ggaggagaat cccggcccca tggtgagcaa    1020
gggcgaggag gataacatgg ccatcatcaa ggagttcatg cgcttcaagg tgcacatgga    1080
gggctccgtg aacggccacg agttcgagat cgagggcgag ggcgagggcc gcccctacga    1140
gggcacccag accgccaagc tgaaggtgac caagggtggc ccctgccct tcgcctggga    1200 catcctgtcc cctcagttca tgtacggctc caaggcctac gtgaagcacc ccgccgacat    1260
ccccgactac ttgaagctgt ccttccccga gggcttcaag tgggagcgcg tgatgaactt    1320
cgaggacggc ggcgtggtga ccgtgaccca ggactcctcc ctgcaggacg gcgagttcat    1380
ctacaaggtg aagctgcgcg gcaccaactt ccctccgac ggccccgtaa tgcagaagaa    1440
gaccatgggc tgggaggcct cctccgagcg gatgtacccc gaggacgcg ccctgaaggg    1500 cgagatcaag cagaggctga agctgaagga cggcggccac tacgacgctg aggtcaagac    1560
cacctacaag gccaagaagc ccgtgcagct gccggcgcc tacaacgtca acatcaagtt    1620
ggacatcacc tcccacaacg aggactacac catcgtggaa cagtacgaac gcgccgaggg    1680
ccgccactcc accggcggca tggacgagct gtacaagtaa ctcgag                   1726
```

<210> SEQ ID NO 19
<211> LENGTH: 223
<212> TYPE: PRT
<213> ORGANISM: Homo sapiens

<400> SEQUENCE: 19

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 20
<211> LENGTH: 289
<212> TYPE: PRT
<213> ORGANISM: Homo sapiens

<400> SEQUENCE: 20

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
            100                 105                 110

-continued

```
Tyr Arg Cys Ser Ala Asn Phe Gln Ser Asn Leu Ile Glu Ser His Ser
            115                 120                 125

Thr Thr Leu Tyr Val Thr Asp Val Lys Ser Ala Ser Glu Arg Pro Ser
        130                 135                 140

Lys Asp Glu Met Ala Ser Arg Pro Trp Leu Leu Tyr Ser Leu Leu Pro
145                 150                 155                 160

Leu Gly Gly Leu Pro Leu Leu Ile Thr Thr Cys Phe Cys Leu Phe Cys
                    165                 170                 175

Cys Leu Arg Arg His Gln Gly Lys Gln Asn Glu Leu Ser Asp Thr Ala
                180                 185                 190

Gly Arg Glu Ile Asn Leu Val Asp Ala His Leu Lys Ser Glu Gln Thr
                195                 200                 205

Glu Ala Ser Thr Arg Gln Asn Ser Gln Val Leu Leu Ser Glu Thr Gly
        210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                    245                 250                 255

Tyr Ala Ser Leu Asn His Ser Val Ile Gly Pro Asn Ser Arg Leu Ala
                260                 265                 270

Arg Asn Val Lys Glu Ala Pro Thr Glu Tyr Ala Ser Ile Cys Val Arg
                275                 280                 285

Ser

<210> SEQ ID NO 21
<211> LENGTH: 301
<212> TYPE: PRT
<213> ORGANISM: Homo sapiens

<400> SEQUENCE: 21

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190
```

```
Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300

<210> SEQ ID NO 22
<211> LENGTH: 525
<212> TYPE: PRT
<213> ORGANISM: Homo sapiens

<400> SEQUENCE: 22

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
```

```
            260                 265                 270
Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Gly Gly Gly
            290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Leu Leu Phe Leu Ile Leu Gly Val Leu Ser Leu Leu Leu Leu
            450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
            515                 520                 525

<210> SEQ ID NO 23
<211> LENGTH: 244
<212> TYPE: PRT
<213> ORGANISM: Homo sapiens

<400> SEQUENCE: 23

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
            35                  40                  45

Ser Thr Thr Ala Gln Val Thr Gln Val Asn Trp Glu Gln Gln Asp Gln
            50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110
```

```
Tyr Pro Asp Gly Thr Tyr Thr Gly Arg Ile Phe Leu Glu Val Leu Glu
            115                 120                 125

Ser Ser Val Ala Glu His Gly Ala Arg Phe Gln Ile Pro Leu Leu Gly
        130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly
```

<210> SEQ ID NO 24
<211> LENGTH: 287
<212> TYPE: PRT
<213> ORGANISM: Homo sapiens

<400> SEQUENCE: 24

```
Met Ser Pro His Pro Thr Ala Leu Leu Gly Leu Val Leu Cys Leu Ala
1               5                   10                  15

Gln Thr Ile His Thr Gln Glu Glu Asp Leu Pro Arg Pro Ser Ile Ser
            20                  25                  30

Ala Glu Pro Gly Thr Val Ile Pro Leu Gly Ser His Val Thr Phe Val
        35                  40                  45

Cys Arg Gly Pro Val Gly Val Gln Thr Phe Arg Leu Glu Arg Asp Ser
    50                  55                  60

Arg Ser Thr Tyr Asn Asp Thr Glu Asp Val Ser Gln Ala Ser Pro Ser
65                  70                  75                  80

Glu Ser Glu Ala Arg Phe Arg Ile Asp Ser Val Arg Glu Gly Asn Ala
                85                  90                  95

Gly Leu Tyr Arg Cys Ile Tyr Tyr Lys Pro Pro Lys Trp Ser Glu Gln
            100                 105                 110

Ser Asp Tyr Leu Glu Leu Leu Val Lys Glu Ser Ser Gly Gly Pro Asp
        115                 120                 125

Ser Pro Asp Thr Glu Pro Gly Ser Ser Ala Gly Pro Thr Gln Arg Pro
    130                 135                 140

Ser Asp Asn Ser His Asn Glu His Ala Pro Ala Ser Gln Gly Leu Lys
145                 150                 155                 160

Ala Glu His Leu Tyr Ile Leu Ile Gly Val Ser Val Val Phe Leu Phe
                165                 170                 175

Cys Leu Leu Leu Leu Val Leu Phe Cys Leu His Arg Gln Asn Gln Ile
            180                 185                 190

Lys Gln Gly Pro Pro Arg Ser Lys Asp Glu Glu Gln Lys Pro Gln Gln
        195                 200                 205

Arg Pro Asp Leu Ala Val Asp Val Leu Glu Arg Thr Ala Asp Lys Ala
    210                 215                 220

Thr Val Asn Gly Leu Pro Glu Lys Asp Arg Glu Thr Asp Thr Ser Ala
225                 230                 235                 240
```

```
Leu Ala Ala Gly Ser Ser Gln Glu Val Thr Tyr Ala Gln Leu Asp His
                245                 250                 255

Trp Ala Leu Thr Gln Arg Thr Ala Arg Ala Val Ser Pro Gln Ser Thr
            260                 265                 270

Lys Pro Met Ala Glu Ser Ile Thr Tyr Ala Ala Val Ala Arg His
        275                 280                 285

<210> SEQ ID NO 25
<211> LENGTH: 370
<212> TYPE: PRT
<213> ORGANISM: Homo sapiens

<400> SEQUENCE: 25

Met Leu Gly Gln Val Val Thr Leu Ile Leu Leu Leu Leu Lys Val
1               5                   10                  15

Tyr Gln Gly Lys Gly Cys Gln Gly Ser Ala Asp His Val Val Ser Ile
                20                  25                  30

Ser Gly Val Pro Leu Gln Leu Gln Pro Asn Ser Ile Gln Thr Lys Val
            35                  40                  45

Asp Ser Ile Ala Trp Lys Lys Leu Leu Pro Ser Gln Asn Gly Phe His
        50                  55                  60

His Ile Leu Lys Trp Glu Asn Gly Ser Leu Pro Ser Asn Thr Ser Asn
65                  70                  75                  80

Asp Arg Phe Ser Phe Ile Val Lys Asn Leu Ser Leu Leu Ile Lys Ala
                85                  90                  95

Ala Gln Gln Gln Asp Ser Gly Leu Tyr Cys Leu Glu Val Thr Ser Ile
                100                 105                 110

Ser Gly Lys Val Gln Thr Ala Thr Phe Gln Val Phe Val Phe Glu Ser
            115                 120                 125

Leu Leu Pro Asp Lys Val Glu Lys Pro Arg Leu Gln Gly Gln Gly Lys
        130                 135                 140

Ile Leu Asp Arg Gly Arg Cys Gln Val Ala Leu Ser Cys Leu Val Ser
145                 150                 155                 160

Arg Asp Gly Asn Val Ser Tyr Ala Trp Tyr Arg Gly Ser Lys Leu Ile
                165                 170                 175

Gln Thr Ala Gly Asn Leu Thr Tyr Leu Asp Glu Val Asp Ile Asn
            180                 185                 190

Gly Thr His Thr Tyr Thr Cys Asn Val Ser Asn Pro Val Ser Trp Glu
            195                 200                 205

Ser His Thr Leu Asn Leu Thr Gln Asp Cys Gln Asn Ala His Gln Glu
        210                 215                 220

Phe Arg Phe Trp Pro Phe Leu Val Ile Ile Val Ile Leu Ser Ala Leu
225                 230                 235                 240

Phe Leu Gly Thr Leu Ala Cys Phe Cys Val Trp Arg Arg Lys Arg Lys
                245                 250                 255

Glu Lys Gln Ser Glu Thr Ser Pro Lys Glu Phe Leu Thr Ile Tyr Glu
            260                 265                 270

Asp Val Lys Asp Leu Lys Thr Arg Arg Asn His Glu Gln Glu Gln Thr
        275                 280                 285

Phe Pro Gly Gly Gly Ser Thr Ile Tyr Ser Met Ile Gln Ser Gln Ser
        290                 295                 300

Ser Ala Pro Thr Ser Gln Glu Pro Ala Tyr Thr Leu Tyr Ser Leu Ile
305                 310                 315                 320

Gln Pro Ser Arg Lys Ser Gly Ser Arg Lys Arg Asn His Ser Pro Ser
                325                 330                 335
```

```
Phe Asn Ser Thr Ile Tyr Glu Val Ile Gly Lys Ser Gln Pro Lys Ala
            340                 345                 350

Gln Asn Pro Ala Arg Leu Ser Arg Lys Glu Leu Glu Asn Phe Asp Val
        355                 360                 365

Tyr Ser
    370

<210> SEQ ID NO 26
<211> LENGTH: 181
<212> TYPE: PRT
<213> ORGANISM: Homo sapiens

<400> SEQUENCE: 26

Met Leu Leu Glu Pro Gly Arg Gly Cys Cys Ala Leu Ala Ile Leu Leu
1               5                   10                  15

Ala Ile Val Asp Ile Gln Ser Gly Gly Cys Ile Asn Ile Thr Ser Ser
            20                  25                  30

Ala Ser Gln Glu Gly Thr Arg Leu Asn Leu Ile Cys Thr Val Trp His
        35                  40                  45

Lys Lys Glu Glu Ala Glu Gly Phe Val Val Phe Leu Cys Lys Asp Arg
    50                  55                  60

Ser Gly Asp Cys Ser Pro Glu Thr Ser Leu Lys Gln Leu Arg Leu Lys
65                  70                  75                  80

Arg Asp Pro Gly Ile Asp Gly Val Gly Glu Ile Ser Ser Gln Leu Met
                85                  90                  95

Phe Thr Ile Ser Gln Val Thr Pro Leu His Ser Gly Thr Tyr Gln Cys
            100                 105                 110

Cys Ala Arg Ser Gln Lys Ser Gly Ile Arg Leu Gln Gly His Phe Phe
        115                 120                 125

Ser Ile Leu Phe Thr Glu Thr Gly Asn Tyr Thr Val Thr Gly Leu Lys
    130                 135                 140

Gln Arg Gln His Leu Glu Phe Ser His Asn Glu Gly Thr Leu Ser Ser
145                 150                 155                 160

Gly Phe Leu Gln Glu Lys Val Trp Val Met Leu Val Thr Ser Leu Val
                165                 170                 175

Ala Leu Gln Ala Leu
        180

<210> SEQ ID NO 27
<211> LENGTH: 592
<212> TYPE: PRT
<213> ORGANISM: Homo sapiens

<400> SEQUENCE: 27

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95
```

```
Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Val Ile Phe Gln Val
            180                 185                 190

Thr Gly Ile Ser Leu Leu Pro Pro Leu Gly Val Ala Ile Ser Val Ile
            195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
                260                 265                 270

Thr Leu Val Gly Lys Gly Arg Phe Ala Glu Val Tyr Lys Ala Lys Leu
            275                 280                 285

Lys Gln Asn Thr Ser Glu Gln Phe Glu Thr Val Ala Val Lys Ile Phe
    290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
            355                 360                 365

Trp Glu Asp Leu Arg Lys Leu Gly Ser Ser Leu Ala Arg Gly Ile Ala
    370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
            420                 425                 430

Leu Ser Val Asp Asp Leu Ala Asn Ser Gly Gln Val Gly Thr Ala Arg
            435                 440                 445

Tyr Met Ala Pro Glu Val Leu Glu Ser Arg Met Asn Leu Glu Asn Val
            450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
            500                 505                 510
```

-continued

```
Lys Asp Asn Val Leu Arg Asp Arg Gly Arg Pro Glu Ile Pro Ser Phe
        515                 520                 525

Trp Leu Asn His Gln Gly Ile Gln Met Val Cys Glu Thr Leu Thr Glu
        530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ser Gly Gly Gly Ser
1               5

<210> SEQ ID NO 29
<211> LENGTH: 4
<212> TYPE: PRT
<213> ORGANISM: Homo sapiens

<400> SEQUENCE: 29

Tyr Val Lys Met
1
```